United States Patent
Donald et al.

(10) Patent No.: US 11,236,087 B2
(45) Date of Patent: Feb. 1, 2022

(54) HIGHLY ACTIVE PYRAZOLO-PIPERIDINE SUBSTITUTED INDOLE-2-CARBOXAMIDES ACTIVE AGAINST THE HEPATITIS B VIRUS (HBV)

(71) Applicant: AiCuris GmbH & Co. KG, Wuppertal (DE)

(72) Inventors: Alastair Donald, Wuppertal (DE); Andreas Urban, Sprockhovel (DE); Susanne Bonsmann, Cologne (DE); Anita Wegert, Aldenhofen (DE); Jasper Springer, Diepenveen (NL)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 16/760,929

(22) PCT Filed: Nov. 2, 2018

(86) PCT No.: PCT/EP2018/000503
§ 371 (c)(1),
(2) Date: May 1, 2020

(87) PCT Pub. No.: WO2019/086142
PCT Pub. Date: May 9, 2019

(65) Prior Publication Data
US 2021/0179608 A1   Jun. 17, 2021

(30) Foreign Application Priority Data
Nov. 2, 2017 (EP) .................... 17199676.2

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
USPC ........................................................ 514/303
See application file for complete search history.

(56) References Cited

U.S. PATENT DOCUMENTS

| | | |
|---|---|---|
| 8,273,765 B2 | 9/2012 | Fancelli et al. |
| 8,309,578 B2 | 11/2012 | Mantegani et al. |
| 2017/0158691 A1 | 6/2017 | Hartman et al. |

FOREIGN PATENT DOCUMENTS

| | | |
|---|---|---|
| WO | 0212242 A2 | 2/2002 |
| WO | 10060854 A1 | 6/2010 |
| WO | 2018056453 * | 3/2019 |

OTHER PUBLICATIONS

Liudi Tang et al: "The current status and future directions of hepatitis B antiviral drug discovery", Expert Opinion on Drug Discovery, vol. 12, No. 1, Nov. 11, 2016 (Nov. 11, 2016), London, GB, pp. 5-15, XP055435640, ISSN: 1746-0441.
Zhi Chen et al: "patents and development of HBV and HCV clinical treatment: from 2001 to Apr. 2005", Expert Opinion on Therapeutic Patents, Informa Healthcare, GB, vol. 15, No. 8, Jan. 1, 2005 (Jan. 1, 2005), pp. 1027-1039, XP002384991, ISSN: 1354-3776.
Murali Dhar et al: "Synthesis and SAR of p38alpha MAP kinase inhibitors based on heterobicyclic scaffolds", Bioorganic & Medicinal Chemistry Letters, Pergamon, Amsterdam, NL, vol. 17, No. 18, Sep. 15, 2007 (Sep. 15, 2007), pp. 5019-5024, XP022206815, ISSN: 0960-894X.
Database Registry [online] Chemical Abstracts Service, Columbus, Ohio, US; May 12, 2016 (May 12, 2016), XP002776843, retrieved from STN Database accession No. 1909100-90-8.
Database Registry [online] Chemical Abstracts Service, Columbus, Ohio, US; Sep. 26, 2014 (Sep. 26, 2014), XP002776844, retrieved from STN Database accession No. 1626950-85-3.
Database Registry [online] Chemical Abstracts Service, Columbus, Ohio, US; Sep. 23, 2014 (Sep. 23, 2014), XP002776845, retrieved from STN Database accession No. 1624680-56-3.
Database Registry [online] Chemical Abstracts Service, Columbus, Ohio, US; Sep. 14, 2011 (Sep. 14, 2011), XP002776846, retrieved from STN Database accession No. 1332166-27-4.
International Search Report PCT/EP2018/000503 dated Feb. 14, 2019 (pp. 1-6).

* cited by examiner

*Primary Examiner* — Niloofar Rahmani
(74) *Attorney, Agent, or Firm* — Millen White Zelano and Branigan, PC; Richard Traverso

(57) ABSTRACT

The present invention relates generally to novel antiviral agents. Specifically, the present invention relates to compounds which can inhibit the protein(s) encoded by hepatitis B virus (HBV) or interfere with the function of the HBV replication cycle, compositions comprising such compounds, methods for inhibiting HBV viral replication, methods for treating or preventing HBV infection, and processes and intermediates for making the compounds.

8 Claims, No Drawings

Specification includes a Sequence Listing.

HIGHLY ACTIVE PYRAZOLO-PIPERIDINE SUBSTITUTED INDOLE-2-CARBOXAMIDES ACTIVE AGAINST THE HEPATITIS B VIRUS (HBV)

INTRODUCTION

A series of novel, highly active pyrazolo-piperidine substituted indole-2-carboxamides active against the hepatitis B virus (HBV), having general structure I were identified. This novel class of anti-HBV agent demonstrates excellent in vitro potency, along with good metabolic stability, acceptable solubility, and high permeability.

TECHNICAL FIELD

The present invention relates generally to novel antiviral agents. Specifically, the present invention relates to compounds which can inhibit the protein(s) encoded by hepatitis B virus (HBV) or interfere with the function of the HBV replication cycle, compositions comprising such compounds, methods for inhibiting HBV viral replication, methods for treating or preventing HBV infection, and processes for making the compounds.

BACKGROUND OF THE INVENTION

Chronic HBV infection is a significant global health problem, affecting over 5% of the world population (over 350 million people worldwide and 1.25 million individuals in the US). Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact.

The low cure rates of HBV are attributed at least in part to the fact that complete suppression of virus production is difficult to achieve with a single antiviral agent, and to the presence and persistence of covalently closed circular DNA (cccDNA) in the nucleus of infected hepatocytes. However, persistent suppression of HBV DNA slows liver disease progression and helps to prevent hepatocellular carcinoma (HCC).

Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid protein (HBV-CP) plays essential roles in HBV replication. The predominant biological function of HBV-CP is to act as a structural protein to encapsidate pre-genomic RNA and form immature capsid particles, which spontaneously self-assemble from many copies of capsid protein dimers in the cytoplasm.

HBV-CP also regulates viral DNA synthesis through differential phosphorylation states of its C-terminal phosphorylation sites. Also, HBV-CP might facilitate the nuclear translocation of viral relaxed circular genome by means of the nuclear localization signals located in the arginine-rich domain of the C-terminal region of HBV-CP.

In the nucleus, as a component of the viral cccDNA mini-chromosome, HBV-CP could play a structural and regulatory role in the functionality of cccDNA mini-chromosomes. HBV-CP also interacts with viral large envelope protein in the endoplasmic reticulum (ER), and triggers the release of intact viral particles from hepatocytes.

HBV-CP related anti-HBV compounds have been reported. For example, phenylpropenamide derivatives, including compounds named AT-61 and AT-130 (Feld J. et al. Antiviral Res. 2007, 76, 168), and a class of thiazolidin-4-ones from Valeant (WO2006/033995), have been shown to inhibit pre-genomic RNA (pgRNA) packaging.

F. Hoffmann-La Roche AG have disclosed a series of 3-substituted tetrahydro-pyrazolo[1,5-a]pyrazines for the therapy of HBV (WO2016/113273, WO2017/198744, WO2018/011162, WO2018/011160, WO2018/011163).

Heteroaryldihydropyrimidines (HAPs) were discovered in a tissue culture-based screening (Weber et al., Antiviral Res. 2002, 54, 69). These HAP analogs act as synthetic allosteric activators and are able to induce aberrant capsid formation that leads to degradation of HBV-CP (WO 99/54326, WO 00/58302, WO 01/45712, WO 01/6840). Further HAP analogs have also been described (J. Med. Chem. 2016, 59 (16), 7651-7666).

A subclass of HAPs from F. Hoffman-La Roche also shows activity against HBV (WO2014/184328, WO2015/132276, and WO2016/146598). A similar subclass from Sunshine Lake Pharma also shows activity against HBV (WO2015/144093). Further HAPs have also been shown to possess activity against HBV (WO2013/102655, Bioorg. Med. Chem. 2017, 25(3) pp. 1042-1056, and a similar subclass from Enanta Therapeutics shows similar activity (WO2017/011552). A further subclass from Medshine Discovery shows similar activity (WO2017/076286). A further subclass (Janssen Pharma) shows similar activity (WO2013/102655).

A subclass of pyridazones and triazinones (F. Hoffman-La Roche) also show activity against HBV (WO2016/023877), as do a subclass of tetrahydropyridopyridines (WO2016/177655). A subclass of tricyclic 4-pyridone-3-carboxylic acid derivatives from Roche also show similar anti-HBV activity (WO2017/013046).

A subclass of sulfamoyl-arylamides from Novira Therapeutics (now part of Johnson & Johnson Inc.) also shows activity against HBV (WO2013/006394, WO2013/096744, WO2014/165128, WO2014/184365, WO2015/109130, WO2016/089990, WO2016/109663, WO2016/109684, WO2016/109689, WO2017/059059). A similar subclass of thioether-arylamides (also from Novira Therapeutics) shows activity against HBV (WO2016/089990). Additionally, a subclass of aryl-azepanes (also from Novira Therapeutics) shows activity against HBV (WO2015/073774). A similar subclass of arylamides from Enanta Therapeutics show activity against HBV (WO2017/015451).

Sulfamoyl derivatives from Janssen Pharma have also been shown to possess activity against HBV (WO2014/033167, WO2014/033170, WO2017/001655, J. Med. Chem, 2018, 61(14) 6247-6260). A similar class of glyoxamide substituted pyrrolamides (Gilead Sciences) has also been described (WO2018/039531).

A subclass of glyoxamide substituted pyrrolamide derivatives also from Janssen Pharma have also been shown to possess activity against HBV (WO2015/011281) A subclass of sulfamoyl- and oxalyl-heterobiaryls from Enanta Therapeutics also show activity against HBV (WO2016/161268, WO2016/183266, WO2017/015451, WO2017/136403 & US20170253609).

A subclass of aniline-pyrimidines from Assembly Biosciences also show activity against HBV (WO2015/057945, WO2015/172128). A subclass of fused tri-cycles from Assembly Biosciences (dibenzo-thiazepinones, dibenzo-diazepinones, dibenzo-oxazepinones) show activity against HBV (WO2015/138895, WO2017/048950).

A series of cyclic sulfamides has been described as modulators of HBV-CP function by Assembly Biosciences (WO2018/160878).

Arbutus Biopharma have disclosed a series of benzamides for the therapy of HBV (WO2018/052967, WO2018/172852).

It was also shown that the small molecule bis-ANS acts as a molecular 'wedge' and interferes with normal capsid-protein geometry and capsid formation (Zlotnick A et al. J. Virol. 2002, 4848).

US 2017/0158691 A1 (published Jun. 8, 2017) from Novira Therapeutics disclosed compounds against HBV infections.

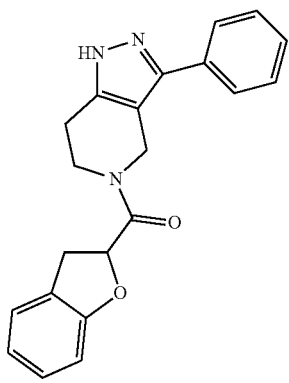 [SMILES: O=C(C1Cc2ccccc2O1)N1CCc2[nH]nc(-c3ccccc3)c2C1]

WO2016/03845 discloses an indazole compound of Formula shown below useful as anti-trypanosomal agents.

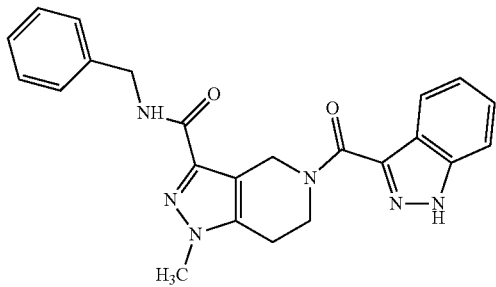 [SMILES: Cn1nc(C(=O)NCc2ccccc2)c2c1CCN(C(=O)c1n[nH]c3ccccc13)C2]

WO2006/105289 discloses compounds of Formula shown below useful as anti-bacterial agents (Examples 15, 21 and 76).

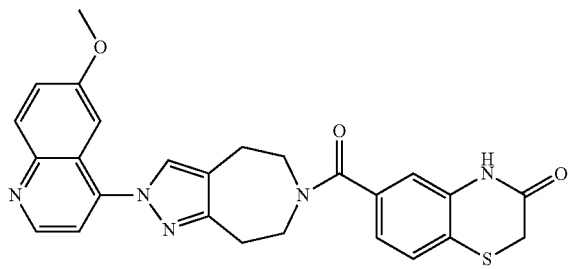

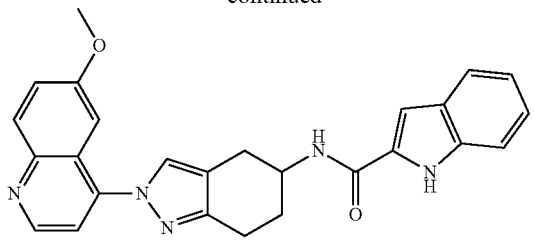

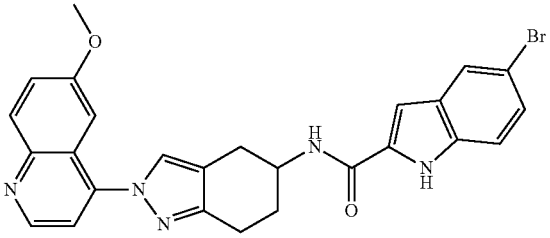

Problems that HBV direct acting antivirals may encounter are toxicity, mutagenicity, lack of selectivity, poor efficacy, poor bioavailability, low solubility and difficulty of synthesis. There is a thus a need for additional inhibitors for the treatment, amelioration or prevention of HBV that may overcome at least one of these disadvantages or that have additional advantages such as increased potency or an increased safety window.

Administration of such therapeutic agents to an HBV infected patient, either as monotherapy or in combination with other HBV treatments or ancillary treatments, will lead to significantly reduced virus burden, improved prognosis, diminished progression of the disease and/or enhanced sero-conversion rates.

SUMMARY OF THE INVENTION

Provided herein are compounds useful for the treatment or prevention of HBV infection in a subject in need thereof, and intermediates useful in their preparation. The subject matter of the invention is a compound of Formula I:

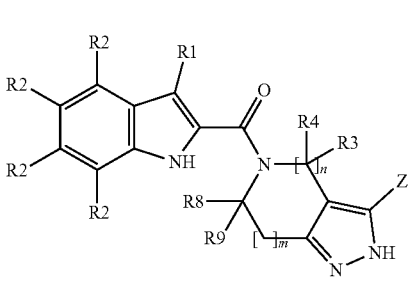

in which
Z is H, D, C(=O)N(R5)(R6), C(=O)N(R5)O(R6), C(=O)N(R5)N(R6)(R7), N(R5)(R6), N(R5)C(=O)(R6), N(R5)SO$_2$(R6), C(=O)O(R5), CH$_2$—N(R5)(R6), C(R5)=NO(R6), alkyl, cycloalkyl, heterocycloalkyl, aryl, and heteroaryl
R1 is H, D, F, Cl, Br, NH$_2$
R2 is for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C=C, C≡C, C≡N, C(CH$_3$)$_2$OH, Si(CH$_3$)$_3$, SMe, OH, OCH$_3$ R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, and C2-C6-hydroxyalkyl, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy R5 and R6 are optionally connected to form a C4-C7-heterocyclic ring containing 1 or 2 nitrogen, sulfur or oxygen atoms.

n is 1 or 2 m is 0 or 1

In one embodiment of the invention subject matter of the invention is a compound of Formula I in which Z is $C(=O)N(R5)(R6)$, $C(=O)N(R5)O(R6)$, $C(=O)N(R5)N(R6)(R7)$, aryl, heterocyclyl, and heteroaryl R1 is H R2 is for each position independently selected from the group comprising H, $CF_2H$, $CF_3$, $CF_2CH_3$, F, Cl, Br, $CH_3$, Et, i-Pr R3, R4, R8 and R9 are for each position independently selected from the group comprising H and methyl R3 and R4 are optionally connected to form a cyclopropyl ring.

R5, R6 and R7 are independently selected from the group comprising H, C1-C6-alkyl, C3-C6-cycloalkyl, C4-C7-heterocycloalkyl and C2-C6-hydroxyalkyl optionally substituted with OH, halo, C1-C6-alkoxy, C3-C7-cycloalkyl, C1-C6-hydroxyalkyl and C3-C7-heterocycloalkyl.

R5 and R6 are optionally connected to form a C4-C7-heterocyclic ring containing 1 or 2 nitrogen, sulfur or oxygen atoms.

n is 1 m is 1

In one embodiment of the invention subject matter of the invention is a compound of Formula I in which Z is $C(=O)N(R5)(R6)$ and heteroaryl R1 is H R2 is for each position independently selected from the group comprising H, $CF_2H$, $CF_3$, $CF_2CH_3$, F, Cl, $CH_3$, and Et.

R3, R4, R8 and R9 are H

R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C3-C7-cycloalkyl, C1-C6-hydroxyalkyl and C3-C7-heterocycloalkyl.

n is 1 m is 1

In one embodiment subject matter of the present invention is a compound according to Formula I in which Z is H, D, $C(=O)N(R5)(R6)$, $C(=O)N(R5)O(R6)$, $C(=O)N(R5)N(R6)(R7)$, $N(R5)(R6)$, $N(R5)C(=O)(R6)$, $N(R5)SO_2(R6)$, $C(=O)O(R5)$, $CH_2N(R5)(R6)$, alkyl, cycloalkyl, heterocycloalkyl, aryl, and heteroaryl.

In one embodiment subject matter of the present invention is a compound according to Formula I in which R1 is H, D, F, Cl, Br, $NH_2$, preferably H.

In a preferred embodiment subject matter of the present invention is a compound according to Formula I in which Z is $C(=O)N(R5)(R6)$, cycloalkyl, heterocycloalkyl or heteroaryl and R1 is H.

In one embodiment subject matter of the present invention is a compound according to Formula I in which R2 is for each position independently selected from the group comprising H, $CF_2H$, $CF_3$, $CF_2CH_3$, F, Cl, Br, $CH_3$, Et, i-Pr, c-Pr, D, $CH_2H$, $CH(CH_3)OH$, $CH_2F$, $C(F)CH_3$, I, C=C, C≡C, C≡N, $C(CH_3)_2OH$, $Si(CH_3)_3$, SMe, OH, $OCH_3$, preferably H, $CF_2H$, $CF_3$, $CF_2CH_3$, F, Cl, Br, $CH_3$, Et, i-Pr, and most preferably H, $CF_2H$, $CF_3$, $CF_2CH_3$, F, Cl, $CH_3$, and Et.

In a preferred embodiment subject matter of the present invention is a compound according to Formula I in which R1 is H and R2 is for each position independently selected from the group comprising H, $CF_2H$, $CF_3$, $CF_2CH_3$, F, Cl, $CH_3$, and Et.

In a another preferred embodiment subject matter of the present invention is a compound according to Formula I in which Z is $C(=O)N(R5)(R6)$, cycloalkyl, heterocycloalkyl or heteroaryl and R2 is for each position independently selected from the group comprising H, $CF_2H$, $CF_3$, $CF_2CH_3$, F, Cl, $CH_3$, and Et.

In another more preferred embodiment of the present invention is a compound according to Formula I in which Z is $C(=O)N(R5)(R6)$, cycloalkyl, heterocycloalkyl or heteroaryl, R1 is H, and R2 is for each position independently selected from the group comprising H, $CF_2H$, $CF_3$, $CF_2CH_3$, F, Cl, $CH_3$, and Et.

In one embodiment subject matter of the present invention is a compound according to Formula I in which R3 and R4 are for each position independently selected from the group comprising H, methyl and ethyl, preferably H and methyl, most preferably H.

In one embodiment subject matter of the present invention is a compound according to Formula I in which R3, R4, R8 and R9 are for each position independently selected from the group comprising H, methyl and ethyl, preferably H and methyl, most preferably H.

In a preferred embodiment subject matter of the present invention is a compound according to Formula I in which R3 is H, R4 is H, R8 is H, and R9 is H or methyl.

In a more preferred embodiment subject matter of the present invention is a compound according to Formula I in which Z is $C(=O)N(R5)(R6)$, cycloalkyl, heterocycloalkyl or heteroaryl, R3 is H, R4 is H, R8 is H and R9 is H or methyl.

In a another more preferred embodiment subject matter of the present invention is a compound according to Formula I in which R1 is H, R3 is H, R4 is H, R8 is H and R9 is H or methyl.

In another even more preferred embodiment subject matter of the present invention is a compound according to Formula I in which R1 is H, R2 is for each position independently selected from the group comprising H, $CF_2H$, $CF_3$, $CF_2CH_3$, F, Cl, $CH_3$, and Et, R3 is H, R4 is H, R8 is H and R9 is H or methyl.

In one embodiment subject matter of the present invention is a compound according to Formula I in which R5, R6 and R7 are independently selected from the group comprising H, D, C1-C6-alkyl, C3-C6-cycloalkyl, C4-C7-heterocycloalkyl, C2-C6-aminoalkyl, C1-C4-carboxyalkyl, C1-C4- acylsulfonamido-alkyl and C2-C6-hydroxyalkyl, optionally substituted with 1, 2, or 3 groups each independently selected from OH, halo, acyl, SO₂Me, SO₃H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl and C3-C7-heterocycloalkyl.

In a preferred embodiment subject-matter of the present invention is a compound according to Formula I in which R5 is C1-C6-alkyl optionally substituted with 1,2, or 3 halogens, and R6 is selected from the group comprising C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO₂Me, SO₃H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl or C3-C7-heterocycloalkyl.

In a more preferred embodiment subject matter of the present invention is a compound according to Formula I in which R5 is methyl, ethyl, 2,2-difluoroethyl, or 2,2,2-trifluoroethyl and R6 is selected from the group comprising C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO₂Me, SO₃H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl or C3-C7-heterocycloalkyl.

In one embodiment subject matter of the present invention is a compound according to Formula I in which n is 1.

In one embodiment subject matter of the present invention is a compound according to Formula I in which m is 1.

In a preferred embodiment subject matter of the present invention is a compound according to Formula I in which n is 1 and m is 1.

In a more preferred embodiment subject matter of the present invention is a compound according to Formula I in which n is 1, m is 1 and R1 is H.

In an even more preferred embodiment subject matter of the present invention is a compound according to Formula I in which n is 1, m is 1, R1 is H and R2 is for each position independently selected from the group comprising H, CF₂H, CF₃. CF₂CH₃, F, Cl, CH₃, and Et.

One embodiment of the invention is a compound of Formula I or a pharmaceutically acceptable salt thereof according to the invention, for use in the prevention or treatment of an HBV infection in subject.

One embodiment of the invention is a pharmaceutical composition comprising a compound of Formula I or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula I or a pharmaceutically acceptable salt thereof according to the present invention.

A further embodiment of the invention is a compound of Formula II or a pharmaceutically acceptable salt thereof according to the invention, for use in the prevention or treatment of an HBV infection in subject in need thereof.

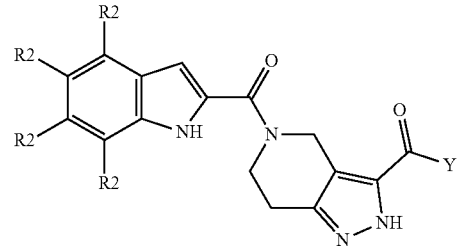

II in which
Y is N(R5)(R6), N(R5)O(R6), or N(R5)N(R6)(R7)
R2 is for each position independently selected from the group comprising H, CF₂H, CF₃, CF₂CH₃, F, Cl, Br, CH₃, Et, i-Pr
R5, R6, and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, SO₂Me, SO₃H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy
R5 and R6 are optionally connected to form a C4-C7-heterocyclic ring containing 1 or 2 nitrogen, sulfur or oxygen atoms
n is 1 or 2
m is 0 or 1
In one embodiment subject matter of the present invention is a compound according to Formula II in which
Y is N(R5)(R6)
R2 is for each position independently selected from the group comprising H, CF₂H, CF₃, CF₂CH₃, F, Cl, CH₃, and Et
R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl
R5 and R6 are optionally connected to form a C4-C7-heterocyclic ring containing 1 or 2 nitrogen, sulfur or oxygen atoms
n is 1
m is 1
In one embodiment subject matter of the present invention is a compound according to Formula II in which Y is N(R5)(R6), N(R5)O(R6), or N(R5)N(R6)(R7)
In one embodiment subject matter of the present invention is a compound according to Formula II in which R2 is for each position independently selected from the group comprising H, CF$_2$H, CF$_3$, CF$_2$CH$_3$, F, Cl, Br, CH$_3$, Et, i-Pr, preferably H, CF$_2$H, CF$_3$, CF$_2$CH$_3$, F, Cl, CH$_3$, and Et.

In a preferred embodiment subject matter of the present invention is a compound according to Formula II in which R2 is for each position independently selected from the group comprising H, CF$_2$H, CF$_3$, CF$_2$CH$_3$, F, Cl, CH$_3$, and Et, and Y is N(R5)(R6).

In one embodiment subject matter of the present invention is a compound according to Formula II in which R5, R6 and R7 are independently selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula II in which R5 is C1-C6-alkyl optionally substituted with 1, 2, or 3 halogens, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula II in which R5 is methyl, ethyl, 2,2-difluoroethyl, or 2,2,2-trifluoroethyl, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In another more preferred embodiment subject matter of the present invention is a compound according to Formula II in which R2 is for each position independently selected from the group comprising H, CF$_2$H, CF$_3$, CF$_2$CH$_3$, F, Cl, CH$_3$, and Et, Y is N(R5)(R6), and R5 is methyl, ethyl, 2,2-difluoroethyl, or 2,2,2-trifluoroethyl.

One embodiment of the invention is a compound of formula II or a pharmaceutically acceptable salt thereof according to the invention, for use in the prevention or treatment of an HBV infection in subject.

One embodiment of the invention is a pharmaceutical composition comprising a compound of formula II or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of formula II or a pharmaceutically acceptable salt thereof according to the present invention.

A further embodiment of the invention is a compound of Formula III or a pharmaceutically acceptable salt thereof according to the invention, for use in the prevention or treatment of an HBV infection in subject in need thereof.

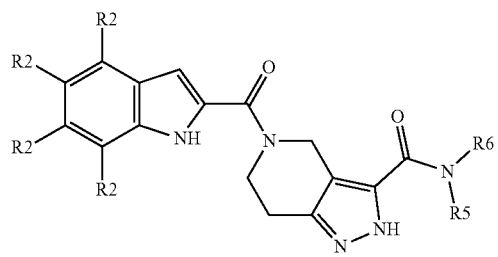

in which
R2 is for each position independently selected from the group comprising H, CH$_2$F, CF$_2$H, CF$_3$, C(F)CH$_3$, CF$_2$CH$_3$, F, Cl, Br, CH$_3$, Et
R5 is selected from the group comprising C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, C1-C4-acylsulfonamido-alkyl, optionally substituted with 1, 2, or 3 groups each independently selected from OH, halo, amino, acyl, SO$_2$Me, SO$_3$H, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy or C1-C6 alkenyloxy
R6 is selected from the group comprising methyl and ethyl.

In one embodiment subject matter of the present invention is a compound according to Formula III in which R2 is for each position independently selected from the group comprising H, CF$_2$H, CF$_3$, CF$_2$CH$_3$, F, Cl, Br, CH$_3$, Et, i-Pr, preferably H, CF$_2$H, CF$_3$, CF$_2$CH$_3$, F, Cl, CH$_3$, and Et.

In a more preferred embodiment subject matter of the present invention is a compound according to Formula III in which R2 is for each position independently selected from the group comprising H, CF$_2$H, CF$_3$, CF$_2$CH$_3$, F, Cl, CH$_3$, and Et, Y is N(R5)(R6), and R5 is methyl, ethyl, 2,2-difluoroethyl, or 2,2,2-trifluoroethyl.

In one embodiment subject matter of the present invention is a compound according to Formula III in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In a preferred embodiment of the present invention is a compound according to Formula III in which R5 is C1-C6-alkyl optionally substituted with 1, 2, or 3 halogens, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula III in which R5 is methyl, ethyl, 2,2-difluoroethyl, or 2,2,2-trifluoroethyl, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

One embodiment of the invention is a compound of formula III or a pharmaceutically acceptable salt thereof according to the invention, for use in the prevention or treatment of an HBV infection in subject.

One embodiment of the invention is a pharmaceutical composition comprising a compound of formula III or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of formula III or a pharmaceutically acceptable salt thereof according to the present invention.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof. All before mentioned doses refer to daily doses per patient.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example containing about 1 to about 500 mg, or about 1 to about 300 mg or about 1 to about 100 mg, or about 2 to about 50 mg of active ingredient per unit dosage form.

The compounds of the invention may, depending on their structure, exist as salts, solvates or hydrates. The invention therefore also encompasses the salts, solvates or hydrates and respective mixtures thereof.

The compounds of the invention may, depending on their structure, exist in tautomeric or stereoisomeric forms (enantiomers, diastereomers). The invention therefore also encompasses the tautomers, enantiomers or diastereomers and respective mixtures thereof. The stereoisomerically uniform constituents can be isolated in a known manner from such mixtures of enantiomers and/or diastereomers.

A further embodiment of the invention is a compound of Formula Ia or a pharmaceutically acceptable salt thereof according to the invention, for use in the prevention or treatment of an HBV infection in subject in need thereof.

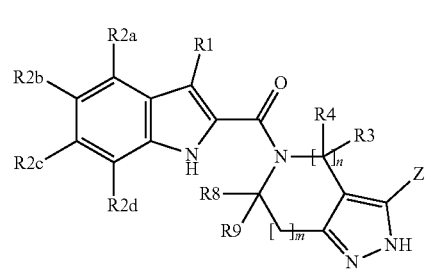

Ia in which
- Z is H, D, C(=O)N(R5)(R6), C(=O)N(R5)O(R6), C(=O)N(R5)N(R6)(R7), N(R5)(R6), N(R5)SO$_2$(R6), C(=O)O(R5), CH$_2$—N(R5)(R6), C(R5)=NO(R6), O—R5, SO$_2$N(R5)(R6), SO$_2$—R5, alkyl, cycloalkyl, heterocycloalkyl, heteroaryl, or heteroaryl substituted with C2-C6 alkenyl, wherein cycloalkyl is optionally substituted with carboxy, carboxyl ester, halo, C1-C6 alkyl, C1-C6-haloalkyl or NH$_2$
- R1 is H, D, F, Cl, Br or NH$_2$
- R2a, R2b, R2c and R2d are for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C=C, C≡C, C≡N, C(CH$_3$)$_2$OH, Si(CH$_3$)$_3$, SMe, and OH, with the proviso that when Z is H, R2b is not F and R2c is not Cl or CH$_3$
- R3, R4, R8 and R9 are for each position independently selected from the group comprising H, methyl and ethyl
- R3 and R4 are optionally connected to form a C3-C5-cycloalkyl ring R3 and R8 are optionally connected to form a bridged heterobicyclic ring R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, and C2-C6-hydroxyalkyl, C2-C6-alkynyl, optionally substituted with 1, 2, or 3 groups each independently selected from OH, halo, C≡N, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C4-carboxamidoalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, or C≡N R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1 or 2 m is 0 or 1.

In one embodiment of the invention subject matter of the invention is a compound of Formula Ia in which Z is C(=O)N(R5)(R6), C(=O)N(R5)O(R6), C(=O)N(R5)N(R6)(R7), heterocyclyl, or heteroaryl R1 is H R2a, R2b, R2c and R2d are for each position independently selected from the group comprising H, $CF_2H$, $CF_3$, $CF_2CH_3$, F, Cl, Br, $CH_3$, Et, and i-Pr R3, R4, R8 and R9 are for each position independently selected from the group comprising H and methyl R3 and R4 are optionally connected to form a cyclopropyl ring R5, R6 and R7 are independently selected from the group comprising H, C1-C6-alkyl, C3-C6-cycloalkyl, C4-C7-heterocycloalkyl and C2-C6-hydroxyalkyl optionally substituted with OH, halo, C1-C6-alkoxy, C3-C7-cycloalkyl, C1-C6-hydroxyalkyl, C1-C6-alkyl-O-C1-C6-alkyl and C3-C7-heterocycloalkyl R5 and R6 are optionally connected to form a C4-C7-heterocyclic ring containing 1 or 2 nitrogen, sulfur or oxygen atoms n is 1 m is 1.

In one embodiment of the invention subject matter of the invention is a compound of Formula Ia in which Z is C(=O)N(R5)(R6) or heteroaryl R1 is H R2a, R2b, R2c and R2d are for each position independently selected from the group comprising H, $CF_2H$, $CF_3$, $CF_2CH_3$, F, Cl, $CH_3$, and Et R3, R4, R8 and R9 are H R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C3-C7-cycloalkyl, C1-C6-hydroxyalkyl, C1-C6-alkyl-O-C1-C6-alkyl and C3-C7-heterocycloalkyl n is 1 m is 1.

In one embodiment subject matter of the present invention is a compound according to Formula Ia in which Z is H, D, C(=O)N(R5)(R6), C(=O)N(R5)O(R6), C(=O)N(R5)N(R6)(R7), N(R5)(R6), N(R5)$SO_2$(R6), C(=O)O(R5), $CH_2$N(R5)(R6), alkyl, cycloalkyl, heterocycloalkyl, or heteroaryl.

In one embodiment subject matter of the present invention is a compound according to Formula Ia in which R1 is H, D, F, Cl, Br, or $NH_2$, preferably H.

In a preferred embodiment subject matter of the present invention is a compound according to Formula Ia in which Z is C(=O)N(R5)(R6), cycloalkyl, heterocycloalkyl or heteroaryl and R1 is H.

In one embodiment subject matter of the present invention is a compound according to Formula Ia in which R2a, R2b, R2c and R2d are for each position independently selected from the group comprising H, $CF_2H$, $CF_3$, $CF_2CH_3$, F, Cl, Br, $CH_3$, Et, i-Pr, c-Pr, D, $CH_2H$, $CH(CH_3)OH$, $CH_2F$, C(F)$CH_3$, I, C=C, C≡C, C≡N, C($CH_3$)$_2$OH, Si($CH_3$)$_3$, SMe, and OH, preferably H, $CF_2H$, $CF_3$, $CF_2CH_3$, F, Cl, Br, $CH_3$, Et, and i-Pr, and most preferably H, $CF_2H$, $CF_3$, $CF_2CH_3$, F, Cl, $CH_3$, and Et.

In a preferred embodiment subject matter of the present invention is a compound according to Formula Ia in which Z is C(=O)N(R5)(R6), cycloalkyl, heterocycloalkyl or heteroaryl and R2a, R2b, R2c and R2d are for each position independently selected from the group comprising H, $CF_2H$, $CF_3$, $CF_2CH_3$, F, Cl, $CH_3$, and Et.

In a more preferred embodiment subject matter of the present invention is a compound according to Formula Ia in which Z is C(=O)N(R5)(R6), cycloalkyl, heterocycloalkyl or heteroaryl, R1 is H, and R2a, R2b, R2c and R2d are for each position independently selected from the group comprising H, $CF_2H$, $CF_3$, $CF_2CH_3$, F, Cl, $CH_3$, and Et.

In another preferred embodiment subject matter of the present invention is a compound according to Formula Ia in which R1 is H and R2a, R2b, R2c and R2d are for each position independently selected from the group comprising H, $CF_2H$, $CF_3$, $CF_2CH_3$, F, Cl, $CH_3$, and Et, with the proviso that when Z is H, R2b is not F and R2c is not Cl or $CH_3$.

In one embodiment subject matter of the present invention is a compound according to Formula Ia in which R3 and R4 are for each position independently selected from the group comprising H, methyl and ethyl, preferably H and methyl, most preferably H.

In one embodiment subject matter of the present invention is a compound according to Formula Ia in which R3, R4, R8 and R9 are for each position independently selected from the group comprising H, methyl and ethyl, preferably H and methyl, most preferably H, with the proviso that when Z is H, R2b is not F and R2c is not Cl or $CH_3$.

In a preferred embodiment subject matter of the present invention is a compound according to Formula Ia in which R3 is H, R4 is H, R8 is H, and R9 is H or methyl, with the proviso that when Z is H, R2b is not F and R2c is not Cl or $CH_3$.

In a more preferred embodiment subject matter of the present invention is a compound according to Formula Ia in which R1 is H, R3 is H, R4 is H, R8 is H and R9 is H or methyl, with the proviso that when Z is H, R2b is not F and R2c is not Cl or $CH_3$.

In a most preferred embodiment subject matter of the present invention is a compound according to Formula Ia in which R1 is H, R2a, R2b, R2c and R2d are for each position independently selected from the group comprising H, $CF_2H$, $CF_3$, $CF_2CH_3$, F, Cl, $CH_3$, and Et, R3 is H, R4 is H, R8 is H and R9 is H or methyl, with the proviso that when Z is H, R2b is not F and R2c is not Cl or $CH_3$.

In a most preferred embodiment subject matter of the present invention is a compound according to Formula Ia in which Z is C(=O)N(R5)(R6), cycloalkyl, heterocycloalkyl or heteroaryl, R3 is H, R4 is H, R8 is H and R9 is H or methyl.

In one embodiment subject matter of the present invention is a compound according to Formula Ia in which R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, and C2-C6-hydroxyalkyl, and C2-C6-alkynyl, optionally substituted with 1, 2, or 3 groups each independently selected from OH, halo, C≡N, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C4-carboxamidoalkyl, C1-C6-haloalkyl, C1-C6-alkoxy, C1-C6-alkyl-O-C1-C6-alkyl, C1-C6-hydroxyalkyl and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, C≡N, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl, C1-C6-alkyl-O-C1-C6-alkyl or C3-C7-heterocycloalkyl.

In a preferred embodiment subject matter of the present invention is a compound according to Formula Ia in which R5 is C1-C6-alkyl optionally substituted with 1, 2, or 3 halogens, and R6 is selected from the group comprising C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6-alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl or C3-C7-heterocycloalkyl.

In a more preferred embodiment subject matter of the present invention is a compound according to Formula Ia in which R5 is methyl, ethyl, 2,2-difluoroethyl, or 2,2,2-trifluoroethyl and R6 is selected from the group comprising C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C3-C7-cycloalkyl, C6-hydroxyalkyl or C3-C7-heterocycloalkyl.

In one embodiment subject matter of the present invention is a compound according to Formula Ta in which n is 1.

In one embodiment subject matter of the present invention is a compound according to Formula Ia in which m is 1.

In a preferred embodiment subject matter of the present invention is a compound according to Formula Ia in which n is 1 and m is 1, with the proviso that when Z is H, R2b is not F and R2c is not Cl or $CH_3$.

In a more preferred embodiment subject matter of the present invention is a compound according to Formula Ia in which n is 1, m is 1 and R1 is H with the proviso that when Z is H, R2b is not F and R2c is not Cl or $CH_3$.

In an even more preferred embodiment subject matter of the present invention is a compound according to Formula Ia in which n is 1, m is 1, R1 is H and R2 is for each position independently selected from the group comprising H, $CF_2H$, $CF_3$, $CF_2CH_3$, F, Cl, $CH_3$, and Et, with the proviso that when Z is H, R2b is not F and R2c is not Cl or $CH_3$.

One embodiment of the invention is a compound of Formula Ia or a pharmaceutically acceptable salt thereof according to the invention, for use in the prevention or treatment of an HBV infection in subject.

One embodiment of the invention is a pharmaceutical composition comprising a compound of Formula Ia or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula Ia or a pharmaceutically acceptable salt thereof according to the present invention.

A further embodiment of the invention is a compound of Formula II or a pharmaceutically acceptable salt thereof according to the invention, for use in the prevention or treatment of an HBV infection in subject in need thereof.

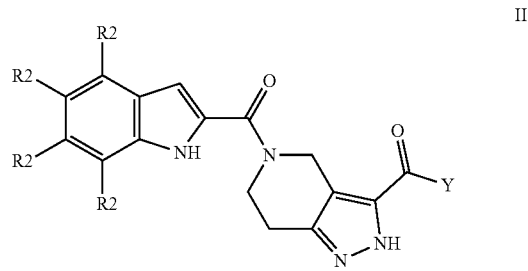

II in which
Y is N(R5)(R6), N(R5)O(R6), or N(R5)N(R6)(R7)
R2 is for each position independently selected from the group comprising H, $CF_2H$, $CF_3$, $CF_2CH_3$, F, Cl, Br, $CH_3$, Et, and i-Pr
R5, R6, and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, or C≡N R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy.

In one embodiment subject matter of the present invention is a compound according to Formula II in which Y is N(R5)(R6)

R2 is for each position independently selected from the group comprising H, $CF_2H$, $CF_3$, $CF_2CH_3$, F, Cl, $CH_3$, and Et R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl, C1-C6-alkyl-O-C1-C6-alkyl or C3-C7-heterocycloalkyl.

R5 and R6 are optionally connected to form a C4-C7-heterocyclic ring containing 1 or 2 nitrogen, sulfur or oxygen atoms.

n is 1 m is 1.

In one embodiment subject matter of the present invention is a compound according to Formula II in which Y is N(R5)(R6), N(R5)O(R6), or N(R5)N(R6)(R7).

In one embodiment subject matter of the present invention is a compound according to Formula II in which R2 is for each position independently selected from the group comprising H, $CF_2H$, $CF_3$, $CF_2CH_3$, F, Cl, Br, $CH_3$, Et, and i-Pr, preferably H, $CF_2H$, $CF_3$, $CF_2CH_3$, F, Cl, $CH_3$, and Et.

In a preferred embodiment subject matter of the present invention is a compound according to Formula II in which R2 is for each position independently selected from the group comprising H, $CF_2H$, $CF_3$, $CF_2CH_3$, F, Cl, $CH_3$, and Et, and Y is N(R5)(R6).

In one embodiment subject matter of the present invention is a compound according to Formula II in which R5, R6 and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, C≡N, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula TT in which R5 is C1-C6-alkyl optionally substituted with 1, 2, or 3 halogens, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula II in which R5 is methyl, ethyl, 2,2-difluoroethyl, or 2,2,2-trifluoroethyl, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula II in which R2 is for each position independently selected from the group comprising H, $CF_2H$, $CF_3$, $CF_2CH_3$, F, Cl, $CH_3$, and Et, Y is N(R5)(R6), and R5 is methyl, ethyl, 2,2-difluoroethyl, or 2,2,2-trifluoroethyl.

One embodiment of the invention is a compound of formula II or a pharmaceutically acceptable salt thereof according to the invention, for use in the prevention or treatment of an HBV infection in subject.

One embodiment of the invention is a pharmaceutical composition comprising a compound of Formula II or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula II or a pharmaceutically acceptable salt thereof according to the present invention.

A further embodiment of the invention is a compound of Formula III or a pharmaceutically acceptable salt thereof according to the invention, for use in the prevention or treatment of an HBV infection in subject in need thereof.

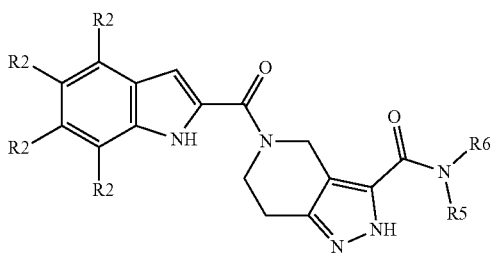

III in which
R2 is for each position independently selected from the group comprising H, CH$_2$F, CF$_2$H, CF$_3$, C(F)CH$_3$, CF$_2$CH$_3$, F, Cl, Br, CH$_3$, and Et R5 is selected from the group comprising C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, and C1-C4-acylsulfonamido-alkyl, optionally substituted with 1, 2, or 3 groups each independently selected from OH, halo, amino, acyl, SO$_2$Me, SO$_3$H, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO$_2$-C1-C6-alkyl, or C≡N R6 is selected from the group comprising methyl and ethyl.

In one embodiment subject matter of the present invention is a compound according to Formula III in which R2 is for each position independently selected from the group comprising H, CF$_2$H, CF$_3$, CF$_2$CH$_3$, F, Cl, Br, CH$_3$, Et, and i-Pr, preferably H, CF$_2$, CF$_3$, CF$_2$CH$_3$, F, Cl, CH$_3$, and Et.

In one embodiment subject matter of the present invention is a compound according to Formula III in which R5 and R6 are independently selected from the group comprising H, D, C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, and C1-C4-acylsulfonamido-alkyl, optionally substituted with 1, 2, or 3 groups each independently selected from OH, halo, amino, acyl, SO$_2$Me, SO$_3$H, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO$_2$—C1-C6-alkyl, or C≡N, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula III in which R5 is C1-C6-alkyl optionally substituted with 1, 2, or 3 halogens, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In a more preferred embodiment subject matter of the present invention is a compound according to Formula III in which R5 is methyl, ethyl, 2,2-difluoroethyl, or 2,2,2-trifluoroethyl, and R6 is selected from the group comprising H, D, C1-C6-alkyl, C3-C6-cycloalkyl, C4-C7-heterocycloalkyl, C2-C6-aminoalkyl, C1-C4-carboxyalkyl, C1-C4-acylsulfonamido-alkyl and C2-C6-hydroxyalkyl, optionally substituted with 1, 2, or 3 groups each independently selected from OH, halo, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment of the present invention is a compound according to Formula III in which R2 is for each position independently selected from the group comprising H, CF$_2$H, CF$_3$, CF$_2$CH$_3$, F, Cl, CH$_3$, and Et, Y is N(R5)(R6), and R5 is methyl, ethyl, 2,2-difluoroethyl, or 2,2,2-trifluoroethyl.

One embodiment of the invention is a compound of Formula III or a pharmaceutically acceptable salt thereof according to the invention, for use in the prevention or treatment of an HBV infection in subject.

One embodiment of the invention is a pharmaceutical composition comprising a compound of Formula III or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula III or a pharmaceutically acceptable salt thereof according to the present invention.

A further embodiment of the invention is a compound of Formula VI or a pharmaceutically acceptable salt thereof according to the invention, for use in the prevention or treatment of an HBV infection in subject in need thereof

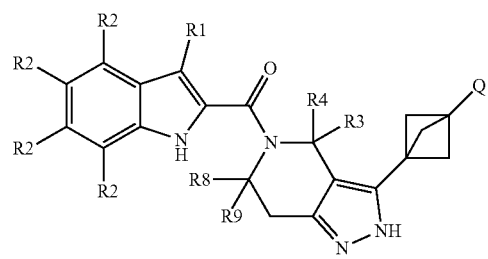

VI in which
Q is H, carboxy, carboxyl ester, halo, C1-C6 alkyl, C1-C6-haloalkyl or NH$_2$ R1 is H, D, F, Cl, Br or $NH_2$ R2 is for each position independently selected from the group comprising H, $CF_2H$, $CF_3$, $CF_2CH_3$, F, Cl, Br, $CH_3$, Et, and i-Pr R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring.

In one embodiment subject matter of the present invention is a compound according to Formula VI in which Q is H, carboxy or carboxyl ester R1 is H, D, F, Cl, Br or $NH_2$ R2 is for each position independently selected from the group comprising H, $CF_2H$, $CF_3$, $CF_2CH_3$, F, Cl, Br, $CH_3$, Et, and i-Pr R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring In one embodiment subject matter of the present invention is a compound according to Formula VI in which Q is H, carboxy, carboxyl ester, halo, C1-C6 alkyl, C1-C6-haloalkyl or $NH_2$ R1 is H, D, F, Cl, Br or $NH_2$ R2 is for each position independently selected from the group comprising H, $CF_2H$, $CF_3$, $CF_2CH_3$, F, Cl, Br, $CH_3$, Et, and i-Pr R3, R4, R8 and R9 are for each position independently selected from the group comprising H, methyl and ethyl.

In one embodiment subject matter of the present invention is a compound according to Formula VI in which Q is H, carboxy, carboxyl ester, halo, C1-C6 alkyl, C1-C6-haloalkyl or $NH_2$ R1 is H, D, F, Cl, Br or $NH_2$ R2 is for each position independently selected from the group comprising H, $CF_2H$, $CF_3$, $CF_2CH_3$, F, Cl, Br, $CH_3$, Et, and i-Pr.

In one embodiment subject matter of the present invention is a compound according to Formula VI in which Q is H, carboxy or carboxyl ester R1 is H, D, F, Cl, Br or $NH_2$ R2 is for each position independently selected from the group comprising H, $CF_2H$, $CF_3$, $CF_2CH_3$, F, Cl, Br, $CH_3$, Et, and i-Pr.

In one embodiment subject matter of the present invention is a compound according to Formula VI in which R1 is H, D, F, Cl, Br or $NH_2$.

In one embodiment subject matter of the present invention is a compound according to Formula VI in which R2 is for each position independently selected from the group comprising H, $CF_2H$, $CF_3$, $CF_2CH_3$, F, Cl, Br, $CH_3$, Et, and i-Pr.

In one embodiment subject matter of the present invention is a compound according to Formula VI in which R3, R4, R8 and R9 are for each position independently selected from the group comprising H, methyl and ethyl.

One embodiment of the invention is a compound of formula VI or a pharmaceutically acceptable salt thereof according to the invention, for use in the prevention or treatment of an HBV infection in subject.

One embodiment of the invention is a pharmaceutical composition comprising a compound of formula VI or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of formula VI or a pharmaceutically acceptable salt thereof according to the present invention.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof. All before mentioned doses refer to daily doses per patient.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example containing about 1 to about 500 mg, or about 1 to about 300 mg or about 1 to about 100 mg, or about 2 to about 50 mg of active ingredient per unit dosage form.

The compounds of the invention may, depending on their structure, exist as salts, solvates or hydrates. The invention therefore also encompasses the salts, solvates or hydrates and respective mixtures thereof.

The compounds of the invention may, depending on their structure, exist in tautomeric or stereoisomeric forms (enantiomers, diastereomers). The invention therefore also encompasses the tautomers, enantiomers or diastereomers and respective mixtures thereof. The stereoisomerically uniform constituents can be isolated in a known manner from such mixtures of enantiomers and/or diastereomers.

Further embodiments within the scope of the present invention are set out below:

1. Compounds of Formula I

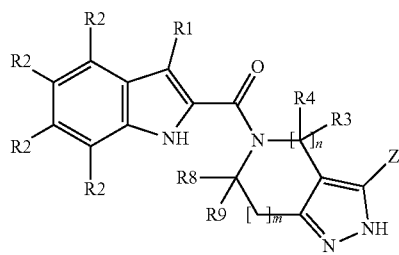

I in which
Z is H, D, C(=O)N(R5)(R6), C(=O)N(R5)O(R6), C(=O)N(R5)N(R6)(R7), N(R5)(R6), N(R5)C(=O)(R6), N(R5)SO$_2$(R6), C(=O)O(R5), CH$_2$—N(R5)(R6), C(R5)=NO(R6), alkyl, cycloalkyl, heterocycloalkyl, aryl, and heteroaryl R1 is H, D, F, Cl, Br, NH$_2$ R2 is for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C=C, C≡C, C≡N, C(CH$_3$)$_2$OH, Si(CH$_3$)$_3$, SMe, OH, OCH$_3$ R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, and C2-C6-hydroxyalkyl, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy R5 and R6 are optionally connected to form a C4-C7-heterocyclic ring containing 1 or 2 nitrogen, sulfur or oxygen atoms.

n is 1 or 2 m is 0 or 1.

or a pharmaceutically acceptable salt thereof or a solvate of a compound of Formula I or the pharmaceutically acceptable salt thereof or a prodrug of a compound of Formula I or a pharmaceutically acceptable salt or a solvate thereof.

2. A compound of Formula I according to embodiment 1 that is a compound of Formula II

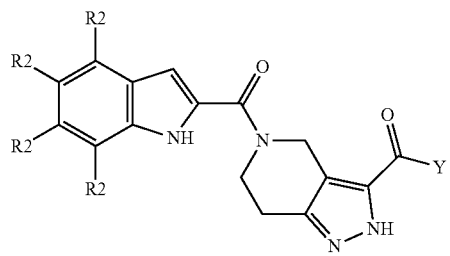

in which
Y is N(R5)(R6), N(R5)O(R6), or N(R5)N(R6)(R7)

R2 is for each position independently selected from the group comprising H, CF$_2$H, CF$_3$, CF$_2$CH$_3$, F, Cl, Br, CH$_3$, Et, i-Pr R5, R6, and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy R5 and R6 are optionally connected to form a C4-C7-heterocyclic ring containing 1 or 2 nitrogen, sulfur or oxygen atoms.

or a pharmaceutically acceptable salt thereof or a solvate of a compound of Formula II or the pharmaceutically acceptable salt thereof or a prodrug of a compound of Formula II or a pharmaceutically acceptable salt or a solvate thereof 3. A compound of Formula I according to embodiments 1 or 2 that is a compound of Formula III

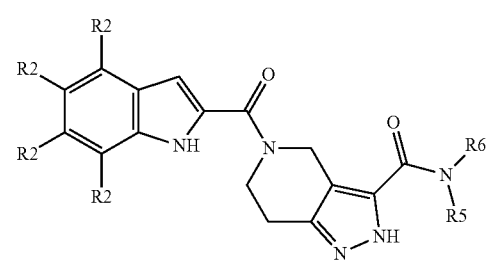

in which
R2 is for each position independently selected from the group comprising H, CH$_2$F, CF$_2$H, CF$_3$, C(F)CH$_3$, CF$_2$CH$_3$, F, Cl, Br, CH$_3$, Et R5 is selected from the group comprising C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, C1-C4-acylsulfonamido-alkyl, optionally substituted with 1, 2, or 3 groups each independently selected from OH, halo, amino, acyl, SO$_2$Me, SO$_3$H, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy or C1-C6 alkenyloxy R6 is selected from the group comprising methyl and ethyl or a pharmaceutically acceptable salt thereof or a solvate of a compound of Formula III or the pharmaceutically acceptable salt thereof or a prodrug of a compound of Formula III or a pharmaceutically acceptable salt or a solvate thereof.

4. A compound according to any of embodiments 1 to 3 or a pharmaceutically acceptable salt thereof or a solvate of said compound or the pharmaceutically acceptable salt thereof or a prodrug of said compound or a pharmaceutically acceptable salt or a solvate thereof for use in the prevention or treatment of an HBV infection in subject.

5. A pharmaceutical composition comprising a compound according to any of embodiments 1 to 3 or a pharmaceutically acceptable salt thereof or a solvate of said compound or the pharmaceutically acceptable salt thereof or a prodrug of said compound or a pharmaceutically acceptable salt or a solvate thereof, together with a pharmaceutically acceptable carrier.

6. A method of treating an HBV infection in an individual in need thereof, comprising administering to the individual a therapeutically effective amount of a compound according to any of embodiments 1 to 3 or a pharmaceutically acceptable salt thereof or a solvate of said compound or the pharmaceutically acceptable salt thereof or a prodrug of said compound or a pharmaceutically acceptable salt or a solvate thereof.

7. Method for the preparation of a compound of Formula I according to embodiment 1 by reacting a compound of Formula IV

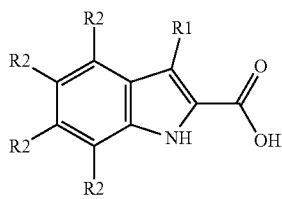

IV in which R1 and R2 are as defined in embodiment 1, with a compound of Formula V

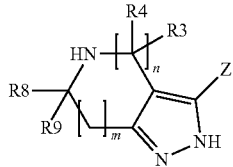

V in which n, m, Z, R3, R4, R8 and R9 are as defined in embodiment 1.

Further embodiments within the scope of the present invention are set out below:

1. Compound of Formula Ia

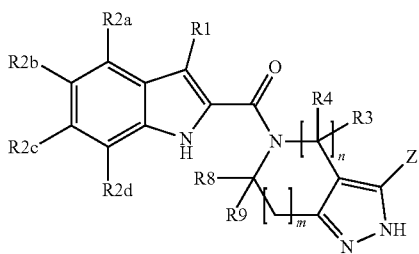

Ia in which
- Z is H, D, C(=O)N(R5)(R6), C(=O)N(R5)O(R6), C(=O)N(R5)N(R6)(R7), N(R5)(R6), N(R5)SO$_2$(R6), C(=O)O(R5), CH$_2$—N(R5)(R6), C(R5)=NO(R6), O—R5, SO$_2$N(R5)(R6), SO$_2$—R5, alkyl, cycloalkyl, heterocycloalkyl, heteroaryl, or heteroaryl substituted with C2-C6 alkenyl, wherein cycloalkyl is optionally substituted with carboxy, carboxyl ester, halo, C1-C6 alkyl, C1-C6-haloalkyl or NH$_2$
- R1 is H, D, F, Cl, Br or NH$_2$
- R2a, R2b, R2c and R2d are for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C=C, C≡C, C≡N, C(CH$_3$)$_2$OH, Si(CH$_3$)$_3$, SMe, and OH, with the proviso that when Z is H, R2b is not F and R2c is not Cl or CH$_3$
- R3, R4, R8 and R9 are for each position independently selected from the group comprising H, methyl and ethyl
- R3 and R4 are optionally connected to form a C3-C5-cycloalkyl ring
- R3 and R8 are optionally connected to form a bridged heterobicyclic ring
- R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, C2-C6-hydroxyalkyl, and C2-C6-alkynyl, optionally substituted with 1, 2, or 3 groups each independently selected from OH, halo, C≡N, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C4-carboxamidoalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO$_2$—C1-C6-alkyl, or C≡N
- R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy
- n is 1 or 2
- m is 0 or 1 or a pharmaceutically acceptable salt thereof or a solvate of a compound of Formula Ia or the pharmaceutically acceptable salt thereof or a prodrug of a compound of Formula Ia or a pharmaceutically acceptable salt or a solvate thereof.

2. A compound of Formula Ia according to embodiment 1 that is a compound of Formula II

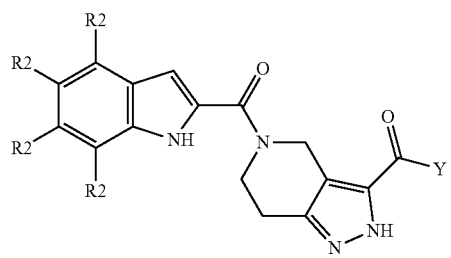

II in which
- Y is N(R5)(R6), N(R5)O(R6), or N(R5)N(R6)(R7)
- R2 is for each position independently selected from the group comprising H, CF$_2$H, CF$_3$, CF$_2$CH$_3$, F, Cl, Br, CH$_3$, Et, and i-Pr
- R5, R6, and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, or C≡N R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, $SO_2Me$, $SO_3H$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy or a pharmaceutically acceptable salt thereof or a solvate of a compound of Formula II or the pharmaceutically acceptable salt thereof or a prodrug of a compound of Formula II or a pharmaceutically acceptable salt or a solvate thereof.

3. A compound of Formula Ia according to embodiments 1 or 2 that is a compound of Formula III

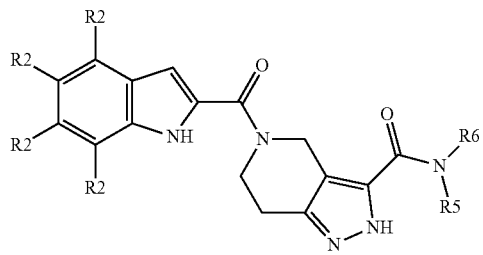

in which

R2 is for each position independently selected from the group comprising H, $CH_2F$, $CF_2H$, $CF_3$, $C(F)CH_3$, $CF_2CH_3$, F, Cl, Br, $CH_3$, and Et R5 is selected from the group comprising C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, and C1-C4-acylsulfonamido-alkyl, optionally substituted with 1, 2, or 3 groups each independently selected from OH, halo, amino, acyl, $SO_2Me$, $SO_3H$, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, and C1-C6 alkenyloxy, wherein C1-C6-alkyl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, $SO_2$—C1-C6-alkyl, or C≡N R6 is selected from the group comprising methyl and ethyl or a pharmaceutically acceptable salt thereof or a solvate of a compound of Formula III or the pharmaceutically acceptable salt thereof or a prodrug of a compound of Formula III or a pharmaceutically acceptable salt or a solvate thereof.

4. A compound of Formula Ia according to embodiment 1 that is a compound of Formula VI

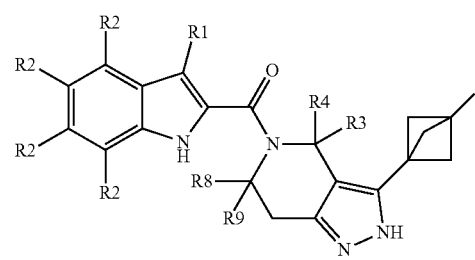

in which,

Q is H, carboxy, carboxyl ester, halo, C1-C6 alkyl, C1-C6-haloalkyl or $NH_2$

R1 is H, D, F, Cl, Br or $NH_2$

R2 is for each position independently selected from the group comprising H, $CF_2H$, $CF_3$, $CF_2CH_3$, F, Cl, Br, $CH_3$, Et, and i-Pr R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring or a pharmaceutically acceptable salt thereof or a solvate of a compound of Formula VI or the pharmaceutically acceptable salt thereof or a prodrug of a compound of Formula VI or a pharmaceutically acceptable salt or a solvate thereof.

5. A compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof for use in the prevention or treatment of an HBV infection in subject.

6. A pharmaceutical composition comprising a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof, together with a pharmaceutically acceptable carrier.

7. A method of treating an HBV infection in an individual in need thereof, comprising administering to the individual a therapeutically effective amount of a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof.

8. Method for the preparation of a compound of Formula Ia according to embodiment 1 by reacting a compound of Formula IV

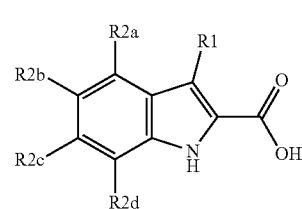

in which R1, R2a, R2b, R2c and R2d are as defined in embodiment 1, with a compound of Formula V

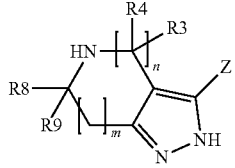

in which n, m, Z, R3, R4, R8 and R9 are as defined in embodiment 1.

Definitions

Listed below are definitions of various terms used to describe this invention. These definitions apply to the terms as they are used throughout this specification and claims unless otherwise limited in specific instances either individually or as part of a larger group.

Unless defined otherwise all technical and scientific terms used herein generally have the same meaning as commonly understood by one of ordinary skill in the art to which this invention belongs. Generally the nomenclature used herein and the laboratory procedures in cell culture, molecular genetics, organic chemistry and peptide chemistry are those well known and commonly employed in the art.

As used herein the articles "a" and "an" refer to one or to more than one (i.e. to at least one) of the grammatical object of the article. By way of example, "an element" means one element or more than one element. Furthermore, use of the term "including" as well as other forms such as "include", "includes" and "included", is not limiting.

As used herein the term "capsid assembly modulator" refers to a compound that disrupts or accelerates or inhibits or hinders or delays or reduces or modifies normal capsid assembly (e.g. during maturation) or normal capsid disassembly (e.g. during infectivity) or perturbs capsid stability, thereby inducing aberrant capsid morphology or aberrant capsid function. In one embodiment, a capsid assembly modulator accelerates capsid assembly or disassembly thereby inducing aberrant capsid morphology. In another embodiment a capsid assembly modulator interacts (e.g. binds at an active site, binds at an allosteric site or modifies and/or hinders folding and the like), with the major capsid assembly protein (HBV-CP), thereby disrupting capsid assembly or disassembly. In yet another embodiment a capsid assembly modulator causes a perturbation in the structure or function of HBV-CP (e.g. the ability of HBV-CP to assemble, disassemble, bind to a substrate, fold into a suitable conformation or the like which attenuates viral infectivity and/or is lethal to the virus).

As used herein the term "treatment" or "treating" is defined as the application or administration of a therapeutic agent i.e., a compound of the invention (alone or in combination with another pharmaceutical agent) to a patient, or application or administration of a therapeutic agent to an isolated tissue or cell line from a patient (e.g. for diagnosis or ex vivo applications) who has an HBV infection, a symptom of HBV infection, or the potential to develop an HBV infection with the purpose to cure, heal, alleviate, relieve, alter, remedy, ameliorate, improve or affect the HBV infection, the symptoms of HBV infection or the potential to develop an HBV infection. Such treatments may be specifically tailored or modified based on knowledge obtained from the field of pharmacogenomics.

As used herein the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein the term "patient", "individual" or "subject" refers to a human or a non-human mammal. Non-human mammals include for example livestock and pets such as ovine, bovine, porcine, feline, and murine mammals. Preferably the patient, subject, or individual is human.

As used herein the terms "effective amount", "pharmaceutically effective amount", and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein the term "pharmaceutically acceptable" refers to a material such as a carrier or diluent which does not abrogate the biological activity or properties of the compound and is relatively non-toxic i.e. the material may be administered to an individual without causing undesirable biological effects or interacting in a deleterious manner with any of the components of the composition in which it is contained.

As used herein the term "pharmaceutically acceptable salt" refers to derivatives of the disclosed compounds wherein the parent compound is modified by converting an existing acid or base moiety to its salt form. Examples of pharmaceutically acceptable salts include but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent or in a mixture of the two; generally non-aqueous media like ether, ethyl acetate, ethanol, isopropanol, or acetonitrile are preferred. Lists of suitable salts are found in Remington's Pharmaceutical Sciences 17$^{th}$ ed. Mack Publishing Company, Easton, Pa., 1985 p. 1418 and Journal of Pharmaceutical Science, 66, 2 (1977), each of which is incorporated herein by reference in its entirety.

As used herein the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including but not limited to intravenous, oral, aerosol, rectal, parenteral, ophthalmic, pulmonary and topical administration.

As used herein the term "pharmaceutically acceptable carrier" means a pharmaceutically acceptable material, composition or carrier such as a liquid or solid filler, stabilizer, dispersing agent, suspending agent, diluent, excipient, thickening agent, solvent or encapsulating material involved in carrying or transporting a compound useful within the invention within or to the patient such that it may perform its intended function. Typically such constructs are carried or transported from one organ, or portion of the body, to another organ or portion of the body. Each carrier must be "acceptable" in the sense of being compatible with the other ingredients of the formulation including the compound use within the invention and not injurious to the patient. Some examples of materials that may serve as pharmaceutically acceptable carriers include: sugars, such as lactose, glucose and sucrose; starches such as corn starch and potato starch; cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents, such as magnesium hydroxide and aluminium hydroxide; surface active agents; alginic acid; pyrogen-free water; isotonic saline; Ringer's solution; ethyl alcohol; phosphate buffer solutions and other non-toxic compatible substances employed in pharmaceutical formulations.

As used herein "pharmaceutically acceptable carrier" also includes any and all coatings, antibacterial and antifungal agents and absorption delaying agents and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described for example in Remington's Pharmaceutical Sciences (Genaro, Ed., Mack Publishing Company, Easton, Pa., 1985) which is incorporated herein by reference.

As used herein, the term "substituted" means that an atom or group of atoms has replaced hydrogen as the substituent attached to another group.

As used herein, the term "comprising" also encompasses the option "consisting of".

As used herein, the term "alkyl" by itself or as part of another substituent means, unless otherwise stated, a straight or branched chain hydrocarbon having the number of carbon atoms designated (i.e. C1-C6-alkyl means one to six carbon atoms) and includes straight and branched chains. Examples include methyl, ethyl, propyl, isopropyl, butyl, isobutyl, tert-butyl, pentyl, neopentyl, and hexyl. In addition, the term "alkyl" by itself or as part of another substituent can also mean a C1-C3 straight chain hydrocarbon substituted with a C3-C5-carbocylic ring. Examples include (cyclopropyl)methyl, (cyclobutyl)methyl and (cyclopentyl)methyl. For the avoidance of doubt, where two alkyl moieties are present in a group, the alkyl moieties may be the same or different.

As used herein the term "alkenyl" denotes a monovalent group derived from a hydrocarbon moiety containing at least two carbon atoms and at least one carbon-carbon double bond of either E or Z stereochemistry. The double bond may or may not be the point of attachment to another group. Alkenyl groups (e.g. C2-C8-alkenyl) include, but are not limited to for example ethenyl, propenyl, prop-1-en-2-yl, butenyl, methyl-2-buten-1-yl, heptenyl and octenyl. For the avoidance of doubt, where two alkenyl moieties are present in a group, the alkyl moieties may be the same or different.

As used herein, a C2-C6-alkynyl group or moiety is a linear or branched alkynyl group or moiety containing from 2 to 6 carbon atoms, for example a C2-C4 alkynyl group or moiety containing from 2 to 4 carbon atoms. Exemplary alkynyl groups include —C≡CH or —CH$_2$—C≡C, as well as 1- and 2-butynyl, 2-pentynyl, 3-pentynyl, 4-pentynyl, 2-hexynyl, 3-hexynyl, 4-hexynyl and 5-hexynyl. For the avoidance of doubt, where two alkynyl moieties are present in a group, they may be the same or different.

As used herein, the term "halo" or "halogen" alone or as part of another substituent means unless otherwise stated a fluorine, chlorine, bromine, or iodine atom, preferably fluorine, chlorine, or bromine, more preferably fluorine or chlorine. For the avoidance of doubt, where two halo moieties are present in a group, they may be the same or different.

As used herein, an C1-C6-alkoxy group or C1-C6-alkenyloxy group is typically a said C1-C6-alkyl (e.g. a C1-C4 alkyl) group or a said C2-C6-alkenyl (e.g. a C2-4 alkenyl) group respectively which is attached to an oxygen atom.

As used herein the term "aryl" employed alone or in combination with other terms, means unless otherwise stated a carbocyclic aromatic system containing one or more rings (typically one, two or three rings) wherein such rings may be attached together in a pendant manner such as a biphenyl, or may be fused, such as naphthalene. Examples of aryl groups include phenyl, anthracyl, and naphthyl. Preferred examples are phenyl (e.g. C6-aryl) and biphenyl (e.g. C12-aryl). In some embodiments aryl groups have from six to sixteen carbon atoms. In some embodiments aryl groups have from six to twelve carbon atoms (e.g. C6-C12-aryl). In some embodiments, aryl groups have six carbon atoms (e.g. C6-aryl).

As used herein the terms "heteroaryl" and "heteroaromatic" refer to a heterocycle having aromatic character containing one or more rings (typically one, two or three rings). Heteroaryl substituents may be defined by the number of carbon atoms e.g. C1-C9-heteroaryl indicates the number of carbon atoms contained in the heteroaryl group without including the number of heteroatoms. For example a C1-C9-heteroaryl will include an additional one to four heteroatoms. A polycyclic heteroaryl may include one or more rings that are partially saturated. Non-limiting examples of heteroaryls include:

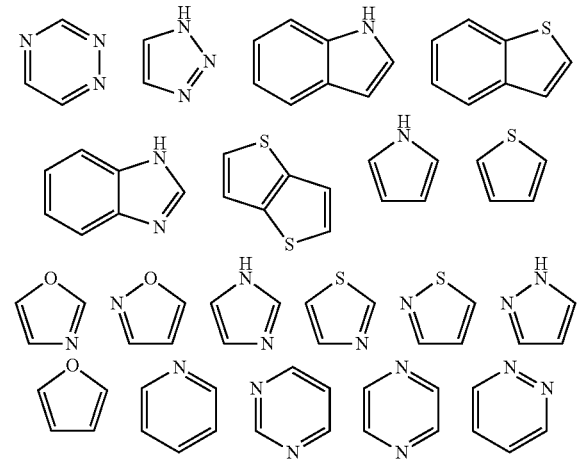

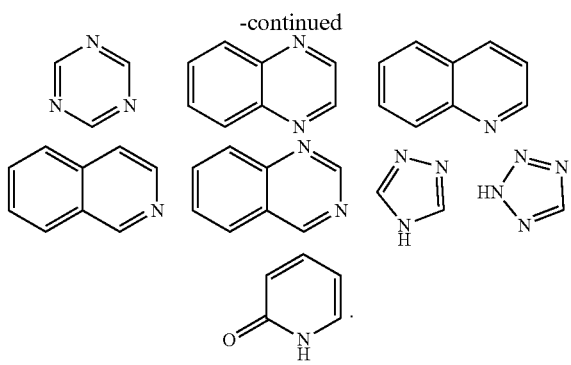

Additional non-limiting examples of heteroaryl groups include pyridyl, pyrazinyl, pyrimidinyl (including e.g. 2- and 4-pyrimidinyl), pyridazinyl, thienyl, furyl, pyrrolyl (including e.g., 2-pyrrolyl), imidazolyl, thiazolyl, oxazolyl, pyrazolyl (including e.g. 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Non-limiting examples of polycyclic heterocycles and heteroaryls include indolyl (including 3-, 4-, 5-, 6- and 7-indolyl), indolinyl, quinolyl, tetrahydroquinolyl, isoquinolyl (including, e.g. 1- and 5-isoquinolyl), 1,2,3,4-tetrahydroisoquinolyl, cinnolinyl, quinoxalinyl (including, e.g 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g. 3-, 4-, 5-, 6-, and 7-benzofuryl), 2,3-dihydrobenzofuryl, 1,2-benzisoxazolyl, benzothienyl (including e.g. 3-, 4-, 5-, 6-, and 7-benzothienyl), benzoxazolyl, benzothiazolyl (including e.g. 2-benzothiazolyl and 5-benzothiazolyl), purinyl, benzimidazolyl (including e.g., 2-benzimidazolyl), benzotriazolyl, thioxanthinyl, carbazolyl, carbolinyl, acridinyl, pyrrolizidinyl and quinolizidinyl.

As used herein the term "haloalkyl" is typically a said alkyl, alkenyl, alkoxy or alkenoxy group respectively wherein any one or more of the carbon atoms is substituted with one or more said halo atoms as defined above. Haloalkyl embraces monohaloalkyl, dihaloalkyl, and polyhaloalkyl radicals. The term "haloalkyl" includes but is not limited to fluoromethyl, 1-fluoroethyl, difluoromethyl, 2,2-difluoroethyl, 2,2,2-trifluoroethyl, trifluoromethyl, chloromethyl, dichloromethyl, trichloromethyl, pentafluoroethyl, difluoromethoxy, and trifluoromethoxy.

As used herein, a C1-C6-hydroxyalkyl group is a said C1-C6 alkyl group substituted by one or more hydroxy groups. Typically, it is substituted by one, two or three hydroxyl groups. Preferably, it is substituted by a single hydroxy group.

As used herein, a C1-C6-aminoalkyl group is a said C1-C6 alkyl group substituted by one or more amino groups. Typically, it is substituted by one, two or three amino groups. Preferably, it is substituted by a single amino group.

As used herein, a C1-C4-carboxyalkyl group is a said C1-C4 alkyl group substituted by carboxyl group.

As used herein, a C1-C4-carboxamidoalkyl group is a said C1-C4 alkyl group substituted by a substituted or unsubstituted carboxamide group.

As used herein, a C1-C4-acylsulfonamido-alkyl group is a said C1-C4 alkyl group substituted by an acylsulfonamide group of general formula C(=O)NHSO$_2$CH$_3$ or C(=O)NHSO$_2$-c-Pr.

As used herein the term "cycloalkyl" refers to a monocyclic or polycyclic nonaromatic group wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms (C3-C10-cycloalkyl), groups having 3 to 8 ring atoms (C3-C8-cycloalkyl), groups having 3 to 7 ring atoms (C3-C7-cycloalkyl) and groups having 3 to 6 ring atoms (C3-C6-cycloalkyl). Illustrative examples of cycloalkyl groups include, but are not limited to the following moieties:

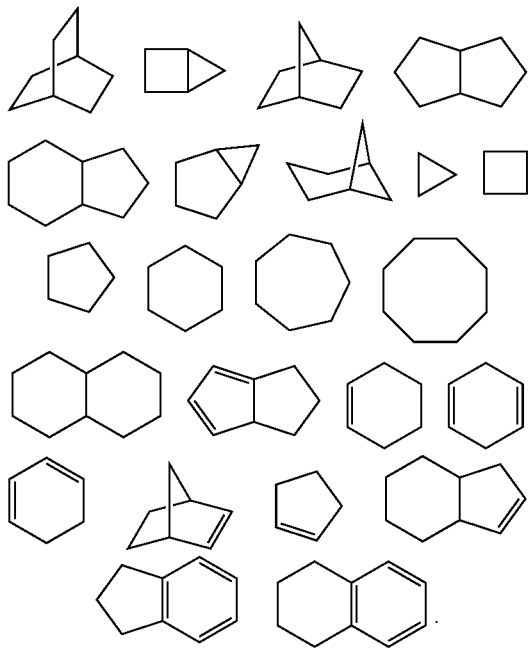

Monocyclic cycloalkyls include but are not limited to cyclopropyl, cyclobutyl, cyclopentyl, cyclohexyl, cycloheptyl, and cyclooctyl. Dicyclic cycloalkyls include but are not limited to tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups both of which refer to a nonaromatic carbocycle as defined herein which contains at least one carbon-carbon double bond or one carbon-carbon triple bond.

As used herein the terms "heterocycloalkyl" and "heterocyclyl" refer to a heteroalicyclic group containing one or more rings (typically one, two or three rings), that contains one to four ring heteroatoms each selected from oxygen, sulfur and nitrogen. In one embodiment each heterocyclyl group has from 3 to 10 atoms in its ring system with the proviso that the ring of said group does not contain two adjacent oxygen or sulfur atoms. In one embodiment each heterocyclyl group has a fused bicyclic ring system with 3 to 10 atoms in the ring system, again with the proviso that the ring of said group does not contain two adjacent oxygen or sulfur atoms. In one embodiment each heterocyclyl group has a bridged bicyclic ring system with 3 to 10 atoms in the ring system, again with the proviso that the ring of said group does not contain two adjacent oxygen or sulfur atoms. In one embodiment each heterocyclyl group has a spirobicyclic ring system with 3 to 10 atoms in the ring system, again with the proviso that the ring of said group does not contain two adjacent oxygen or sulfur atoms. Heterocyclyl substituents may be alternatively defined by the number of carbon atoms e.g. C2-C8-heterocyclyl indicates the number of carbon atoms contained in the heterocyclic group without including the number of heteroatoms. For example a C2-C8-heterocyclyl will include an additional one to four heteroatoms. In another embodiment the heterocycloalkyl group is fused with an aromatic ring. In another embodiment the heterocycloalkyl group is fused with a heteroaryl ring. In one embodiment the nitrogen and sulfur heteroatoms may be optionally oxidized and the nitrogen atom may be optionally quaternized. The heterocyclic system may be attached, unless otherwise stated, at any heteroatom or carbon atom that affords a stable structure. An example of a 3-membered heterocyclyl group includes and is not limited to aziridine. Examples of 4-membered heterocycloalkyl groups include, and are not limited to azetidine and a beta-lactam. Examples of 5-membered heterocyclyl groups include, and are not limited to pyrrolidine, oxazolidine and thiazolidinedione. Examples of 6-membered heterocycloalkyl groups include, and are not limited to, piperidine, morpholine, piperazine, N-acetylpiperazine and N-acetylmorpholine. Other non-limiting examples of heterocyclyl groups are

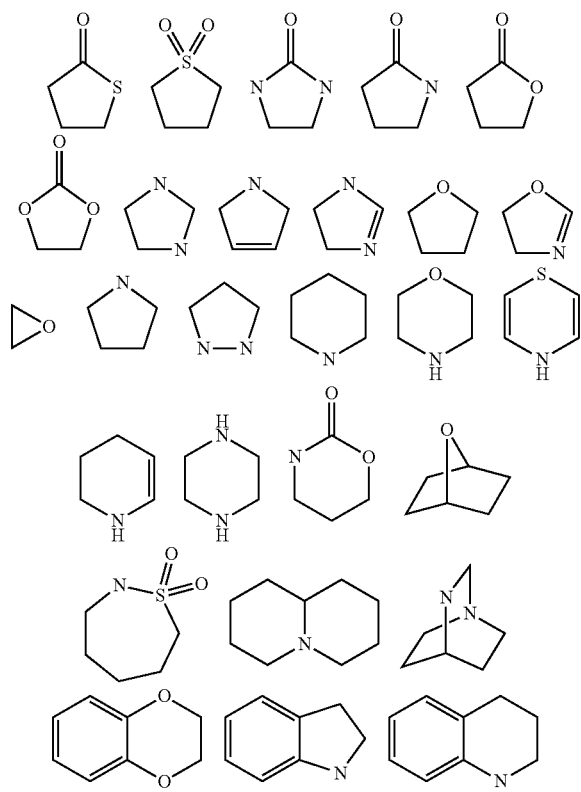

Examples of heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, 1,3-dioxolane, homopiperazine, homopiperidine, 1,3-dioxepane, 47-dihydro-1,3-dioxepin, and hexamethyleneoxide.

As used herein, the term "aromatic" refers to a carbocycle or heterocycle with one or more polyunsaturated rings and having aromatic character i.e. having (4n+2) delocalized π (pi) electrons where n is an integer.

As used herein, the term "acyl", employed alone or in combination with other terms, means, unless otherwise stated, to mean to an alkyl, cycloalkyl, heterocycloalkyl, aryl or heteroaryl group linked via a carbonyl group.

As used herein, the terms "carbamoyl" and "substituted carbamoyl", employed alone or in combination with other terms, means, unless otherwise stated, to mean a carbonyl group linked to an amino group optionally mono or di-substituted by hydrogen, alkyl, cycloalkyl, heterocycloalkyl, aryl or heteroaryl, optionally substituted with said carboxy or carboxyl ester. In some embodiments, the nitrogen substituents will be connected to form a heterocyclyl ring as defined above.

As used herein, the term "carboxy" and by itself or as part of another substituent means, unless otherwise stated, a group of formula C(=O)OH.

As used herein, a C1-C6-alkyl-O-C1-C6-alkyl group is a said C1-C6-alkoxy group attached to a said C1-C6-alkyl group, wherein any one or more of the carbon atoms is optionally substituted with one or more said halo atoms as defined above. C1-C6-alkyl-O-C1-C6-alkyl groups include, but are not limited to, for example, ethoxymethyl, methoxymethyl, methoxyethyl, difluoromethoxymethyl, difluoromethoxyethyl and trifluoromethoxymethyl.

As used herein, the term "acyloxy", employed alone or in combination with other terms, means, unless otherwise stated, a said acyl group attached to an oxygen atom.

As used herein, a C2-C6-alkynyloxy group is typically a said C2-C6-alkynyl (e.g. a C2-C4 alkynyl) group which is attached to an oxygen atom.

As used herein, the term "spirocyclic" refers to any compound containing two or more rings wherein two of the rings have one ring carbon in common.

As used herein, the term "carboxyl ester" by itself or as part of another substituent means, unless otherwise stated, a group of formula C(=O)OX, wherein X is selected from the group consisting of C1-C6-alkyl, C3-C7-cycloalkyl, and aryl.

As used herein the term "prodrug" represents a derivative of a compound of Formula I or Formula II or Formula III which is administered in a form which, once administered, is metabolised in vivo into an active metabolite also of Formula I or Formula II or Formula III.

Subject matter of the present invention are also the prodrugs of a compound of Formula I or Formula II or Formula III, whether in generalized form or in a specifically mentioned form below.

Various forms of prodrug are known in the art. For examples of such prodrugs see: Design of Prodrugs, edited by H. Bundgaard, (Elsevier, 1985) and Methods in Enzymology, Vol. 42, p. 309-396, edited by K. Widder, et al. (Academic Press, 1985); A Textbook of Drug Design and Development, edited by Krogsgaard-Larsen and H. Bundgaard, Chapter 5 "Design and Application of Prodrugs" by H. Bundgaard p. 113-191 (1991); H. Bundgaard, Advanced Drug Delivery Reviews 8, 1-38 (1992); H. Bundgaard, et al., Journal of Pharmaceutical Sciences, 77, 285 (1988); and N. Kakeya, et al., Chem. Pharm. Bull., 32, 692 (1984).

Examples of prodrugs include cleavable esters of compounds of Formula I, II and/or III. An in vivo cleavable ester of a compound of the invention containing a carboxy group is, for example, a pharmaceutically acceptable ester which is cleaved in the human or animal body to produce the parent acid. Suitable pharmaceutically acceptable esters for carboxy include C1-C6 alkyl ester, for example methyl or ethyl esters; C1-C6 alkoxymethyl esters, for example methoxymethyl ester; C1-C6 alkanoyloxymethyl esters; phthalidyl esters; C3-C8 cycloalkoxycarbonyloxyC1-C6 alkyl esters, for example 1-cyclohexylcarbonyloxyethyl; 1-3-dioxolan-2-ylmethylesters, for example 5-methyl-1,3-dioxolan-2-ylmethyl; C1-C6 alkoxycarbonyloxyethyl esters, for example 1-methoxycarbonyloxyethyl; aminocarbonylmethyl esters and mono- or di-N—(C1-C6 alkyl) versions thereof, for example N, N-dimethylaminocarbonylmethyl esters and N-ethylaminocarbonylmethyl esters; and may be formed at any carboxy group in the compounds of the invention.

An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include C1-C6-alkanoyl esters, for example acetyl esters; and benzoyl esters wherein the phenyl group may be substituted with aminomethyl or N-substituted mono- or di-C1-C6 alkyl aminomethyl, for example 4-aminomethylbenzoyl esters and 4-N,N-dimethylaminomethylbenzoylesters.

Preferred prodrugs of the invention include acetyloxy and carbonate derivatives. For example, a hydroxy group of a compound of Formula I can be present in a prodrug as —O—COR$^i$ or —O—C(O)OR$^i$ where R$^i$ is unsubstituted or substituted C1-C4 alkyl. Substituents on the alkyl groups are as defined earlier. Preferably the alkyl groups in R$^i$ is unsubstituted, preferable methyl, ethyl, isopropyl or cyclopropyl.

Other preferred prodrugs of the invention include amino acid derivatives. Suitable amino acids include α-amino acids linked to compounds of Formula I via their C(O)OH group. Such prodrugs cleave in vivo to produce compounds of Formula I bearing a hydroxy group. Accordingly, such amino acid groups are preferably employed positions of Formula I where a hydroxy group is eventually required. Exemplary prodrugs of this embodiment of the invention are therefore compounds of Formula I bearing a group of Formula —OC(O)—CH(NH$_2$)R$^{ii}$ where R$^{ii}$ is an amino acid side chain. Preferred amino acids include glycine, alanine, valine and serine. The amino acid can also be functionalised, for example the amino group can be alkylated. A suitable functionalised amino acid is N,N-dimethylglycine. Preferably the amino acid is valine.

Other preferred prodrugs of the invention include phosphoramidate derivatives. Various forms of phosphoramidate prodrugs are known in the art. For example of such prodrugs see Serpi et al., Curr. Protoc. Nucleic Acid Chem. 2013, Chapter 15, Unit 15.5 and Mehellou et al., ChemMedChem, 2009, 4 pp. 1779-1791. Suitable phosphoramidates include (phenoxy)-α-amino acids linked to compounds of Formula I via their —OH group. Such prodrugs cleave in vivo to produce compounds of Formula I bearing a hydroxy group. Accordingly, such phosphoramidate groups are preferably employed positions of Formula I where a hydroxy group is eventually required. Exemplary prodrugs of this embodiment of the invention are therefore compounds of Formula I bearing a group of Formula —OP(O)(OR$^{iii}$)R$^{iv}$ where R$^{iii}$ is alkyl, cycloalkyl, aryl or heteroaryl, and R$^{iv}$ is a group of Formula —NH—CH(R$^v$)C(O)OR$^{vi}$, wherein R$^v$ is an amino acid side chain and R$^{vi}$ is alkyl, cycloalkyl, aryl or heterocyclyl. Preferred amino acids include glycine, alanine, valine and serine. Preferably the amino acid is alanine. R$^v$ is preferably alkyl, most preferably isopropyl.

Subject matter of the present invention is also a method of preparing the compounds of the present invention. Subject matter of the invention is, thus, a method for the preparation of a compound of Formula I according to the present invention by reacting a compound of Formula IV

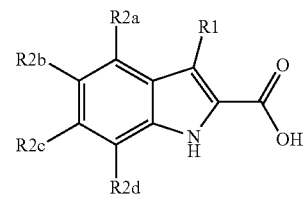

IV in which R1, R2a, R2b, R2c and R2d are as above-defined, with a compound of Formula V

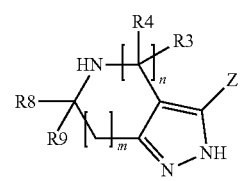

V in which n, m, Z, R3, R4, R8 and R9 are as above-defined.

Subject matter of the invention is, also, a method for the preparation of a compound of Formula II, III, IV and V in the same manner, and as will be outlined in the Examples in more detail.

EXAMPLES

The invention is now described with reference to the following Examples. These Examples are provided for the purpose of illustration only, and the invention is not limited to these Examples, but rather encompasses all variations that are evident as a result of the teachings provided herein.

The HBV core protein modulators can be prepared in a number of ways. Schemes 1-6 illustrate the main routes employed for their preparation for the purpose of this application. To the chemist skilled in the art it will be apparent that there are other methodologies that will also achieve the preparation of these intermediates and Examples.

In a preferred embodiment compounds of Formula I can be prepared as shown in General scheme 1 below.

General scheme 1: Synthesis of compounds of Formula I

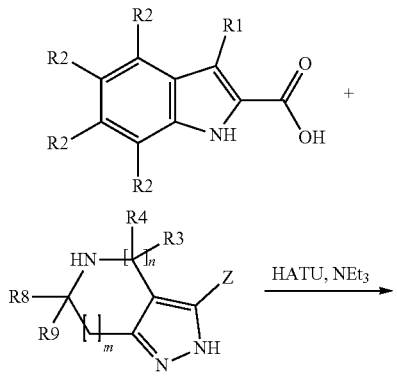

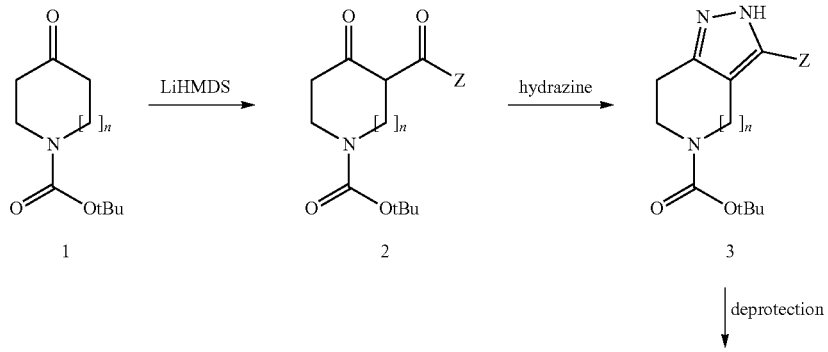

An amide coupling of indole-2-carboxylic acids of general structure 1 with amines of general structure 2 according to methods known in literature (A. El-Faham, F. Albericio, Chem. Rev. 2011, 111, 6557-6602), e.g. with HATU results in compounds of Formula I.

In another preferred embodiment the synthesis of the compounds according to the invention follows the following general synthesis scheme:

In a preferred embodiment compounds of Formula I can be prepared as shown in General scheme 2 below.

General scheme 2: Synthesis of compounds of Formula I

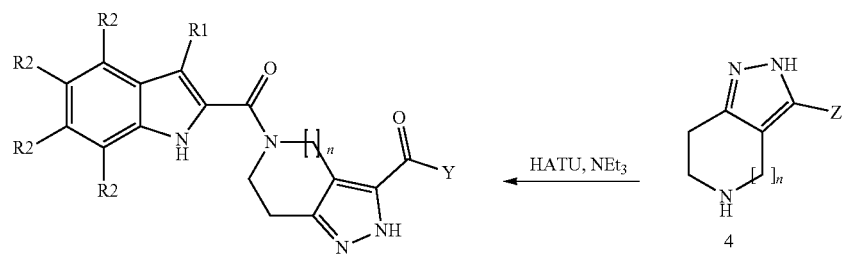

In step 1 ketone 1 is converted into compound 2 under basic conditions (M. Andres et al., Eur. J. Med. Chem., 2014, 71, 168-184) (for compounds where Z is hetero(aryl)). Compound 2 is cyclized in step 2 with hydrazine into pyrazole 3 (M. Andres et al., Eur. J. Med. Chem., 2014, 71, 168-184). In step 3 deprotection of the nitrogen protective group (A. Isidro-Llobet et al., Chem. Rev., 2009, 109, 2455-2504), drawn as but not limited to Boc, e.g. with HCl gives amine 4. An amide coupling in step 4 with methods known in literature (A. El-Faham, F. Albericio, Chem. Rev. 2011, 111, 6557-6602), e.g. with HATU results in compounds of Formula I.

In another preferred embodiment compounds of Formula II can be prepared as shown in General scheme 3 below.

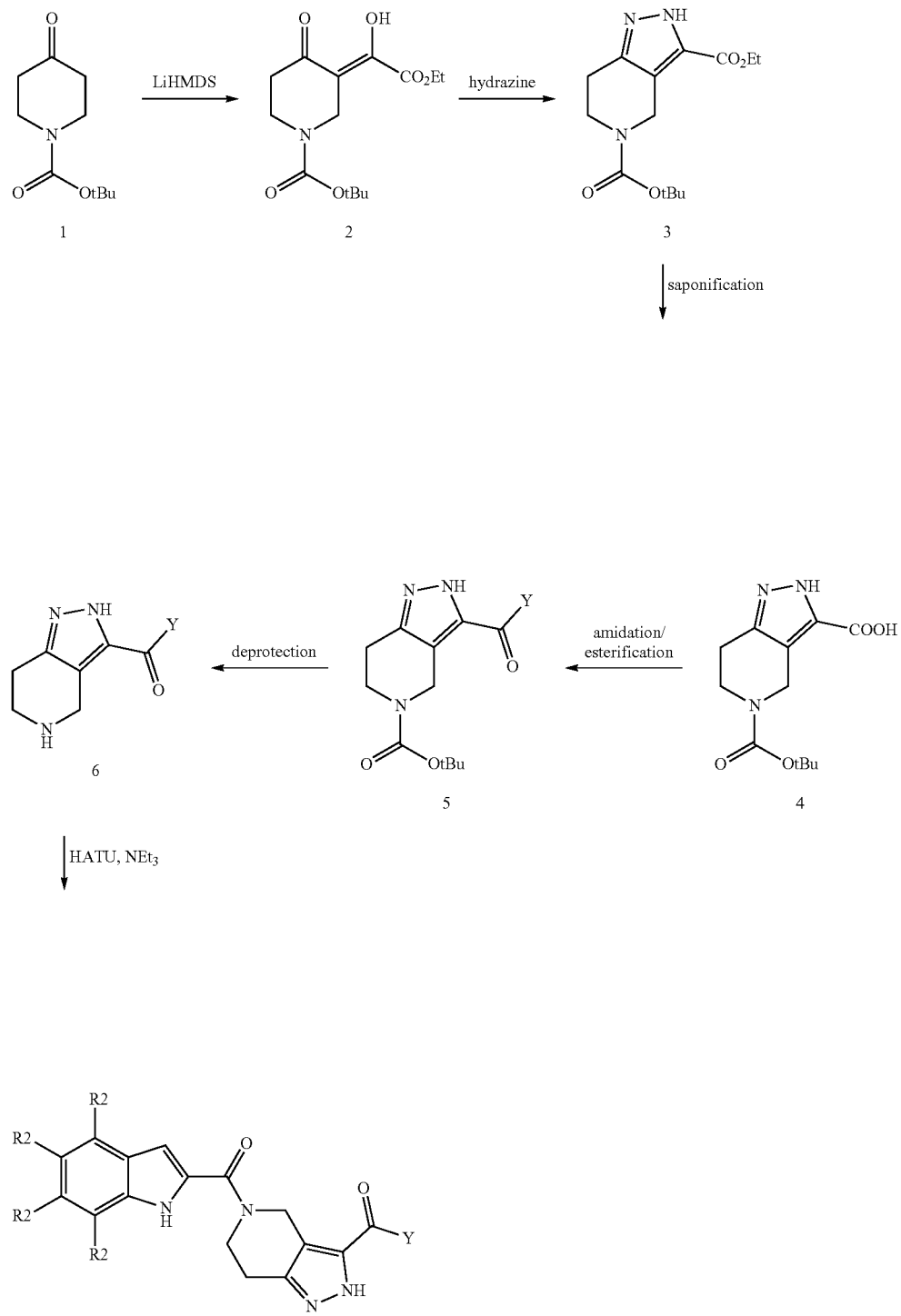

In step 1 ketone 1 is converted into compound 2 under basic conditions (WO200722280). Compound 2 is cyclized in step 2 with hydrazine into pyrazole 3 (WO200722280). The ester of compound 3, drawn as but not limited to ethyl, is hydrolysed by methods known from the literature (WO200722280) to give acid 4. By methods known from the literature, acid 4 in step 4 is amidated (A. El-Faham, F. Albericio, Chem. Rev. 2011, 111, 6557-6602), or esterified (J. K. Twibanire, T. B. Grindley, Org. Lett. 2011, 13, 2988-2991) to give compounds with the general structure 5.

In step 5 deprotection of the nitrogen protective group (A. Isidro-Llobet et al., Chem. Rev., 2009, 109, 2455-2504), drawn as but not limited to Boc, e.g. with TFA gives aminea 6. An amide coupling in step 6 with methods known in literature (A. El-Faham, F. Albericio, Chem. Rev. 2011, 111, 6557-6602), e.g. with HATU results in compounds of Formula II.

In another preferred embodiment compounds of Formula III can be prepared as shown in General scheme 4 below.

General scheme 4: Synthesis of compounds of Formula III

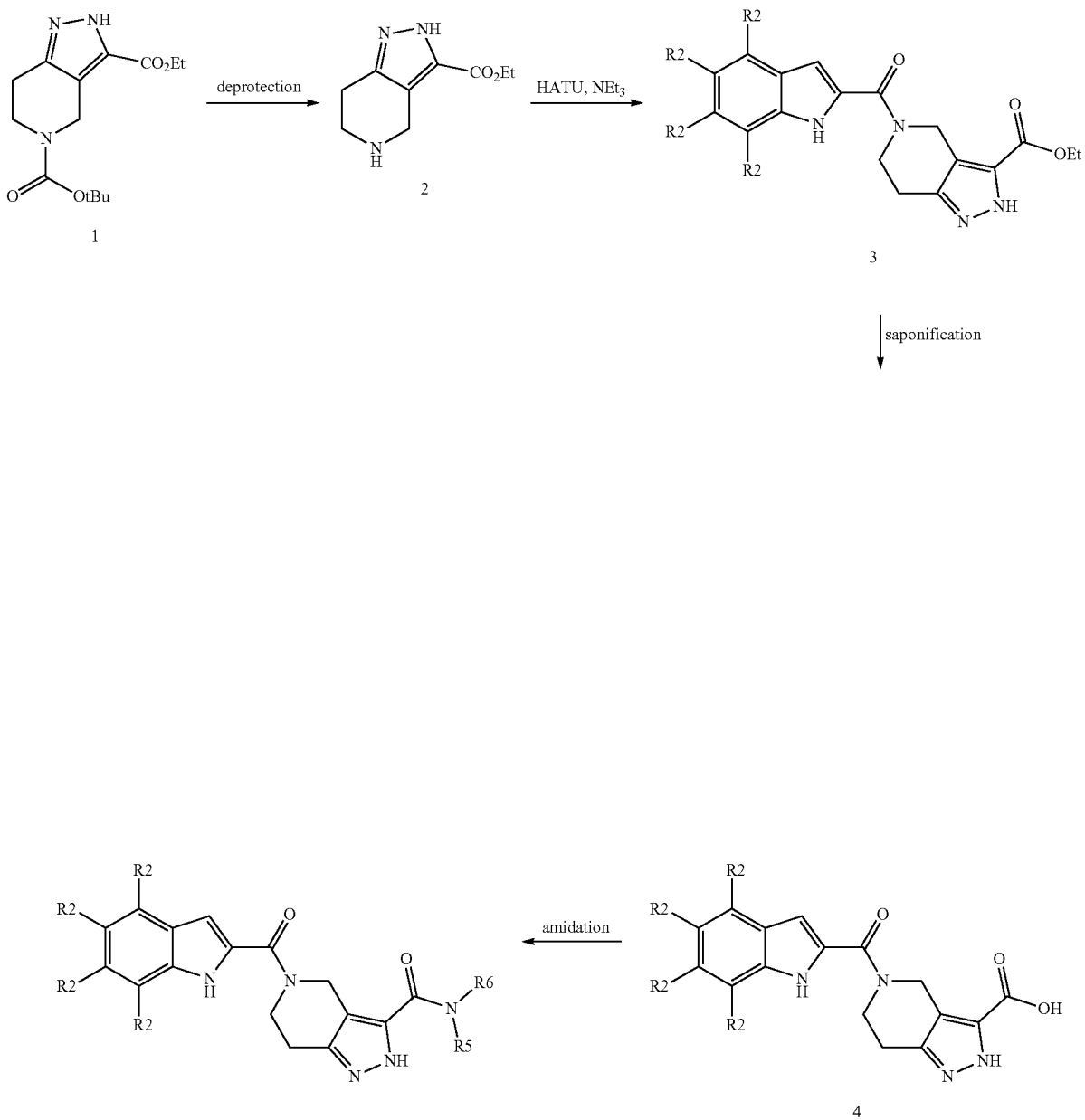

In step 1 deprotection of the nitrogen protective group (A. Isidro-Llobet et al., Chem. Rev., 2009, 109, 2455-2504) from compound 1 described in general scheme 4, drawn as In another preferred embodiment the synthesis of the compounds according to the invention follows the General scheme 5.

General scheme 5: Synthesis of compounds of the invention

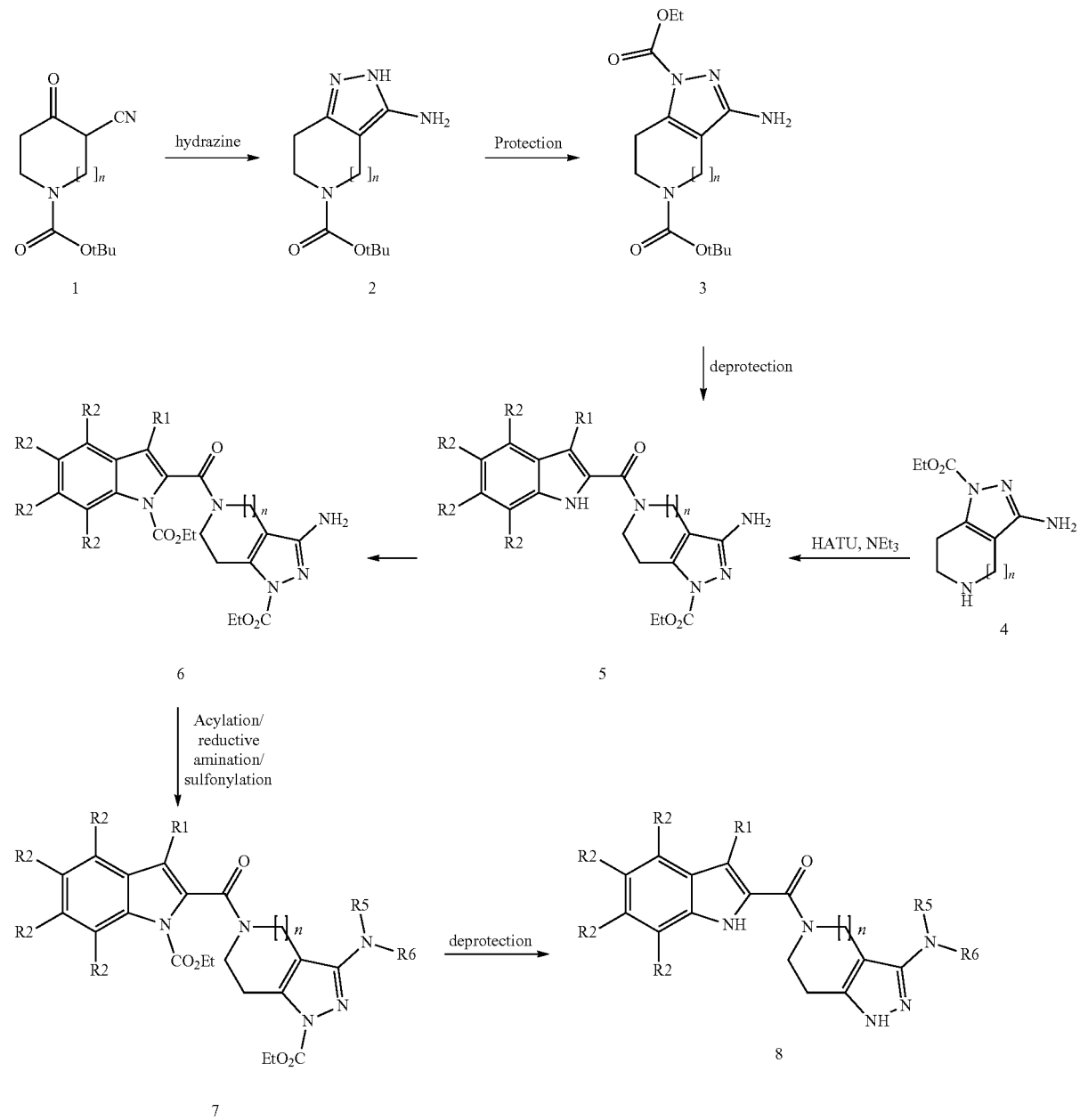

but not limited to Boc, e.g. with HCl gives amine 2. An amide coupling in step 2 with methods known in literature (A. El-Faham, F. Albericio, Chem. Rev. 2011, 111, 6557-6602), e.g. with HATU results in a compound with the general structure 3. In step 3 the ester of compound 3, drawn as but not limited to ethyl, is hydrolysed by methods known from the literature (WO200722280) to give acid 4. By methods known from the literature, acid 4 in step 4 is amidated (A. El-Faham, F. Albericio, Chem. Rev. 2011, 111, 6557-6602) to give compounds of Formula III.

In step 1 compound 1 is cyclized with hydrazine to give an amino-pyrazole 2 (WO201686200). The pyrazole is then protected in step 2, drawn as but not limited to ethoxycarbamate, to give compound 3 (WO200480457). In step 3 deprotection of the nitrogen protective group (A. Isidro-Llobet et al., Chem. Rev., 2009, 109, 2455-2504), drawn as but not limited to Boc, e.g. with HCl gives amine 4. An amide coupling in step 4 with methods known in literature (A. El-Faham, F. Albericio, Chem. Rev. 2011, 111, 6557-6602), e.g. with HATU results in a compound with the general structure 5. The indole N—H is protected in step 5, drawn as but not limited to ethoxycarbamate, to give compound 6 (A. Monge et al., J. Het. Chem., 1984, 21, 397-400). By methods known from the literature, in step 6 the nitrogen of the amino-pyrazole 6 is acylated (A. El-Faham, F. Albericio, Chem. Rev. 2011, 111, 6557-6602), reductively aminated (US2015315198), or sulfonylated (WO201167145) to give compounds with the general structure 7. Reductive amination on 6 can potentially also be followed by acylation (A. El-Faham, F. Albericio, Chem. Rev. 2011, 111, 6557-6602), or sulfonylation (WO201167145) to obtain compounds also with the general structure 7. In step 7 deprotection (S. O. Ochiana et al., Eur. J. Med. Chem., 2013, 62, 777-784) gives compounds with the general structure 8.

In another preferred embodiment the synthesis of the compounds according to the invention follows the following general scheme 6:

General scheme 6: Synthesis of compounds of the invention

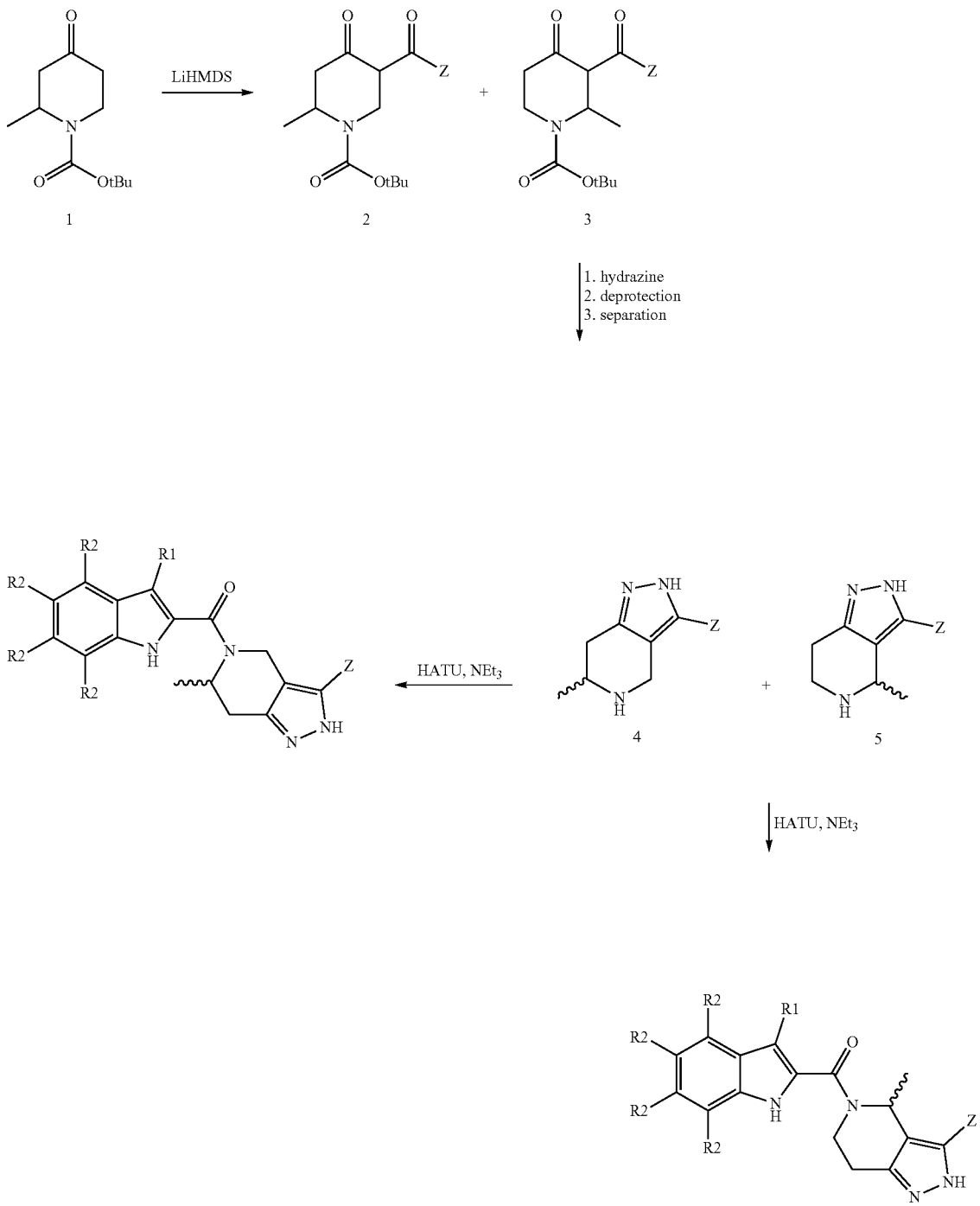

In step 1 ketone 1 is converted into isomeric diketones 2 and 3 (M. Andres et al., Eur. J. Med. Chem., 2014, 71, 168-184). Intermediates 2 and 3 are converted into the pyrazoles with hydrazine (WO0200722280), followed by deprotection of the nitrogen protective group, drawn as but not limited to Boc, e.g. with HCl (A. Isidro-Llobet et al., Chem. Rev., 2009, 109, 2455-2504), to give amines 4 and 5. Mixtures of regio- and stereo-isomeric products can be separated at this stage by standard chromatographic techniques. An amide coupling on 4 or 5 with methods known in literature (A. El-Faham, F. Albericio, Chem. Rev. 2011, 111, 6557-6602), e.g. with HATU results in compounds of Formula I.

The required substituted indole-2-carboxylic acids may be prepared in a number of ways; the main routes employed being outlined in Schemes 7-10. To the chemist skilled in the art it will be apparent that there are other methodologies that will also achieve the preparation of these intermediates.

Substituted indole-2-carboxylic acids can be prepared via the Hemetsberger-Knittel reaction (Organic Letters, 2011, 13(8) pp. 2012-2014, and Monatshefte für Chemie, 103(1), pp. 194-204) (Scheme 7).

Scheme 7: Indoles from vinyl azides

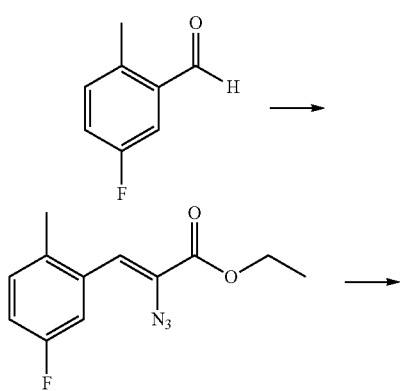

Substituted indoles may also be prepared using the Fischer method (Berichte der Deutschen Chemischen Gesellschaft. 17 (1): 559-568) (Scheme 8)

Scheme 8: The Fischer indole synthesis

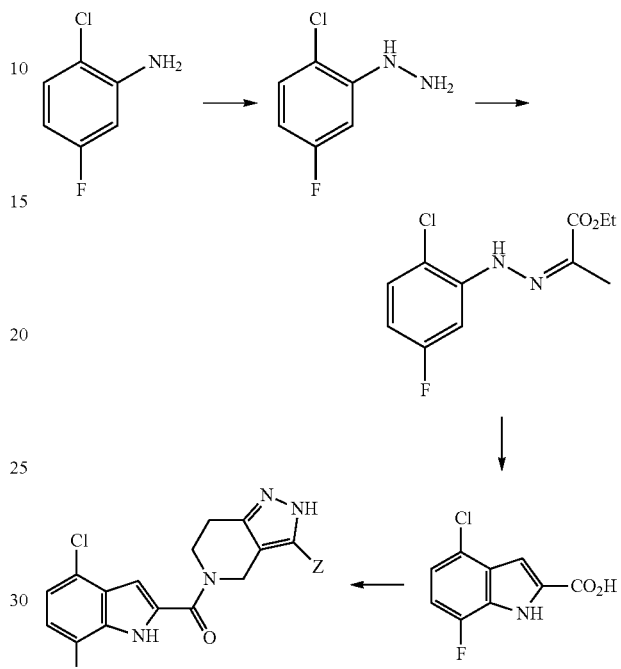

A further method for the preparation of substituted indoles is the palladium catalysed alkyne annulation reaction (Journal of the American Chemical Society, 1991, pp. 6690-6692) (Scheme 9).

Scheme 9: Preparation of indoles via alkyne annulation

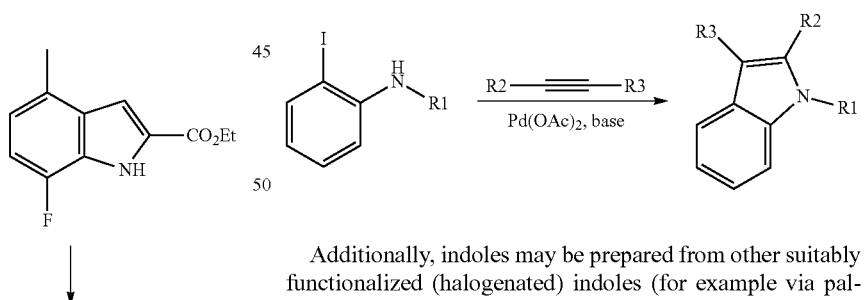

Additionally, indoles may be prepared from other suitably functionalized (halogenated) indoles (for example via palladium catalysed cross coupling or nucleophilic substitution reactions) as illustrated in Scheme 10.

Scheme 10: Palladium catalysed functionalization of halogenated indoles

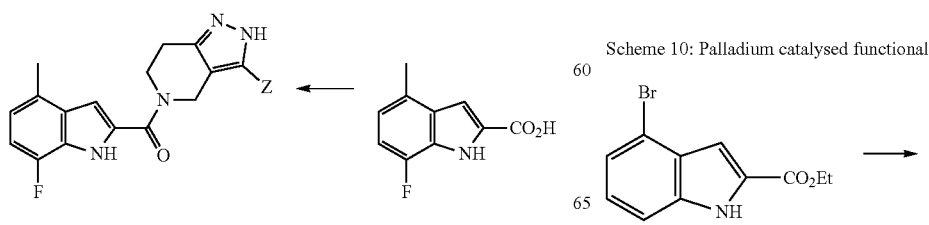

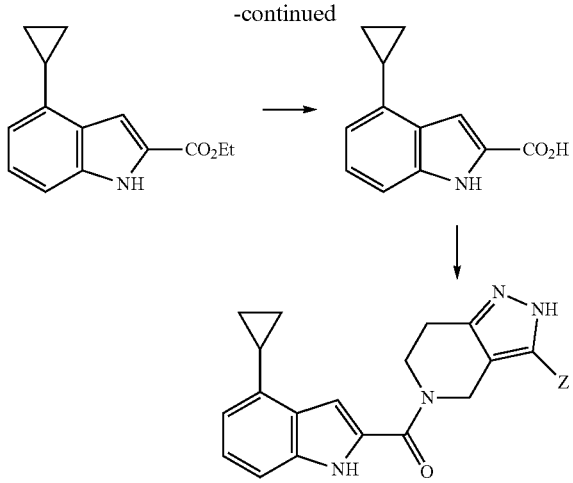

Chemists skilled in the art will appreciate that other methods are available for the synthesis of suitably functionalized indole-2-carboxylic acids and activated esters thereof.

The following examples illustrate the preparation and properties of some specific compounds of the invention. The following abbreviations are used:
A—DNA nucleobase adenine
ACN—acetonitrile
Ar—argon
BBQ—BlackBerry Quencher 650
BODIPY-FL—4,4-difluoro-5,7-dimethyl-4-bora-3a,4a-diaza-s-indacene-3-propionic acid (fluorescent dye)
Boc—tert-butoxycarbonyl
n-BuLi—n-butyl lithium
t-BuLi—t-butyl lithium
C—DNA nucleobase cytosine
$CC_{50}$—half-maximal cytotoxic concentration
$CO_2$—carbon dioxide
CuCN—copper (I) cyanide
DAST—diethylaminosulfur trifluoride
DHBV—duck hepatitis B virus
DCE—dichloroethane
DCM—dichloromethane
Dess-Martinperiodinane-1,1,1-triacetoxy-1,1-dihydro-1,2-benziodoxol-3(1H)-one
DIPEA—diisopropylethylamine
DIPE—di-isopropyl ether
DMAP—4-dimethylaminopyridine
DMF—N,N-dimethylformamide
DMP—Dess-Martin periodinane
DMSO—dimethyl sulfoxide
DNA—deoxyribonucleic acid
DTT—dithiothreitol
$EC_{50}$—half-maximal effective concentration
EDCI—N-(3-dimethylaminopropyl)-N'-ethylcarbodiimide hydrochloride
$Et_2O$—diethyl ether
EtOAc—ethyl acetate
EtOH—ethanol
FAM—6-fluorescein amidite
FL-—five prime end labled with fluorescein
$NEt_3$—triethylamine
ELS—Evaporative Light Scattering
g—gram(s)
G—DNA nucleobase guanine
HBV—hepatitis B virus
HATU—2-(1H-7-azabenzotriazol-1-yl)-1,1,3,3-tetramethyl uronium hexafluorophosphate
HCl—hydrochloric acid
HDI—hydrodynamic injection
HEPES—4-(2-hydroxyethyl)-1-piperazineethanesulfonic acid
HOAt—1-hydroxy-7-azabenzotriazole
HOBt—1-hydroxybenzotriazole
HPLC—high performance liquid chromatography
$IC_{50}$—half-maximal inhibitory concentration
LC640—3 prime end modification with fluorescent dye LightCycler® Red 640
LC/MS—liquid chromatography/mass spectrometry
$LiAlH_4$—lithium aluminium hydride
LiOH—lithium hydroxide
MeOH—methanol
MeCN—acetonitrile
$MgSO_4$—magnesium sulfate
mg—milligram(s)
min—minutes
mol—moles
mmol—millimole(s)
mL—millilitre(s)
MTBE—methyl tert-butyl ether
$N_2$—nitrogen
$Na_2CO_3$—sodium carbonate
$NaHCO_3$—sodium hydrogen carbonate
$Na_2SO_4$—sodium sulfate
NdeI—restriction enzyme recognizes CA^TATG sites
$NEt_3$—triethylamine
NaH—sodium hydride
NaOH—sodium hydroxide
$NH_3$—ammonia
$NH_4Cl$—ammonium chloride
NMR—nuclear magnetic resonance
PAGE—polyacrylamide gel electrophoresis
PCR—polymerase chain reaction
qPCR—quantitative PCR
Pd/C—palladium on carbon
PEG 400—polyethylene glycol 400
PH—3 prime end phosphate modification
pTSA—4-toluene-sulfonic acid
Rt—retention time
r.t.—room temperature
sat.—saturated aqueous solution
SDS—sodium dodecyl sulfate
SI—selectivity index (=$CC_{50}/EC_{50}$)
STAB—sodium triacetoxyborohydride
T—DNA nucleobase thymine
TBAF—tetrabutylammonium fluoride
Tg—transgenic
TFA—trifluoroacetic acid
THF—tetrahydrofuran
TLC—thin layer chromatography
Tris—tris(hydroxymethyl)-aminomethane
WHV—woodchuck hepatitis virus
XhoI—restriction enzyme recognizes C^TCGAG sites
Compound Identification—NMR For a number of compounds, NMR spectra were recorded using a Bruker DPX400 spectrometer equipped with a 5 mm reverse triple-resonance probe head operating at 400 MHz for the proton and 100 MHz for carbon. Deuterated solvents were chloroform-d (deuterated chloroform, $CDCl_3$) or d6-DMSO (deuterated DMSO, d6-dimethylsulfoxide).
Chemical shifts are reported in parts per million (ppm) relative to tetramethylsilane (TMS) which was used as internal standard.

Compound Identification—HPLC/MS

For a number of compounds, LC-MS spectra were recorded using the following analytical methods.

Method A
Column—Reverse phase Waters Xselect CSH C18 (50× 2.1 mm, 3.5 micron)
Flow—0.8 mL/min, 25 degrees Celsius
Eluent A—95% acetonitrile+5% 10 mM ammonium carbonate in water (pH 9)
Eluent B—10 mM ammonium carbonate in water (pH 9)
Linear gradient t=0 min 5% A, t=3.5 min 98% A. t=6 min 98% A Method B
Column—Reverse phase Waters Xselect CSH C18 (50× 2.1 mm, 3.5 micron)
Flow—0.8 mL/min, 35 degrees Celsius
Eluent A—0.1% formic acid in acetonitrile
Eluent B—0.1% formic acid in water
Linear gradient t=0 min 5% A, t=3.5 min 98% A. t=6 min 98% A Method C
Column—Reverse phase Waters Xselect CSH C18 (50× 2.1 mm, 3.5 micron)
Flow—1 mL/min, 35 degrees Celsius
Eluent A—0.1% formic acid in acetonitrile
Eluent B—0.1% formic acid in water
Linear gradient t=0 min 5% A, t=1.6 min 98% A. t=3 min 98% A Method D
Column—Phenomenex Gemini NX C18 (50×2.0 mm, 3.0 micron)
Flow—0.8 mL/min, 35 degrees Celsius
Eluent A—95% acetonitrile+5% 10 mM ammoniumbicarbonate in water
Eluent B—10 mM ammoniumbicarbonate in water pH=9.0
Linear gradient t=0 min 5% A, t=3.5 min 98% A. t=6 min 98% A Method E
Column—Phenomenex Gemini NX C18 (50×2.0 mm, 3.0 micron)
Flow—0.8 mL/min, 25 degrees Celsius
Eluent A—95% acetonitrile+5% 10 mM ammoniumbicarbonate in water
Eluent B—10 mM ammonium bicarbonate in water (pH 9)
Linear gradient t=0 min 5% A, t=3.5 min 30% A. t=7 min 98% A, t=10 min 98% A Method F
Column—Waters XSelect HSS C18 (150×4.6 mm, 3.5 micron)
Flow—1.0 mL/min, 25 degrees Celsius
Eluent A—0.1% TFA in acetonitrile
Eluent B—0.1% TFA in water
Linear gradient t=0 min 2% A, t=1 min 2% A, t=15 min 60% A, t=20 min 60% A Method G
Column—Zorbax SB-C18 1.8 μm 4.6×15 mm Rapid Resolution cartridge (PN 821975-932)
Flow—3 mL/min
Eluent A—0.1% formic acid in acetonitrile
Eluent B—0.1% formic acid in water
Linear gradient t=0 min 0% A, t=1.8 min 100% A Method H
Column—Waters Xselect CSH C18 (50×2.1 mm, 2.5 micron)
Flow—0.6 mL/min
Eluent A—0.1% formic acid in acetonitrile
Eluent B—0.1% formic acid in water
Linear gradient t=0 min 5% A, t=2.0 min 98% A, t=2.7 min 98% A Method J
Column—Reverse phase Waters Xselect CSH C18 (50× 2.1 mm, 2.5 micron)
Flow—0.6 mL/min
Eluent A—100% acetonitrile
Eluent B—10 mM ammonium bicarbonate in water (pH 7.9)
Linear gradient t=0 min 5% A, t=2.0 min 98% A, t=2.7 min 98% A Preparation of
4-chloro-7-fluoro-1H-indole-2-carboxylic acid

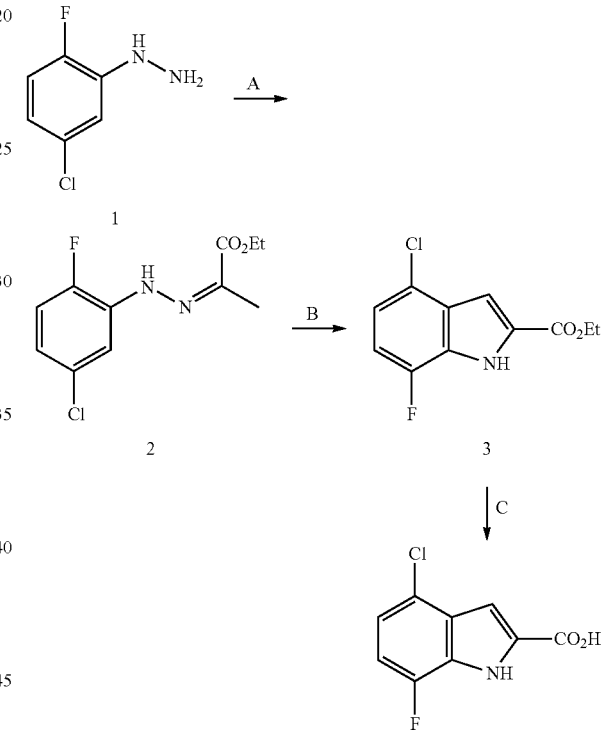

Step A: A mixture of compound 1·HCl (17.0 g, 86.2 mmol), sodium acetate (7.10 g, 86.6 mmol), and ethyl pyruvate (10.0 g, 86.1 mmol) in ethanol (100 mL) was refluxed for 1 h, cooled to r.t., and diluted with water (100 mL). The precipitated solid was collected by filtration and dried to obtain 20.0 g (77.3 mmol, 90%) of compound 2 as a mixture of cis- and trans-isomers.

Step B: A mixture of compound 2 (20.0 g, 77.3 mmol), obtained in the previous step, and $BF_3.Et_2O$ (50.0 g, 352 mmol) in acetic acid (125 mL) was refluxed for 18 h and evaporated under reduced pressure. The residue was mixed with water (100 mL) and extracted with MTBE (2×50 mL). The combined organic extracts were dried over $Na_2SO_4$ and evaporated under reduced pressure. The residue was purified by silica gel column chromatography to give 3.00 g (12.4 mmol, 16%) of compound 3.

Step C: A mixture of compound 3 (3.00 g, 12.4 mmol) and NaOH (0.500 g, 12.5 mmol) in ethanol (30 mL) was refluxed for 30 min and evaporated under reduced pressure. The residue was mixed with water (30 mL) and the insoluble material was filtered off. The filtrate was acidified with concentrated hydrochloric acid (5 mL). The precipitated solid was collected by filtration, washed with water (3 mL), and dried to obtain 2.41 g (11.3 mmol, 91%) of 4-chloro-7-fluoro-1H-indole-2-carboxylic acid.

Rt (Method G) 1.24 mins, m/z 212 [M−H]⁻

The resulting precipitate was filtered, washed with water, and dried to obtain 18.0 g (93.2 mmol, 92%) of 7-fluoro-4-methyl-1H-indole-2-carboxylic acid.

Rt (Method G) 1.12 mins, m/z 192 [M−H]⁻

Preparation of 6,7-difluoro-1H-indole-2-carboxylic acid

Preparation of 7-fluoro-4-methyl-1H-indole-2-carboxylic acid

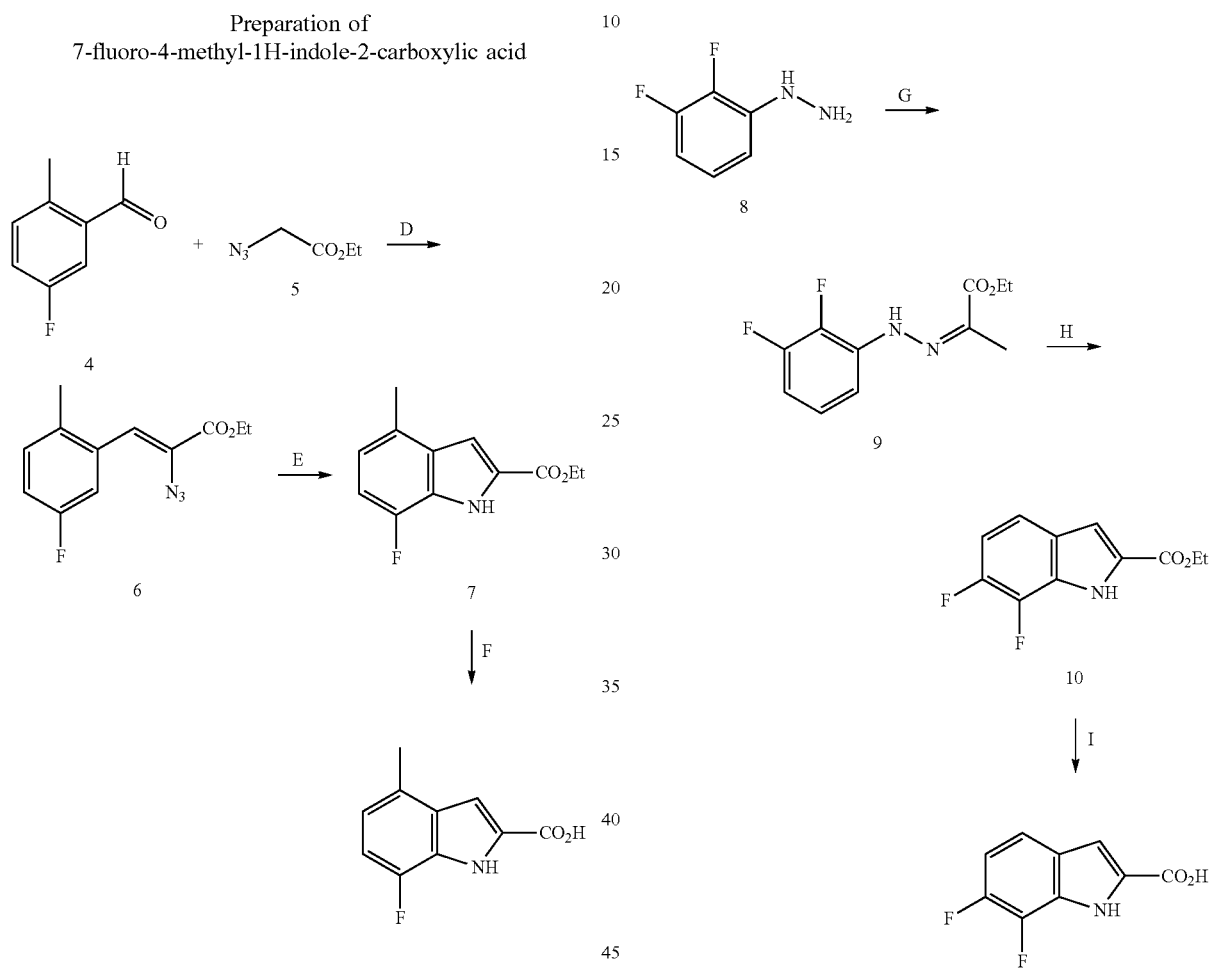

Step D: To a solution of sodium methoxide (21.6 g, 400 mmol) in methanol (300 mL) at −10° C. was added dropwise a solution of compound 4 (26.4 g, 183 mmol) and compound 5 (59.0 g, 457 mmol) in methanol (100 mL). The reaction mass was stirred for 3 h maintaining temperature below 5° C. and then quenched with ice water. The resulting mixture was stirred for 10 min, filtered, and washed with water to afford 35.0 g (156 mmol, 72%) of compound 6 as a white solid.

Step E: A solution of compound 6, obtained in the previous step, (35.0 g, 156 mmol) in xylene (250 mL) was refluxed for 1 h under an argon atmosphere and then evaporated under reduced pressure. The residue was recrystallized form hexane-ethyl acetate mixture (60:40) to give 21.0 g (103 mmol, 60%) of compound 7.

Step F: To a solution of compound 7 (21.0 g, 101 mmol) in ethanol (200 mL) was added 2 N aqueous sodium hydroxide solution (47 mL). The mixture was stirred for 2 h at 60° C. The solvent was evaporated and the residue was acidified with aqueous hydrochloric acid to pH 5-6.

Step G: A mixture of compound 8 (5.00 g, 34.7 mmol), acetic acid (1 m), and ethyl pyruvate (5.00 g, 43.1 mmol) in ethanol (20 mL) was refluxed for 1 h, cooled to r.t., and diluted with water (20 mL). The precipitated solid was collected by filtration and dried to obtain 5.50 g (22.7 mmol, 66%) of compound 9 as a mixture of cis- and trans-isomers.

Step H: A mixture of compound 9 (5.50 g, 22.7 mmol), obtained in the previous step, and BF₃·Et₂O (10.0 g, 70.5 mmol) in acetic acid (25 mL) was refluxed for 18 h and evaporated under reduced pressure. The residue was mixed with water (30 mL) and extracted with MTBE (2×30 mL). The combined organic extracts were dried over Na₂SO₄ and evaporated under reduced pressure. The residue was purified by silica gel column chromatography to give 0.460 g (2.04 mmol, 9%) of compound 10.

Step I: A mixture of compound 10 (0.450 g, 2.00 mmol) and NaOH (0.100 g, 2.50 mmol) in ethanol (10 mL) was refluxed for 30 min and evaporated under reduced pressure. The residue was mixed with water (10 mL) and the insoluble material was filtered off. The filtrate was acidified with concentrated hydrochloric acid (1 mL). The precipitated solid was collected by filtration, washed with water (3 mL), and dried to obtain 0.38 g (1.93 mmol, 95%) of 6,7-difluoro-1H-indole-2-carboxylic acid.

Rt (Method G) 1.10 mins, m/z 196 [M−H]⁻

Preparation of 4-cyano-1H-indole-2-carboxylic acid

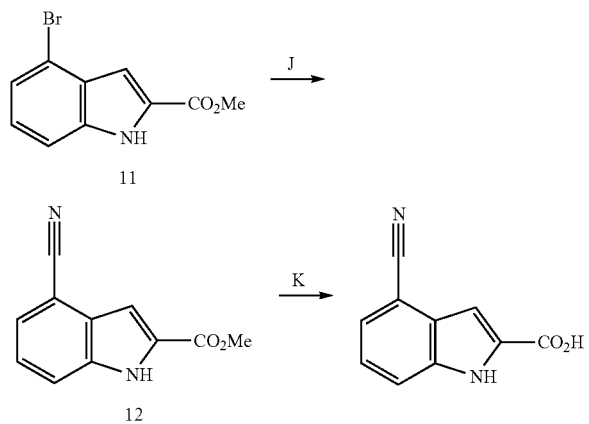

Step J: To a stirred solution of compound 11 (5.00 g, 19.7 mmol) in DMF (50 mL) was added CuCN (3.00 g, 33.5 mmol). The mixture was stirred for 4 h at 150° C. The mixture was then cooled to r.t., and water (100 mL) added. The resulting mixture was extracted with ethyl acetate (4×100 mL). The combined organic extracts were washed with water (50 mL) and brine (50 mL), dried over $Na_2SO_4$, and evaporated under reduced pressure to give 2.50 g (12.5 mmol, 63%) of compound 12, pure enough for the next step.

Step K: To a solution of compound 12 (2.50 g, 12.5 mmol) in ethanol (30 mL) was added $LiOH·H_2O$ (0.600 g, 13.0 mmol). The mixture was refluxed for 10 h. The solvent was evaporated under reduced pressure and the residue diluted with water (50 mL). The aqueous layer was acidified to pH 6 with 10% aq. hydrochloric acid and the precipitated solid was collected by filtration. The residue was washed with water and dried under vacuum to afford 1.20 g (6.45 mmol, 52%) of 4-cyano-1H-indole-2-carboxylic acid as a white solid.

Rt (Method G) 1.00 mins, m/z 197 [M+H]⁺

Preparation of 4-cyano-7-fluoro-1H-indole-2-carboxylic acid

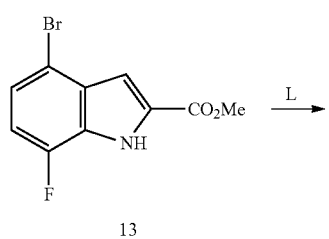

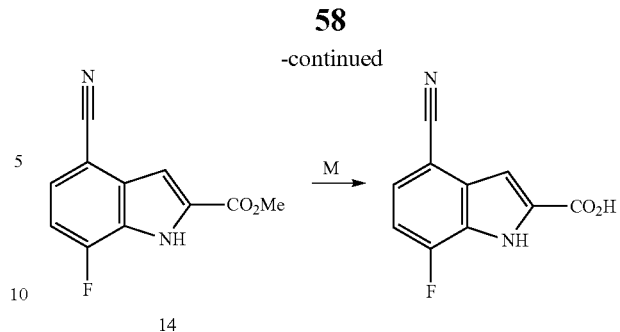

Step L: To a stirred solution of compound 13 (5.00 g, 18.4 mmol) in DMF (50 mL) was added CuCN (2.80 g, 31.2 mmol). The mixture was stirred for 4 h at 150° C. The mixture was then cooled to r.t., and water (100 mL) added. The resulting mixture was extracted with ethyl acetate (4×100 mL). The combined organic extracts were washed with water (50 mL) and brine (50 mL), dried over $Na_2SO_4$, and evaporated under reduced pressure to give 1.50 g (6.87 mmol, 37%) of compound 14, pure enough for the next step.

Step M: To a solution of compound 14 (1.50 g, 6.87 mmol) in ethanol (20 mL) was added $LiOH·H_2O$ (0.400 g, 9.53 mmol). The mixture was refluxed for 10 h. The solvent was evaporated under reduced pressure and the residue diluted with water (40 mL). The aqueous layer was acidified to pH 6.0 with 10% aq. hydrochloric acid and the precipitate was collected by filtration. The residue was washed with water and dried under vacuum to afford 0.400 g (1.95 mmol, 28%) of 4-cyano-7-fluoro-1H-indole-2-carboxylic acid as a white solid.

Rt (Method G) 1.02 mins, m/z 203 [M−H]⁻

Preparation of 4-cyano-5-fluoro-1H-indole-2-carboxylic acid

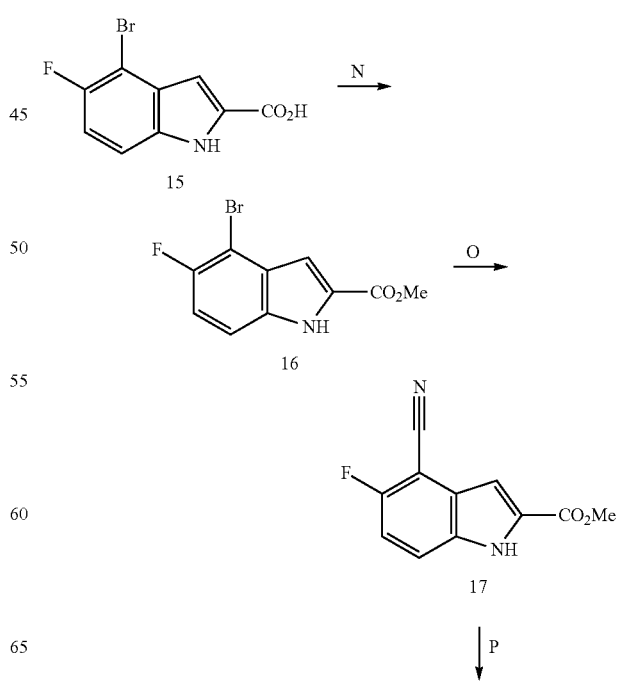

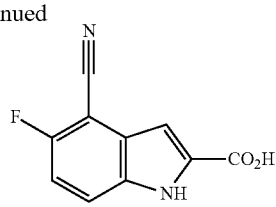

Step N: To a solution of compound 15 (5.00 g, 19.4 mmol) in DMF (50 mL) was added NaHCO₃ (1.59 g, 18.9 mmol) and iodomethane (3 mL). The resulting mixture was stirred overnight at r.t., then diluted with water (50 mL) and extracted with diethyl ether (3×50 mL). The combined organic extracts were dried over Na₂SO₄, and evaporated under reduced pressure to obtain 4.90 g (18.0 mmol, 90%) of compound 16 as white solid.

Step O: To a stirred solution of compound 16 (4.80 g, 17.6 mmol) in DMF (50 mL) was added CuCN (2.70 g, 30.1 mmol). The mixture was stirred for 4 h at 150° C. The mixture was then cooled to r.t., water (100 mL) added. The resulting mixture was extracted with ethyl acetate (4×100 mL). The combined organic extracts were washed with water (50 mL) and brine (50 mL), dried over Na₂SO₄, and evaporated under reduced pressure to give 1.40 g (6.42 mmol, 36%) of compound 17, pure enough for the next step.

Step P: To a solution of compound 17 (1.40 g, 6.42 mmol) in ethanol (20 mL) was added LiOH.H₂O (0.350 g, 8.34 mmol). The mixture was refluxed for 10 h. The solvent was evaporated under reduced pressure and the residue diluted with water (30 mL). The aqueous layer was acidified to pH 6.0 with 10% aq. hydrochloric acid and the precipitate collected by filtration. The residue was washed with water and dried under vacuum to afford 0.500 g (2.45 mmol, 38%) of 4-cyano-5-fluoro-1H-indole-2-carboxylic acid as a white solid.

Rt (Method G) 1.10 mins, m/z 203 [M−H]⁻

Preparation of
4,5,6-trifluoro-1H-indole-2-carboxylic acid

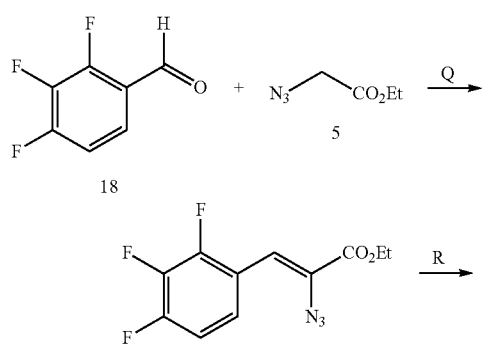

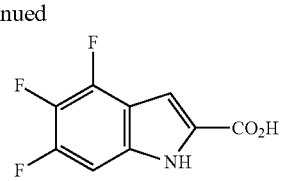

Step Q: To a solution of sodium methoxide (23.0 g, 426 mmol) in methanol (200 mL) at −10° C. was added dropwise a solution of compound 18 (15.0 g, 93.7 mmol) and compound 5 (26.0 g, 201 mmol) in methanol (100 mL). The reaction mixture was stirred for 3 h, maintaining the temperature below 5° C. and then quenched with ice water. The resulting mixture was stirred for 10 min, and the precipitate collected by filtration. The solid was washed with water and dried to afford 12.0 g (46.7 mmol, 72%) of compound 19 as a white solid.

Step R: A solution of compound 19, obtained in the previous step, (12.0 g, 46.7 mmol) in xylene (250 mL) was refluxed for 1 h under an argon atmosphere and then evaporated under reduced pressure. The residue was recrystallized form hexane-ethyl acetate mixture (60:40) to give 7.00 g (30.5 mmol, 65%) of compound 20.

Step S: To a solution of compound 20 (7.00 g, 30.5 mmol) in ethanol (50 mL) was added 2 N aqueous sodium hydroxide solution (18 mL). The mixture was stirred for 2 h at 60° C. The solvent was evaporated and the residue was acidified to pH 5-6 with aqueous hydrochloric acid. The resulting precipitate was collected by filtration, washed with water, and dried to obtain 5.00 g (23.2 mmol, 76%) 4,5,6-trifluoro-1H-indole-2-carboxylic acid.

¹H NMR (400 MHz, d6-dmso) 7.17 (1H, s), 7.22 (1H, dd), 12.3 (1H, br s), 13.3 (1H, br s)

Preparation of
4,6,7-trifluoro-1H-indole-2-carboxylic acid

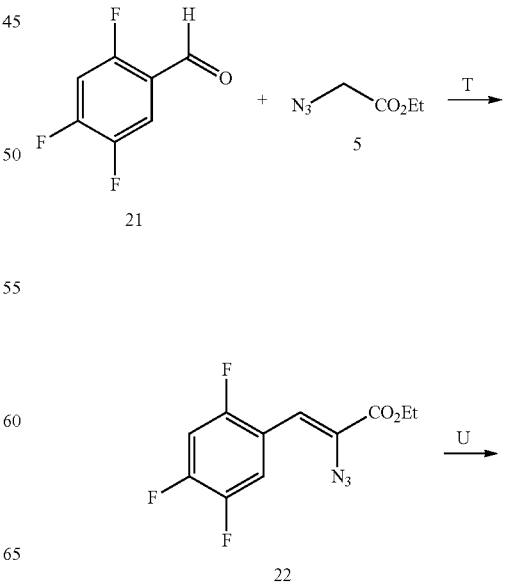

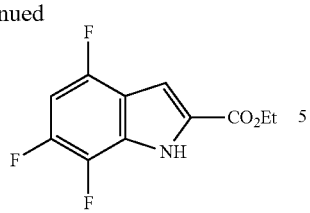

23

↓ V

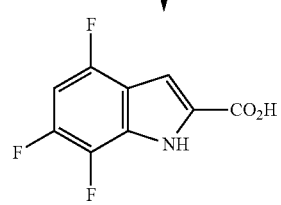

Step T: To a solution of sodium methoxide (23.0 g, 426 mmol) in methanol (200 mL) at −10° C. was added dropwise a solution of compound 21 (15.0 g, 90.3 mmol) and compound 5 (26.0 g, 201 mmol) in methanol (100 mL). The reaction mixture was stirred for 3 h maintaining the temperature below 5° C. and then quenched with ice water. The resulting mixture was stirred for 10 min. The precipitate was collected by filtration, washed with water and dried to afford 10.0 g (38.0 mmol, 42%) of compound 22 as a white solid.

Step U: A solution of compound 22, obtained in the previous step, (10.0 g, 38.0 mmol) in xylene (200 mL) was refluxed for 1 h under an argon atmosphere and then concentrated under reduced pressure. The residue was recrystallized form hexane-ethyl acetate mixture (60:40) to give 6.00 g (26.2 mmol, 69%) of compound 23.

Step V: To a solution of compound 23 (7.00 g, 30.5 mmol) in ethanol (40 mL) was added 2 N aqueous sodium hydroxide solution (16 mL). The mixture was stirred for 2 h at 60° C. The solvent was evaporated and the residue was acidified to pH 5-6 with aqueous hydrochloric acid. The resulting precipitate was collected by filtration, washed with water, and dried to obtain 4.10 g (19.1 mmol, 62%) of 4,6,7-trifluoro-1H-indole-2-carboxylic acid.

Rt (Method G) 1.16 mins, m/z 214 [M−H]⁻

Preparation of
4-cyano-6-fluoro-1H-indole-2-carboxylic acid

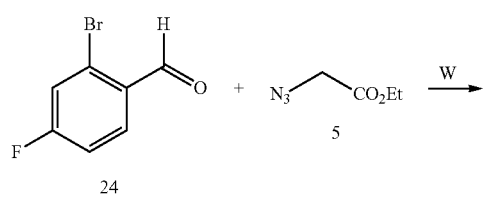

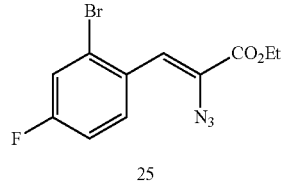

25

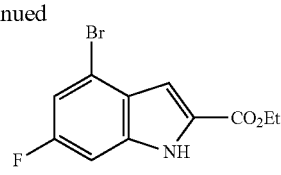

26

↓ Y

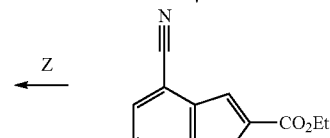

27

Step W: To a solution of sodium methoxide (65.0 g, 1203 mmol) in methanol (500 mL) at −10° C. was added dropwise a solution of compound 24 (60.0 g, 296 mmol) and compound 5 (85.0 g, 658 mmol) in methanol (200 mL). The reaction mixture was stirred for 3 h maintaining the temperature below 5° C. and then quenched with ice water. The resulting mixture was stirred for 10 min. The precipitate was collected by filtration, washed with water and dried to afford 45.0 g (143 mmol, 48%) of compound 25.

Step X: A solution of compound 25, obtained in the previous step, (35.0 g, 111 mmol) in xylene (250 mL) was refluxed for 1 h under an argon atmosphere and then evaporated under reduced pressure. The residue was recrystallized form hexane-ethyl acetate mixture (60:40) to give 11.0 g (38.4 mmol, 35%) of compound 26.

Step Y: To a stirred solution of compound 26 (11.0 g, 38.4 mmol) in DMF (20 mL) was added CuCN (6.60 g, 73.7 mmol). The mixture was stirred for 4 h at 150° C. The mixture was then cooled to r.t., and water (70 mL) added. The mixture was extracted with ethyl acetate (4×50 mL). The combined organic extracts were washed with water (50 mL) and brine (50 mL), dried over Na₂SO₄, and evaporated under reduced pressure to give 2.40 g (10.3 mmol, 27%) of compound 27, pure enough for the next step.

Step Z: To a solution of compound 27 (2.40 g, 6.42 mmol) in ethanol (30 mL) was added LiOH.H₂O (0.600 g, 14.3 mmol). The mixture was refluxed for 10 h. The mixture was concentrated under reduced pressure and the residue diluted with water (50 m). The aqueous layer was acidified to pH 6 with 10% aq. hydrochloric acid and the precipitate was collected by filtration. The solid was washed with water and dried under vacuum to afford 1.20 g (5.88 mmol, 57%) of 4-cyano-6-fluoro-1H-indole-2-carboxylic acid as a white solid.

Rt (Method G) 1.06 mins, m/z 203 [M−H]⁻

Preparation of 4-ethyl-1H-indole-2-carboxylic acid

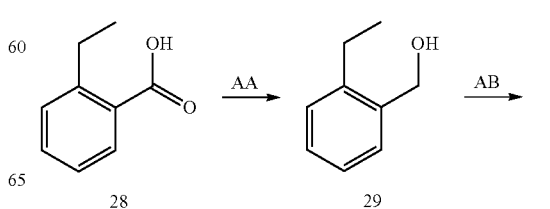

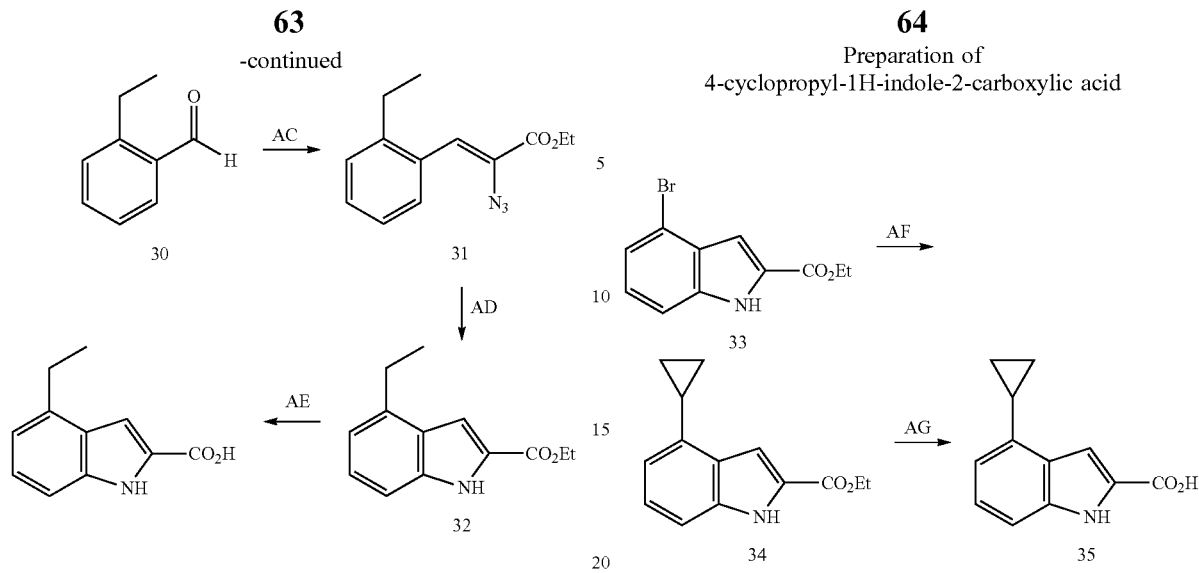

Preparation of
4-cyclopropyl-1H-indole-2-carboxylic acid

Step AA: A solution of compound 28 (70.0 g, 466 mmol) in dry THF (500 mL) was treated with 10 M solution of $BH_3$ in THF (53 mL, 53.0 mmol of $BH_3$) at 0° C. The reaction mass was stirred at r.t. for 24 h before methanol (150 mL) was slowly added thereto. The resulting mixture was stirred for 45 min, and evaporated under reduced pressure to yield 55.0 g (404 mmol, 87%) of compound 29, pure enough for the next step.

Step AB: To a cooled (0° C.) solution of compound 29 (55.0 g, 404 mmol) in $CH_2Cl_2$ (400 mL) was added Dess-Martin periodinane (177 g, 417 mmol) portionwise. After stirring for 1 h at r.t., the reaction mixture was quenched with saturated aqueous $Na_2S_2O_3$ (300 mL) and saturated aqueous $NaHCO_3$ (500 mL). The mixture was extracted with $CH_2Cl_2$ (3×300 mL). The combined organic extracts were washed with water and brine, dried over $Na_2SO_4$ and concentrated to yield 51.0 g of crude compound 30 as a yellow solid.

Step AC: To a solution of sodium methoxide (107 g, 1981 mmol) in methanol (600 mL) at −10° C. was added dropwise a solution of compound 30, obtained in the previous step, (51.0 g) and compound 5 (126 g, 976 mmol) in methanol (300 mL). The reaction mixture was stirred for 4 h maintaining temperature below 5° C., then quenched with ice water. The resulting mixture was stirred for 10 min, and the precipitate collected by filtration. The solid was washed with water and dried to afford 35.0 g (151 mmol, 37% over 2 steps) of compound 31.

Step AD: A solution of compound 31, obtained in the previous step, (35.0 g, 151 mmol) in xylene (500 mL) was refluxed for 1 h under an argon atmosphere and then concentrated under reduced pressure. The residue was recrystallized form hexane-ethyl acetate mixture (60:40) to give 21.0 g (103 mmol, 68%) of compound 32.

Step AE: To a solution of compound 32 (21.0 g, 103 mmol) in ethanol (200 mL) was added 2 N aqueous sodium hydroxide solution (47 mL). The mixture was stirred for 2 h at 60° C. The mixture was concentrated under reduced pressure, and the residue acidified to pH 5-6 with aqueous hydrochloric acid. The precipitate was collected by filtration, washed with water, and dried to obtain 19 g (100 mmol, 97%) of 4-ethyl-1H-indole-2-carboxylic acid.

Rt (Method G) 1.20 mins, m/z 188 [M−H]⁻

$^1$H NMR (400 MHz, d6-dmso) δ 1.25 (t, 3H), 2.88 (q, 2H), 6.86 (1H, d), 7.08-7.20 (2H, m), 7.26 (1H, d), 11.7 (1H, br s), 12.9 (1H, br s)

Step AF: To a degassed suspension of compound 33 (2.00 g, 7.80 mmol), cyclopropylboronic acid (0.754 g, 8.78 mmol), $K_3PO_4$ (5.02 g, 23.6 mmol), tricyclohexyl phosphine (0.189 g, 0.675 mmol), and water (2.0 mL) in toluene (60.0 mL) was added palladium (II) acetate (0.076 g, 0.340 mmol). The reaction mixture was stirred at 100° C. for 4 h. The reaction progress was monitored by diluting an aliquot of the reaction mixture with water and extracting with ethyl acetate. The organic layer was spotted over an analytical silica gel TLC plate and visualized using 254 nm UV light. The reaction progressed to completion with the formation of a polar spot. The $R_f$ values of the starting material and product were 0.3 and 0.2, respectively. The reaction mixture was allowed to cool to r.t. and filtered through a pad of celite. The filtrate was concentrated under reduced pressure and the crude product was purified by flash column using 230-400 mesh silica gel and eluted with 10% ethyl acetate in petroleum ether to afford 1.10 g (5.11 mmol, 63%) of compound 34 as a brown liquid. TLC system: 5% ethyl acetate in petroleum ether.

Step AG: A mixture of compound 34 (1.10 g, 5.11 mmol) in ethanol (40 mL) and 2 N aqueous sodium hydroxide (15 mL) was stirred for 2 h at 60° C. The mixture was concentrated under reduced pressure, and the residue acidified to pH 5-6 with aqueous hydrochloric acid. The precipitate was collected by filtration, washed with water, and dried to yield 1.01 g (5.02 mmol, 92%) of 4-cyclopropyl-1H-indole-2-carboxylic acid.

Rt (Method G) 1.17 mins, m/z 200 [M−H]⁻

Preparation of
4-chloro-5-fluoro-1H-indole-2-carboxylicacid

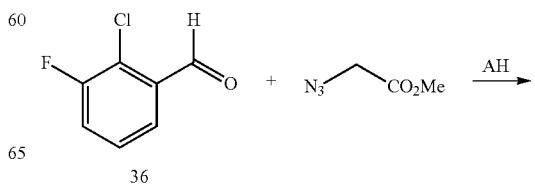

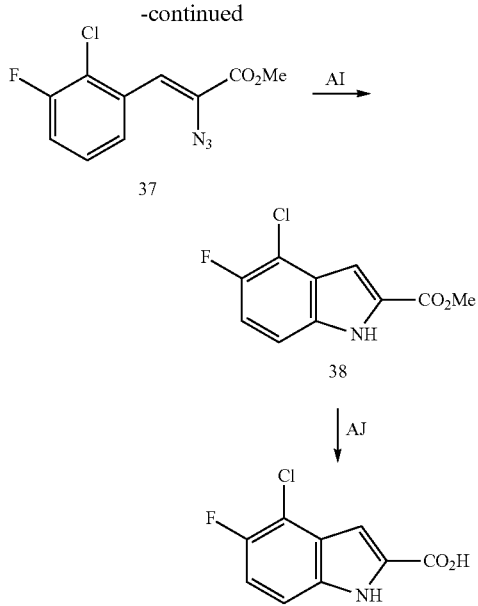

Step AH: To a solution of sodium methoxide (39.9 g, 738 mmol) in methanol (300 mL) at −10° C. was added dropwise a solution of compound 36 (28.8 g, 182 mmol) and methyl azidoacetate (52.1 g, 404 mmol) in methanol (150 mL). The reaction mixture was stirred for 3 h maintaining temperature below 5° C., then quenched with ice water. The resulting mixture was stirred for 10 min. The precipitate was collected by filtration, washed with water and dried to afford 20.0 g (78.2 mmol, 43%) of compound 37.

Step AI: A solution of compound 37 (19.4 g, 76.0 mmol) in xylene (250 mL) was refluxed for 1 h under an argon atmosphere and then concentrated under reduced pressure. The residue was recrystallized from hexane-ethyl acetate (50:50) to give 9.00 g (39.5 mmol, 52%) of compound 38.

Step AJ: To a solution of compound 38 (8.98 g, 39.4 mmol) in ethanol (100 mL) was added 2 N aqueous sodium hydroxide solution (18 mL). The mixture was stirred for 2 h at 60° C. The mixture was concentrated under reduced pressure, and the residue acidified to pH 5-6 with aqueous hydrochloric acid. The resulting precipitate was collected by filtration, washed with water, and dried to obtain 7.75 g (36.3 mmol, 92%) of 4-chloro-5-fluoro-1H-indole-2-carboxylic acid.

Rt (Method G) 1.15 mins, m/z 212 [M−H]⁻

$^1$H NMR (400 MHz, d6-dmso) 7.08 (1H, s), 7.28 (1H, dd) 7.42 (1H, dd), 12.2 (1H, br s), 13.2 (1H, br s)

Preparation of 5-fluoro-4-(1-hydroxyethyl)-1H-indole-2-carboxylic acid

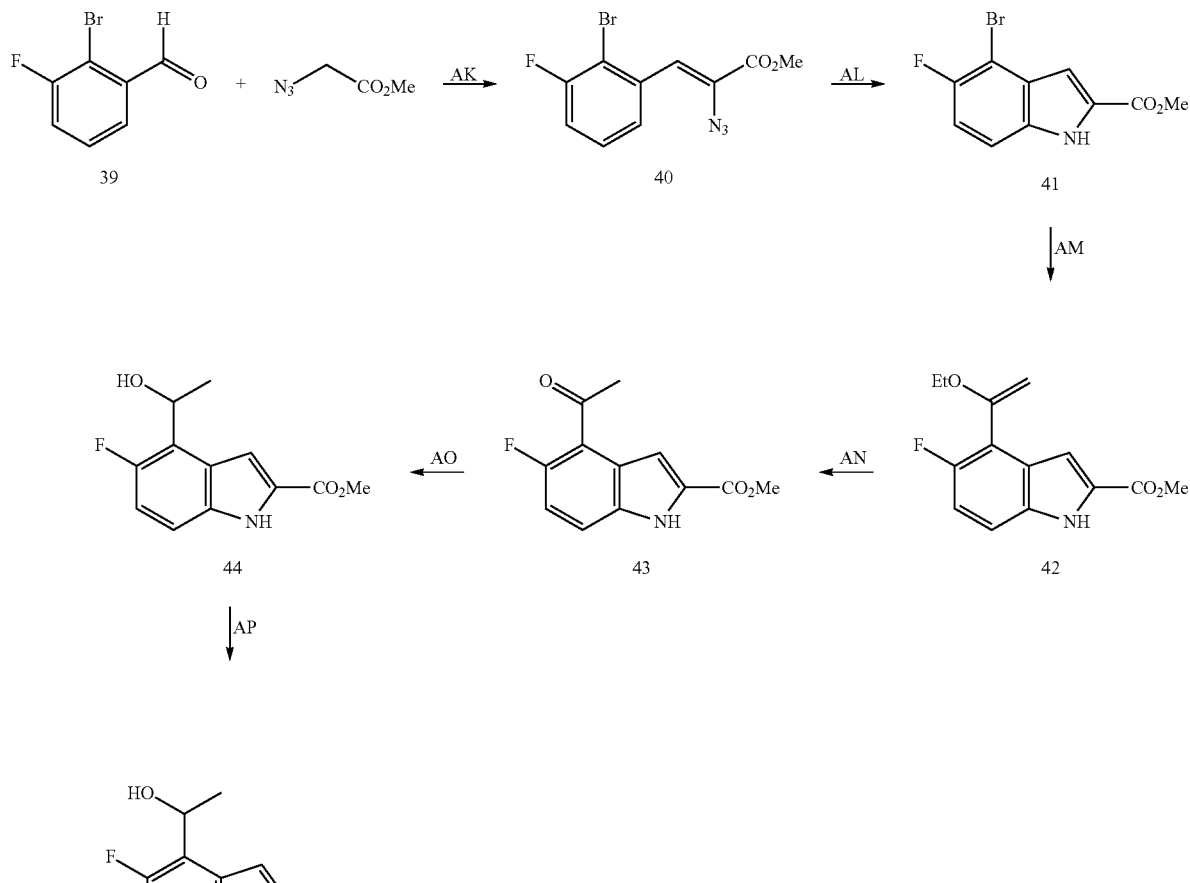

Step AK: To a solution of sodium methoxide (50.0 g, 926 mmol) in methanol (300 mL) at −10° C. was added dropwise a solution of compound 39 (45.0 g, 222 mmol) and methyl azidoacetate (59.0 g, 457 mmol) in methanol (100 mL). The reaction mixture was stirred for 3 h maintaining the temperature below 5° C., then quenched with ice water. The resulting mixture was stirred for 10 min. The precipitate was collected by filtration, washed with water and dried to afford 35.0 g (133 mmol, 60%) of compound 40 as a white solid.

Step AL: A solution of compound 40, obtained in the previous step, (35.0 g, 133 mmol) in xylene (250 mL) was refluxed for 1 h under an argon atmosphere and then evaporated under reduced pressure. The residue was recrystallized from hexane-ethyl acetate (60:40) to give 21.0 g (77.2 mmol, 58%) of compound 41.

Step AM: To a degassed solution of compound 41 (4.00 g, 14.7 mmol) and tributyl(1-ethoxyvinyl)stannane (5.50 g, 15.2 mmol) in toluene (50 mL) under nitrogen was added bis(triphenylphosphine) palladium(II) dichloride (1.16 g, 1.65 mmol). The reaction mixture was stirred at 60° C. for 20 h. The reaction mixture was cooled to room temperature and filtered. The filtrate was concentrated under reduced pressure and the residue purified by silica gel chromatography to afford 2.50 g (9.50 mmol, 65%) of compound 42 as a pale yellow solid.

Step AN: To a solution of compound 42 (2.40 g, 9.12 mmol) in 1,4-dioxane (30 mL) was added 2M hydrochloric acid (15 mL). The resulting mixture was stirred at room temperature for 30 min. The mixture was concentrated under vacuum and the residue partitioned between ethyl acetate and water. The organic extract was washed with water and brine, dried over sodium sulfate, filtered, and evaporated. The residue was triturated with 5% ether in isohexane and dried to afford 1.80 g (7.65 mmol, 84%) of compound 43 as a white solid.

Step AO: A suspension of compound 43 (1.70 g, 7.23 mmol) and NaBH$_4$ (2.50 g, 66.1 mmol) in ethanol (13 mL) was refluxed for 2 h, then cooled to room temperature, and filtered. The filtrate was concentrated under reduced pressure and the residue dissolved in ethyl acetate. The solution was washed with 1N hydrochloric acid and brine, dried over Na$_2$SO$_4$, and evaporated under reduced pressure to give 1.60 g (6.74 mmol, 93%) of compound 44 as a colourless oil.

Step AP: To a solution of compound 44 (1.50 g, 6.32 mmol) in methanol (40 mL) was added 2N aqueous NaOH (10 mL). The mixture was stirred for 2 h at 60° C. The mixture was concentrated under reduced pressure and the residue acidified to pH 5-6 with 10% hydrochloric acid. The precipitate was collected by filtration, washed with water (3×15 mL), and dried to obtain 1.30 g (5.82 mmol, 92%) of 5-fluoro-4-(1-hydroxyethyl)-1H-indole-2-carboxylic acid.

Rt (Method G) 1.00 mins, m/z 222 [M−H]$^−$

Preparation of
4-ethyl-5-fluoro-1H-indole-2-carboxylic acid

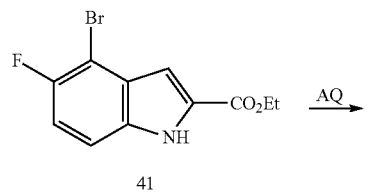

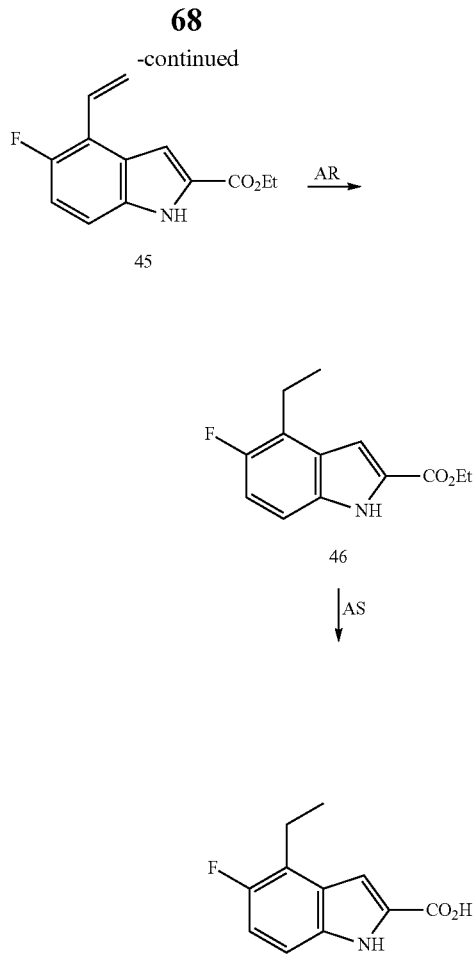

Step AQ: To a heated (90° C.) solution of compound 41 (4.00 g, 14.7 mmol) in anhydrous DMF under nitrogen (10 mL) were added tri-n-butyl(vinyl)tin (3.60 g, 11.4 mmol) and Pd(PPh$_3$)$_2$Cl$_2$ (0.301 g, 0.757 mmol). The resulting mixture was stirred at 90° C. for 1 h. The mixture was then cooled to room temperature and purified by silica gel column chromatography (60-80% ethyl acetate in hexane) to give 2.20 g (10.0 mmol, 68%) of compound 45 as yellow solid.

Step AR: A mixture of compound 45 (1.50 g, 6.84 mmol) and Pd/C (0.300 g, 10% wt.) in methanol (20 mL) was stirred under an atmosphere of hydrogen at room temperature for 16 h. The mixture was filtered, then concentrated under reduced pressure to give 1.45 g (6.55 mmol, 96%) of compound 46.

Step AS: To a solution of compound 46 (1.40 g, 6.33 mmol) in methanol (40 mL) was added 2N aqueous NaOH (10 mL). The mixture was stirred for 2 h at 60° C. The mixture was concentrated under vacuum, then the residue was acidified to pH 5-6 with 10% hydrochloric acid. The precipitate was collected by filtration, washed with water (3×15 mL), and dried to obtain 1.20 g (5.79 mmol, 91%) of target compound 4-ethyl-5-fluoro-1H-indole-2-carboxylic acid.

Rt (Method G) 1.33 mins, m/z 206 [M−H]$^−$

Preparation of
4-ethyl-6-fluoro-1H-indole-2-carboxylic acid

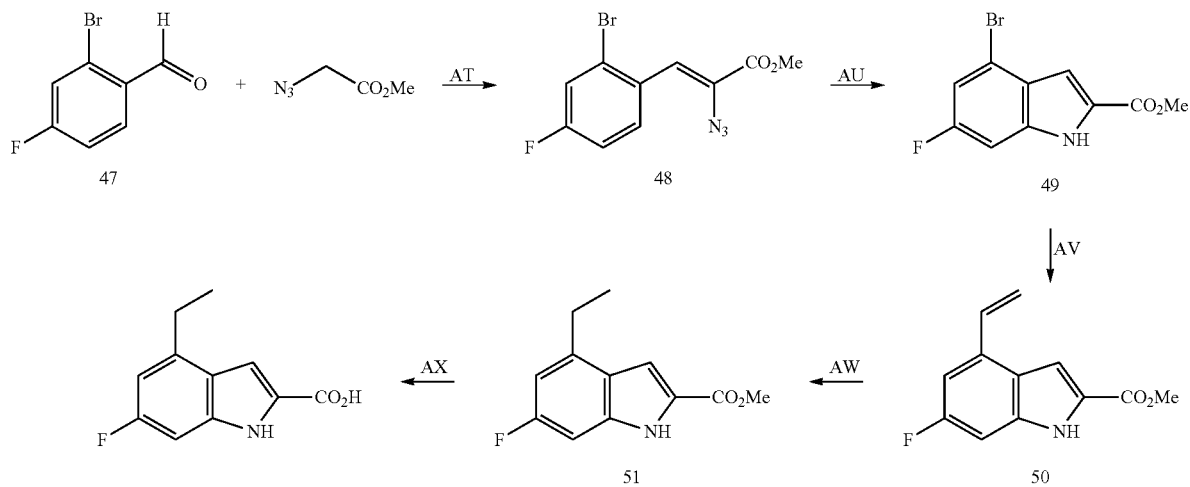

Step AT: To a solution of sodium methoxide (50.0 g, 926 mmol) in methanol (300 mL) at −10° C. was added dropwise a solution of compound 47 (45.0 g, 202 mmol) and methyl azidoacetate (59.0 g, 457 mmol) in methanol (100 mL). The reaction mixture was stirred for 3 h maintaining temperature below 5° C., then quenched with ice water. The resulting mixture was stirred for 10 min. The precipitate was collected by filtration, washed with water and dried to afford 38.5 g (128 mmol, 63%) of compound 48 as a white solid.

Step AU: A solution of compound 48, obtained in the previous step, (38.5 g, 128 mmol) in xylene (250 mL) was refluxed for 1 h under an argon atmosphere and then concentrated under reduced pressure. The residue was recrystallized hexane-ethyl acetate (60:40) to give 18.0 g (67.3 mmol, 53%) of compound 49.

Step AV: To a heated (90° C.) solution of compound 49 (4.00 g, 14.7 mmol) in anhydrous DMF under nitrogen (10 mL) were added tri-n-butyl(vinyl)tin (3.60 g, 11.4 mmol) and Pd(PPh$_3$)$_2$Cl$_2$ (0.301 g, 0.757 mmol). The resulting mixture was stirred at 90° C. for 1 h. The mixture was then cooled to room temperature and purified by silica gel column chromatography (60-80% ethyl acetate in hexane) to give 2.00 g (9.12 mmol, 62%) of compound 50 as yellow solid.

Step AW: A mixture of compound 50 (1.50 g, 6.84 mmol) and Pd/C (0.300 g, 10% wt.) in methanol (20 mL) was stirred under an atmosphere of hydrogen at room temperature for 16 h. The mixture was filtered and concentrated to give 1.40 g (6.33 mmol, 93%) of compound 51.

Step AX: To a solution of compound 51 (1.10 g, 4.97 mmol) in methanol (40 mL) was added 2N aqueous NaOH (10 mL). The mixture was stirred for 2 h at 60° C. The mixture was concentrated under reduced pressure, then acidified to pH 5-6 with 10% hydrochloric acid. The precipitate was collected by filtration, washed with water (3×15 mL), and dried to obtain 0.900 g (4.34 mmol, 87%) of target compound 4-ethyl-6-fluoro-1H-indole-2-carboxylic acid.

Rt (Method G) 1.29 mins, m/z 206 [M−H]$^-$

Preparation of
6-fluoro-4-(1-hydroxyethyl)-1H-indole-2-carboxylic acid

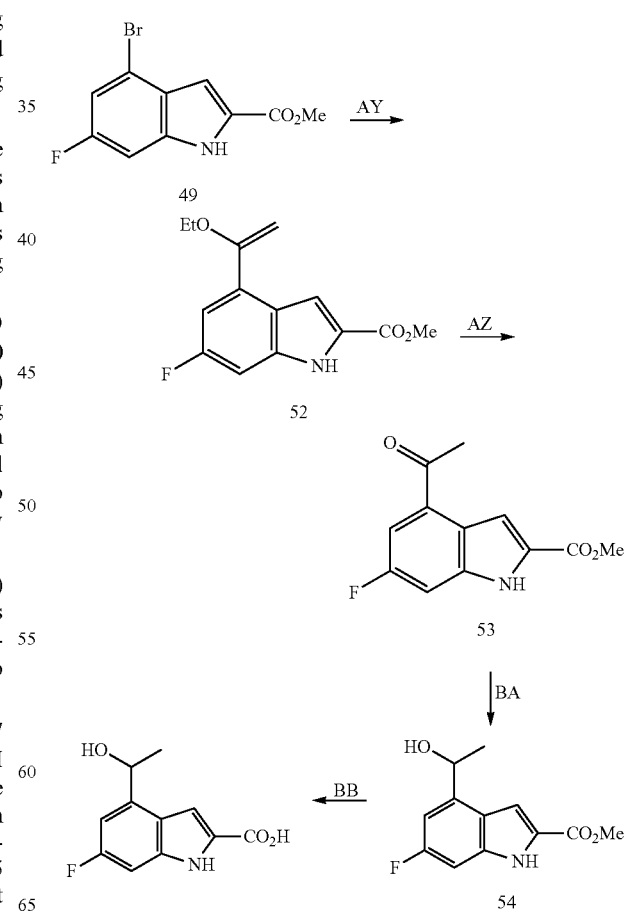

Step AY: To a degassed solution of compound 49 (4.00 g, 14.7 mmol) and tributyl(1-ethoxyvinyl)stannane (5.50 g, 15.2 mmol) in toluene (50 mL) under nitrogen were added bis(triphenylphosphine) palladium(II) dichloride (1.16 g, 1.65 mmol). The reaction mixture was stirred at 60° C. for 20 h. The reaction mixture was cooled to room temperature and filtered. The filtrate was concentrated under reduced pressure and the residue purified by silica gel chromatography to give 2.10 g (7.98 mmol, 54%) of compound 52 as a pale yellow solid.

Step AZ: To a solution of compound 52 (2.10 g, 7.98 mmol) in 1,4-dioxane (30 mL) was added 2M hydrochloric acid (15 mL). The resulting mixture was stirred at room temperature for 30 min. The mixture was concentrated under reduced pressure, and residue partitioned between ethyl acetate and water. The organic extract was washed with water and brine, dried over sodium sulfate, filtered, and concentrated. The residue was triturated with 5% ether in isohexane and dried to afford 1.70 g (7.23 mmol, 91%) of compound 53 as a white solid.

Step BA: A suspension of compound 53 (1.70 g, 7.23 mmol) and $NaBH_4$ (2.50 g, 66.1 mmol) in ethanol (13 mL) was refluxed for 2 h, cooled to room temperature, and filtered. The filtrate was concentrated under reduced pressure and the residue was dissolved in ethyl acetate. The solution was washed with 1N hydrochloric acid and brine, dried over $Na_2SO_4$, and concentrated under reduced pressure to give 1.60 g (6.74 mmol, 93%) of compound 54 as a colourless oil.

Step BB: To a solution of compound 54 (1.40 g, 5.90 mmol) in methanol (40 mL) was added 2N aqueous NaOH (10 mL). The mixture was stirred for 2 h at 60° C. The mixture was concentrated and the residue acidified to pH 5-6 with 10% hydrochloric acid. The precipitate was collected by filtration, washed with water (3×15 mL), and dried to obtain 1.10 g (4.93 mmol, 48%) of target compound 6-fluoro-4-(1-hydroxyethyl)-1H-indole-2-carboxylic acid.

Rt (Method G) 1.00 mins, m/z 222 [M−H]⁻

Preparation of
4-ethyl-7-fluoro-1H-indole-2-carboxylic acid

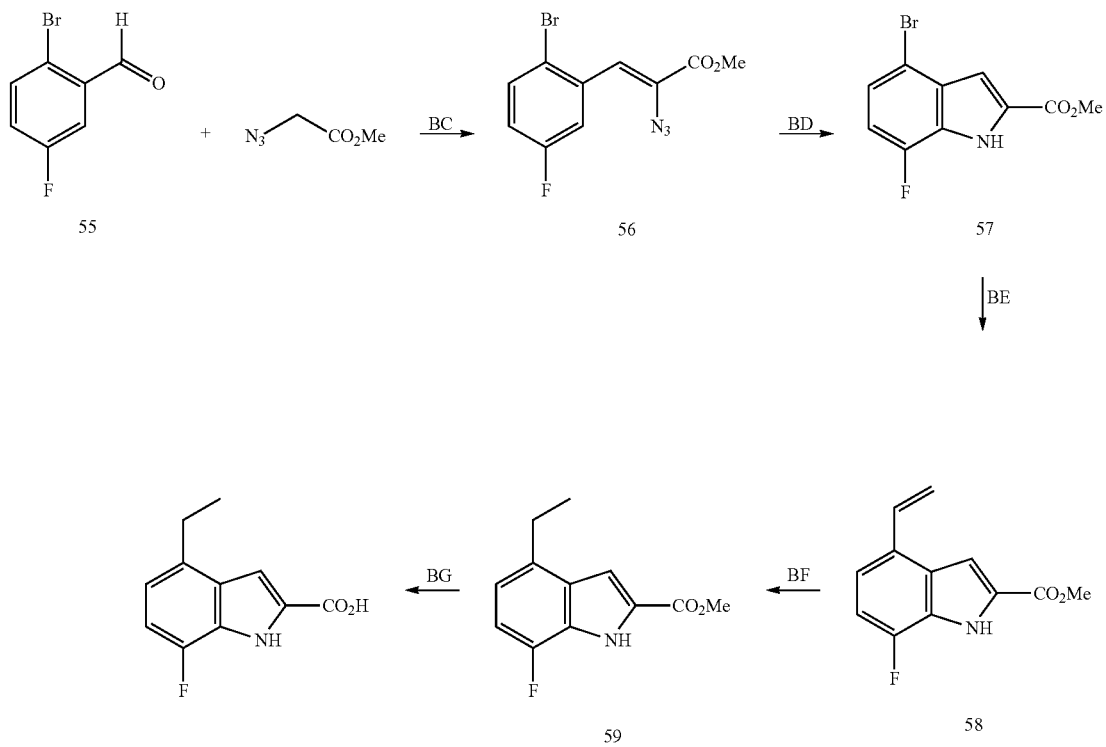

Step BC: To a solution of sodium methoxide (50.0 g, 926 mmol) in methanol (300 mL) −10° C. was added dropwise a solution of compound 55 (45.0 g, 222 mmol) and methyl azidoacetate (59.0 g, 457 mmol) in methanol (100 mL). The reaction mixture was stirred for 3 h maintaining temperature below 5° C., then quenched with ice water. The resulting mixture was stirred for 10 min. The precipitate was collected by filtration, washed with water and dried to afford 33.0 g (110 mmol, 50%) of compound 56 as a white solid.

Step BD: A solution of compound 56, obtained in the previous step, (33.0 g, 110 mmol) in xylene (250 mL) was refluxed for 1 h under an argon atmosphere and then concentrated under reduced pressure. The residue was recrystallized from hexane-ethyl acetate (60:40) to give 21.5 g (79.0 mmol, 72%) of compound 57.

Step BE: To a heated (90° C.) solution of compound 57 (4.00 g, 14.7 mmol) in anhydrous DMF under nitrogen (10 mL) were added tri-n-butyl(vinyl)tin (3.60 g, 11.4 mmol) and $Pd(PPh_3)_2Cl_2$ (0.301 g, 0.757 mmol). The resulting mixture was stirred at 90° C. for 1 h. The mixture was cooled to room temperature and purified by silica gel column chromatography (60-80% EtOAc in hexane). The combined product fractions of the product were concentrated, washed with water (3×100 mL), dried over Na$_2$SO$_4$, and concentrated to give 1.80 g (8.21 mmol, 56%) of compound 58 as yellow solid.

Step BF: A mixture of compound 58 (1.50 g, 6.84 mmol) and Pd/C (0.300 g, 10% wt.) in methanol (20 mL) was stirred under atmosphere of hydrogen at room temperature for 16 h. The mixture was filtered and concentrated to give 1.25 g (5.65 mmol, 83%) of compound 59.

Step BG: To a solution of compound 59 (1.40 g, 6.33 mmol) in methanol (40 mL) was added 2N aqueous NaOH (10 mL). The mixture was stirred for 2 h at 60° C. The mixture was concentrated under reduced pressure, and the residue acidified to pH 5-6 with 10% hydrochloric acid. The precipitate was collected by filtration, washed with water (3×15 mL), and dried to obtain 1.25 g (6.03 mmol, 95%) of target compound 4-ethyl-7-fluoro-1H-indole-2-carboxylic acid.

Rt (Method G) 1.27 mins, m/z 206 [M–H]$^-$

Step BH: To a degassed solution of compound 57 (4.00 g, 14.7 mmol) and tributyl(1-ethoxyvinyl)stannane (5.50 g, 15.2 mmol) in toluene (50 mL) under nitrogen was added bis(triphenylphosphine) palladium(II) dichloride (1.16 g, 1.65 mmol). The reaction mixture was stirred at 60° C. for 20 h. The mixture was cooled to room temperature and filtered. The filtrate was concentrated under reduced pressure and the residue purified by silica gel chromatography to afford 2.70 g (10.3 mmol, 70%) of compound 60 as a pale yellow solid.

Step BI: To a solution of compound 60 (2.40 g, 9.12 mmol) in 1,4-dioxane (30 mL) was added 2M hydrochloric acid (15 mL). The mixture was stirred at room temperature for 30 min. The majority of the solvent was evaporated and the residue was partitioned between ethyl acetate and water. The combined organic extracts were washed with water and brine, dried over sodium sulfate, filtered, and evaporated. The residue was triturated with 5% ether in isohexane and dried to afford 1.90 g (8.08 mmol, 86%) of compound 61 as a white solid.

Step BJ: A suspension of compound 61 (1.70 g, 7.23 mmol) and NaBH$_4$ (2.50 g, 66.1 mmol) in ethanol (13 mL) was refluxed for 2 h, cooled to room temperature, and filtered. The filtrate was evaporated under reduced pressure and the residue was dissolved in ethyl acetate. The solution was washed with 1N hydrochloric acid and brine, dried over Na$_2$SO$_4$, and evaporated under reduced pressure to give 1.50 g (6.32 mmol, 87%) of compound 62 as a colourless oil.

Step BK: To a solution of compound 62 (1.50 g, 6.32 mmol) in methanol (40 mL) was added 2N aqueous NaOH (10 mL). The mixture was stirred for 2 h at 60° C. The mixture was concentrated under reduced pressure and the residue acidified to pH 5-6 with 10% hydrochloric acid. The precipitate was collected by filtration, washed with water (3×15 mL), and dried to obtain 1.35 g (6.05 mmol, 96%) of target compound 7-fluoro-4-(1-hydroxyethyl)-1H-indole-2-carboxylic acid.

Rt (Method G) 0.90 mins, m/z 222 [M–H]$^-$

Preparation of
7-fluoro-4-(1-hydroxyethyl)-1H-indole-2-carboxylic acid

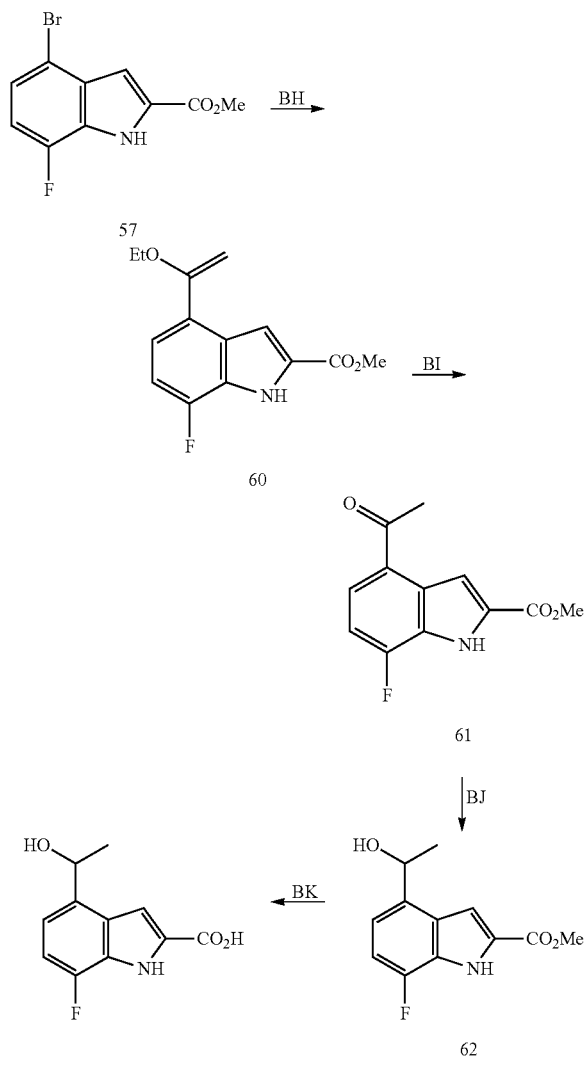

Preparation of
4-(hydroxymethyl)-1H-indole-2-carboxylic acid

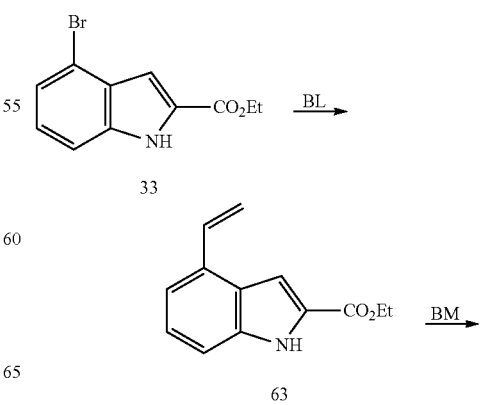

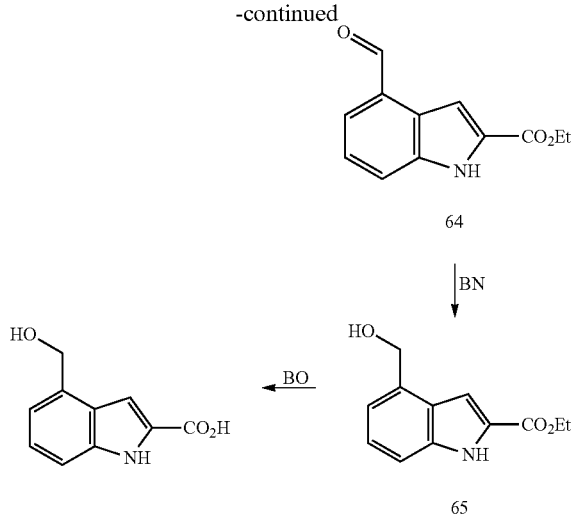

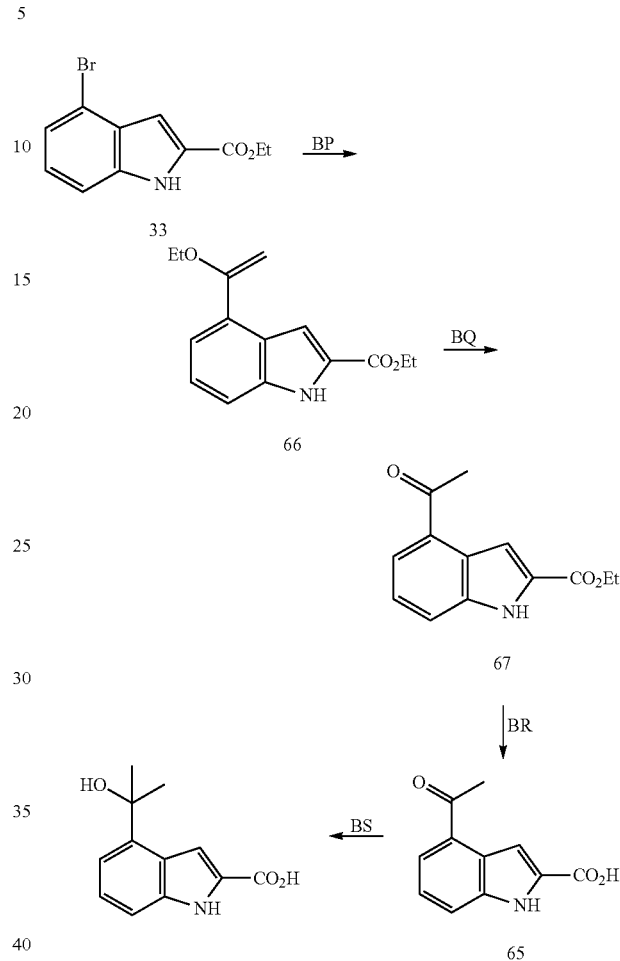

Preparation of 4-(2-hydroxypropan-2-yl)-1H-indole-2-carboxylic acid

Step BL: To a solution of compound 33 (10.0 g, 39.4 mmol) in a mixture of dioxane (200 mL) and water (50 mL) were added potassium vinyltrifluoroborate (11.0 g, 82.1 mmol), triethylamine (30 mL, 248 mmol) and Pd(dppf)Cl$_2$ (1.00 g, 1.37 mmol). The mixture was stirred at 80° C. for 48 h. The mixture was concentrated under vacuum, and the residue was dissolved in ethyl acetate. The solution was washed with water and concentrated under reduced pressure. The obtained material was purified by silica gel column chromatography to give 2.50 g (12.4 mmol, 38%) of compound 63.

Step BM: To a mixture of compound 63 (2.50 g, 12.4 mmol), acetone (200 m), and water (40 mL) were added OsO$_4$ (0.100 g, 0.393 mmol) and NaIO$_4$ (13.4 g, 62.6 mmol). The reaction was stirred for 10 h at room temperature. The acetone was distilled off and the remaining aqueous solution extracted with dichloromethane. The organic layer was washed with saturated NaHCO$_3$ solution (2×50 mL) and brine (2×50 mL), dried over Na$_2$SO$_4$, and concentrated under reduced pressure to obtain 1.50 g (7.40 mmol, 60%) of compound 64.

Step BN: To a cooled (0° C.) solution of compound 64 (1.50 g, 7.38 mmol) in THF/methanol mixture (100 mL) was added NaBH$_4$ (0.491 g, 13.0 mmol). The reaction mixture was stirred for 12 h at room temperature. Then the mixture was cooled to 0° C., treated with 2N hydrochloric acid (40 mL), and concentrated. The residue was extracted with ethyl acetate. The organic extract was washed with water, dried over Na$_2$SO$_4$, and concentrated under reduced pressure to obtain 1.00 g (4.87 mmol, 65%) of compound 65, pure enough for the next step.

Step BO: To a solution of compound 65, obtained in the previous step, (1.00 g, 4.87 mmol) in THF (50 mL), was added 1N aqueous LiOH (9 mL). The resulting mixture was stirred for 48 h at room temperature, then concentrated and diluted with 1N aqueous NaHSO$_4$ (9 mL). The mixture was extracted with ethyl acetate. The organic extract was dried over Na$_2$SO$_4$, and concentrated under reduced pressure. The residue was recrystallized from MTBE to obtain 0.250 g (1.30 mmol, 27%) of target compound 4-(hydroxymethyl)-1H-indole-2-carboxylic acid.

Rt (Method G) 0.98 mins, m/z 190 [M–H]$^-$

Steps BP and BQ: To a degassed solution of compound 33 (1.00 g, 3.94 mmol) and tributyl-(1-ethoxyvinyl)stannane (1.58 g, 4.37 mmol) in DMF (25 mL) under argon was added bis(triphenylphosphine)palladium(II) dichloride (0.100 g, 0.142 mmol). The reaction mixture was stirred at room temperature until TLC revealed completion of the reaction (approx. 7 days). The mixture was concentrated under reduced pressure and the residue partitioned between ethyl acetate and water. The organic layer was filtered through a plug of silica gel, dried over MgSO4, and concentrated under reduced pressure. The resulting black oil was dissolved in methanol (100 mL), treated with 5N hydrochloric acid (100 mL), and stirred at room temperature overnight. The mixture was concentrated and the residue dissolved in ethyl acetate. The solution was washed with water, dried over Na$_2$SO$_4$, and concentrated under reduced pressure. The crude product was purified by silica gel column chromatography to give 0.500 g (2.30 mmol, 58%) of compound 66.

Step BR: To a solution of compound 66 (1.00 g, 4.60 mmol) in THF (50 mL), was added 1N aqueous LiOH (7 mL). The resulting mixture was stirred for 48 h at room temperature, then concentrated under reduced pressure and diluted with 1N aqueous NaHSO4 (7 mL). The mixture was extracted with ethyl acetate. The organic extract was dried over MgSO$_4$, and concentrated under reduced pressure. The residue was recrystallized from MTBE to obtain 0.900 g (4.43 mmol, 96%) of compound 67.

Step BS: To a cooled (0° C.) solution of compound 67 (0.900 g, 4.43 mmol) in THF (50 mL) under argon was added a 1N solution of MeMgCl (16 mL) in hexane. The resulting mixture was stirred for 48 h at room temperature. The mixture was carefully quenched with 1N NaHSO₄ and extracted with ethyl acetate. The organic extract was dried over Na₂SO₄, and concentrated under reduced pressure. The residue was recrystallized from MTBE to obtain 0.250 g (1.14 mmol, 26%) of target compound 4-(2-hydroxypropan-2-yl)-1H-indole-2-carboxylic acid.

Rt (Method G) 0.99 mins, m/z 202 [M–H]⁻

Preparation of
4-(1-hydroxyethyl)-1H-indole-2-carboxylic acid

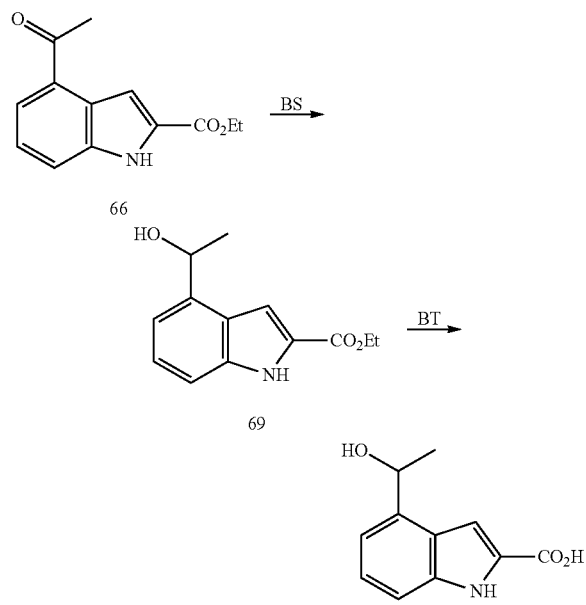

Step BS: To a cooled (0° C.) solution of compound 66 (1.00 g, 4.60 mmol) in THF/methanol mixture (50 mL) was added NaBH₄ (0.385 g, 10.2 mmol). The reaction mixture was stirred for 12 h at room temperature. The mixture was cooled to 0° C., treated with 2N hydrochloric acid (20 mL), and concentrated. The residue was extracted with ethyl acetate. The organic extract was washed with water, dried over Na₂SO₄, and evaporated under reduced pressure to obtain 0.800 g (3.65 mmol, 79%) of compound 69, pure enough for the next step.

Step BT: To a solution of compound 69, obtained in the previous step, (0.800 g, 3.65 mmol) in THF (50 mL), was added 1N aqueous LiOH (6 mL). The resulting mixture was stirred for 48 h at room temperature, then concentrated and diluted with 1N aqueous NaHSO₄ (6 mL). The mixture was extracted with ethyl acetate. The organic extract was dried over MgSO₄, and concentrated under reduced pressure. The residue was recrystallized from MTBE to obtain 0.300 g (1.46 mmol, 40%) of target compound 4-(1-hydroxyethyl)-1H-indole-2-carboxylic acid.

Rt (Method G) 0.82 mins, m/z 204 [M–H]⁻

Preparation of
4-(propan-2-yl)-1H-indole-2-carboxylic acid

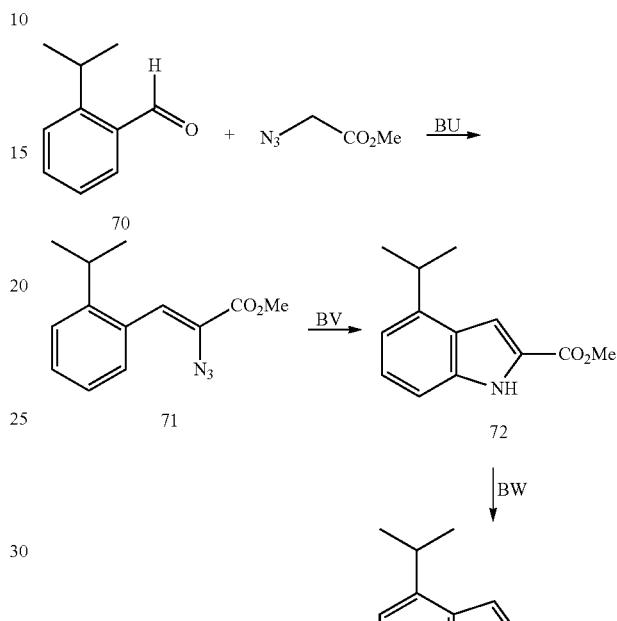

Step BU: To a solution of sodium methoxide (10.0 g, 185 mmol) in methanol (150 mL) at −10° C. was added dropwise a solution of compound 70 (15.0 g, 101 mmol) and methyl azidoacetate (12.0 g, 104 mmol) in methanol (100 mL). The reaction mixture was stirred for 3 h maintaining the temperature below 5° C., then quenched with ice water. The resulting mixture was stirred for 10 min. The precipitate was then collected by filtration, washed with water and dried to afford 7.00 g (23.3 mmol, 23%) of compound 71 as a white solid.

Step BV: A solution of compound 71, obtained in the previous step, (7.00 g, 23.3 mmol) in xylene (200 mL) was refluxed for 1 h under an argon atmosphere and then concentrated under reduced pressure. The residue was recrystallized from hexane-ethyl acetate (60:40) to give 3.50 g (16.1 mmol, 69%) of compound 72.

Step BW: To a solution of compound 72 (3.50 g, 16.1 mmol) in methanol (100 mL) was added 2N aqueous NaOH (40 mL). The mixture was stirred for 2 h at 60° C. The mixture was concentrated under reduced pressure, and then residue acidified to pH 5-6 with 10% hydrochloric acid. The precipitate was collected by filtration, washed with water (3×50 mL), and dried to obtain 2.70 g (13.3 mmol, 83%) of target compound 4-(propan-2-yl)-1H-indole-2-carboxylic acid.

Rt (Method G) 1.32 mins, m/z 202 [M–H]⁻

Preparation of 4-ethenyl-1H-indole-2-carboxylic acid

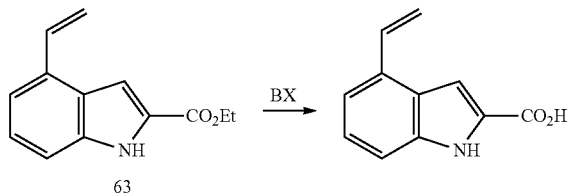 [SMILES: C=Cc1cccc2[nH]c(C(=O)OCC)cc12 ; C=Cc1cccc2[nH]c(C(=O)O)cc12]

Step BX: To a solution of compound 63 (0.900 g, 4.47 mmol) in THF (50 mL), was added 1N aqueous LiOH (8 mL). The resulting mixture was stirred for 48 h at room temperature, then concentrated under reduced pressure and diluted with 1N aqueous NaHSO$_4$ (8 mL). The mixture was extracted with ethyl acetate. The organic extract was dried over MgSO$_4$ and concentrated under reduced pressure. The residue was recrystallized from MTBE to obtain 0.500 g (2.67 mmol, 59%) of target compound 4-ethenyl-1H-indole-2-carboxylic acid.

Rt (Method G) 1.14 mins, m/z 186 [M–H]$^-$

Preparation of 4-ethynyl-1H-indole-2-carboxylic acid

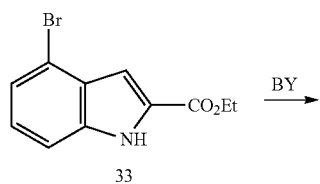

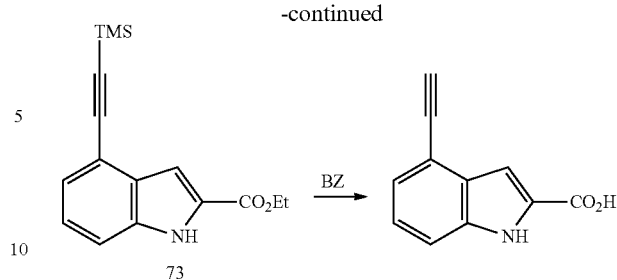

Step BY: To a solution of compound 33 (1.00 g, 3.94 mmol) in THF (50 mL) under argon were added TMS-acetylene (0.68 mL, 4.80 mmol), CuI (0.076 g, 0.399 mmol), triethylamine (2.80 mL, 20.0 mmol), and Pd(dppf)Cl$_2$ (0.100 g, 0.137 mmol). The mixture was stirred at 60° C. until TLC revealed completion of the reaction (approx. 5 days). The mixture was concentrated under reduced pressure, and the residue dissolved in ethyl acetate. The solution was washed with water, dried over Na$_2$SO$_4$, and concentrated under reduced pressure. The residue was purified by silica gel column chromatography to give 0.600 g (2.14 mmol, 56%) of compound 73.

Step BZ: To a solution of compound 73 (0.840 g, 3.10 mmol) in THF (50 mL), was added 1N aqueous LiOH (7 mL). The resulting mixture was stirred for 48 h at room temperature, then concentrated under reduced pressure and diluted with 1N aqueous NaHSO$_4$ (7 mL). The mixture was extracted with ethyl acetate. The organic extract was dried over MgSO$_4$ and concentrated under reduced pressure. The residue was recrystallized from MTBE to obtain 0.400 g (2.17 mmol, 70%) of target compound 4-ethynyl-1H-indole-2-carboxylic acid.

Rt (Method G) 1.12 mins, m/z 184 [M–H]$^-$

Preparation of 4-(1,1-difluoroethyl)-1H-indole-2-carboxylic acid

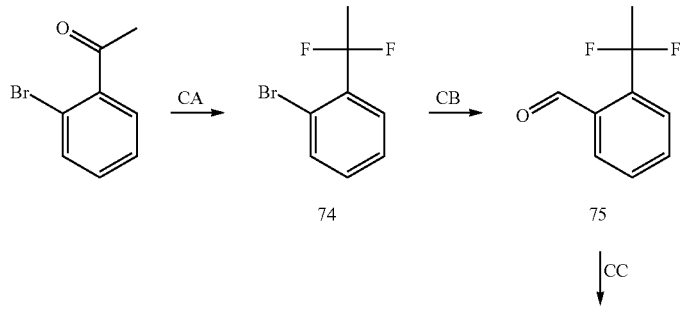

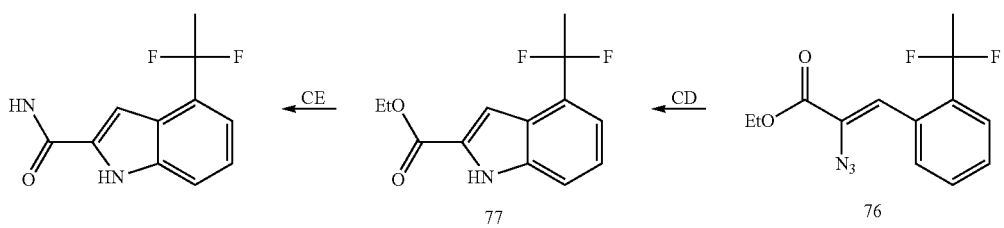

Step CA: To a mixture of 2-bromoacetophenone (63.0 g, 317 mmol), water (0.5 mL), and dichloromethane (100 mL) was added Morph-DAST (121 mL, 992 mmol). The resulting mixture was stirred for 28 days at room temperature. The reaction mixture was then poured into saturated aqueous NaHCO$_3$ (1000 mL) and extracted with ethyl acetate (2×500 mL). The organic layer was dried over Na$_2$SO$_4$ and concentrated under reduced pressure. The residue was purified by silica gel column chromatography to give 16.8 g (76.0 mmol, 12%) of compound 74.

Step CB: To a cooled (−85° C.) solution of compound 74 (16.8 g, 76.0 mmol) in THF (300 mL) under Ar was added 2.5M solution of n-BuLi in hexanes (36.5 mL, 91.5 mmol) over 30 min. The resulting mixture was stirred for 1 h at −85° C. DMF (8.80 mL, 114 mmol) was then added (maintaining temperature below −80° C.) and the reaction stirred for a further 45 min. The reaction was quenched with saturated aqueous NH$_4$Cl (100 mL) and diluted with water (600 mL). The obtained mixture was extracted with ethyl acetate (2×500 mL). The combined organic extracts were dried over Na$_2$SO$_4$, and concentrated under reduced pressure to obtain 12.5 g (73.6 mmol, 97%) of compound 75 (sufficiently pure for the next step).

Step CC: To a cooled (−30° C.) mixture of compound 75 (12.5 g, 73.5 mmol), ethanol (500 mL), and ethyl azidoacetate (28.5 g, 221 mmol) was added a freshly prepared solution of sodium methoxide (prepared by mixing Na (5.00 g, 217 mmol) and methanol (100 mL)) portionwise under Ar (maintaining the temperature below −25° C.). The reaction mixture was warmed to 15° C. and stirred for 12 h. The obtained mixture was poured into saturated aqueous NH$_4$Cl (2500 mL) and stirred for 20 min. The precipitate was collected by filtration, washed with water, and dried to obtain 10.0 g (35.6 mmol, 51%) of compound 76.

Step CD: A solution of compound 76 (10.0 g, 35.6 mmol) in xylene (500 mL) was refluxed until gas evolution ceased (approx. 2 h) and then concentrated under reduced pressure. The orange oil obtained was triturated with hexane/ethyl acetate (5:1), collected by filtration, and dried to obtain 1.53 g (6.04 mmol, 17%) of compound 77.

Step CE: To a solution of compound 77 (1.53 g, 6.04 mmol) in THF/water 9:1 mixture (100 mL) was added LiOH.H$_2$O (0.590 g, 14.1 mmol). The resulting mixture was stirred overnight at r.t. The volatiles were evaporated and the residue mixed with water (50 mL) and 1N hydrochloric acid (10 mL). The mixture was extracted with ethyl acetate (2×100 mL). The combined organic extracts were dried over Na$_2$SO$_4$, and concentrated under reduced pressure. The crude product was purified by silica gel column chromatography to give 0.340 g (1.33 mmol, 24%) of 4-(1,1-difluoroethyl)-1H-indole-2-carboxylic acid.

Rt (Method G) 1.16 mins, m/z 224 [M−H]$^-$

Preparation of
4-(trimethylsilyl)-1H-indole-2-carboxylic acid

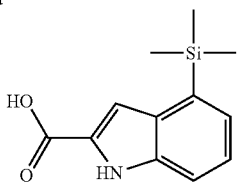

Step CF: To a cooled (−78° C.) solution of 4-bromo-1H-indole (5.00 g, 25.5 mmol) in THF (100 mL) under Ar was added a 2.5M solution of n-BuLi in hexanes (23 mL, 57.5 mmol). The resulting mixture was stirred for 30 min. TMSCl (16 mL, 126 mmol) was added and the reaction mixture warmed to room temperature. After 1 h the mixture was diluted with MTBE (250 mL), washed with water (2×200 mL) and brine (200 mL), then dried over Na$_2$SO$_4$, and concentrated under reduced pressure. The residue was refluxed in methanol (100 mL) for 1 h. The solvent was then distilled off to obtain 3.60 g (19.0 mmol, 74%) of compound 78.

Step CG: To a cooled (−78° C.) solution of compound 78 (1.50 g, 7.92 mmol) in THF (50 mL) under Ar was added a 2.5M solution of n-BuLi in hexanes (3.8 mL, 9.5 mmol). The resulting mixture was stirred for 20 min. CO$_2$ (2 L) was then bubbled through the mixture for 10 min, and the reaction mixture warmed to room temperature. The volatiles were evaporated and the residue dissolved in THF (50 mL). The solution was cooled to −78° C., and a 1.7M solution of t-BuLi (5.6 mL, 9.50 mmol) was added. The mixture was warmed to −30° C., then again cooled to −78° C. CO$_2$ (2 L) was bubbled through the solution for 10 min. The obtained solution was allowed to slowly warm to r.t. then concentrated under reduced pressure. The residue was dissolved in water (50 mL), washed with MTBE (2×50 mL), then acidified to pH 4, and extracted with ethyl acetate (2×50 mL). The organic extract was washed with water (2×50 m), and brine (50 mL), dried over Na$_2$SO$_4$, and evaporated under reduced pressure. The crude product was washed with hexane and dried to obtain 1.24 g (5.31 mmol, 67%) of target compound 4-(trimethylsilyl)-1H-indole-2-carboxylic acid.

Rt (Method G) 1.47 mins, m/z 232 [M−H]$^-$

Preparation of
6-chloro-5-fluoro-1H-indole-2-carboxylic acid

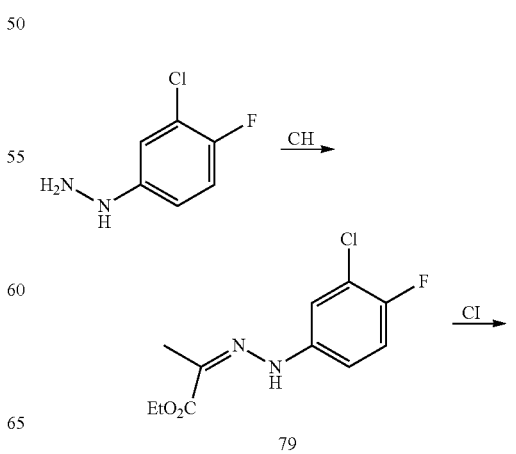

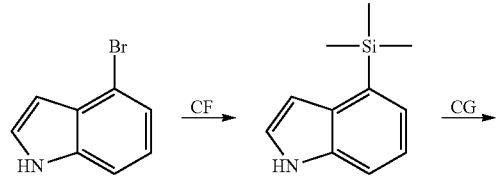

-continued

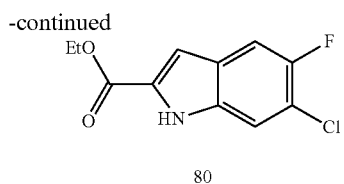
80

↓ CJ

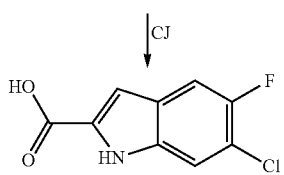

Step CH: To a solution of (3-chloro-4-fluorophenyl)hydrazine (80.0 g, 498 mmol) in ethanol (200 mL) was added ethyl pyruvate (58.0 g, 499 mmol). The mixture was refluxed for 1 h, then concentrated under reduced pressure, and diluted with water (300 m). The solid was collected by filtration then dried to obtain 122 g (472 mmol, 95%) of compound 79.

Step CI: A suspension of compound 79 (122 g, 472 mmol) and pTSA (81.5 g, 473 mmol) in toluene (500 mL) was refluxed for 48 h, then cooled to room temperature. The precipitate was collected by filtration and purified by fractional crystallization from toluene to obtain 4.00 g (16.6 mmol, 4%) of compound 80.

Step CJ: To a refluxing solution of compound 80 (4.00 g, 16.6 mmol) in ethanol (30 mL) was added NaOH (0.660 g, 16.5 mmol). The mixture was refluxed for 1 h, then concentrated under reduced pressure. The residue was triturated with warm water (80° C., 50 mL) and the solution acidified (pH 2) with concentrated hydrochloric acid. The precipitate was collected by filtration, washed with water (2×10 mL), and dried to obtain 3.18 g (14.9 mmol, 90%) of target compound 6-chloro-5-fluoro-1H-indole-2-carboxylic acid.

Rt (Method G) 1.23 mins, m/z 212 [M−H]⁻

Preparation of 4-(difluoromethyl)-6-fluoro-1H-indole-2-carboxylicacid

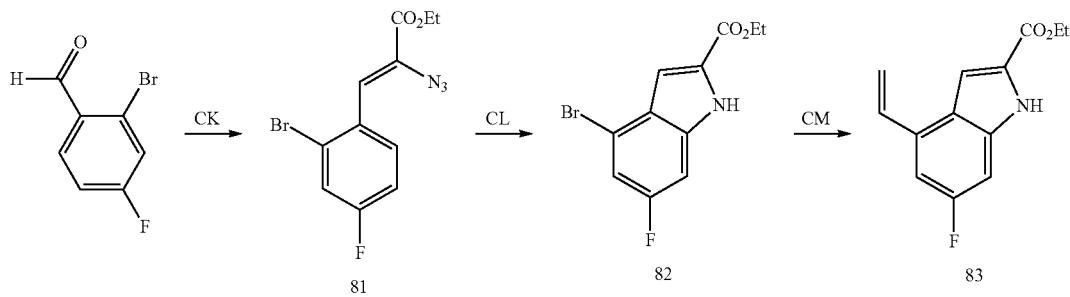

 CN

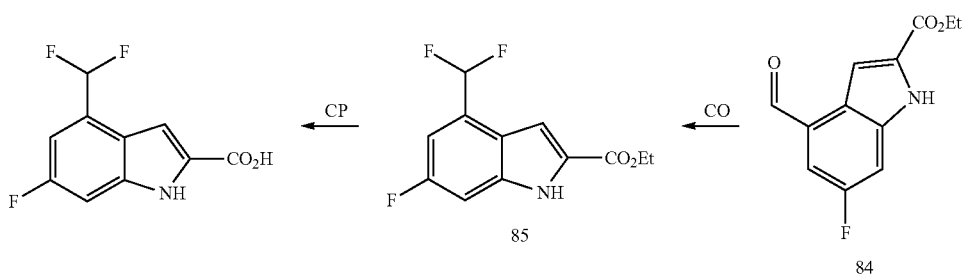

Step CK: To a solution of sodium methoxide (50.0 g, 926 mmol) in methanol (300 mL) at −10° C. was added dropwise a solution of 2-bromo-4-fluorobenzaldehyde (222 mmol) and methyl azidoacetate (59.0 g, 457 mmol) in methanol (100 mL). The reaction mixture was stirred for 3 h, maintaining the temperature below 5° C., then quenched with ice water. The resulting mixture was stirred for 10 min and the solid collected by filtration. The solid was washed with water to afford compound 81 as a white solid (62% yield).

Step CL: A solution of compound 81 (133 mmol) in xylene (250 mL) was refluxed for 1 h under an argon atmosphere and then concentrated under reduced pressure. The residue was recrystallized form hexane-ethyl acetate mixture (60:40) to give compound 82 (58% yield).

Step CM: To a heated (90° C.) solution of compound 82 (14.7 mmol) in anhydrous DMF (10 mL) tri-n-butyl(vinyl) tin (3.60 g, 11.4 mmol) and Pd(PPh3)2Cl2 (0.301 g, 0.757 mmol) were added under nitrogen and the resulting mixture was stirred at 90° C. for 1 h. The mixture was cooled to room temperature and purified by silica gel column chromatography (60-80% ethyl acetate in hexane). The combined product fractions were concentrated, washed with water (3×100 mL), dried over $Na_2SO_4$, and concentrated under reduced pressure to afford compound 83 as a yellow solid (60% yield).

Step CN: To a mixture of compound 83 (12.4 mmol), acetone (200 mL), and water (40 mL) $OsO_4$ (0.100 g, 0.393 mmol) and $NaIO_4$ (13.4 g, 62.6 mmol) were added and the reaction was stirred for 10 h at room temperature. Acetone was distilled off and the aqueous solution was extracted with dichloromethane. The combined organic layer was washed with saturated $NaHCO_3$ solution (2×50 mL) and brine (2×50 m), dried over $Na_2SO_4$, and concentrated under reduced pressure to afford compound 84 (33% yield).

Step CO: To a solution of compound 85 (11.0 mmol) in dichloromethane (50 mL) was added Morph-DAST (4.10 mL, 33.6 mmol). The resulting mixture was stirred until NMR of an aliquot revealed completion of the reaction (2-5 days). The reaction mixture was added dropwise to a cold saturated $NaHCO_3$ solution (1000 mL). The mixture obtained was extracted with ethyl acetate. The organic layer was dried over $MgSO_4$ and concentrated. The residue was purified by column chromatography to give compound 86 as yellow solid (48% yield).

Step CP: To a solution of compound 87 (4.50 mmol) in THF (50 mL), was added 1N aqueous LiOH (8 mL). The resulting mixture was stirred for 48 h at room temperature then concentrated under reduced pressure and diluted with 1N aqueous $NaHSO_4$ (8 mL). The obtained mixture was extracted with ethyl acetate. The organic extract was dried over $MgSO_4$ and concentrated under reduced pressure. The residue was recrystallized from MTBE to obtain 4-(difluoromethyl)-6-fluoro-1H-indole-2-carboxylic acid (87%).

Rt (Method G) 1.22 mins, m/z 228 [M−H]⁻

Preparation of
4-(difluoromethyl)-7-fluoro-1H-indole-2-carboxylic acid

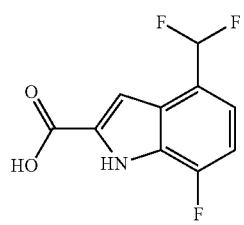 [SMILES: O=C(O)c1cc2c(C(F)F)ccc(F)c2[nH]1]

Prepared as described for 4-(difluoromethyl)-6-fluoro-1H-indole-2-carboxylic acid, starting from 2-bromo-5-fluorobenzaldehyde (2.5% overall yield).

Rt (Method G) 1.13 mins, m/z 228 [M−H]⁻

Preparation of
4-(difluoromethyl)-1H-indole-2-carboxylic acid

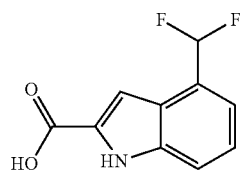 [SMILES: O=C(O)c1cc2c(C(F)F)cccc2[nH]1]

Prepared as described for 4-(difluoromethyl)-6-fluoro-1H-indole-2-carboxylic acid, starting from 4-bromo-1H-indole-2-carboxylic acid (11% overall yield).

Rt (Method G) 1.17 mins, m/z 210 [M−H]⁻

Preparation of 4-(1,1-difluoroethyl)-6-fluoro-1H-indole-2-carboxylic acid

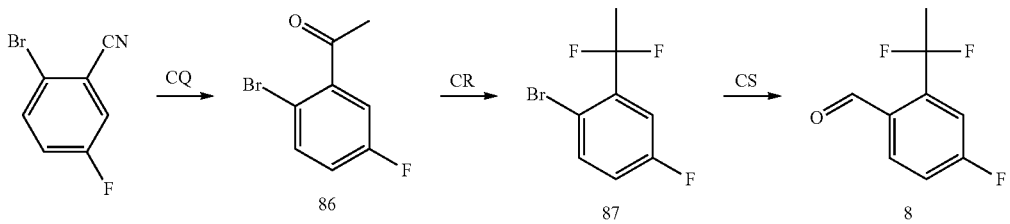

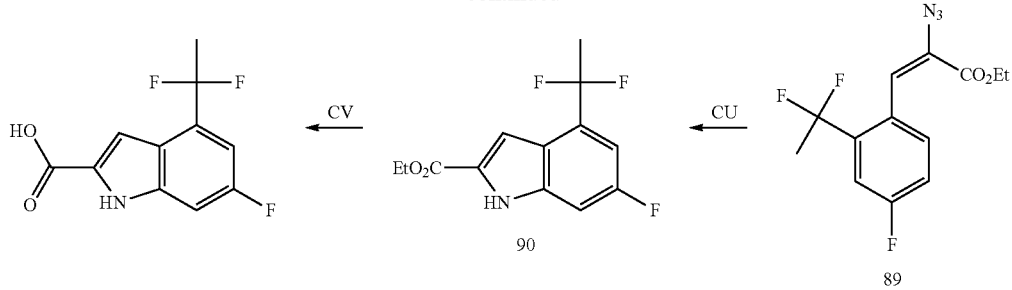

Step CQ: To a solution of 2-bromo-5-fluorobenzonitrile (10.0 g, 48.5 mmol) in anhydrous tetrahydrofuran (100 mL) under nitrogen was added methylmagnesium bromide (3.2M in ether, 19 mL, 60.0 mmol). The resulting mixture was heated to reflux for 4 h. The reaction mixture was then cooled, poured into 2N hydrochloric acid (100 mL), and diluted with methanol (100 mL). The organic solvents were removed and the crude product precipitated out. The reaction mixture was extracted with ethyl acetate, dried over MgSO$_4$, and concentrated. The residue was purified by column chromatography (heptane/dichloromethane) to give 4.88 g (21.9 mmol, 45%) of compound 86 as a pink oil.

Step CR: To a solution of compound 86 (110 mmol) in dichloromethane (50 mL) at room temperature was added Morph-DAST (41 mL, 336 mmol) and a few drops of water. The resulting mixture was stirred for 48 days at room temperature; every 7 days an additional portion of Morph-DAST (41 mL, 336 mmol) was added. After the reaction was complete, the mixture was carefully added dropwise to cold saturated aqueous NaHCO$_3$. The product was extracted with ethyl acetate and the organic extract dried over MgSO$_4$ and concentrated. The residue was purified by column chromatography to give 87 as a colorless liquid (37% yield).

Step CS: To a cooled (−80° C.) solution of compound 87 (21.0 mmol) in THF (150 mL) was added slowly a 2.5M solution of n-BuLi in hexanes (10.0 mL, 25.0 mmol of n-BuLi). The mixture was stirred for 1 h, then DMF (2.62 mL, 33.8 mmol) was added and the mixture stirred for a further 1 h. The reaction was quenched with saturated aqueous NH$_4$Cl (250 mL) and extracted with Et$_2$O (3×150 mL). The organic layer was dried over Na$_2$SO$_4$ and concentrated under reduced pressure. The residue was purified by silica gel chromatography (ethyl acetate/hexane 1:9) to give compound 88 (52% yield).

Step CT: To a solution of sodium methoxide (50.0 g, 926 mmol) in methanol (300 mL) at −10° C. was added dropwise a solution of compound 88 (222 mmol) and methyl azidoacetate (59.0 g, 457 mmol) in methanol (100 mL). The reaction mixture was stirred for 3 h, maintaining the temperature below 5° C., then quenched with ice water. The resulting mixture was stirred for 10 min. The solid obtained was collected by filtration, and washed with water to afford compound 89 as a white solid (66% yield).

Step CU: A solution of compound 89 (120 mmol) in xylene (250 mL) was refluxed for 1 h under an argon atmosphere and then concentrated under reduced pressure. The residue was recrystallized from hexane-ethyl acetate to give compound 90 (70% yield).

Step CV: To a solution of compound 90 (4.40 mmol) in THF (50 mL) was added 1N aqueous LiOH (8 mL). The resulting mixture was stirred for 48 h at room temperature, then concentrated under reduced pressure and diluted with 1N aqueous NaHSO$_4$ (8 mL). The residue obtained was extracted with ethyl acetate. The organic extract was dried over MgSO$_4$ and concentrated under reduced pressure. The residue was recrystallized from MTBE to obtain target compound 4-(1,1-difluoroethyl)-6-fluoro-1H-indole-2-carboxylic acid (95% yield).

Rt (Method G) 1.26 mins, m/z 242 [M−H]$^-$

Preparation of 4-(1,1-difluoroethyl)-7-fluoro-1H-indole-2-carboxylic acid

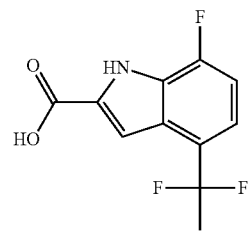 [SMILES: CC(F)(F)c1ccc(F)c2[nH]c(C(=O)O)cc12]

Prepared as described for 4-(1,1-difluoroethyl)-6-fluoro-1H-indole-2-carboxylic acid, starting from 2-bromo-4-fluoroacetophenone (3.6% overall yield).

Rt (Method G) 1.23 mins, m/z 242 [M−H]$^-$

Preparation of 6,6-difluoro-4-azaspiro[2.4]heptane

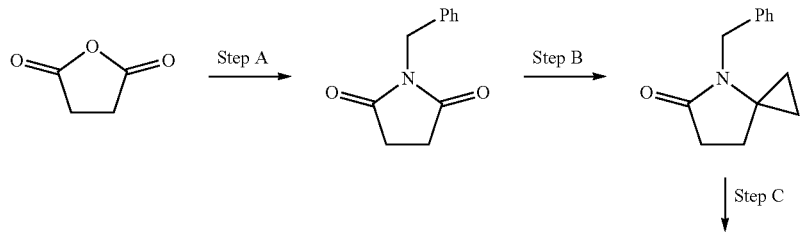

-continued

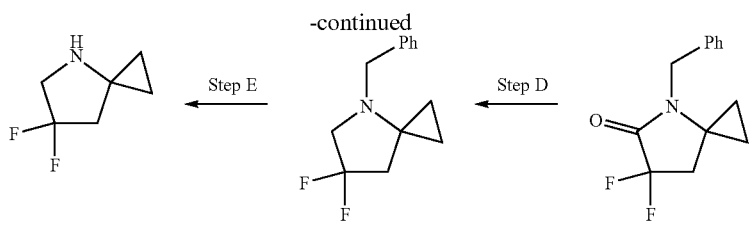

Preparation of 7,7-difluoro-4-azaspiro[2.4]heptane

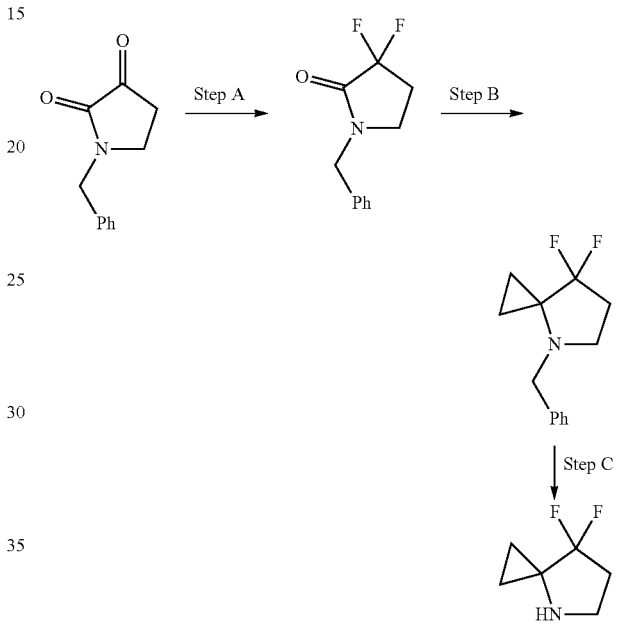

Step A: To a solution of succinic anhydride (100 g, 1000 mmol) in toluene (3000 mL) was added benzylamine (107 g, 1000 mmol). The solution was stirred at room temperature for 24 h, then heated at reflux with a Dean-Stark apparatus for 16 hours. The mixture was then concentrated under reduced pressure to give 1-benzylpyrrolidine-2,5-dione (170 g, 900 mmol, 90% yield).

Step B: To a cooled (0° C.) mixture of 1-benzylpyrrolidine-2,5-dione (114 g, 600 mmol) and Ti(Oi-Pr)$_4$ (170.5 g, 600 mmol) in dry THF (2000 mL) under argon atmosphere was added dropwise a 3.4M solution of ethylmagnesium bromide in THF (1200 mmol). The mixture was warmed to room temperature and stirred for 4 h. BF$_3$.Et$_2$O (170 g, 1200 mmol) was then added dropwise and the solution stirred for 6 h. The mixture was cooled (0° C.) and 3N hydrochloric acid (500 mL) was added. The mixture was extracted twice with Et$_2$O, and the combined organic extracts washed with brine, dried and concentrated under reduced pressure to give 4-benzyl-4-azaspiro[2.4]heptan-5-one (30.2 g, 150 mmol, 25% yield).

Step C: To a cooled (−78° C.) solution of 4-benzyl-4-azaspiro[2.4]heptan-5-one (34.2 g, 170 mmol) in dry THF (1000 mL) under argon was added LiHMDS in THF (1.1M solution, 240 mmol). The mixture was stirred for 1 h, then a solution of N-fluorobenzenesulfonimide (75.7 g, 240 mmol) in THF (200 mL) was added dropwise. The mixture was warmed to room temperature and stirred for 6 h. The mixture was then re-cooled (−78° C.) and LiHMDS added (1.1M solution in THF, 240 mmol).

The solution was stirred for 1 h, then N-fluorobenzenesulfonimide (75.7 g, 240 mmol) in THF (200 mL) was added dropwise. The mixture was warmed to room temperature and stirred for 6 h. The mixture was poured into a saturated solution of NH$_4$Cl (300 mL) and extracted twice with Et$_2$O. The combined organic extracts were washed with brine and concentrated under reduced pressure. Product was purified by column chromatography to provide 4-benzyl-6,6-difluoro-4-azaspiro[2.4]heptan-5-one (18 g, 75.9 mmol, 45% yield).

Step D: To a warmed (40° C.) solution of BH$_3$.Me$_2$S (3.42 g, 45 mmol) in THF (200 mL) was added dropwise 4-benzyl-6,6-difluoro-4-azaspiro[2.4]heptan-5-one (11.9 g, 50 mmol). The mixture was stirred for 24 h at 40° C., then cooled to room temperature. Water (50 mL) was added dropwise, and the mixture extracted with Et$_2$O (2×200 mL). The combined organic extracts were washed brine, diluted with 10% solution of HCl in dioxane (50 mL) and evaporated under reduced pressure to give 4-benzyl-6,6-difluoro-4-azaspiro[2.4]heptane (3 g, 13.4 mmol, 27% yield).

Step E: 4-benzyl-6,6-difluoro-4-azaspiro[2.4]heptane (2.68 g, 12 mmol) and palladium hydroxide (0.5 g) in methanol (500 mL) were stirred at room temperature under an atmosphere of H$_2$ for 24 h. The mixture was filtered and then filtrate concentrated under reduced pressure to obtain 6,6-difluoro-4-azaspiro[2.4]heptane (0.8 g, 6.01 mmol, 50% yield).

Step A: To a cooled (0° C.) solution of 1-benzylpyrrolidine-2,3-dione (8 g, 42.3 mmol) in DCM (100 mL) was added dropwise over 30 minutes DAST (20.4 g, 127 mmol). The mixture was stirred at room temperature overnight, then quenched by dropwise addition of saturated NaHCO$_3$. The organic layer was separated, and the aqueous fraction extracted twice with DCM (2×50 mL). The combined organic layers were dried over Na$_2$SO$_4$ and concentrated under reduced pressure to afford 1-benzyl-3,3-difluoropyrrolidin-2-one (26.0 mmol, 61% yield), which used in the next step without further purification.

Step B: To a solution of crude 1-benzyl-3,3-difluoropyrrolidin-2-one (5.5 g, 26 mmol) and Ti(Oi-Pr)$_4$ (23.4 mL, 78 mmol) in THF (300 mL) was added dropwise under argon atmosphere 3.4 M solution of EtMgBr in 2-MeTHF (45.8 mL, 156 mmol). After stirring for 12 h, water (10 mL) was added to obtain a white precipitate. The precipitate was washed with MTBE (3×50 mL). The combined organic fractions were dried over Na$_2$SO$_4$, concentrated and purified by flash chromatography (hexanes-EtOAc 9:1) to obtain 4-benzyl-7,7-difluoro-4-azaspiro[2.4]heptane (1.3 g, 5.82 mmol, 22% yield) as a pale yellow oil.

Step C: 4-benzyl-7,7-difluoro-4-azaspiro[2.4]heptane (0.55 g, 2.46 mmol) was dissolved in solution of CHCl$_3$ (1 mL) and MeOH (20 mL) and Pd/C (0.2 g, 10%) was added. This mixture was stirred under and an H$_2$ atmosphere for 5 h, then filtered. The filtrate was concentrated to give 7,7-difluoro-4-azaspiro[2.4]heptane (0.164 g, 1.23 mmol, 50% yield)

Synthesis of 1-[(difluoromethoxy)methyl]-N-methylcyclopropan-1-amine

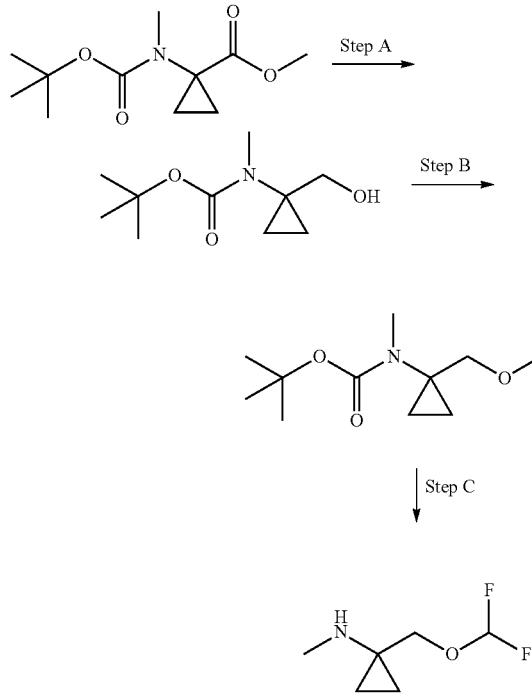

Step A: To a solution of methyl 1-((tertbutoxycarbonyl)(methyl)amino)cyclopropane-1-carboxylate (1.05 g, 4.58 mmol) in dry THF (5 ml) under N₂ was added lithium borohydride (1.259 mL, 4M in THF, 5.04 mmol). The mixture was stirred at r.t. for 4 days. Sodium sulfate and water were added, the mixture was filtered over a pad of sodium sulfate which was rinsed with dichloromethane. The filtrate was concentrated, to give tert-butyl (1-(hydroxymethyl)cyclopropyl)(methyl)carbamate as a white solid (0.904 g, 95% yield).

Step B: To a solution of tert-butyl (1-(hydroxymethyl)cyclopropyl)(methyl)carbamate (0.100 g, 0.497 mmol) and (bromodifluoromethyl)trimethylsilane (0.155 ml, 0.994 mmol) in dichloromethane (0.5 ml) was added one drop of a solution of potassium acetate (0.195 g, 1.987 mmol) in water (0.5 ml). The mixture was stirred for 40 h. The mixture was diluted with dichloromethane and water, the organic layer was separated and concentrated. Purification by flash chromatography (20% ethyl acetate in heptane) gave tert-butyl N-{1[(difluoromethoxy)methyl]cyclopropyl}-N-methylcarbamate as colorless oil (0.058 g, 46% yield)

Step C: To tert-butyl (1-(((difluoromethoxy)methyl)cyclopropyl)(methyl)carbamate (0.058 g, 0.231 mmol) was added HCl in dioxane (4M solution, 2 mL, 8.00 mmol). The mixture was stirred for 30 min at rt, then concentrated to yield the desired product which was used without further purification LC-MS: m/z 152.2 (M+H)+

Synthesis of 3-{bicyclo[1.1.1]pentan-1-yl}-2H,4H,5H,6H,7H-pyrazolo[4,3-c]pyridine

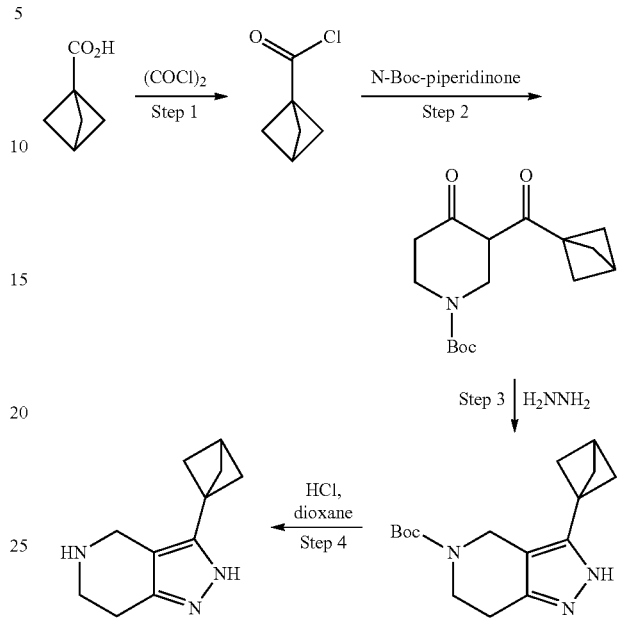

Step 1: To a stirred solution of bicyclo[1.1.1]pentane-1-carboxylic acid (3.86 g, 34.4 mmol) in dry DCM (60 ml), was added drop of DMF followed dropwise addition of oxalyl chloride (5.03 g, 39.6 mmol). The reaction mixture was stirred at r.t. until gas release was complete. The mixture was concentrated and bicyclo[1.1.1]pentane-1-carbonyl chloride (4.49 g, 34.4 mmol, 99.9% yield) was used in the next step without further purification.

Step 2: To a cooled (−65° C.), stirred solution of tert-butyl 4-oxopiperidine-1-carboxylate (13.7 g, 68.8 mmol) in THF (60 mL) under argon was added to a solution of LiHMDS (68.8 mL, 68.8 mmol, 1M) in dry THF (80 mL). The mixture was stirred at −65° C. for 0.5 hr. A solution of bicyclo[1.1.1]pentane-1-carbonyl chloride (4.49 g, 34.4 mmol) in THF (20.00 mL) was added dropwise dropwise. The reaction mixture was stirred for 30 min at −65° C., then warmed to r.t. The mixture was quenched by the addition of saturated NH₄Cl solution (200 mL) and extracted with EtOAc (2×150 mL). The combined organic extracts were washed with brine, dried over Na₂SO₄ and concentrated. The residue was purified by flash column chromatography with EtOAc/pentane (from 1:1 to 100% EtOAc) as an eluent to afford tert-butyl 3-bicyclo[1.1.1]pentane-1-carbonyl-4-oxopiperidine-1-carboxylate (2.2 g, 7.5 mmol, 21.8% yield) as pale yellow solid.

Step 3: To a solution of tert-butyl 3-bicyclo[1.1.1]pentane-1-carbonyl-4-oxopiperidine-1-carboxylate (1.1 g, 3.75 mmol) in EtOH (40 mL) was added hydrazine hydrate (60% in water) (0.5 mL) and acetic acid (0.5 mL). The mixture was heated at reflux for 5 h, then cooled and concentrated. The residue was diluted with water (20 mL) and extracted with CHCl₃ (2×30 mL). The combined organic extracts were washed with brine, sat. aq. solution of NaHCO₃, dried over Na₂SO₄, filtered and concentrated under reduced pressure to afford tert-butyl 3-bicyclo[1.1.1]pentan-1-yl-2H,4H,5H,6H,7H-pyrazolo[4,3-c]pyridine-5-carboxylate (1.1 g, 3.67 mmol, 97.8% yield) as yellow solid.

Step 4: To a stirred solution of tert-butyl 3-bicyclo[1.1.1]pentan-1-yl-2H,4H,5H,6H,7H-pyrazolo[4,3-c]pyridine-5-carboxylate (1.1 g, 3.8 mmol) in dry dioxane (10 mL) was added HCl (4M solution in dioxane, 9.5 mL, 38 mmol). The reaction mixture was stirred for 10 h at r.t. then concentrated. The residue obtained was co-evaporated with water and dried under reduced pressure to afford 3-bicyclo[1.1.1]pentan-1-yl-2H,4H,5H,6H,7H-pyrazolo[4,3-c]pyridine dihydrochloride (628.0 mg, 3.32 mmol, 87.3% yield) as yellow solid.

Synthesis of 3-{2H,4H,5H,6H,7H-pyrazolo[4,3-c]pyridin-3-yl}bicyclo[1.1.1]pentane-1-carboxylic acid dine-1-carboxylate (3.1 g, 8.82 mmol) in MeOH (50 mL) was added acetic acid (1 mL) and hydrazine hydrate 60% in water (0.5 mL). The reaction mixture was stirred at r.t. overnight. The reaction mixture was concentrated, water (30 mL) was added and the product was extracted with EtOAc (3×10 mL). The combined organic extracts were washed with brine, sat. aq. NaHCO₃ solution, dried over Na₂SO4 and concentrated to afford crude tert-butyl 3-[3-(methoxycarbonyl)bicyclo[1.1.1]pentan-1-yl]-2H,4H,5H,6H,7H-pyrazolo[4,3-c]pyridine-5-carboxylate (1.6 g, 2.86 mmol, 32.4% yield) as light yellow solid, that was used in the next step without further purification.

Step 4: To a stirred solution of tert-butyl 3-[3-(methoxycarbonyl)bicyclo[1.1.1]pentan-1-yl]-2H,4H,5H,6H,7H-pyrazolo[4,3-c]pyridine-5-carboxylate (1.6 g, 4.6 mmol) in

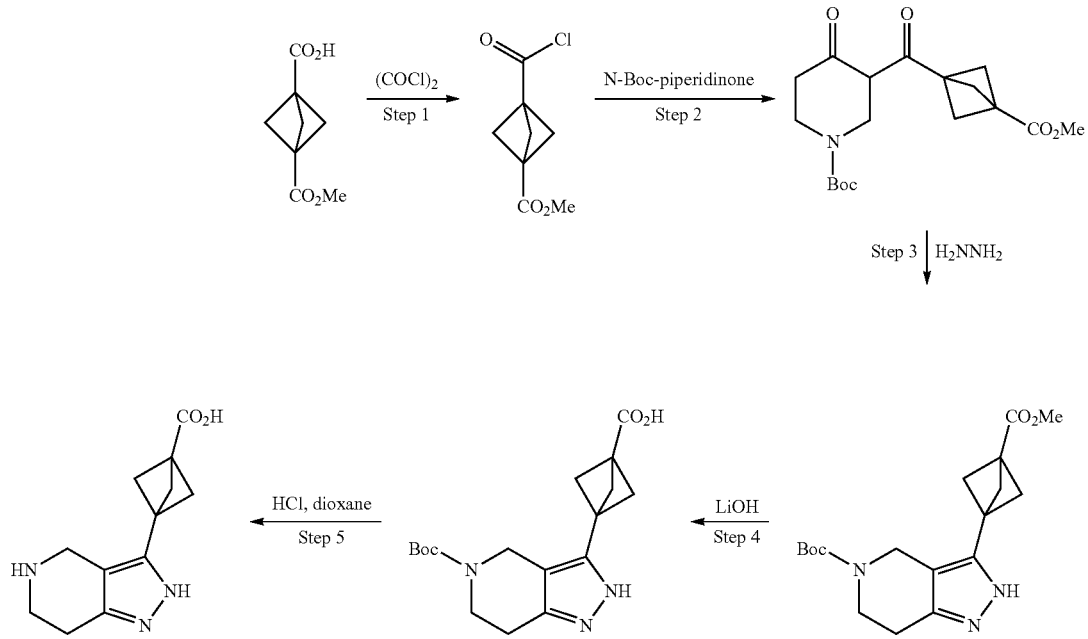

Step 1: To a stirred solution of 3-(methoxycarbonyl)bicyclo[1.1.1]pentane-1-carboxylic acid (1.0 g, 5.88 mmol) in dry DCM (20 mL), was added a drop of DMF. Oxalyl chloride (894.77 mg, 7.05 mmol) was then added dropwise and the mixture was stirred until gas evolution ceased. The mixture was then concentrated to afford methyl 3-(carboxy)bicyclo[1.1.1]pentane-1-carboxylate (1.1 g, 5.83 mmol, 99.3% yield) as yellow solid.

Step 2: To a cooled (−65° C.) solution of LiHMDS (11.6 mL, 11.6 mmol, 1M/L) in THF (20 mL) under argon was added a solution tert-butyl 4-oxopiperidine-1-carboxylate (2.32 g, 11.66 mmol) in THF (20.00 mL). The mixture was stirred at −65° C. for 0.5 h. A solution of methyl 3-(carboxy)bicyclo[1.1.1]pentane-1-carboxylate in THF (5 mL) was added dropwise at −65° C. The solution was warmed to r.t. and stirred for 1 h. The mixture was quenched by addition of saturated NH₄Cl solution (50 mL) and extracted with EtOAc (2×30 mL). The combined organic extracts were washed with brine, dried over Na₂SO₄ and concentrated to afford crude tert-butyl 3-[3-(methoxycarbonyl)bicyclo[1.1.1]pentane-1-carbonyl]-4-oxopiperidine-1-carboxylate (3.1 g, 2.65 mmol, 45.4% yield), that was used in the next step without further purification.

Step 3: To a stirred solution of tert-butyl 3-[3-(methoxycarbonyl)bicyclo[1.1.1]pentane-1-carbonyl]-4-oxopiperi- THF/H₂O (30 mL/5 mL) was added lithium hydroxide monohydrate (580 mg, 13.8 mmol). The mixture was stirred at r.t. overnight. The mixture was then concentrated, and the residue diluted with water (20 mL). The mixture was filtered and the filtrate acidified with 10% aq. HCl acid to pH 5-6. The precipitate was collected by filtration and dissolved in DCM. The solution was dried (Na₂SO₄), filtered and concentrated to afford 3-5-[(tert-butoxy)carbonyl]-2H,4H,5H,6H,7H-pyrazolo[4,3-c]pyridin-3-ylbicyclo[1.1.1]pentane-1-carboxylic acid (650.0 mg, 1.95 mmol, 42.3% yield) as yellow solid.

Step 5: To a stirred solution of 3-5-[(tert-butoxy)carbonyl]-2H,4H,5H,6H,7H-pyrazolo[4,3-c]pyridin-3-ylbicyclo[1.1.1]pentane-1-carboxylic acid (650 mg, 1.95 mmol) in dry DCM (5 ml) was added HCl (4M in dioxane, 4.8 mL, 19.5 mmol). The mixture was stirred overnight then concentrated, and the residue obtained triturated with acetonitrile. The participate was collected by filtration and dried to afford 3-2H,4H,5H,6H,7H-pyrazolo[4,3-c]pyridin-3-ylbicyclo[1.1.1]pentane-1-carboxylic acid dihydrochloride (336 mg, 583 μmol, 73.9% yield) as white solid Synthesis of methyl 3-{2H,4H,5H,6H,7H-pyrazolo[4,3-c]pyridin-3-yl}bicyclo[1.1.1]pentane-1-carboxylate

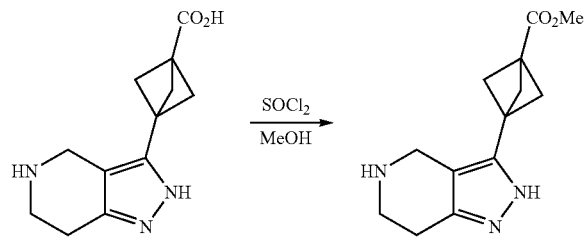 [SMILES: "MeOH" ; O=C(O)C12CC(c3[nH]nc4c3CNCC4)(C1)C2 ; "SOCl2" ; COC(=O)C12CC(c3[nH]nc4c3CNCC4)(C1)C2]

To a cooled (0° C.) solution of thionyl chloride (212 mg, 1.78 mmol, 130 µL) in MeOH (2 mL) was added 3-2H,4H,5H,6H,7H-pyrazolo[4,3-c]pyridin-3-ylbicyclo[1.1.1]pentane-1-carboxylic acid dihydrochloride (200 mg, 653 µmol). The mixture was stirred for 20 h at r.t. then concentrated to afford methyl 3-2H,4H,5H,6H,7H-pyrazolo[4,3-c]pyridin-3-ylbicyclo[1.1.1]pentane-1-carboxylate dihydrochloride (186.0 mg, 580.86 µmol, 88.9% yield) as yellow solid.

Synthesis of N-methyl-1-(5-methyl-1,3,4-oxadiazol-2-yl)cyclopropan-1-amine

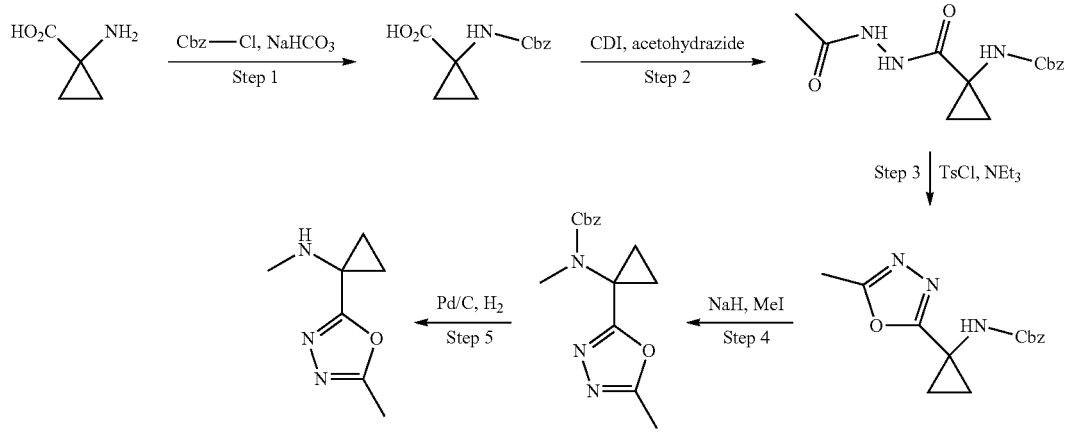

Step 1: 1-Aminocyclopropane-1-carboxylic acid (6.0 g, 59.34 mmol) and sodium hydrogen carbonate (19.94 g, 237.38 mmol) were dissolved in distilled water (50 mL) and the resulting mixture was diluted with THF (50 mL). The mixture was cooled to 0° C. with an ice/water bath and a solution of benzyl chloroformate (11.14 g, 65.28 mmol, 9.28 ml) in THF (10 mL) was added dropwise. The resulting mixture was stirred overnight then washed with EtOAc. The aqueous layer was separated, acidified to pH=1 with conc. HCl, and extracted with EtOAc (2×20 mL). The combine organic extracts were dried ($Na_2SO_4$) and concentrated under reduced pressure to give 1-[(benzyloxy)carbonyl]aminocyclopropane-1-carboxylic acid (6.0 g, 25.51 mmol, 43% yield) which was used for the next step without purification.

Step 2: To a solution of 1-[(benzyloxy)carbonyl]aminocyclopropane-1-carboxylic acid (6.0 g, 25.5 mmol) in DCM (100 mL) at r.t. was added 1-(1H-imidazole-1-carbonyl)-1H-imidazole (6.2 g, 38.3 mmol) in one portion. Upon completion of gas evolution (~20 min) acetohydrazide (3.78 g, 51.01 mmol) was added and the reaction mixture stirred overnight. The precipitate formed was collected by filtration, washed with DCM and dried to give benzyl N-[1-(N'-acetylhydrazinecarbonyl)cyclopropyl]carbamate (4.0 g).

The filtrate was concentrated under reduced pressure. The residue was partitioned between EtOAc (100 mL) and aqueous sodium hydrogensulfate solution (100 mL). The organic phase was washed with water, brine, dried over sodium sulfate and concentrated under reduced pressure to afford second portion of product (2.5 g). Portions were combined to obtain benzyl N-[1-(N'-acetylhydrazinecarbonyl)cyclopropyl]carbamate (6.5 g, 22.31 mmol, 87.5% yield) as a white solid.

Step 3: Benzyl N-[1-(N'-acetylhydrazinecarbonyl)cyclopropyl]carbamate (6.5 g, 22.3 mmol) was suspended in DCM (100 mL). Triethylamine (4.97 g, 49.09 mmol, 6.84 ml) was added in one portion and the resulting mixture was cooled to 0° C. with an ice/water bath. A solution of 4-methylbenzene-1-sulfonyl chloride (4.47 g, 23.4 mmol) in DCM (50 mL) was added. The resulting mixture was then warmed, then heated at reflux. The resulting mixture was washed with water (2×10 mL), sat. aq. sodium bicarbonate, brine, dried over $Na_2SO_4$ and concentrated under reduced pressure. The residue was purified by column chromatography (1st run: Interchim, 220 g SiO2, MTBE/methanol with methanol from 0-10%, flow rate=100 mL/min, Rv=6 CV; 2nd run: Interchim, 80 g SiO2, chloroform/acetonitrile with acetonitrile from 0-50%, flow rate=60 mL/min, Rv=10 CV) to obtain benzyl N-[1-(5-methyl-1,3,4-oxadiazol-2-yl)cyclopropyl]carbamate (2.69 g, 9.82 mmol, 44% yield) as yellow solid.

Step 4: Sodium hydride (126.49 mg, 5.27 mmol) was suspended in dry THF (30 mL). A solution of benzyl N-[1-(5-methyl-1,3,4-oxadiazol-2-yl)cyclopropyl]carbamate (1.2 g, 4.39 mmol) in dry THF (10 mL) was added dropwise at 15° C. (water bath). The resulting mixture was stirred until gas release was complete then cooled to 0° C. Iodomethane (748 mg, 5.27 mmol, 330 µl) was added dropwise, and the resulting mixture was warmed to r.t. and stirred overnight. The mixture was then extracted with EtOAc (2×20 mL), and the combined organic extracts were dried over sodium sulfate then concentrated under reduced pressure to obtain crude benzyl N-methyl-N-[1-(5-methyl-1,3,4-oxadiazol-2-yl)cyclopropyl]carbamate (1.33 g, 4.62 mmol, 105.2% yield) which was used for the next step without purification.

Step 5: To a solution of benzyl N-methyl-N-[1-(5-methyl-1,3,4-oxadiazol-2-yl)cyclopropyl]carbamate (1.33 g, 4.62 mmol) in dry methanol (20 mL) was added 10% Pd/C (100 mg). The resulting mixture was stirred under at atmosphere of H$_2$. When reaction was complete (according to 1H NMR of the reaction mixture) the mixture was filtered and the filtrate concentrated. The residue was purified by HPLC to obtain N-methyl-1-(5-methyl-1,3,4-oxadiazol-2-yl)cyclopropan-1-amine (140 mg, 913 µmol, 19.7% yield).

Synthesis of
N-methyl-1-(1,3-oxazol-2-yl)cyclopropan-1-amine

Step 3: N-(2,2-dimethoxyethyl)-1-(1,3-dioxo-2,3-dihydro-1H-isoindol-2-yl)cyclopropane-1-carboxamide (10.5 g, 33.0 mmol) was added to methanesulfonic acid (100 g) followed by addition of phosphorus pentoxide (7.7 g) and the mixture was stirred at 140° C. overnight. The resulting dark solution was cooled to r.t., poured into ice, and the pH of the resulting mixture was adjusted to 8 with saturated NaHCO$_3$ solution. The product was extracted with ethyl acetate (2×200 mL). The combined organic extracts were washed with brine, dried over sodium sulfate and evaporated.

The residue obtained was triturated with Et$_2$O and product collected by filtration. The resulting white solid was dried to

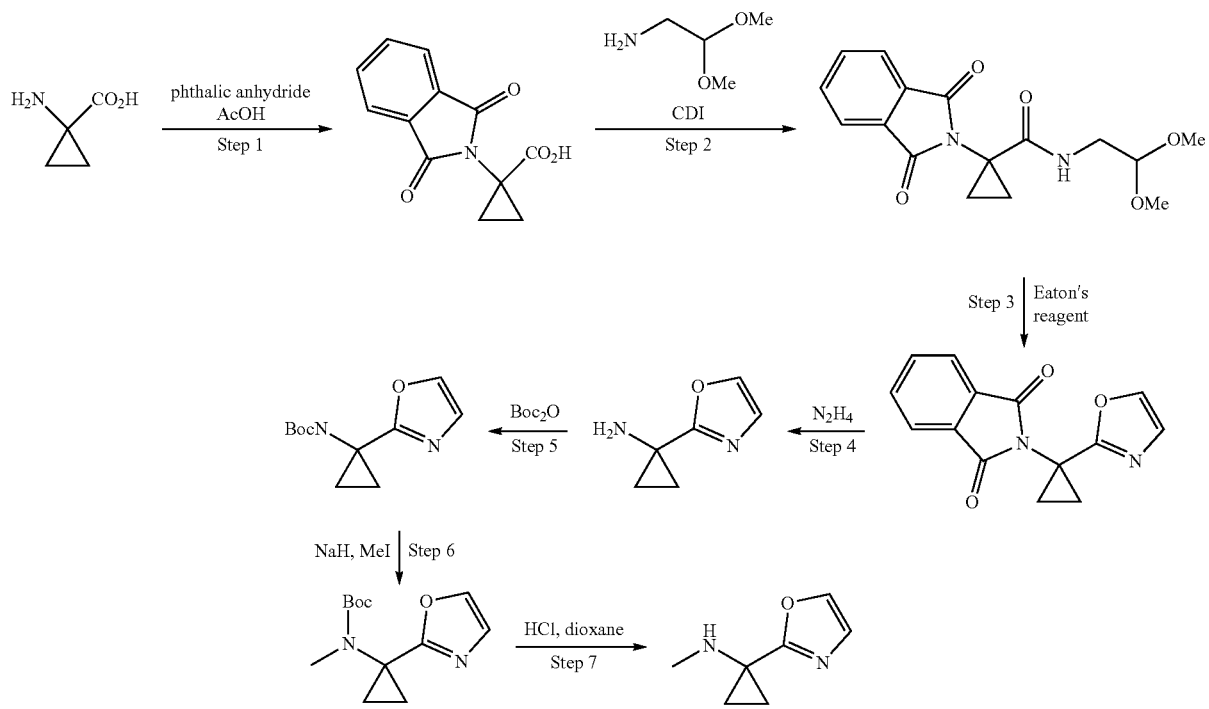

Step 1: 1-Aminocyclopropane-1-carboxylic acid (4.85 g, 48.0 mmol) was suspended in glacial acetic acid (50 mL). Phthalic anhydride (7.11 g, 48.0 mmol) was added and the resulting mixture was stirred at 110° C. overnight. stirring at 110° C. overnight. The mixture was cooled to r.t. and triturated with water (200 mL). The precipitate was collected by filtration, washed with water and dried to obtain 1-(1,3-dioxo-2,3-dihydro-1H-isoindol-2-yl)cyclopropane-1-carboxylic acid (8.8 g, 38.1 mmol, 79.3% yield) as white solid.

Step 2: To a solution of 1-(1,3-dioxo-2,3-dihydro-1H-isoindol-2-yl)cyclopropane-1-carboxylic acid (8.8 g, 38.1 mmol) in DCM (100 mL) and THF (10 mL) at r.t. was added 1-(1H-imidazole-1-carbonyl)-1H-imidazole (6.79 g, 41.9 mmol). After complete reaction (monitored by NMR), 2,2-dimethoxyethan-1-amine (4.4 g, 41.9 mmol, 4.56 ml) was added at r.t and the mixture stirred overnight. The mixture then was concentrated under reduced pressure and the residue was triturated with distilled water (15 mL). The resulting precipitate was collected by filtration, washed with water (2×15 mL) and dissolved in DCM. The organic layer was collected, dried (Na$_2$SO$_4$) and concentrated under reduced pressure to obtain N-(2,2-dimethoxyethyl)-1-(1,3-dioxo-2,3-dihydro-1H-isoindol-2-yl)cyclopropane-1-carboxamide (6.0 g, 18.9 mmol, 49.5% yield).

obtain 2-[1-(1,3-oxazol-2-yl)cyclopropyl]-2,3-dihydro-1H-isoindole-1,3-dione (2.3 g, 9.05 mmol, 27.4% yield).

Step 4: To a solution of 2-[1-(1,3-oxazol-2-yl)cyclopropyl]-2,3-dihydro-1H-isoindole-1,3-dione (2.3 g, 9.05 mmol) in ethanol (50 mL) was added hydrazine hydrate (2.26 g, 45.23 mmol, 2.26 ml). The resulting mixture was stirred at 50° C. overnight. The resulting mixture was cooled to r.t. and concentrated in vacuo. The residue obtained was triturated with DCM. The resulting precipitate was filtered off and the filtrate concentrated under reduced pressure to obtain crude 1-(1,3-oxazol-2-yl)cyclopropan-1-amine (1.24 g, 10.0 mmol) as colorless oil, which was used in the next step without further purification.

Step 5: Di-tert-butyl dicarbonate (2.18 g, 10.0 mmol, 2.3 ml) was added dropwise to a solution of 1-(1,3-oxazol-2-yl)cyclopropan-1-amine (1.24 g, 10.0 mmol) in dry DCM (10 mL). The resulting mixture was stirred until completion (1H NMR), and concentrated under reduced pressure. The residue was purified by flash column chromatography (80 g SiO2, petroleum ether/MTBE with MTBE from 0-40%, flow rate=60 mL/min, Rv=8 CV) to obtain tert-butyl N-[1-(1,3-oxazol-2-yl)cyclopropyl]carbamate (400 mg, 1.78 mmol, 17.8% yield) as yellow oil.

Step 6: Sodium hydride (51.36 mg, 2.14 mmol) was suspended in 10 ml of dry THF. A solution of tert-butyl N-[1-(1,3-oxazol-2-yl)cyclopropyl]carbamate (400 mg, 1.78 mmol) in dry THF (2 mL) was added dropwise (water bath cooling). The resulting mixture was stirred until gas evolution ceased and was then cooled (0° C.). Iodomethane (304 mg, 2.14 mmol, 130 µL) was added dropwise and the resulting mixture was warmed to r.t. and stirred overnight. The reaction mixture was poured into saturated aq. ammonium chloride solution. The resulting mixture was extracted with EtOAc (2×10 mL) and the combined organic extracts were dried over sodium sulfate then concentrated under reduced pressure. The residue was purified by HPLC (column: Waters SunFire C18, 5 mkm, 19 mm×100 mm; mobile phase: water-acetonitrile, 30 mL/min) to obtain tert-butyl N-methyl-N-[1-(1,3-oxazol-2-yl)cyclopropyl]carbamate (29 mg, 122 µmol, 6.8% yield).

Step 7: Tert-butyl N-methyl-N-[1-(1,3-oxazol-2-yl)cyclopropyl]carbamate (29.0 mg, 121.7 µmol) was dissolved in 4M HCl/dioxane (2 mL) at r.t. and the resulting mixture was stirred overnight. The resulting mixture was concentrated under reduced pressure to obtain N-methyl-1-(1,3-oxazol-2-yl)cyclopropan-1-amine hydrochloride (14 mg, 80.17 µmol, 83.3% yield).

Step 3: Tert-butyl N-(1-formylcyclopropyl)-N-methylcarbamate (477 mg, 2.39 mmol) was mixed with 1-isocyanomethanesulfonyl-4-methylbenzene (514 mg, 2.63 mmol) in dry methanol (50 mL) followed by addition of potassium carbonate (695 mg, 5.03 mmol). The resulting mixture was at reflux for 2 hours. Distilled water (20 mL) was then added to the hot reaction mixture and the resulting solution extracted with EtOAc (2×15 mL). The combined organic extracts were dried (sodium sulfate) and concentrated under reduced pressure. The residue was purified by column chromatography (40 g SiO2, chloroform/acetonitrile with acetonitrile from 0 to 20%, flow rate=40 mL/min) to obtain tert-butyl N-methyl-N-[1-(1,3-oxazol-5-yl)cyclopropyl]carbamate (400.0 mg, 1.68 mmol, 70.1% yield).

Step 4: Tert-butyl N-methyl-N-[1-(1,3-oxazol-5-yl)cyclopropyl]carbamate (370 mg, 1.55 mmol) was dissolved in TFA (5 mL) and the resulting mixture was left to stir at r.t. overnight. When the reaction was complete (monitored by LCMS of the reaction mixture) the excess of TFA was evaporated to obtain N-methyl-1-(1,3-oxazol-5-yl)cyclopropan-1-amine trifluoroacetate (360 mg, 2.1 mmol, 100% yield).

Synthesis of
N-methyl-1-(1,3-oxazol-5-yl)cyclopropan-1-amine

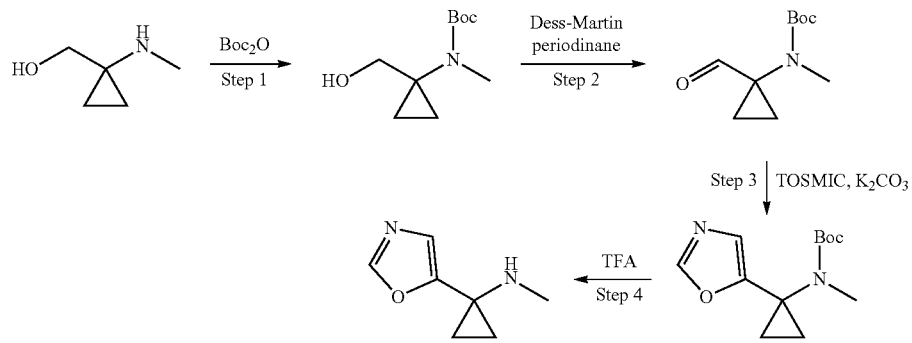

Step 1: Di-tert-butyl dicarbonate (1.75 g, 8.0 mmol) was added portionwise to a mixture of (1-(methylamino)cyclopropyl)methanol hydrochloride (1.0 g, 7.27 mmol) and triethylamine (957 mg, 9.46 mmol) in DCM (20 mL) and left to stir overnight at r.t. After reaction was complete (monitored by 1H NMR) the mixture was washed with water (10 mL), dried over Na₂SO₄ and concentrated in vacuum to give tert-butyl N-[1-(hydroxymethyl)cyclopropyl]-N-methylcarbamate (1.2 g, 5.97 mmol, 82% yield).

Step 2: To a cooled (0° C.) solution of tert-butyl N-[1-(hydroxymethyl)cyclopropyl]-N-methylcarbamate (500.01 mg, 2.48 mmol) in DCM (50 mL) was added 1,1,1-tris(acetoxy)-1,1-dihydro-1,2-benziodoxol-3(1H)-one (1.16 g, 2.73 mmol). When reaction was complete (monitored by 1H NMR) the mixture was poured into an aqueous solution of NaHCO₃ and Na₂S₂O₃, then stirred until organic phase became transparent (~1 h). The layers were separated and the aqueous layer extracted with DCM (3×50 mL). The combined organic extracts were washed with brine, dried over Na₂SO₄ and concentrated under reduced pressure to give crude tert-butyl N-(1-formylcyclopropyl)-N-methylcarbamate (620 mg, 3.11 mmol) which was used for the next step without further purification.

Synthesis of
N-methyl-1-(1,3-oxazol-4-yl)cyclopropan-1-amine

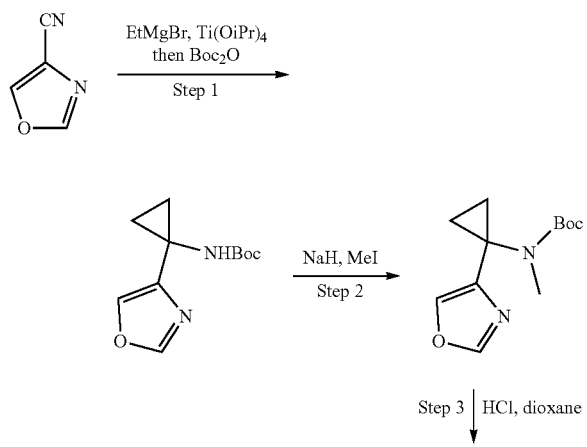

-continued

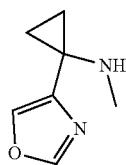

Step 1: To a cooled (−70° C.) solution of 1,3-oxazole-4-carbonitrile (4.0 g, 42.52 mmol) and titanium tetraisopropoxide (13.29 g, 46.77 mmol) in Et$_2$O (220 mL) was added ethylmagnesium bromide (11.9 g, 89.29 mmol). The resulting yellow solution was stirred for 10 min. The solution was warmed to r.t. and stirred for 1 h. Boron trifluoride-diethyl etherate (12.07 g, 85.04 mmol, 10.73 ml) was added and the mixture stirred for a further 1 h. 1N HCl (100 mL) and ether (200 mL) were added. NaOH (10% aq, 200 mL) was added to the resulting two clear phases, followed by addition of di-tert-butyl dicarbonate (46.4 g, 212.59 mmol, 48.84 ml). The resulting biphasic mixture was stirred vigorously overnight. The layers were separated and the aqueous phase was extracted with 300 mL of diethyl ether. The combined organic extracts were dried over Na$_2$SO$_4$, filtered and concentrated under reduced pressure to give viscous yellow oil, which mainly consisted of desired product and Boc$_2$O (shown by 1H NMR). This oil was dissolved in 100 mL of dioxane and the resulting solution was added dropwise to a solution of 2-aminoacetic acid (15.96 g, 212.59 mmol) and sodium carbonate (22.53 g, 212.59 mmol) in 200 mL of water at r.t. The resulting mixture was left stirring overnight before all volatiles were removed under vacuum. The residue was partitioned between 300 mL of water and 150 mL of MTBE. The organic phase was washed with 50 mL of water, brine, dried over Na$_2$SO$_4$ and concentrated under reduced pressure to give tert-butyl N-[1-(1,3-oxazol-4-yl)cyclopropyl]carbamate (7.2 g, 32.11 mmol, 75.5% yield) as light yellow crystalline solid.

Step 2: To a solution of tert-butyl N-[1-(1,3-oxazol-4-yl)cyclopropyl]carbamate (2.0 g, 8.92 mmol) in 50 mL of DMF was added sodium hydride (60%, 321.02 mg, 13.38 mmol) portionwise, maintaining the temperature below 25° C. (water cooling bath). After gas evolution was complete, iodomethane (3.16 g, 22.29 mmol, 1.39 ml) was added dropwise and the resulting mixture was left to stir overnight at r.t. The reaction mixture was poured into 500 mL of water and extracted with 150 mL of ethyl acetate. The organic phase was washed with water (2×100 mL), brine, dried over Na$_2$SO$_4$ and concentrated in vacuo to give tert-butyl N-methyl-N-[1-(1,3-oxazol-4-yl)cyclopropyl]carbamate (2.15 g, 90.0% purity, 8.12 mmol, 91.1% yield) as yellow crystalline solid.

Step 3: Tert-butyl N-methyl-N-[1-(1,3-oxazol-4-yl)cyclopropyl]carbamate (2.15 g, 9.02 mmol) was dissolved in 50 mL of 4M HCl/dioxane at r.t. and the resulting mixture was stirred overnight. The resulting mixture was diluted with 50 mL of diethyl ether and product collected by filtration. The solid was washed with 20 mL of ether, and dried in vacuo to obtain N-methyl-1-(1,3-oxazol-4-yl)cyclopropan-1-amine hydrochloride (1.32 g, 7.56 mmol, 83.8% yield) as light yellow powder.

Synthesis of
N-methyl-1-(1,2-oxazol-5-yl)cyclopropan-1-amine

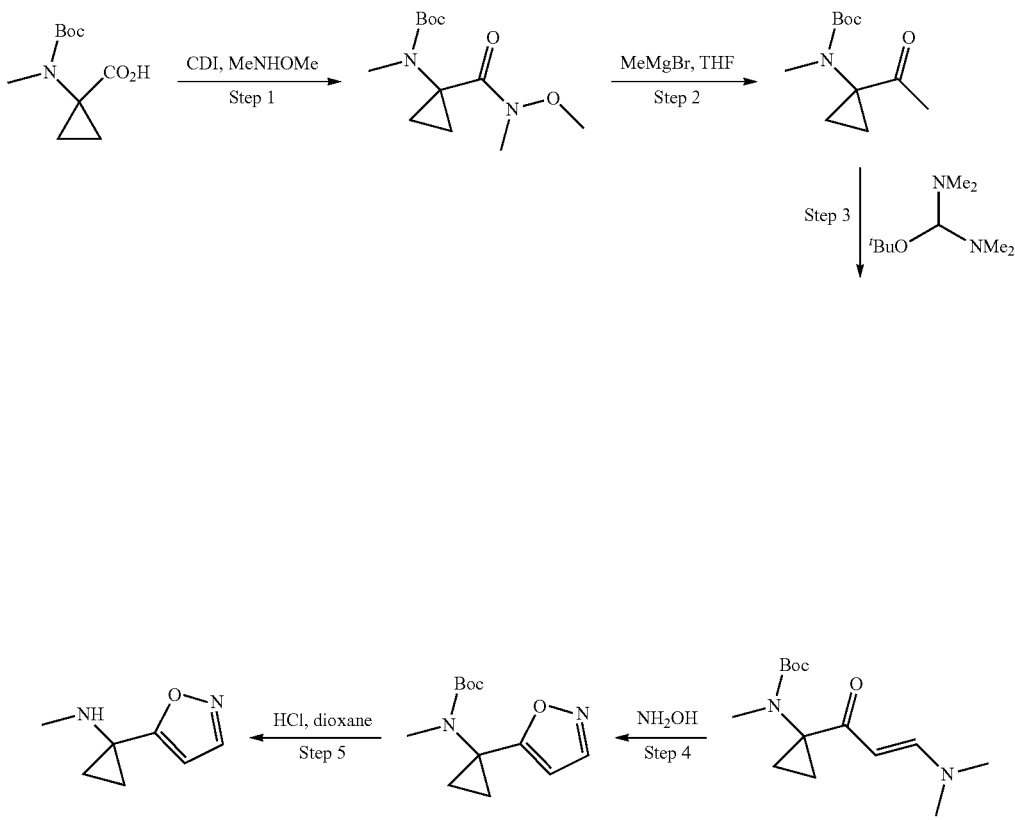

Step 1: To a solution of 1-[(tert-butoxy)carbonyl](methyl) aminocyclopropane-1-carboxylic acid (6.0 g, 27.88 mmol) in dry DCM (300 mL) at r.t. was added 1-(1H-imidazole-1-carbonyl)-1H-imidazole (6.78 g, 41.82 mmol). When gas evolution was complete (~20 min), methoxy(methyl)amine hydrochloride (6.8 g, 69.7 mmol) was added and the resulting mixture was stirred overnight. The reaction mixture was diluted with petroleum ether (300 mL) and washed with water (3×300 mL). The organic phase was separated, washed with brine, dried over sodium sulfate and concentrated under reduced pressure to obtain tert-butyl N-1-[methoxy(methyl)carbamoyl]cyclopropyl-N-methylcarbamate (3.95 g, 96.0% purity, 14.7 mmol, 52.7% yield) as a colorless oil.

Step 2: To a solution of tert-butyl N-1-[methoxy(methyl)carbamoyl]cyclopropyl-N-methylcarbamate (3.77 g, 14.6 mmol) in 100 mL of THF at r.t. under argon atmosphere was added methylmagnesium bromide (5.22 g, 43.8 mmol, 13.7 ml). The mixture was stirred at r.t. overnight, quenched by addition of saturated aqueous NH4Cl solution (50 mL) and concentrated under reduced pressure. The residue was partitioned between 200 mL of water and 200 mL of MTBE. The organic layer was washed with 100 mL of water, brine, dried over Na2SO4 and concentrated under reduced pressure to give tert-butyl N-(1-acetylcyclopropyl)-N-methylcarbamate (2.71 g, 96.0% purity, 12.2 mmol, 83.6% yield) as light yellow liquid.

Step 3: Tert-butyl N-(1-acetylcyclopropyl)-N-methylcarbamate (2.71 g, 12.71 mmol) was dissolved in tert-butoxy bis(dimethylamino)methane (50 mL) and heated at 75° C. overnight. The reaction mixture was concentrated under reduced pressure to obtain 6.65 g of an orange oil. 2 g of this oil were purified by flash chromatography (40 g SiO2, petroleum ether/MTBE with MTBE from 15-100% and MTBE/methanol with methanol from 0-15%, flow rate=40 mL/min, R$^v$=21.5 CV) to obtain tert-butyl N-1-[(2E)-3-(dimethylamino)prop-2-enoyl]cyclopropyl-N-methylcarbamate (580 mg, 2.16 mmol) as a colorless liquid.

Step 4: A mixture of tert-butyl N-1-[(2E)-3-(dimethylamino)prop-2-enoyl]cyclopropyl-N-methylcarbamate (580.0 mg, 2.16 mmol) and hydroxylamine hydrochloride (165 mg, 2.38 mmol) in dry methanol (20 mL) was heated at 50° C. under an argon atmosphere for 20 h. The reaction mixture was then concentrated under reduced pressure. The residue was partitioned between ethyl acetate (20 mL) and water (50 mL). The organic layer was washed with water, brine, dried over Na2SO4 and concentrated under reduced pressure to give tert-butyl N-methyl-N-[1-(1,2-oxazol-5-yl)cyclopropyl]carbamate (455 mg, 1.91 mmol, 88.3% yield) as light yellow oil.

Step 5: Tert-butyl N-methyl-N-[1-(1,2-oxazol-5-yl)cyclopropyl]carbamate (455 mg, 1.91 mmol) was dissolved in 10 mL of 4M HCl/dioxane at r.t. and the resulting mixture was stirred overnight. The resulting mixture was concentrated under reduced pressure and the residue was triturated with ethyl acetate (10 mL). The pale brown solid obtained was collected by filtration and dried under vacuum to give N-methyl-1-(1,2-oxazol-5-yl)cyclopropan-1-amine hydrochloride (210.0 mg, 1.2 mmol, 63.1% yield) as crystalline solid.

Synthesis of
N-methyl-1-(1,2-oxazol-3-yl)cyclopropan-1-amine

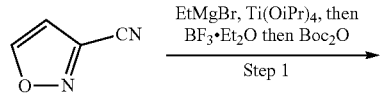

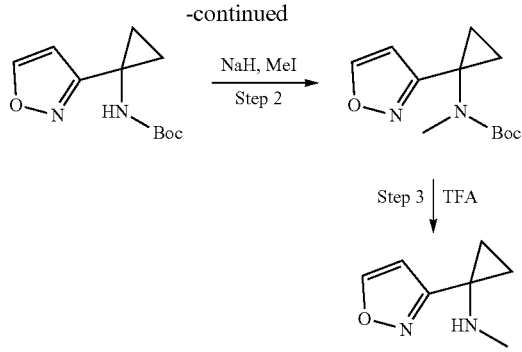

Step 1: To a cooled (~70° C.) to solution of 1,2-oxazole-3-carbonitrile (4.0 g, 42.5 mmol) and titanium tetraisopropoxide (13.3 g, 46.8 mmol) in Et2O (200 mL) was added ethylmagnesium bromide (11.9 g, 89.3 mmol, 26.3 ml). The resulting yellow solution was stirred for 10 min at −70° C. then slowly warmed to r.t. Boron trifluoride-diethyl etherate (12.1 g, 85.1 mmol, 10.7 ml) was then added. After stirring for 1 h, 1N HCl (100 mL) and diethyl ether (200 mL) were added. NaOH (10% aq, 200 mL) was added to the resulting mixture, followed by addition of di-tert-butyl dicarbonate (46.4 g, 212 mmol, 48.9 ml). The resulting biphasic mixture was stirred vigorously overnight. The phases were separated, and the aqueous phase was extracted with diethyl ether (3×100 mL). The combined organic extracts were dried over Na2SO4, filtered and concentrated under reduced pressure to give viscous yellow oil, which mainly consisted of desired product and Boc2O. This oil was dissolved in 50 mL of dioxane. To this solution was added dropwise a solution of 2-aminoacetic acid (15.96 g, 212.66 mmol) and sodium carbonate (22.54 g, 212.66 mmol) in 100 ml of water. The mixture was left to stir overnight then concentrated under reduced pressure. The residue was partitioned between 300 ml of water and 150 ml of MTBE. The organic phase was washed with 5 mL of water, brine, dried over Na2SO4 and concentrated under reduced pressure to give tert-butyl N-[1-(1,2-oxazol-3-yl)cyclopropyl]carbamate (6.0 g, 26.8 mmol, 62.9% yield) as light yellow oil.

Step 2: Sodium hydride (67 mg, 2.81 mmol) was suspended in 10 mL of dry THF. A solution of tert-butyl N-[1-(1,2-oxazol-3-yl)cyclopropyl]carbamate (524 mg, 2.34 mmol) in 2 mL of dry THF was then added dropwise (water bath cooling). The resulting mixture was stirred until gas evolution ceased and then cooled to 0° C. Iodomethane (498 mg, 3.51 mmol, 220 μL) was added dropwise and the resulting mixture was warmed to r.t. and then stirred overnight. The reaction mixture was poured into saturated aq. ammonium chloride solution. The resulting mixture was extracted EtOAc (2×10 mL). The combined organic extracts were combined, dried over sodium sulfate and concentrated under reduced pressure giving crude tert-butyl N-methyl-N-[1-(1,2-oxazol-3-yl)cyclopropyl]carbamate (537 mg, 2.25 mmol, 96.4% yield) which was used in next step without purification.

Step 3: tert-Butyl N-methyl-N-[1-(1,2-oxazol-3-yl)cyclopropyl]carbamate (536 mg, 2.25 mmol) was dissolved in 50 ml of dry DCM. 2,2,2-Trifluoroacetic acid (770 mg, 6.75 mmol, 520 μl) was added in one portion and the resulting mixture was stirred at r.t. overnight. The reaction mixture was concentrated under reduced pressure to obtain N-methyl-1-(1,2-oxazol-3-yl)cyclopropan-1-amine (64 mg, 463 μmol, 20.6% yield).

Synthesis of N-methyl-1-(3-methyl-1,2,4-oxadiazol-5-yl)cyclopropan-1-amine

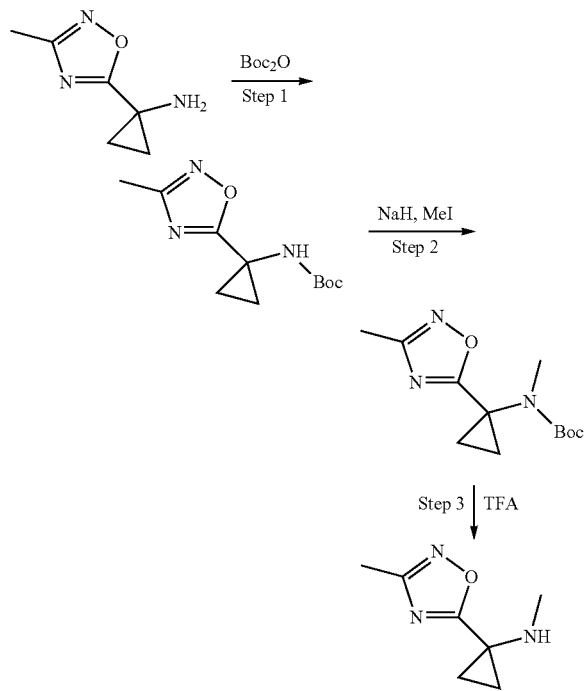

Step 1: 1-(3-Methyl-1,2,4-oxadiazol-5-yl)cyclopropan-1-amine hydrochloride (1.5 g, 8.54 mmol) and di-tert-butyl dicarbonate (2.05 g, 9.39 mmol, 2.16 mL) were mixed in dichloromethane (50 mL), and triethylamine (949.0 mg, 9.38 mmol, 1.31 mL) was added dropwise at 0° C. The reaction mixture was stirred at ambient temperature overnight then washed with water (2×10 mL), dried over sodium sulfate and evaporated in vacuo to give tert-butyl N-[1-(3-methyl-1,2,4-oxadiazol-5-yl)cyclopropyl]carbamate (1.61 g, 6.72 mmol, 78.9% yield).

Step 2: Sodium hydride (209.7 mg, 8.74 mmol) was suspended in dry THF (10 mL). A solution of tert-butyl N-[1-(3-methyl-1,2,4-oxadiazol-5-yl)cyclopropyl]carbamate (1.61 g, 6.72 mmol) in dry THF (10 mL) was added dropwise (water bath cooling). The resulting mixture was stirred until gas release was complete, and then cooled to 0° C. Iodomethane (1.05 g, 7.4 mmol, 460.0 µL) was added dropwise. The resulting mixture was warmed to r.t. and then stirred overnight. The reaction mixture was poured into saturated aq. ammonium chloride solution and extracted twice with 20 mL of CH$_2$Cl$_2$. The combined organic extracts were dried over sodium sulfate and concentrated. The residue (1.56 g) was purified by column chromatography on silica gel using hexane/MTBE (gradient 100/0 to 50/50) as eluent to obtain tert-butyl N-methyl-N-[1-(3-methyl-1,2,4-oxadiazol-5-yl)cyclopropyl]carbamate (914.0 mg, 3.61 mmol, 53.7% yield) as colorless oil.

Step 3: tert-Butyl N-methyl-N-[1-(3-methyl-1,2,4-oxadiazol-5-yl)cyclopropyl]carbamate (914.0 mg, 3.61 mmol) was dissolved in 50 ml of dry DCM. 2,2,2-Trifluoroacetic acid (2.06 g, 18.04 mmol, 1.39 mL) was added in one portion and the resulting mixture was stirred at r.t. overnight. The reaction mixture was concentrated giving N-methyl-1-(3-methyl-1,2,4-oxadiazol-5-yl)cyclopropan-1-amine trifluoroacetate (522.0 mg, 1.95 mmol, 54.1% yield)

Synthesis of 1-amino-N-methylcyclopropane-1-carboxamide

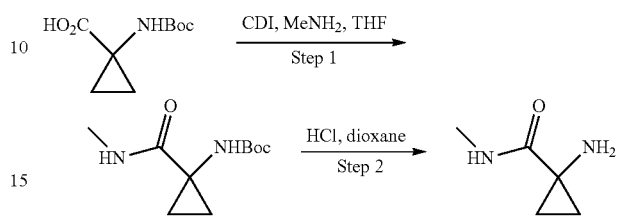

Step 1: 1-(1H-imidazole-1-carbonyl)-1H-imidazole (2.42 g, 14.9 mmol) was added to a solution of 1-((tert-butoxycarbonyl)amino)cyclopropanecarboxylic acid (2.0 g, 9.94 mmol) in 10 mL of dry THF at r.t. When the gas release completed (~20 min), a solution of methanamine (50 mL, 20% solution in methanol) was added dropwise. The resulting solution was stirred overnight. The solvent was evaporated in vacuo and the residue was partitioned between DCM (30 mL) and water (10 mL). The organic phase was separated, washed with water, brine, dried over sodium sulfate and concentrated under reduced pressure to obtain tert-butyl N-[1-(methylcarbamoyl)cyclopropyl]carbamate (1.9 g, 8.89 mmol, 89.4% yield) as a white solid.

Step 2: Tert-butyl N-[1-(methylcarbamoyl)cyclopropyl]carbamate (1.9 g, 8.89 mmol) was dissolved in 25 mL of 4M HCl in dioxane. and the resulting mixture was stirred overnight. The mixture was concentrated under reduced pressure to obtain 1-amino-N-methylcyclopropane-1-carboxamide hydrochloride (1.29 g, 8.58 mmol, 96.4% yield) as a white solid.

Synthesis of N-methyl-1-(oxolan-2-yl)cyclopropan-1-amine

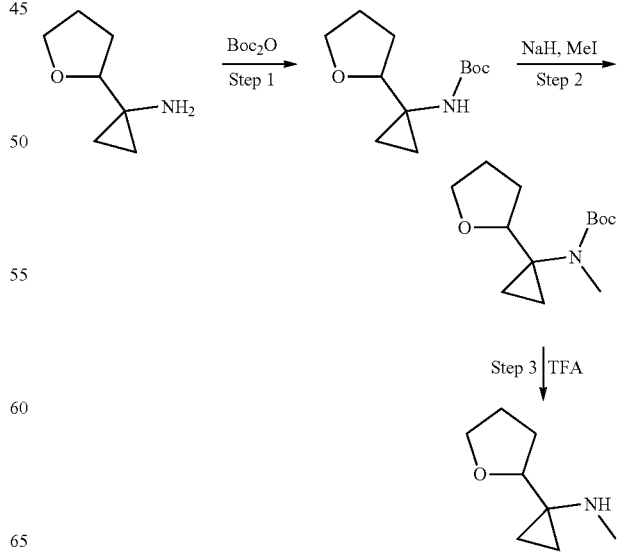

Step 1: To a stirred solution of 1-(oxolan-2-yl)cyclopropan-1-amine (669 mg, 5.26 mmol) in dry DCM (10 ml) was added di-tert-butyl dicarbonate (1.15 g, 5.26 mmol). The reaction mixture was stirred at r.t. for 4 h. The reaction mixture was concentrated to afford tert-butyl N-[1-(oxolan-2-yl)cyclopropyl]carbamate (1.19 g, 95.0% purity, 4.97 mmol, 94.5% yield) as white solid.

Step 2: To a cooled (0° C.) stirred suspension of sodium hydride (0.376 g, 15.7 mmol) in dry THF (20 mL) was added dropwise a solution of tert-butyl N-[1-(oxolan-2-yl)cyclopropyl]carbamate (1.19 g, 5.23 mmol) in THF (5 ml). The reaction mixture was stirred for 30 min at r.t. and cooled again to 0° C. Iodomethane (2.23 g, 15.7 mmol) was added dropwise and the reaction mixture was stirred overnight at r.t. The reaction mixture was carefully poured into brine (20 mL) and extracted with EtOAc (3×15 mL). The combined organic extracts were washed with brine, dried over Na$_2$SO$_4$, filtered and concentrated to afford tert-butyl N-methyl-N-[1-(oxolan-2-yl)cyclopropyl]carbamate (1.0 g, 4.14 mmol, 79.2% yield) as yellow oil.

Step 3: To a cooled (0° C.) solution of tert-butyl N-methyl-N-[1-(oxolan-2-yl)cyclopropyl]carbamate (1.0 g, 4.14 mmol) in dry DCM (5 ml) was added 2,2,2-trifluoroacetic acid (2.36 g, 20.7 mmol, 1.6 ml). The reaction mixture was stirred for 4 h at r.t., concentrated under reduced pressure and the residue was co-evaporated with water, and dried under vacuum to afford N-methyl-1-(oxolan-2-yl)cyclopropan-1-amine trifluoroacetate (580 mg, 2.39 mmol, 99.1% yield) as brown oil.

Synthesis of 7-fluoro-4-azaspiro[2.5]octane

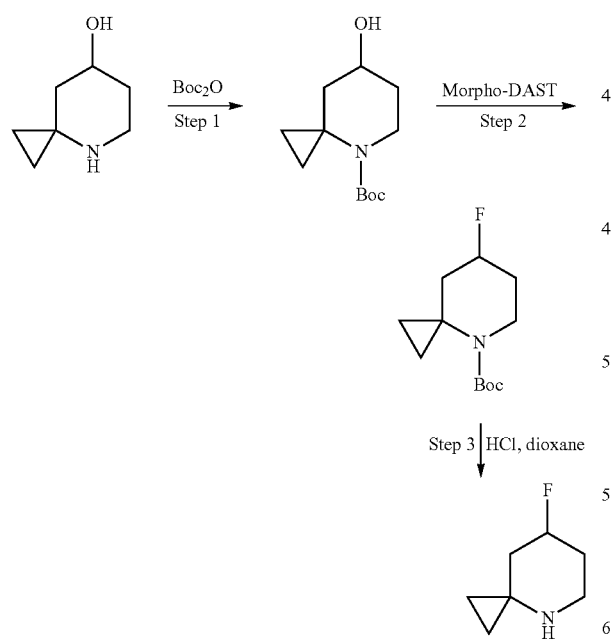

Step 1: To a stirred suspension of 4-azaspiro[2.5]octan-7-ol hydrochloride (1.06 g, 6.48 mmol) in dry DCM (30 mL) was added di-tert-butyl dicarbonate (1.41 g, 6.48 mmol), followed by triethylamine (655 mg, 6.48 mmol, 900.0 µl). The reaction mixture was stirred at r.t. overnight. The reaction mixture was concentrated, the residue was diluted with MTBE (30 mL), the precipitate of triethylamine hydrochloride was filtered off and the filtrate was evaporated to afford tert-butyl 7-hydroxy-4-azaspiro[2.5]octane-4-carboxylate (1.45 g, 6.38 mmol, 98.5% yield) as yellow oil.

Step 2: To a cooled (−40° C.) solution of tert-butyl 7-hydroxy-4-azaspiro[2.5]octane-4-carboxylate (1.45 g, 6.37 mmol) in dry DCM (25 ml) under argon was added dropwise 4-morpholinylsulfur trifluoride (2.46 g, 14.0 mmol, 1.71 ml). The reaction mixture was warmed to r.t. and stirred overnight. The reaction mixture diluted with DCM and quenched with sat. aq. sodium bicarbonate. The organic phase was washed with brine and concentrated. The residue was dissolved in DCM (30 ml), a saturated aq. solution of potassium permanganate (50 ml) was added and the reaction mixture was stirred for 2 h. The organic phase was separated, washed with brine, dried over sodium sulfate and concentrated. The residue was purified by column chromatography on silica with hexane-EtOAc 9:1 as an eluent to afford tert-butyl 7-fluoro-4-azaspiro[2.5]octane-4-carboxylate (290 mg, 1.26 mmol, 19.8% yield) as yellow oil.

Step 3: To a solution of tert-butyl 7-fluoro-4-azaspiro[2.5]octane-4-carboxylate (290.0 mg, 1.26 mmol) in DCM (5 mL) was added HCl (4M in dioxane, 2 mL). The reaction mixture was stirred overnight then concentrated The residue was dried under reduced pressure to afford 7-fluoro-4-azaspiro[2.5]octane hydrochloride (209 mg, 92.0% purity, 1.16 mmol, quan. yield) as white solid.

Synthesis of 4-azaspiro[2.6]nonane

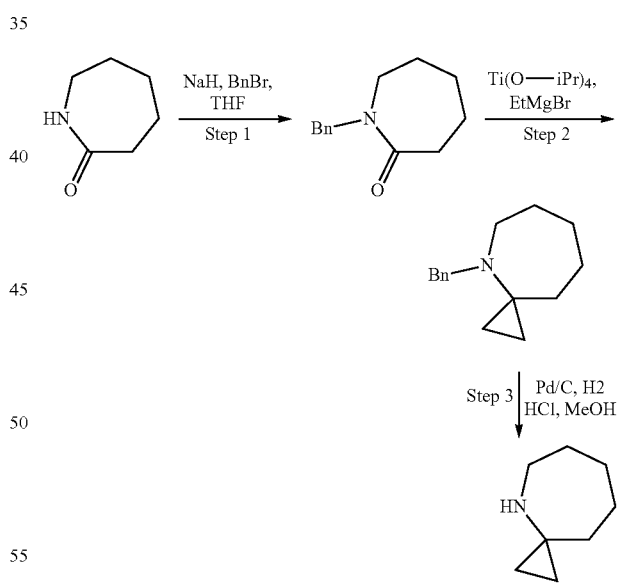

Step 1: To a solution of azepan-2-one (681 mg, 6.02 mmol) in THF (15 mL) was added sodium hydride (159 mg, 6.62 mmol) in small portions, maintaining temperature below 25° C. with a water cooling bath. After gas evolution ceased (bromomethyl)benzene (1.13 g, 6.62 mmol) was added dropwise and the resulting mixture was left stirring overnight at r.t. The reaction mixture was quenched with 5 mL of saturated aq. NH$_4$Cl solution and concentrated under reduced pressure. The residue was partitioned between 40 mL of water 30 mL of MTBE. The organic phase was washed with water (2×30 mL), brine, dried over Na$_2$SO$_4$ and concentrated in vacuo to give 1-benzylazepan-2-one (1.3 g, 86.0% purity, 5.5 mmol, 91.3% yield) as colorless oil.

Step 2: To a vigorously stirred solution of 1-benzylazepan-2-one (800 mg, 3.94 mmol) and titanium tetraisopropoxide (4.47 g, 15.7 mmol, 4.66 mL) in anhydrous THF (78 mL) was added ethylmagnesium bromide (4.2 g, 31.5 mmol, 9.26 mL), diluted with 30 mL of dry THF. The resulting mixture was stirred at 40° C. for 12 h. The reaction mixture was quenched by addition of sat. aqueous NH4$_c$l solution (100 mL), and the resulting mixture was stirred for 1 h until color changed from brown-black to white-yellow. The mixture filtered, and the filter cake washed with THF (50 mL). The filtrate was basified (pH>11) by addition of 15% aq. NaOH solution and extracted with Et$_2$O (3×150 mL). The combined organic extracts were washed with brine, dried (MgSO$_4$), and concentrated under reduced pressure. The residue (636 mg) was purified by HPLC to give the 4-benzyl-4-azaspiro[2.6]nonane (176.0 mg, 817.33 μmol, 20.8% yield) as a yellow liquid.

Step 3: 4-Benzyl-4-azaspiro[2.6]nonane (175 mg, 813 μmol) was dissolved in 2 mL of 1 M HCl solution in methanol. The resulting solution was concentrated under reduced pressure and re-evaporated three times with dry methanol to remove excess of HCl. The residue was dissolved in dry methanol (3 mL) and 25 mg of 10% Pd/C, dried from water beforehand, was added to the resulting solution under argon atmosphere. The resulting suspension was left to stir overnight at r.t under an atmosphere of H$_2$. The mixture was stirred until complete consumption of the starting material (as assessed by 1H NMR). The reaction mixture was filtered and the filtrate concentrated under reduced pressure to give 4-azaspiro[2.6]nonane hydrochloride (87.0 mg, 538 μmol, 66.4% yield) as yellow solid.

Examples 1 and 2

Intentionally left blank

Example 3

5-[4-(difluoromethyl)-6-fluoro-1H-indole-2-carbonyl]-N-(2-hydroxyethyl)-N-methyl-1H,4H,5H,6H,7H-pyrazolo[4,3-c]pyridine-3-carboxamide

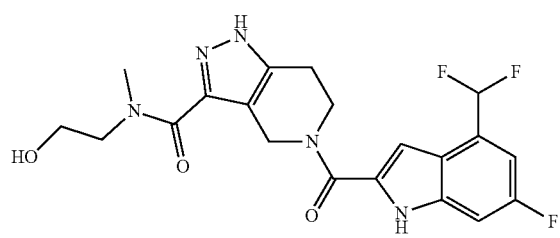 [SMILES: CN(CCO)C(=O)c1n[nH]c2c1CN(C(=O)c1cc3c(C(F)F)cc(F)cc3[nH]1)CC2]

Rt (Method A) 2.85 mins, m/z 436 [M+H]+

1H NMR (400 MHz, DMSO-d6) δ 13.06 (s, 1H), 12.10 (s, 1H), 7.51-7.16 (m, 3H), 6.99 (s, 1H), 5.14-4.54 (m, 3H), 4.06-3.79 (m, 3H), 3.66-3.37 (m, 4H), 3.04-2.79 (m, 4H).

Example 4

5-[4-(difluoromethyl)-1H-indole-2-carbonyl]-N-(2-hydroxyethyl)-N-methyl-1H,4H,5H,6H,7H-pyrazolo[4,3-c]pyridine-3-carboxamide

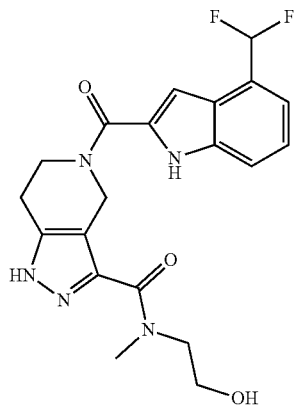 [SMILES: CN(CCO)C(=O)c1n[nH]c2c1CN(C(=O)c1cc3c(C(F)F)cccc3[nH]1)CC2]

Rt (Method A) 2.75 mins, m/z 416 [M+H]+

1H NMR (400 MHz, DMSO-d6) δ 13.05 (s, 1H), 12.01 (s, 1H), 7.60 (t, J=4.3 Hz, 1H), 7.48-7.14 (m, 3H), 6.97 (s, 1H), 5.07-4.60 (m, 3H), 4.06-3.78 (m, 3H), 3.70-3.38 (m, 4H), 3.07-2.77 (m, 4H).

Example 5

5-[4-(1,1-difluoroethyl)-1H-indole-2-carbonyl]-N-(2-hydroxyethyl)-N-methyl-1H,4H,5H,6H,7H-pyrazolo[4,3-c]pyridine-3-carboxamide

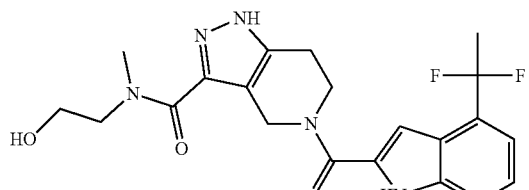

Rt (Method A) 2.86 mins, m/z 430 [M+H]+

1H NMR (400 MHz, DMSO-d6) δ 13.05 (s, 1H), 11.97 (s, 1H), 7.55 (d, J=7.7 Hz, 1H), 7.27 (t, J=7.7 Hz, 1H), 7.23 (d, J=6.9 Hz, 1H), 6.86 (s, 1H), 5.22-4.53 (m, 3H), 4.07-3.78 (m, 3H), 3.69-3.39 (m, 4H), 3.06-2.76 (m, 4H), 2.08 (t, J=18.8 Hz, 3H).

Example 6

5-(6-chloro-5-fluoro-1H-indole-2-carbonyl)-N-(2-hydroxyethyl)-N-methyl-1H,4H,5H,6H,7H-pyrazolo[4,3-c]pyridine-3-carboxamide

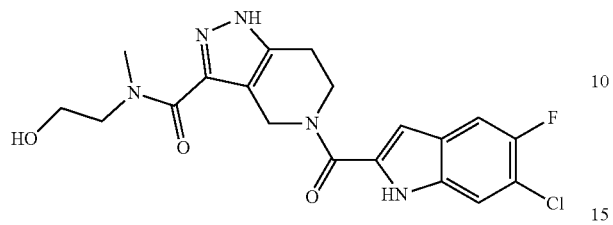

Rt (Method A) 2.91 mins, m/z 420/422 [M+H]+
1H NMR (400 MHz, DMSO-d6) δ 13.08 (s, 1H), 11.89 (s, 1H), 7.65 (d, J=7.8 Hz, 1H), 7.54 (d, J=6.5 Hz, 1H), 6.90 (s, 1H), 5.12-4.39 (m, 3H), 4.07-3.76 (m, 3H), 3.66-3.37 (m, 4H), 3.07-2.70 (m, 4H).

Example 7

5-(5,6-difluoro-1H-indole-2-carbonyl)-N-(2-hydroxyethyl)-N-methyl-1H,4H,5H,6H,7H-pyrazolo[4,3-c]pyridine-3-carboxamide

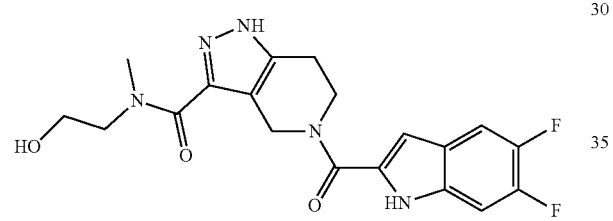

Rt (Method A) 2.78 mins, m/z 404 [M+H]+
1H NMR (400 MHz, DMSO-d6) δ 12.99 (s, 1H), 11.82 (s, 1H), 7.71-7.60 (m, 1H), 7.35 (dd, J=11.0, 7.0 Hz, 1H), 6.90 (s, 1H), 5.08-4.55 (m, 3H), 4.04-3.79 (m, 3H), 3.68-3.36 (m, 4H), 3.04-2.74 (m, 4H).

Example 8

N-(2-hydroxyethyl)-N-methyl-5-(4,5,6-trifluoro-1H-indole-2-carbonyl)-1H,4H,5H,6H,7H-pyrazolo[4,3-c]pyridine-3-carboxamide

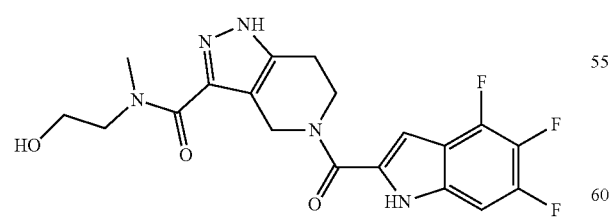

Rt (Method A) 2.89 mins, m/z 422 [M+H]+
1H NMR (400 MHz, DMSO-d6) δ 13.05 (s, 1H), 12.15 (s, 1H), 7.25 (dd, J=10.2, 5.8 Hz, 1H), 7.02 (s, 1H), 5.10-4.60 (m, 3H), 4.07-3.78 (m, 3H), 3.62-3.38 (m, 4H), 3.06-2.75 (m, 4H).

Example 9

5-(4-ethyl-7-fluoro-1H-indole-2-carbonyl)-N-(2-hydroxyethyl)-N-methyl-1H,4H,5H,6H,7H-pyrazolo[4,3-c]pyridine-3-carboxamide

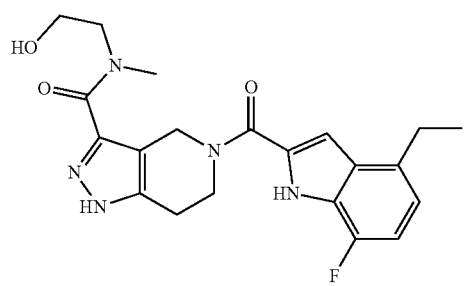 [SMILES: CCc1ccc(F)c2[nH]c(C(=O)N3CCc4[nH]nc(C(=O)N(C)CCO)c4C3)cc12]

Rt (Method A) 2.95 mins, m/z 414 [M+H]+
1H NMR (400 MHz, DMSO-d6) δ 13.08 (s, 1H), 11.68 (s, 1H), 6.96 (dd, J=9.8, 2.2 Hz, 1H), 6.93 (s, 1H), 6.77 (dd, J=10.8, 2.3 Hz, 1H), 5.11-4.56 (m, 3H), 4.08-3.91 (m, 2H), 3.90-3.78 (m, 1H), 3.64-3.54 (m, 2H), 3.52-3.36 (m, 2H), 3.02-2.84 (m, 5H), 1.28 (t, J=7.5 Hz, 3H).

Example 10

5-(4-ethyl-6-fluoro-1H-indole-2-carbonyl)-N-(2-hydroxyethyl)-N-methyl-1H,4H,5H,6H,7H-pyrazolo[4,3-c]pyridine-3-carboxamide

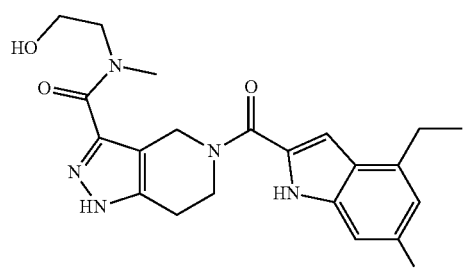

Rt (Method A) 2.97 mins, m/z 414 [M+H]+
1H NMR (400 MHz, DMSO-d6) δ 13.08 (s, 1H), 11.68 (s, 1H), 6.96 (dd, J=9.8, 2.2 Hz, 1H), 6.93 (s, 1H), 6.77 (dd, J=10.8, 2.3 Hz, 1H), 5.11-4.56 (m, 3H), 4.08-3.91 (m, 2H), 3.90-3.78 (m, 1H), 3.64-3.54 (m, 2H), 3.52-3.36 (m, 2H), 3.02-2.84 (m, 5H), 1.28 (t, J=7.5 Hz, 3H).

Example 11

4,5,6-trifluoro-2-[3-(1,3-thiazol-4-yl)-2H,4H,5H,6H,7H-pyrazolo[4,3-c]pyridine-5-carbonyl]-1H-indole

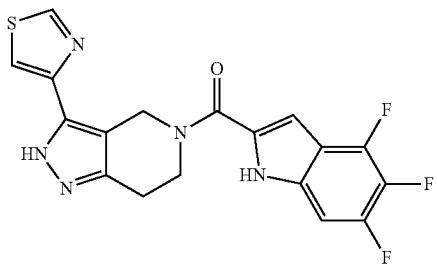 [SMILES: O=C(c1cc2c(F)c(F)c(F)cc2[nH]1)N1CCc2n[nH]c(-c3cscn3)c2C1]

Rt (Method A) 3.26 mins, m/z 404 [M+H]+

Example 12

4-ethyl-6-fluoro-2-[3-(1,3-thiazol-4-yl)-2H,4H,5H,6H,7H-pyrazolo[4,3-c]pyridine-5-carbonyl]-1H-indole

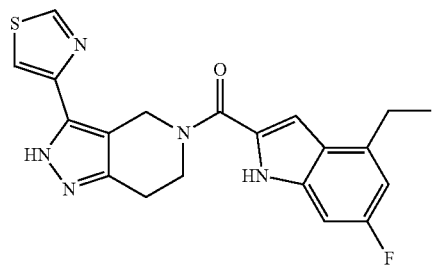 [SMILES: CCc1cc(F)cc2[nH]c(C(=O)N3CCc4n[nH]c(-c5cscn5)c4C3)cc12]

Rt (Method A) 3.35 mins, m/z 396 [M+H]+
1H NMR (400 MHz, DMSO-d6) δ 13.21-12.81 (m, 1H), 11.68 (s, 1H), 9.20 (s, 1H), 7.91 (s, 1H), 7.03-6.90 (m, 2H), 6.77 (dd, J=10.7, 2.2 Hz, 1H), 5.55-4.65 (m, 2H), 4.22-3.88 (m, 2H), 3.05-2.71 (m, 4H), 1.28 (t, J=7.5 Hz, 3H).

Example 13

4-chloro-5-fluoro-2-[3-(1,3-thiazol-4-yl)-2H,4H,5H,6H,7H-pyrazolo[4,3-c]pyridine-5-carbonyl]-1H-indole

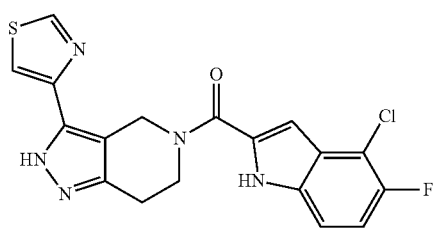 [SMILES: O=C(c1cc2c(Cl)c(F)ccc2[nH]1)N1CCc2n[nH]c(-c3cscn3)c2C1]

Rt (Method A) 3.26 mins, m/z 402/404 [M+H]+

Example 14

5,6-difluoro-2-[3-(1,3-thiazol-4-yl)-2H,4H,5H,6H,7H-pyrazolo[4,3-c]pyridine-5-carbonyl]-1H-indole

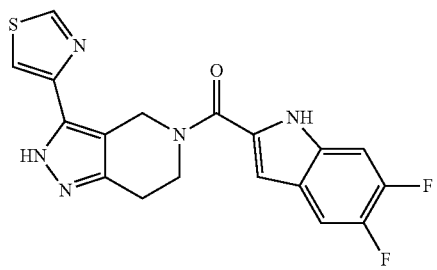 [SMILES: O=C(c1cc2cc(F)c(F)cc2[nH]1)N1CCc2n[nH]c(-c3cscn3)c2C1]

Rt (Method A) 3.14 mins, m/z 386 [M+H]+

Example 15

6-bromo-2-[3-(1,3-thiazol-4-yl)-2H,4H,5H,6H,7H-pyrazolo[4,3-c]pyridine-5-carbonyl]-1H-indole

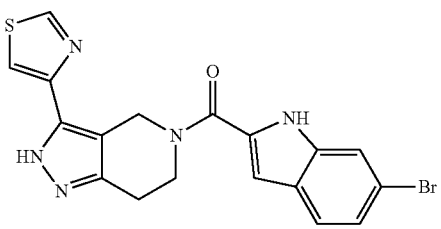 [SMILES: O=C(c1cc2ccc(Br)cc2[nH]1)N1CCc2n[nH]c(-c3cscn3)c2C1]

Rt (Method A) 3.28 mins, m/z 428/430 [M+H]+

Example 16

6-chloro-2-[3-(1,3-thiazol-4-yl)-2H,4H,5H,6H,7H-pyrazolo[4,3-c]pyridine-5-carbonyl]-1H-indole

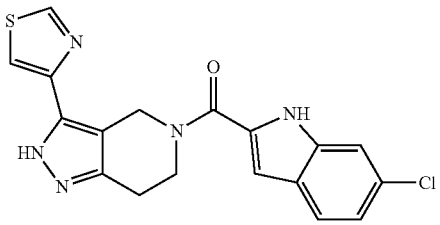 [SMILES: O=C(c1cc2ccc(Cl)cc2[nH]1)N1CCc2n[nH]c(-c3cscn3)c2C1]

Rt (Method A) 3.23 mins, m/z 384/386 [M+H]+

Example 17

4,7-difluoro-2-[3-(1,3-thiazol-4-yl)-2H,4H,5H,6H,7H-pyrazolo[4,3-c]pyridine-5-carbonyl]-1H-indole

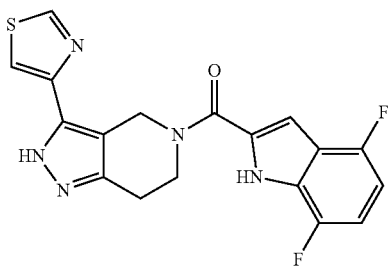 [SMILES: O=C(c1cc2c(F)ccc(F)c2[nH]1)N1CCc2n[nH]c(-c3cscn3)c2C1]

Rt (Method A) 3.12 mins, m/z 386 [M+H]+

1H NMR (400 MHz, DMSO-d6) δ 13.21-12.82 (m, 1H), 12.48 (s, 1H), 9.39-9.02 (m, 1H), 7.91 (s, 1H), 7.06-6.90 (m, 2H), 6.86-6.76 (m, 1H), 5.21-4.76 (m, 2H), 4.09-3.86 (m, 2H), 3.04-2.73 (m, 2H).

Example 18

4-ethyl-2-[3-(1,3-thiazol-4-yl)-2H,4H,5H,6H,7H-pyrazolo[4,3-c]pyridine-5-carbonyl]-1H-indole

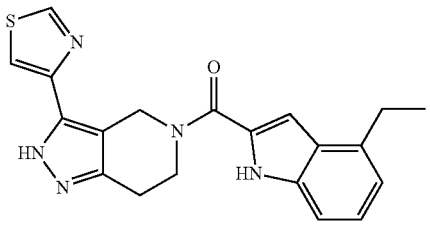 [SMILES: CCc1cccc2[nH]c(C(=O)N3CCc4n[nH]c(-c5cscn5)c4C3)cc12]

Rt (Method A) 3.28 mins, m/z 378 [M+H]+

Example 19

4-chloro-2-[3-(1,3-thiazol-4-yl)-2H,4H,5H,6H,7H-pyrazolo[4,3-c]pyridine-5-carbonyl]-1H-indole

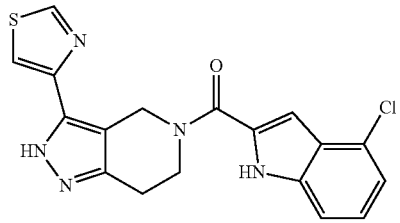 [SMILES: O=C(c1cc2c(Cl)cccc2[nH]1)N1CCc2n[nH]c(-c3cscn3)c2C1]

Rt (Method A) 3.23 mins, m/z 384/386 [M+H]+

Example 20

4,6-difluoro-2-[3-(1,3-thiazol-4-yl)-2H,4H,5H,6H,7H-pyrazolo[4,3-c]pyridine-5-carbonyl]-1H-indole

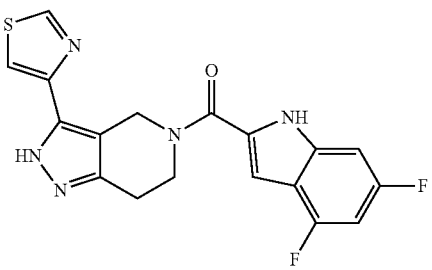 [SMILES: O=C(c1cc2c(F)cc(F)cc2[nH]1)N1CCc2n[nH]c(-c3cscn3)c2C1]

Rt (Method A) 3.18 mins, m/z 386 [M+H]+

Example 21

2-[3-(1,3-thiazol-4-yl)-2H,4H,5H,6H,7H-pyrazolo[4,3-c]pyridine-5-carbonyl]-4-(trifluoromethyl)-1H-indole

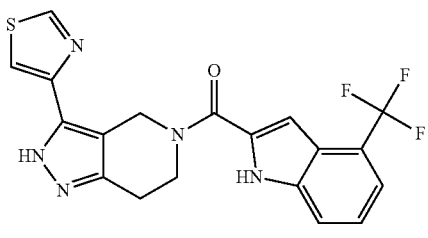 [SMILES: O=C(c1cc2c(C(F)(F)F)cccc2[nH]1)N1CCc2n[nH]c(-c3cscn3)c2C1]

Rt (Method A) 3.32 mins, m/z 418 [M+H]+

Example 22

4,5-difluoro-2-[3-(1,3-thiazol-4-yl)-2H,4H,5H,6H,7H-pyrazolo[4,3-c]pyridine-5-carbonyl]-1H-indole

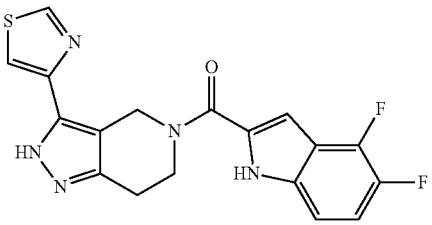 [SMILES: O=C(c1cc2c(F)c(F)ccc2[nH]1)N1CCc2n[nH]c(-c3cscn3)c2C1]

Rt (Method A) 3.15 mins, m/z 386 [M+H]+

Example 23

4-methyl-2-[3-(1,3-thiazol-4-yl)-2H,4H,5H,6H,7H-pyrazolo[4,3-c]pyridine-5-carbonyl]-1H-indole

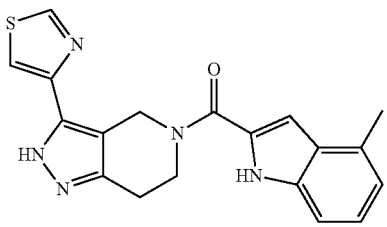 [SMILES: Cc1cccc2[nH]c(C(=O)N3CCc4n[nH]c(-c5cscn5)c4C3)cc12]

Rt (Method A) 3.13 mins, m/z 364 [M+H]+

Example 24

Intentionally left blank

Example 25

4-ethyl-5-fluoro-2-[3-(1,3-thiazol-4-yl)-2H,4H,5H,6H,7H-pyrazolo[4,3-c]pyridine-5-carbonyl]-1H-indole

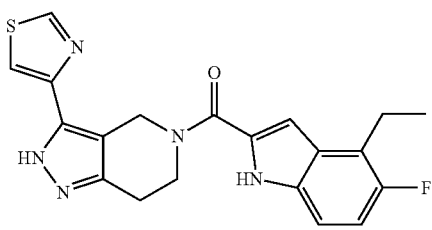 [SMILES: CCc1c(F)ccc2[nH]c(C(=O)N3CCc4n[nH]c(-c5cscn5)c4C3)cc12]

Rt (Method A) 3.38 mins, m/z 396 [M+H]+

Example 26

6-fluoro-4-methyl-2-[3-(1,3-thiazol-4-yl)-2H,4H,5H,6H,7H-pyrazolo[4,3-c]pyridine-5-carbonyl]-1H-indole

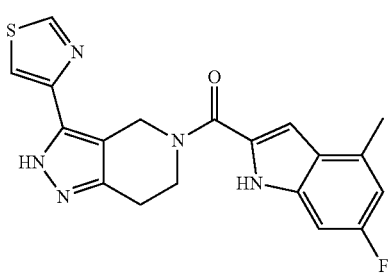 [SMILES: Cc1cc(F)cc2[nH]c(C(=O)N3CCc4n[nH]c(-c5cscn5)c4C3)cc12]

Rt (Method A) 3.2 mins, m/z 382 [M+H]+

Example 27

5-[4-(1,1-difluoroethyl)-6-fluoro-1H-indole-2-carbonyl]-N-(2-hydroxyethyl)-N-methyl-1H,4H,5H,6H,7H-pyrazolo[4,3-c]pyridine-3-carboxamide

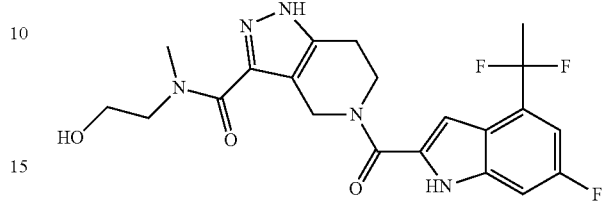

Rt (Method A) 2.96 mins, m/z 450 [M+H]+
1H NMR (400 MHz, DMSO-d6) δ 13.95-11.39 (m, 2H), 7.34-7.25 (m, 1H), 7.11 (dd, J=10.2, 2.0 Hz, 1H), 6.88 (s, 1H), 5.12-4.38 (m, 3H), 4.08-3.76 (m, 3H), 3.66-3.37 (m, 4H), 3.08-2.79 (m, 4H), 2.09 (t, J=18.9 Hz, 3H).

Example 28

5-(4,6-difluoro-1H-indole-2-carbonyl)-N-(2-hydroxyethyl)-N-methyl-1H,4H,5H,6H,7H-pyrazolo[4,3-c]pyridine-3-carboxamide

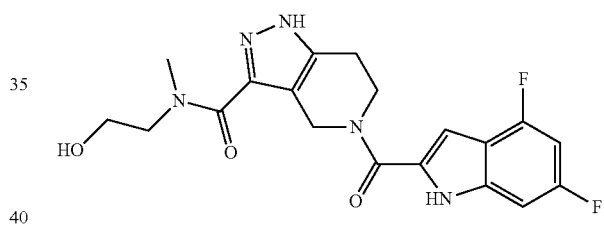

Rt (Method A) 2.81 mins, m/z 404 [M+H]+
1H NMR (400 MHz, DMSO-d6) δ 13.05 (s, 1H), 12.07 (s, 1H), 7.04 (dd, J=9.4, 1.6 Hz, 1H), 6.97-6.87 (m, 2H), 5.12-4.58 (m, 3H), 4.08-3.76 (m, 3H), 3.68-3.36 (m, 4H), 3.06-2.75 (m, 4H).

Example 29

5-(6-bromo-1H-indole-2-carbonyl)-N-(2-hydroxyethyl)-N-methyl-1H,4H,5H,6H,7H-pyrazolo[4,3-c]pyridine-3-carboxamide

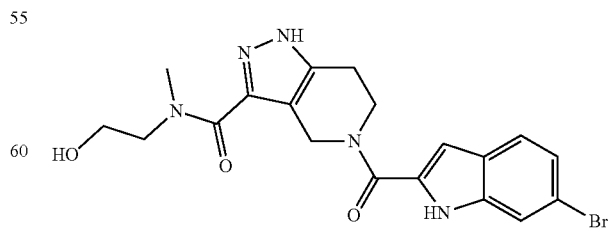

Rt (Method A) 2.9 mins, m/z 446/448 [M+H]+
1H NMR (400 MHz, DMSO-d6) δ 13.06 (s, 1H), 11.79 (s, 1H), 7.62 (d, J=8.5 Hz, 1H), 7.58 (s, 1H), 7.19 (dd, J=8.5, 1.7 Hz, 1H), 6.92 (s, 1H), 5.16-4.63 (m, 3H), 4.08-3.76 (m, 3H), 3.62-3.36 (m, 4H), 3.04-2.74 (m, 4H).

Example 30

5-(4-bromo-1H-indole-2-carbonyl)-N-(2-hydroxyethyl)-N-methyl-1H,4H,5H,6H,7H-pyrazolo[4,3-c]pyridine-3-carboxamide

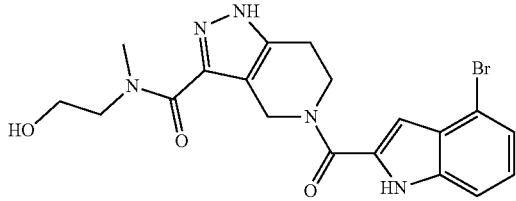 [SMILES: CN(CCO)C(=O)c1n[nH]c2c1CN(C(=O)c1cc3c(Br)cccc3[nH]1)CC2]

Rt (Method A) 2.87 mins, m/z 446/448 [M+H]+

1H NMR (400 MHz, DMSO-d6) δ 13.02 (s, 1H), 12.07 (s, 1H), 7.45 (d, J=8.2 Hz, 1H), 7.30 (d, J=7.4 Hz, 1H), 7.17-7.10 (m, 1H), 6.75 (s, 1H), 5.08-4.56 (m, 3H), 4.09-3.90 (m, 2H), 3.90-3.77 (m, 1H), 3.63-3.37 (m, 4H), 3.05-2.76 (m, 4H).

Example 31

2-methyl-2-(methylamino)propyl 5-(1H-indole-2-carbonyl)-1H,4H,5H,6H,7H-pyrazolo[4,3-c]pyridine-3-carboxylate

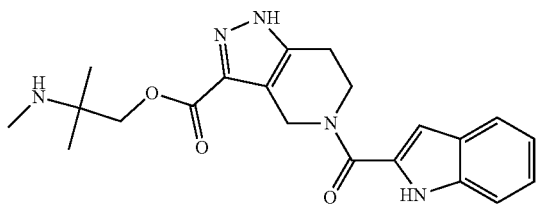 [SMILES: CNC(C)(C)COC(=O)c1n[nH]c2c1CN(C(=O)c1cc3ccccc3[nH]1)CC2]

Rt (Method B) 2.35 mins, m/z 396 [M+H]+

1H NMR (400 MHz, DMSO-d6) δ 11.66 (s, 1H), 8.32 (s, 1H), 7.63 (d, J=8.0 Hz, 1H), 7.42 (d, J=8.2 Hz, 1H), 7.24-7.15 (m, 1H), 7.10-7.02 (m, 1H), 6.89 (s, 1H), 5.22-4.76 (m, 2H), 4.25-4.06 (m, 2H), 4.06-3.88 (m, 2H), 3.00-2.80 (m, 2H), 2.29 (s, 3H), 1.13 (s, 6H).

Example 32

[1-(methylamino)cyclopropyl]methyl 5-(1H-indole-2-carbonyl)-1H,4H,5H,6H,7H-pyrazolo[4,3-c]pyridine-3-carboxylate

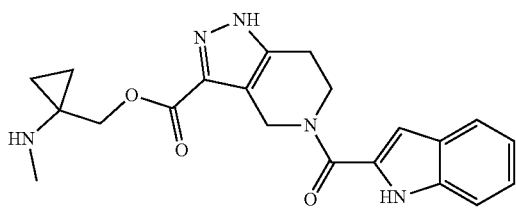 [SMILES: CNC1(COC(=O)c2n[nH]c3c2CN(C(=O)c2cc4ccccc4[nH]2)CC3)CC1]

Rt (Method A) 2.95 mins, m/z 394 [M+H]+

1H NMR (400 MHz, DMSO-d6) δ 13.91-13.13 (m, 1H), 11.65 (s, 1H), 7.63 (d, J=8.0 Hz, 1H), 7.42 (d, J=8.2 Hz, 1H), 7.24-7.14 (m, 1H), 7.11-7.01 (m, 1H), 6.94-6.86 (m, 2H), 5.33-4.62 (m, 2H), 4.35-4.09 (m, 2H), 4.09-3.87 (m, 2H), 3.00-2.79 (m, 2H), 2.27 (s, 3H), 0.56 (s, 4H).

Example 33

N-[1-(hydroxymethyl)cyclopropyl]-5-(1H-indole-2-carbonyl)-N-methyl-1H,4H,5H,6H,7H-pyrazolo[4,3-c]pyridine-3-carboxamide

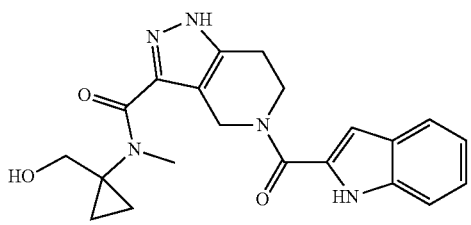 [SMILES: CN(C(=O)c1n[nH]c2c1CN(C(=O)c1cc3ccccc3[nH]1)CC2)C1(CO)CC1]

Rt (Method A) 2.81 mins, m/z 394 [M+H]+

1H NMR (400 MHz, DMSO-d6) δ 13.05 (s, 1H), 11.63 (s, 1H), 7.64 (d, J=7.6 Hz, 1H), 7.42 (d, J=8.3 Hz, 1H), 7.23-7.16 (m, 1H), 7.10-7.03 (m, 1H), 6.88 (s, 1H), 5.42 (s, 1H), 5.19-4.50 (m, 3H), 4.11-3.82 (m, 2H), 3.79-3.47 (m, 2H), 3.09-2.74 (m, 4H), 0.95-0.41 (m, 4H).

Example 34

1-[5-(1H-indole-2-carbonyl)-1H,4H,5H,6H,7H-pyrazolo[4,3-c]pyridine-3-carbonyl]-3-methylazetidin-3-ol

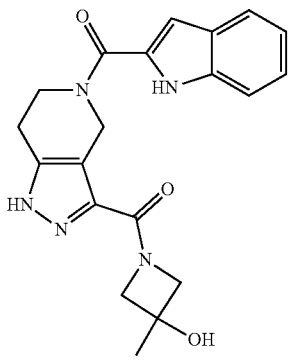 [SMILES: CC1(O)CN(C(=O)c2n[nH]c3c2CN(C(=O)c2cc4ccccc4[nH]2)CC3)C1]

Rt (Method A) 2.68 mins, m/z 380 [M+H]+

1H NMR (400 MHz, DMSO-d6) δ 13.09 (s, 1H), 11.62 (s, 1H), 7.64 (d, J=8.0 Hz, 1H), 7.42 (d, J=8.2 Hz, 1H), 7.23-7.16 (m, 1H), 7.06 (t, J=7.5 Hz, 1H), 6.87 (s, 1H), 5.61 (s, 1H), 5.17-4.60 (m, 2H), 4.38-4.19 (m, 2H), 4.07-3.90 (m, 2H), 3.90-3.72 (m, 2H), 3.00-2.74 (m, 2H), 1.37 (s, 3H).

Example 35

4-chloro-6-fluoro-2-[4-methyl-3-(1,3-thiazol-4-yl)-1H,4H,5H,6H,7H-pyrazolo[4,3-c]pyridine-5-carbonyl]-1H-indole

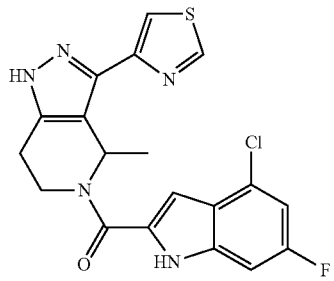 [SMILES: CC1c2c(-c3cscn3)n[nH]c2CCN1C(=O)c1cc2c(Cl)cc(F)cc2[nH]1]

Rt (Method A) 3.46 mins, m/z 416/418 [M+H]+

1H NMR (400 MHz, DMSO-d6) δ 12.97 (s, 1H), 12.13 (s, 1H), 9.35-9.07 (m, 1H), 8.03-7.81 (m, 1H), 7.17 (d, J=9.5 Hz, 2H), 6.85 (s, 1H), 6.08-5.94 (m, 1H), 4.73-4.41 (m, 1H), 3.69-3.38 (m, 1H), 3.11-2.75 (m, 2H), 1.71-1.36 (m, 3H).

Example 37

4-chloro-6-fluoro-2-[6-methyl-3-(1,3-thiazol-4-yl)-1H,4H,5H,6H,7H-pyrazolo[4,3-c]pyridine-5-carbonyl]-1H-indole

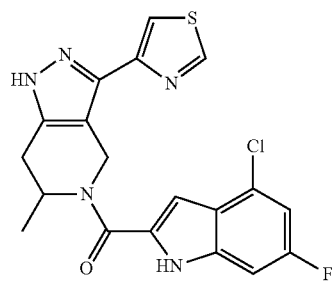

Rt (Method A) 3.42 mins, m/z 416/418 [M+H]+

1H NMR (400 MHz, DMSO-d6) δ 13.00 (s, 1H), 12.10 (s, 1H), 9.23 (s, 1H), 7.92 (s, 1H), 7.23-7.12 (m, 2H), 6.88 (s, 1H), 5.50 (d, J=16.7 Hz, 1H), 5.34-5.02 (m, 1H), 4.92-4.10 (m, 1H), 3.22-2.99 (m, 1H), 2.69 (d, J=16.0 Hz, 1H), 1.24 (d, J=6.8 Hz, 3H).

Example 36

2-[4-methyl-3-(1,3-thiazol-4-yl)-1H,4H,5H,6H,7H-pyrazolo[4,3-c]pyridine-5-carbonyl]-1H-indole

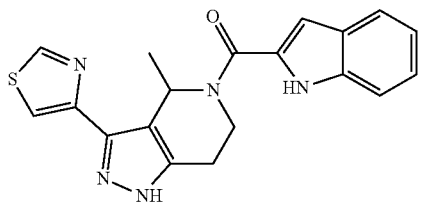 [SMILES: CC1c2c(-c3cscn3)n[nH]c2CCN1C(=O)c1cc2ccccc2[nH]1]

Rt (Method A) 3.14 mins, m/z 364 [M+H]+

1H NMR (400 MHz, DMSO-d6) δ 12.93 (s, 1H), 11.64 (s, 1H), 9.40-9.07 (m, 1H), 8.01-7.79 (m, 1H), 7.64 (d, J=7.5 Hz, 1H), 7.42 (d, J=8.2 Hz, 1H), 7.25-7.13 (m, 1H), 7.11-7.00 (m, 1H), 6.88 (s, 1H), 6.06-5.91 (m, 1H), 4.67-4.50 (m, 1H), 3.71-3.36 (m, 1H), 3.16-2.71 (m, 2H), 1.79-1.36 (m, 3H).

Example 38

2-[6-methyl-3-(1,3-thiazol-4-yl)-1H,4H,5H,6H,7H-pyrazolo[4,3-c]pyridine-5-carbonyl]-1H-indole

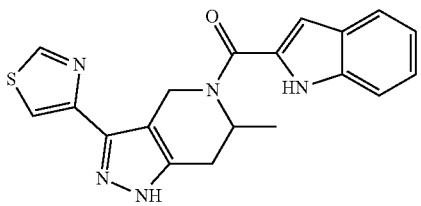 [SMILES: CC1Cc2[nH]nc(-c3cscn3)c2CN1C(=O)c1cc2ccccc2[nH]1]

Rt (Method A) 3.09 mins, m/z 364 [M+H]+

1H NMR (400 MHz, DMSO-d6) δ 12.97 (s, 1H), 11.62 (s, 1H), 9.23 (s, 1H), 7.92 (s, 1H), 7.64 (d, J=8.0 Hz, 1H), 7.43 (d, J=8.2 Hz, 1H), 7.25-7.13 (m, 1H), 7.11-7.00 (m, 1H), 6.88 (s, 1H), 5.50 (d, J=16.7 Hz, 1H), 5.30-5.10 (m, 1H), 4.94-4.03 (m, 1H), 3.21-3.00 (m, 1H), 2.68 (d, J=15.7 Hz, 1H), 1.23 (d, J=6.8 Hz, 3H).

Example 39

2-{1-[5-(1H-indole-2-carbonyl)-1H,4H,5H,6H,7H-pyrazolo[4,3-c]pyridine-3-carbonyl]azetidin-3-yl}propan-2-ol

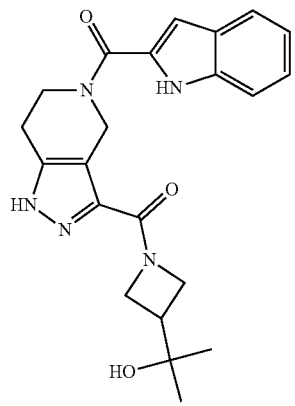 [SMILES: CC(C)(O)C1CN(C(=O)c2n[nH]c3c2CN(C(=O)c2cc4ccccc4[nH]2)CC3)C1]

Rt (Method A) 2.79 mins, m/z 408 [M+H]+

1H NMR (400 MHz, DMSO-d6) δ 13.09 (s, 1H), 11.63 (s, 1H), 7.64 (d, J=8.0 Hz, 1H), 7.42 (d, J=8.3 Hz, 1H), 7.22-7.16 (m, 1H), 7.09-7.03 (m, 1H), 6.86 (s, 1H), 5.14-4.60 (m, 2H), 4.55-4.44 (m, 1H), 4.39-4.30 (m, 2H), 4.08-3.78 (m, 4H), 3.00-2.78 (m, 2H), 2.62-2.53 (m, 1H), 1.03 (s, 6H).

Example 40

1-[5-(1H-indole-2-carbonyl)-1H,4H,5H,6H,7H-pyrazolo[4,3-c]pyridine-3-carbonyl]azetidin-3-ol

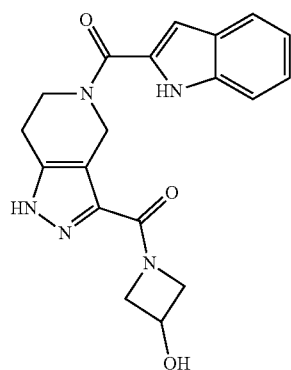 [SMILES: O=C(c1cc2ccccc2[nH]1)N1CCc2[nH]nc(C(=O)N3CC(O)C3)c2C1]

Rt (Method A) 2.61 mins, m/z 366 [M+H]+

1H NMR (400 MHz, DMSO-d6) δ 13.09 (s, 1H), 11.63 (s, 1H), 7.64 (d, J=8.0 Hz, 1H), 7.42 (d, J=8.2 Hz, 1H), 7.23-7.16 (m, 1H), 7.09-7.03 (m, 1H), 6.86 (s, 1H), 5.75-5.60 (m, 1H), 5.23-4.70 (m, 2H), 4.70-4.55 (m, 1H), 4.55-4.40 (m, 1H), 4.26-4.11 (m, 2H), 4.06-3.87 (m, 2H), 3.78-3.62 (m, 1H), 3.02-2.75 (m, 2H).

Example 41

N-(2-hydroxypropyl)-5-(1H-indole-2-carbonyl)-N-methyl-1H,4H,5H,6H,7H-pyrazolo[4,3-]pyridine-3-carboxamide

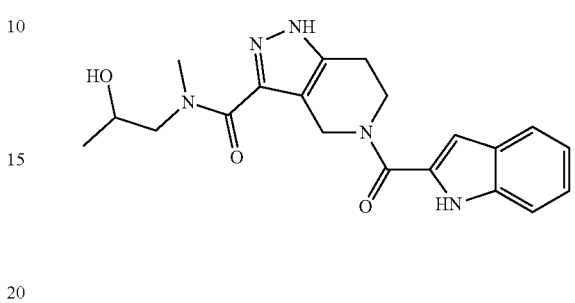

Rt (Method A) 2.7 mins, m/z 382 [M+H]+

1H NMR (400 MHz, DMSO-d6) δ 13.03 (s, 1H), 11.63 (s, 1H), 7.64 (d, J=8.0 Hz, 1H), 7.42 (d, J=8.2 Hz, 1H), 7.19 (t, J=7.3 Hz, 1H), 7.06 (t, J=7.4 Hz, 1H), 6.87 (s, 1H), 5.17-4.48 (m, 3H), 4.09-3.73 (m, 3H), 3.71-3.43 (m, 1H), 3.43-3.36 (m, 1H), 3.31-3.11 (m, 1H), 3.09-2.74 (m, 4H), 1.13-0.88 (m, 3H). A mixture of conformers was observed

Example 42

N-(1-hydroxypropan-2-yl)-5-(1H-indole-2-carbonyl)-N-methyl-1H,4H,5H,6H,7H-pyrazolo[4,3-c]pyridine-3-carboxamide

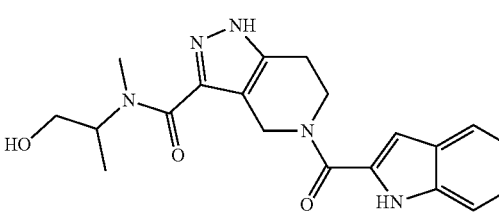

Rt (Method A) 2.69 mins, m/z 382 [M+H]+

1H NMR (400 MHz, DMSO-d6) δ 12.97 (s, 1H), 11.63 (s, 1H), 7.64 (d, J=7.9 Hz, 1H), 7.42 (d, J=8.2 Hz, 1H), 7.22-7.16 (m, 1H), 7.09-7.01 (m, 1H), 6.87 (s, 1H), 5.15-4.48 (m, 4H), 4.15-3.79 (m, 2H), 3.54-3.38 (m, 1H), 3.23-3.06 (m, 1H), 3.00-2.68 (m, 4H), 1.20-0.92 (m, 3H). A mixture of conformers was observed.

Example 43

N-(2-hydroxy-2-methylpropyl)-5-(1H-indole-2-carbonyl)-N-methyl-1H,4H,5H,6H,7H-pyrazolo[4,3-c]pyridine-3-carboxamide

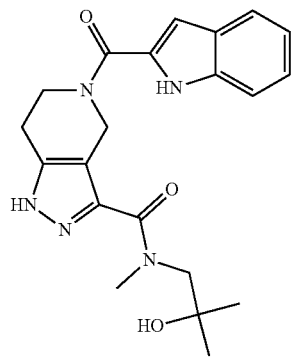 [SMILES: CN(CC(C)(C)O)C(=O)c1n[nH]c2c1CN(C(=O)c1cc3ccccc3[nH]1)CC2]

Rt (Method A) 2.76 mins, m/z 396 [M+H]+ 1H NMR (400 MHz, DMSO-d6) δ 13.05 (s, 1H), 11.62 (s, 1H), 7.63 (d, J=7.7 Hz, 1H), 7.42 (d, J=8.2 Hz, 1H), 7.19 (t, J=7.6 Hz, 1H), 7.06 (t, J=7.5 Hz, 1H), 6.86 (s, 1H), 5.09-4.44 (m, 3H), 4.10-3.82 (m, 3H), 3.45-3.39 (m, 2H), 3.12-2.99 (m, 2H), 2.97-2.78 (m, 2H), 1.17-0.92 (m, 6H). A mixture of conformers was observed

Example 44

2-{1-[5-(1H-indole-2-carbonyl)-1H,4H,5H,6H,7H-pyrazolo[4,3-c]pyridine-3-carbonyl]azetidin-3-yl}ethan-1-ol

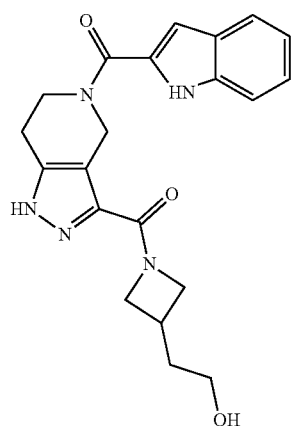 [SMILES: O=C(c1cc2ccccc2[nH]1)N1CCc2[nH]nc(C(=O)N3CC(CCO)C3)c2C1]

Rt (Method A) 2.67 mins, m/z 394 [M+H]+

1H NMR (400 MHz, DMSO-d6) δ 13.07 (s, 1H), 11.62 (s, 1H), 7.64 (d, J=8.0 Hz, 1H), 7.42 (d, J=8.2 Hz, 1H), 7.23-7.16 (m, 1H), 7.06 (t, J=7.6 Hz, 1H), 6.86 (s, 1H), 5.14-4.68 (m, 2H), 4.56-4.51 (m, 1H), 4.43 (t, J=4.9 Hz, 1H), 4.15-3.88 (m, 4H), 3.70-3.55 (m, 1H), 3.45-3.36 (m, 2H), 2.98-2.77 (m, 2H), 2.75-2.61 (m, 1H), 1.76-1.67 (m, 2H).

Example 45

{1-[5-(1H-indole-2-carbonyl)-1H,4H,5H,6H,7H-pyrazolo[4,3-c]pyridine-3-carbonyl]azetidin-3-yl}methanol

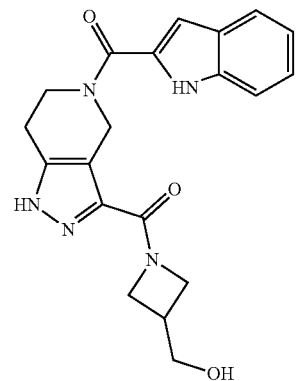 [SMILES: O=C(c1cc2ccccc2[nH]1)N1CCc2[nH]nc(C(=O)N3CC(CO)C3)c2C1]

Rt (Method A) 2.64 mins, m/z 380 [M+H]+

1H NMR (400 MHz, DMSO-d6) δ 13.08 (s, 1H), 11.62 (s, 1H), 7.64 (d, J=8.1 Hz, 1H), 7.42 (d, J=8.2 Hz, 1H), 7.23-7.16 (m, 1H), 7.06 (t, J=7.5 Hz, 1H), 6.86 (s, 1H), 5.14-4.62 (m, 3H), 4.44 (t, J=9.2 Hz, 1H), 4.27-4.11 (m, 1H), 4.04-3.88 (m, 3H), 3.77-3.63 (m, 1H), 3.57-3.47 (m, 2H), 3.02-2.75 (m, 2H), 2.75-2.60 (m, 1H).

Example 46

4-chloro-6-fluoro-2-[3-(1,3-thiazol-4-yl)-1H,4H,5H,6H,7H-pyrazolo[4,3-c]pyridine-5-carbonyl]-1H-indole

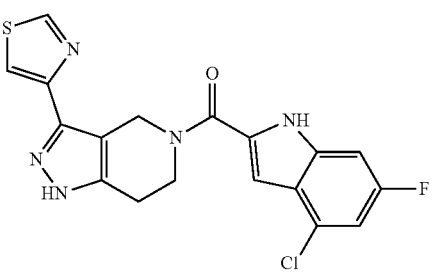 [SMILES: O=C(c1cc2c(Cl)cc(F)cc2[nH]1)N1CCc2[nH]nc(-c3cscn3)c2C1]

Rt (Method A) 3.32 mins, m/z 402/404 [M+H]+

1H NMR (400 MHz, DMSO-d6) δ 13.39-12.72 (m, 1H), 12.12 (s, 1H), 9.23 (s, 1H), 7.91 (s, 1H), 7.26-7.13 (m, 2H), 6.90 (s, 1H), 5.44-4.75 (m, 2H), 4.16-3.87 (m, 2H), 3.08-2.72 (m, 2H).

Example 47

2-[3-(1,3-thiazol-4-yl)-1H,4H,5H,6H,7H-pyrazolo[4,3-c]pyridine-5-carbonyl]-1H-indole

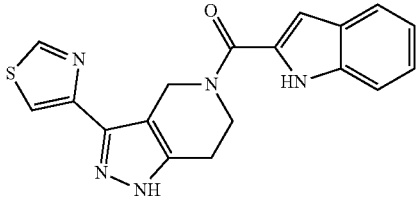 [SMILES: O=C(c1cc2ccccc2[nH]1)N1CCc2[nH]nc(-c3cscn3)c2C1]

Rt (Method A) 3.00 mins, m/z 350 [M+H]+

1H NMR (400 MHz, DMSO-d6) δ 13.48-12.48 (m, 1H), 11.64 (s, 1H), 9.23 (s, 1H), 7.91 (s, 1H), 7.64 (d, J=7.9 Hz, 1H), 7.43 (d, J=8.2 Hz, 1H), 7.27-7.12 (m, 1H), 7.10-7.00 (m, 1H), 6.91 (s, 1H), 5.39-4.66 (m, 2H), 4.33-3.76 (m, 2H), 3.09-2.74 (m, 2H).

Example 48

2-{1-[5-(1H-indole-2-carbonyl)-1H,4H,5H,6H,7H-pyrazolo[4,3-c]pyridin-3-yl]-N-methylformamido}ethyl (2S)-2-amino-3-methylbutanoate

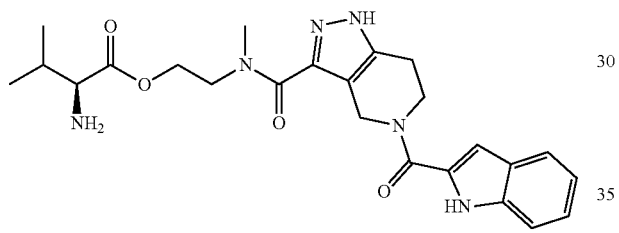

Rt (Method A) 2.88 mins, m/z 467 [M+H]+

1H NMR (400 MHz, DMSO-d6) δ 13.06 (s, 1H), 11.63 (s, 1H), 7.64 (d, J=7.9 Hz, 1H), 7.42 (d, J=8.2 Hz, 1H), 7.19 (m, 1H), 7.06 (m, 1H), 6.87 (s, 1H), 4.88 (m, 2H), 4.28-4.16 (m, 3H), 3.98 (m, 2H), 3.71-3.65 (m, 1H), 3.39 (m, 1H), 3.07-2.87 (m, 5H), 1.82-1.67 (m, 2H), 0.83-0.69 (m, 6H)

Example 49

5-[6-fluoro-4-(1-hydroxyethyl)-1H-indole-2-carbonyl]-N-(2-hydroxyethyl)-N-methyl-1H,4H,5H,6H,7H-pyrazolo[4,3-c]pyridine-3-carboxamide

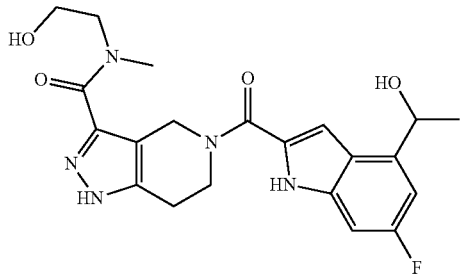 [SMILES: CC(O)c1cc(F)cc2[nH]c(C(=O)N3CCc4[nH]nc(C(=O)N(C)CCO)c4C3)cc12]

Rt (Method A) 2.5 mins, m/z 428 [M+H]+

1H NMR (400 MHz, DMSO-d6) δ 13.03 (s, 1H), 11.69 (s, 1H), 7.02-6.91 (m, 3H), 5.34 (d, J=4.1 Hz, 1H), 5.21-5.08 (m, 1H), 5.07-4.63 (m, 3H), 4.09-3.80 (m, 3H), 3.67-3.35 (m, 4H), 3.09-2.94 (m, 2H), 2.93-2.77 (m, 4H), 1.42 (d, J=6.4 Hz, 3H).

Example 50

N-(2-hydroxyethyl)-5-[4-(1-hydroxyethyl)-1H-indole-2-carbonyl]-N-methyl-1H,4H,5H,6H,7H-pyrazolo[4,3-c]pyridine-3-carboxamide

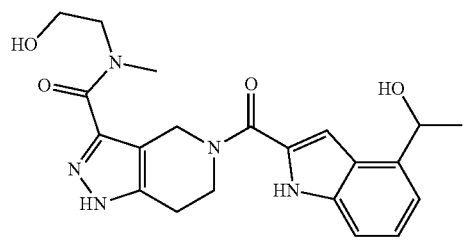 [SMILES: CC(O)c1cccc2[nH]c(C(=O)N3CCc4[nH]nc(C(=O)N(C)CCO)c4C3)cc12]

Rt (Method A) 2.4 mins, m/z 410 [M+H]+

1H NMR (400 MHz, DMSO-d6) δ 13.03 (s, 1H), 11.60 (s, 1H), 7.28 (d, J=8.1 Hz, 1H), 7.19-7.11 (m, 1H), 7.08 (d, J=7.1 Hz, 1H), 6.95 (s, 1H), 5.22-5.16 (m, 1H), 5.16-5.07 (m, 1H), 5.00-4.62 (m, 3H), 4.09-3.80 (m, 3H), 3.66-3.35 (m, 4H), 3.06-2.77 (m, 4H), 1.43 (d, J=6.4 Hz, 3H).

Example 51

5-(4-chloro-5-fluoro-1H-indole-2-carbonyl)-N-(2-hydroxyethyl)-N-methyl-1H,4H,5H,6H,7H-pyrazolo[4,3-c]pyridine-3-carboxamide

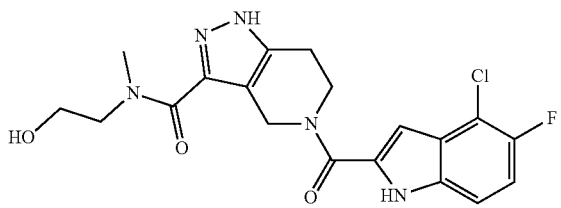

Rt (Method A) 2.88 mins, m/z 420/422 [M+H]+

1H NMR (400 MHz, DMSO-d6) δ 13.05 (s, 1H), 12.14 (s, 1H), 7.41 (dd, J=8.9, 3.9 Hz, 1H), 7.28-7.20 (m, 1H), 6.87 (s, 1H), 5.12-4.56 (m, 3H), 4.16-3.91 (m, 2H), 3.91-3.75 (m, 1H), 3.63-3.37 (m, 4H), 3.13-2.75 (m, 4H).

Example 52

5-(4,5-difluoro-1H-indole-2-carbonyl)-N-(2-hydroxyethyl)-N-methyl-1H,4H,5H,6H,7H-pyrazolo[4,3-c]pyridine-3-carboxamide

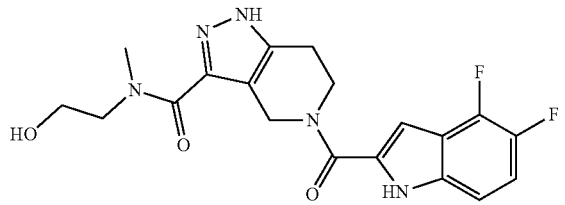 [SMILES: CN(CCO)C(=O)c1n[nH]c2c1CN(C(=O)c1cc3c(F)c(F)ccc3[nH]1)CC2]

Rt (Method A) 2.79 mins, m/z 404 [M+H]+

1H NMR (400 MHz, DMSO-d6) δ 13.06 (s, 1H), 12.07 (s, 1H), 7.32-7.16 (m, 2H), 6.97 (s, 1H), 5.13-4.57 (m, 3H), 4.10-3.90 (m, 2H), 3.90-3.77 (m, 1H), 3.66-3.36 (m, 4H), 3.10-2.72 (m, 4H).

Example 53

5-(4,7-difluoro-1H-indole-2-carbonyl)-N-(2-hydroxyethyl)-N-methyl-1H,4H,5H,6H,7H-pyrazolo[4,3-c]pyridine-3-carboxamide

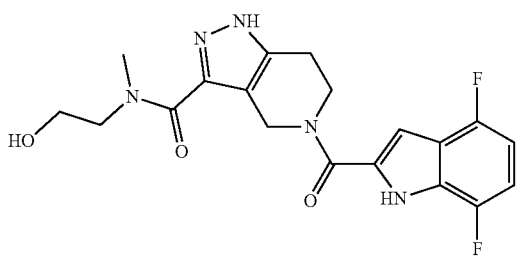 [SMILES: CN(CCO)C(=O)c1n[nH]c2c1CN(C(=O)c1cc3c(F)ccc(F)c3[nH]1)CC2]

Rt (Method A) 2.75 mins, m/z 404 [M+H]+

1H NMR (400 MHz, DMSO-d6) δ 13.05 (s, 1H), 12.47 (s, 1H), 7.06-6.95 (m, 1H), 6.93 (d, J=2.6 Hz, 1H), 6.87-6.76 (m, 1H), 4.99-4.57 (m, 3H), 4.03-3.69 (m, 3H), 3.71-3.35 (m, 4H), 3.10-2.73 (m, 4H).

Example 54

5-(1H-indole-2-carbonyl)-N-(2-methoxyethyl)-N-methyl-1H,4H,5H,6H,7H-pyrazolo[4,3-c]pyridine-3-carboxamide

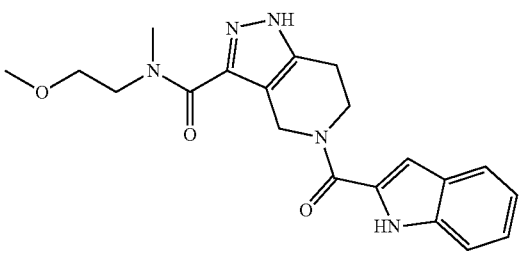 [SMILES: COCCN(C)C(=O)c1n[nH]c2c1CN(C(=O)c1cc3ccccc3[nH]1)CC2]

Rt (Method A) 2.79 mins, m/z 382 [M+H]+

1H NMR (400 MHz, DMSO-d6) δ 13.03 (s, 1H), 11.62 (s, 1H), 7.64 (d, J=8.0 Hz, 1H), 7.42 (d, J=8.3 Hz, 1H), 7.23-7.15 (m, 1H), 7.09-7.02 (m, 1H), 6.87 (s, 1H), 5.16-4.58 (m, 2H), 4.08-3.88 (m, 3H), 3.63-3.45 (m, 3H), 3.40-3.34 (m, 1H), 3.27-3.09 (m, 3H), 3.03-2.78 (m, 4H).

Example 55 propan-2-yl (2S)-2-({[2-({N-methyl-1-[5-(4-methyl-1H-indole-2-carbonyl)-1H,4H,5H,6H,7H-pyrazolo[4,3-c]pyridin-3-yl]formamido}oxy)ethoxy](phenoxy)phosphoryl}amino)propanoate

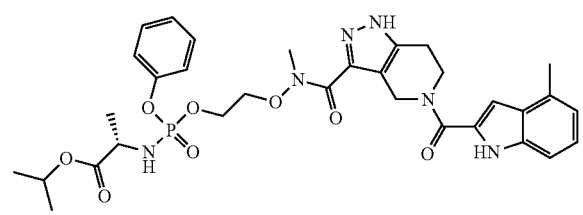 [SMILES: Cc1cccc2[nH]c(C(=O)N3CCc4[nH]nc(C(=O)N(C)OCCOP(=O)(N[C@@H](C)C(=O)OC(C)C)Oc5ccccc5)c4C3)cc12]

Rt (Method A) 3.47 mins, m/z 667 [M+H]+

1H NMR (400 MHz, DMSO-d6) δ 13.17 (s, 1H), 11.60 (s, 1H), 7.35 (d, 2H), 7.25-7.10 (m, 4H), 7.08 (m, 1H), 6.87 (m, 2H), 5.96 (m, 1H), 4.88-4.81 (m, 3H), 4.22-4.17 (m, 4H), 3.99 (m, 2H), 3.78 (m, 1H) 3.42 (m, 2H), 2.89 (m, 2H), 1.22-1.12 (m, 9H)

Example 56 propan-2-yl (2S)-2-({[2-({1-[5-(4-chloro-1H-indole-2-carbonyl)-1H,4H,5H,6H,7H-pyrazolo[4,3-c]pyridin-3-yl]-N-methylformamido}oxy)ethoxy](phenoxy)phosphoryl}amino)propanoate

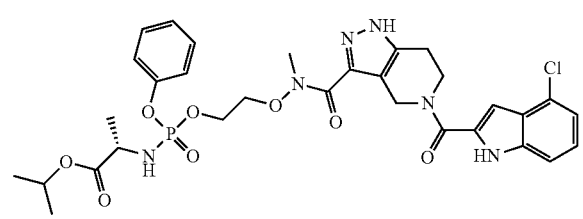

Rt (Method A) 3.54 mins, m/z 687/689 [M+H]+

1H NMR (400 MHz, DMSO-d6) δ 13.13 (s, 1H), 12.05 (s, 1H), 7.42-7.33 (m, 3H), 7.22-7.14 (m, 5H), 6.84 (s, 1H), 5.96 (m, 1H), 4.94-4.81 (m, 3H), 4.22-4.16 (m, 4H), 3.98 (m, 2H), 3.82-3.75 (m, 1H) 3.40 (m, 3H), 2.89 (m, 2H), 1.22-1.12 (m, 9H)

Example 57

5-(6-chloro-1H-indole-2-carbonyl)-N-(2-hydroxyethyl)-N-methyl-1H,4H,5H,6H,7H-pyrazolo[4,3-c]pyridine-3-carboxamide

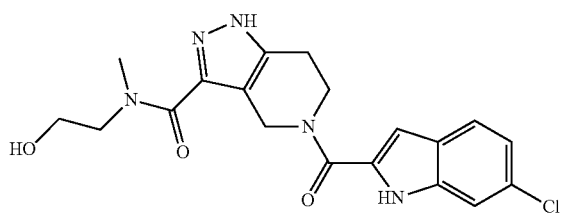 [SMILES: CN(CCO)C(=O)c1n[nH]c2c1CN(C(=O)c1cc3ccc(Cl)cc3[nH]1)CC2]

Rt (Method A) 2.84 mins, m/z 402/404 [M+H]+
1H NMR (400 MHz, DMSO-d6) δ 13.07 (s, 1H), 11.79 (s, 1H), 7.67 (d, J=8.5 Hz, 1H), 7.43 (d, J=1.6 Hz, 1H), 7.08 (dd, J=8.5, 1.9 Hz, 1H), 6.92 (s, 1H), 5.15-4.58 (m, 3H), 4.11-3.89 (m, 2H), 3.90-3.75 (m, 1H), 3.67-3.51 (m, 2H), 3.51-3.43 (m, 1H), 3.43-3.36 (m, 1H), 3.05-2.78 (m, 4H).

Example 58

5-(4-chloro-1H-indole-2-carbonyl)-N-(2-hydroxyethyl)-N-methyl-1H,4H,5H,6H,7H-pyrazolo[4,3-c]pyridine-3-carboxamide

Rt (Method A) 2.81 mins, m/z 402/404 [M+H]+
1H NMR (400 MHz, DMSO-d6) δ 12.93 (s, 1H), 12.05 (s, 1H), 7.41 (d, J=8.0 Hz, 1H), 7.20 (t, J=7.8 Hz, 1H), 7.17-7.12 (m, 1H), 6.84 (s, 1H), 5.09-4.61 (m, 3H), 4.02-3.92 (m, 2H), 3.88-3.81 (m, 1H), 3.63-3.52 (m, 2H), 3.51-3.42 (m, 1H), 3.42-3.36 (m, 1H), 3.05-2.74 (m, 4H).

Example 59

N-(2-hydroxyethyl)-N-methyl-5-[4-(trifluoromethyl)-1H-indole-2-carbonyl]-1H,4H,5H,6H,7H-pyrazolo[4,3-c]pyridine-3-carboxamide

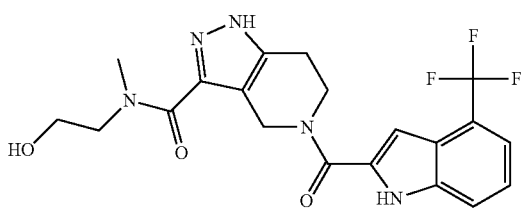 [SMILES: CN(CCO)C(=O)c1n[nH]c2c1CN(C(=O)c1cc3c(C(F)(F)F)cccc3[nH]1)CC2]

Rt (Method A) 2.92 mins, m/z 436 [M+H]+
1H NMR (400 MHz, DMSO-d6) δ 13.00 (s, 1H), 12.25 (s, 1H), 7.73 (d, J=8.2 Hz, 1H), 7.46 (d, J=7.4 Hz, 1H), 7.37 (t, J=7.8 Hz, 1H), 6.85 (s, 1H), 5.20-4.48 (m, 3H), 4.02-3.92 (m, 2H), 3.90-3.79 (m, 1H), 3.63-3.51 (m, 2H), 3.51-3.43 (m, 1H), 3.42-3.36 (m, 1H), 3.05-2.76 (m, 4H).

Example 60

5-(4-chloro-6-fluoro-1H-indole-2-carbonyl)-N-(2-hydroxyethyl)-N-methyl-1H,4H,5H,6H,7H-pyrazolo[4,3-c]pyridine-3-carboxamide

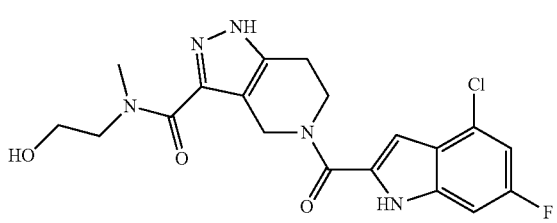 [SMILES: CN(CCO)C(=O)c1n[nH]c2c1CN(C(=O)c1cc3c(Cl)cc(F)cc3[nH]1)CC2]

Rt (Method A) 2.91 mins, m/z 420/422 [M+H]+
1H NMR (400 MHz, DMSO-d6) δ 13.07 (s, 1H), 12.13 (s, 1H), 7.20-7.15 (m, 2H), 6.86 (s, 1H), 5.09-4.62 (m, 3H), 4.09-3.90 (m, 2H), 3.90-3.77 (m, 1H), 3.68-3.52 (m, 2H), 3.52-3.43 (m, 1H), 3.43-3.36 (m, 1H), 3.05-2.93 (m, 2H), 2.93-2.78 (m, 2H).

Example 61

5-(6-fluoro-4-methyl-1H-indole-2-carbonyl)-N-(2-hydroxyethyl)-N-methyl-1H,4H,5H,6H,7H-pyrazolo[4,3-c]pyridine-3-carboxamide

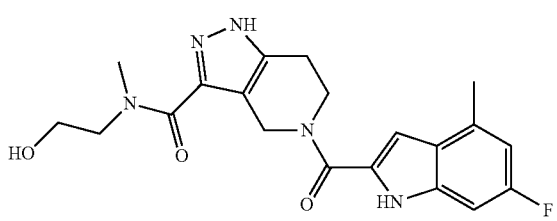 [SMILES: Cc1cc(F)cc2[nH]c(C(=O)N3CCc4[nH]nc(C(=O)N(C)CCO)c4C3)cc12]

Rt (Method A) 2.81 mins, m/z 400 [M+H]+
1H NMR (400 MHz, DMSO-d6) δ 13.07 (s, 1H), 11.68 (s, 1H), 6.99-6.89 (m, 2H), 6.76 (d, J=10.6 Hz, 1H), 5.20-4.50 (m, 2H), 4.06-3.91 (m, 2H), 3.88-3.80 (m, 1H), 3.63-3.53 (m, 2H), 3.52-3.43 (m, 1H), 3.41-3.37 (m, 1H), 3.02-2.94 (m, 2H), 2.94-2.83 (m, 2H)—One peak (3H) coincides with DMSO signal.

Example 62

5-(4-ethyl-1H-indole-2-carbonyl)-N-(2-hydroxyethyl)-N-methyl-1H,4H,5H,6H,7H-pyrazolo[4,3-c]pyridine-3-carboxamide

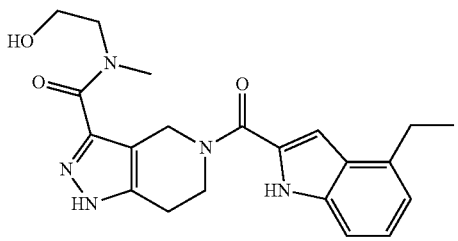 [SMILES: CCc1cccc2[nH]c(C(=O)N3CCc4[nH]nc(C(=O)N(C)CCO)c4C3)cc12]

Rt (Method A) 2.87 mins, m/z 396 [M+H]+

1H NMR (400 MHz, DMSO-d6) δ 13.02 (s, 1H), 11.59 (s, 1H), 7.25 (d, J=8.2 Hz, 1H), 7.11 (t, J=7.5 Hz, 1H), 6.92-6.84 (m, 2H), 5.28-4.51 (m, 3H), 4.03-3.94 (m, 2H), 3.88-3.80 (m, 1H), 3.63-3.52 (m, 2H), 3.51-3.42 (m, 1H), 3.42-3.36 (m, 1H), 3.04-2.94 (m, 2H), 2.93-2.81 (m, 4H), 1.28 (t, J=7.5 Hz, 3H).

Example 63

N-(2-hydroxyethyl)-N-methyl-5-(4-methyl-1H-indole-2-carbonyl)-1H,4H,5H,6H,7H-pyrazolo[4,3-c]pyridine-3-carboxamide

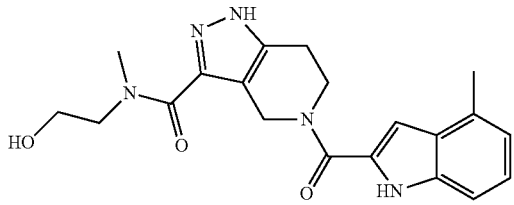 [SMILES: Cc1cccc2[nH]c(C(=O)N3CCc4[nH]nc(C(=O)N(C)CCO)c4C3)cc12]

Rt (Method A) 2.74 mins, m/z 382 [M+H]+

1H NMR (400 MHz, DMSO-d6) δ 13.03 (s, 1H), 11.59 (s, 1H), 7.24 (d, J=8.2 Hz, 1H), 7.08 (t, J=7.6 Hz, 1H), 6.91-6.82 (m, 2H), 5.09-4.48 (m, 3H), 4.10-3.91 (m, 2H), 3.91-3.78 (m, 1H), 3.66-3.52 (m, 2H), 3.52-3.43 (m, 1H), 3.43-3.37 (m, 1H), 3.06-2.94 (m, 2H), 2.94-2.80 (m, 2H)—One signal (3H) coincides with DMSO signal.

Example 64 propan-2-yl (2S)-2-({[2-({1-[5-(1H-indole-2-carbonyl)-1H,4H,5H,6H,7H-pyrazolo[4,3-c]pyridin-3-yl]-N-methylformamido}oxy)ethoxy](phenoxy)phosphoryl}amino)propanoate

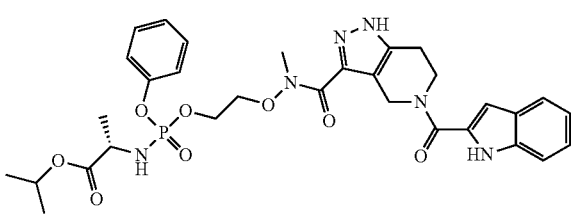 [SMILES: CC(C)OC(=O)[C@H](C)NP(=O)(OCCON(C)C(=O)c1n[nH]c2c1CN(C(=O)c1cc3ccccc3[nH]1)CC2)Oc1ccccc1]

Rt (Method A) 3.37 mins, m/z 653 [M+H]+

1H NMR (400 MHz, DMSO-d6) δ 13.17 (s, 1H), 11.63 (s, 1H), 7.64 (d, J=8.0 Hz, 1H), 7.42 (d, J=8.2 Hz, 1H), 7.35 (m, 2H), 7.25-7.11 (m, 4H), 7.06 (m, 1H), 6.87 (s, 1H), 5.96 (m, 1H), 5.13-4.59 (m, 3H), 4.27-4.08 (m, 4H), 3.99 (m, 2H), 3.78 (m, 1H) 3.43 (m, 2H), 2.88 (m, 2H), 1.23-1.09 (m, 9H).

Example 65

Intentionally left blank

Example 66 propan-2-yl (2S)-2-{[(3-{1-[5-(4-chloro-1H-indole-2-carbonyl)-1H,4H,5H,6H,7H-pyrazolo[4,3-c]pyridin-3-yl]-N-methylformamido}propoxy)(phenoxy)phosphoryl]amino}propanoate

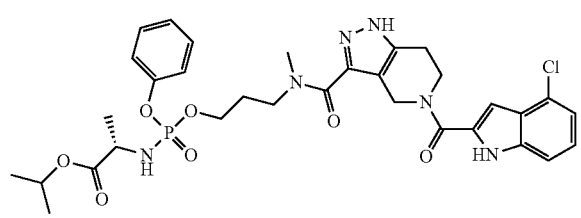 [SMILES: CC(C)OC(=O)[C@H](C)NP(=O)(OCCCN(C)C(=O)c1n[nH]c2c1CN(C(=O)c1cc3c(Cl)cccc3[nH]1)CC2)Oc1ccccc1]

Rt (Method A) 3.51 mins, m/z 685/687 [M+H]+

1H NMR (400 MHz, DMSO-d6) δ 13.07 (s, 1H), 12.04 (s, 1H), 7.41 (d, J=8.0 Hz, 1H), 7.35 (m, 2H), 7.24-7.11 (m, 5H), 6.83 (s, 1H), 5.89 (m, 1H), 4.94-4.80 (m, 3H), 3.98-3.75 (m, 6H), 3.46 (m, 1H), 2.89 (m, 3H), 1.96 (m, 2H), 1.20-1.12 (m, 9H) (one signal (2H) coincides with water signal).

Example 67 propan-2-yl (2S)-2-{[(2-{1-[5-(4-chloro-1H-indole-2-carbonyl)-1H,4H,5H,6H,7H-pyrazolo[4,3-c]pyridin-3-yl]-N-methylformamido}ethoxy)(phenoxy)phosphoryl]amino}propanoate Rt (Method A) 3.46 mins, m/z 671/673 [M+H]+

1H-NMR (400 MHz, DMSO-d6) δ 13.09 (s, 1H), 12.03 (s, 1H), 7.40 (d, J=8.0 Hz, 1H), 7.32 (m, 2H), 7.22-7.09 (m, 5H), 6.83 (s, 1H), 5.92 (m, 1H), 4.85-4.79 (m, 3H), 4.18-4.11 (m, 3H), 3.96 (m, 2H), 3.74-3.67 (m, 2H), 3.39 (m, 1H), 2.96-2.88 (m, 4H), 1.23-1.10 (m, 9H)

Example 68

5-(1H-indole-2-carbonyl)-1H,4H,5H,6H-pyrrolo[3,4-c]pyrazol-3-amine

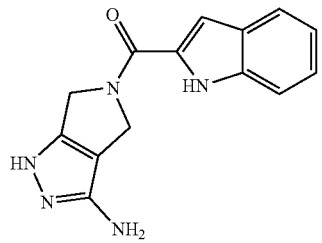 [SMILES: Nc1n[nH]c2c1CN(C(=O)c1cc3ccccc3[nH]1)C2]

Rt (Method A) 2.58 mins, m/z 268 [M+H]+

Example 69

5-(4,6-difluoro-1H-indole-2-carbonyl)-1H,4H,5H,6H-pyrrolo[3,4-c]pyrazol-3-amine

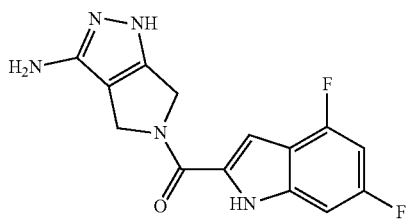 [SMILES: Nc1n[nH]c2c1CN(C(=O)c1cc3c(F)cc(F)cc3[nH]1)C2]

Rt (Method A) 2.80 mins, m/z 304 [M+H]+

Example 70 propan-2-yl (2S)-2-{[(3-{1-[5-(1H-indole-2-carbonyl)-1H,4H,5H,6H,7H-pyrazolo[4,3-c]pyridin-3-yl]-N-methylformamido}propoxy)(phenoxy)phosphoryl]amino}propanoate

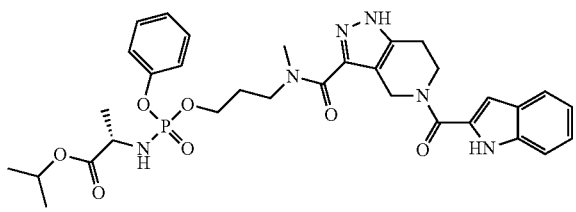 [SMILES: CC(C)OC(=O)[C@H](C)NP(=O)(OCCCN(C)C(=O)c1n[nH]c2c1CN(C(=O)c1cc3ccccc3[nH]1)CC2)Oc1ccccc1]

Rt (Method A) 3.35 mins, m/z 651 [M+H]+

1H NMR (400 MHz, DMSO-d6) δ 13.06 (s, 1H), 11.63 (s, 1H), 7.64 (d, J=8.0 Hz, 1H), 7.42 (d, J=8.2 Hz, 1H), 7.35 (m, 2H), 7.21-7.13 (m, 4H), 7.06 (m, 1H), 6.87 (s, 1H), 5.89 (m, 1H), 4.92-4.80 (m, 3H), 3.99-3.73 (m, 6H), 3.46 (m, 1H), 2.91 (m, 3H), 1.92 (m, 2H), 1.21-1.12 (m, 9H) (one signal (2H) coincides with water signal).

Example 71 propan-2-yl (2S)-2-{[(2-{1-[5-(1H-indole-2-carbonyl)-1H,4H,5H,6H,7H-pyrazolo[4,3-c]pyridin-3-yl]-N-methylformamido}ethoxy)(phenoxy)phosphoryl]amino}propanoate

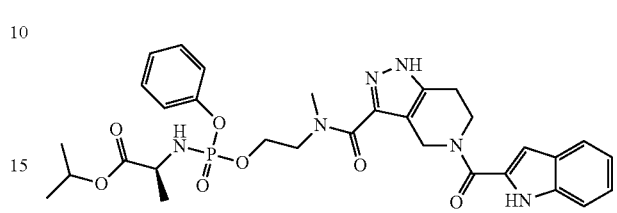

Rt (Method D) 3.29 mins, m/z 637 [M+H]+

1H NMR (400 MHz, DMSO-d6) δ 13.08 (m, 1H), 11.62 (m, 1H), 7.64 (d, J=8.0 Hz, 1H), 7.42 (d, J=8.2 Hz, 1H), 7.32 (m, 2H), 7.25-7.00 (m, 5H), 6.87 (s, 1H), 5.92 (m, 1H), 5.13-4.53 (m, 3H), 4.17 (m, 3H), 3.96 (m, 2H), 3.73-3.63 (m, 2H), 3.40 (m, 1H), 2.97-2.88 (m, 4H), 1.22-1.09 (m, 9H)

Examples 72 and 73

Intentionally left blank

Example 74

N-[5-(1H-indole-2-carbonyl)-1H,4H,5H,6H,7H-pyrazolo[4,3-c]pyridin-3-yl]-N-methylmethanesulfonamide

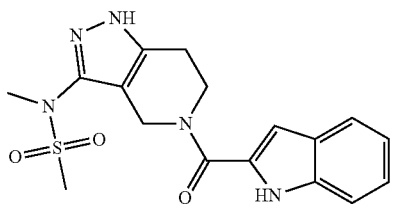 [SMILES: CN(c1n[nH]c2c1CN(C(=O)c1cc3ccccc3[nH]1)CC2)S(C)(=O)=O]

Rt (Method D) 2.78 mins, m/z 374 [M+H]+

1H NMR (400 MHz, DMSO-d6) δ 12.71 (s, 1H), 11.63 (s, 1H), 7.64 (d, J=7.9 Hz, 1H), 7.42 (d, J=8.2 Hz, 1H), 7.26-7.15 (m, 1H), 7.11-7.01 (m, 1H), 6.89 (s, 1H), 5.08-4.35 (m, 2H), 4.14-3.82 (m, 2H), 3.14 (s, 3H), 3.05-2.78 (m, 5H).

Example 75

5-(1H-indole-2-carbonyl)-N,N-dimethyl-1H,4H,5H,6H,7H-pyrazolo[4,3-c]pyridin-3-amine

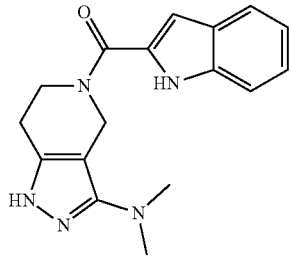 [SMILES: CN(C)c1n[nH]c2c1CN(C(=O)c1cc3ccccc3[nH]1)CC2]

Rt (Method D) 2.73 mins, m/z 310 [M+H]+
1H NMR (400 MHz, DMSO-d6) δ 11.75-11.40 (m, 2H), 7.64 (d, J=8.0 Hz, 1H), 7.43 (d, J=8.2 Hz, 1H), 7.27-7.15 (m, 1H), 7.13-7.02 (m, 1H), 6.90 (s, 1H), 5.10-4.44 (m, 2H), 4.12-3.77 (m, 2H), 2.98-2.60 (m, 8H).

Examples 76 to 78

Intentionally left blank

Example 79

N-(cyclopropylmethyl)-5-(1H-indole-2-carbonyl)-1H,4H,5H,6H,7H-pyrazolo[4,3-c]pyridin-3-amine

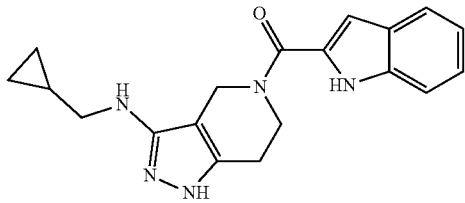 [SMILES: O=C(c1cc2ccccc2[nH]1)N1CCc2[nH]nc(NCC3CC3)c2C1]

Rt (Method D) 2.9 mins, m/z 336 [M+H]+ 1H NMR (400 MHz, DMSO-d6) δ 11.61 (s, 1H), 11.20 (s, 1H), 7.63 (d, J=8.0 Hz, 1H), 7.43 (d, J=8.1 Hz, 1H), 7.24-7.14 (m, 1H), 7.11-7.02 (m, 1H), 6.89 (s, 1H), 5.07 (s, 1H), 4.86-4.30 (m, 2H), 4.14-3.75 (m, 2H), 3.02-2.57 (m, 4H), 1.16-0.93 (m, 1H), 0.50-0.31 (m, 2H), 0.27-0.07 (m, 2H).

Example 80

N-ethyl-5-(1H-indole-2-carbonyl)-1H,4H,5H,6H,7H-pyrazolo[4,3-c]pyridin-3-amine

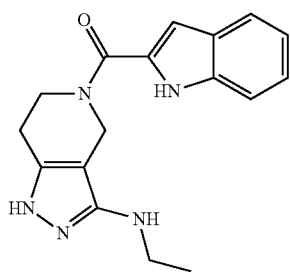 [SMILES: CCNc1n[nH]c2c1CN(C(=O)c1cc3ccccc3[nH]1)CC2]

Rt (Method D) 2.72 mins, m/z 310 [M+H]+
1H NMR (400 MHz, DMSO-d6) δ 11.61 (s, 1H), 11.20 (s, 1H), 7.63 (d, J=7.9 Hz, 1H), 7.42 (d, J=8.2 Hz, 1H), 7.25-7.14 (m, 1H), 7.12-7.02 (m, 1H), 6.88 (s, 1H), 4.96 (s, 1H), 4.80-4.26 (m, 2H), 4.10-3.74 (m, 2H), 3.18-2.96 (m, 2H), 2.92-2.58 (m, 2H), 1.10 (t, J=6.8 Hz, 3H).

Example 81

5-(1H-indole-2-carbonyl)-N-[(oxan-4-yl)methyl]-1H,4H,5H,6H,7H-pyrazolo[4,3-c]pyridin-3-amine

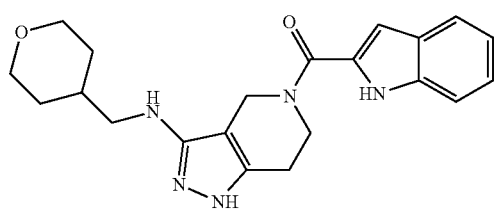 [SMILES: O=C(c1cc2ccccc2[nH]1)N1CCc2[nH]nc(NCC3CCOCC3)c2C1]

Rt (Method D) 2.75 mins, m/z 380 [M+H]+
1H NMR (400 MHz, DMSO-d6) δ 11.61 (s, 1H), 11.19 (s, 1H), 7.62 (d, J=8.0 Hz, 1H), 7.42 (d, J=8.2 Hz, 1H), 7.22-7.15 (m, 1H), 7.10-7.02 (m, 1H), 6.88 (s, 1H), 5.13 (s, 1H), 4.85-4.26 (m, 2H), 4.05-3.73 (m, 4H), 3.29-3.13 (m, 2H), 3.00-2.83 (m, 2H), 2.85-2.58 (m, 2H), 1.88-1.70 (m, 2H), 1.70-1.51 (m, 2H), 1.30-1.01 (m, 2H).

Example 82

N-[5-(1H-indole-2-carbonyl)-1H,4H,5H,6H,7H-pyrazolo[4,3-c]pyridin-3-yl]methanesulfonamide

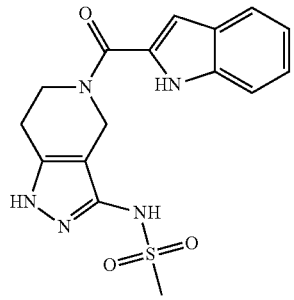 [SMILES: CS(=O)(=O)Nc1n[nH]c2c1CN(C(=O)c1cc3ccccc3[nH]1)CC2]

Rt (Method D) 2.2 mins, m/z 360 [M+H]+
1H NMR (400 MHz, DMSO-d6) δ 12.45 (bs, 1H), 11.61 (s, 1H), 9.28 (bs, 1H), 7.64 (d, J=8.0 Hz, 1H), 7.42 (d, J=8.2 Hz, 1H), 7.24-7.14 (m, 1H), 7.10-7.01 (m, 1H), 6.88 (s, 1H), 5.08-4.37 (m, 2H), 4.11-3.80 (m, 2H), 3.19-2.63 (m, 5H).

Example 83

5-(1H-indole-2-carbonyl)-N-(1-methylpiperidin-4-yl)-1H,4H,5H,6H,7H-pyrazolo[4,3-c]pyridine-3-carboxamide

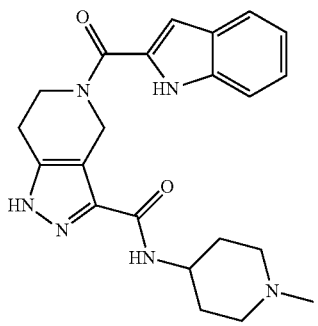 [SMILES: CN1CCC(NC(=O)c2n[nH]c3c2CN(C(=O)c2cc4ccccc4[nH]2)CC3)CC1]

Rt (Method A) 3.01 mins, m/z 407 [M+H]+

1H NMR (400 MHz, DMSO-d6) δ 13.09 (s, 1H), 11.63 (s, 1H), 7.85 (d, J=8.2 Hz, 1H), 7.64 (d, J=7.9 Hz, 1H), 7.42 (d, J=8.2 Hz, 1H), 7.23-7.15 (m, 1H), 7.10-7.02 (m, 1H), 6.87 (s, 1H), 5.23-4.64 (m, 2H), 4.03-3.91 (m, 2H), 3.74-3.56 (m, 1H), 3.00-2.78 (m, 2H), 2.76-2.65 (m, 2H), 2.13 (s, 3H), 1.96-1.84 (m, 2H), 1.72-1.52 (m, 4H).

Example 84

2-{2H,4H,5H,6H,7H,8H-pyrazolo[3,4-d]azepine-6-carbonyl}-1H-indole

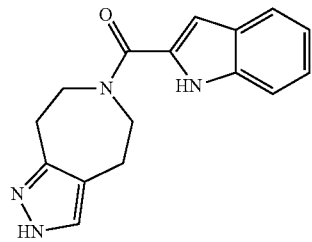 [SMILES: O=C(c1cc2ccccc2[nH]1)N1CCc2c[nH]nc2CC1]

Rt (Method A) 2.85 mins, m/z 281 [M+H]+

1H NMR (400 MHz, DMSO-d6) δ 12.33 (s, 1H), 11.59 (s, 1H), 7.63 (d, J=8.0 Hz, 1H), 7.46-7.28 (m, 2H), 7.24-7.14 (m, 1H), 7.10-7.00 (m, 1H), 6.87 (s, 1H), 4.13-3.69 (m, 4H), 3.05-2.86 (m, 2H), 2.85-2.71 (m, 2H).

Example 85

5-(1H-indole-2-carbonyl)-N-methyl-N-[(oxan-4-yl)methyl]-1H,4H,5H,6H,7H-pyrazolo[4,3-c]pyridine-3-carboxamide

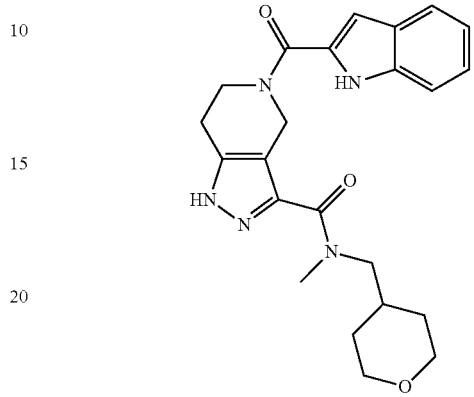

Rt (Method A) 2.82 mins, m/z 422 [M+H]+

1H NMR (400 MHz, DMSO-d6) δ 13.04 (s, 1H), 11.63 (s, 1H), 7.64 (d, J=8.0 Hz, 1H), 7.42 (d, J=8.2 Hz, 1H), 7.25-7.14 (m, 1H), 7.06 (t, J=7.4 Hz, 1H), 6.87 (s, 1H), 5.17-4.51 (m, 2H), 4.11-3.89 (m, 2H), 3.89-3.62 (m, 3H), 3.32-2.71 (m, 8H), 2.02-1.82 (m, 1H), 1.58-1.31 (m, 2H), 1.31-0.96 (m, 2H).

Example 86

Intentionally left blank

Example 87

N-cyclohexyl-5-(1H-indole-2-carbonyl)-1H,4H,5H,6H,7H-pyrazolo[4,3-c]pyridine-3-carboxamide

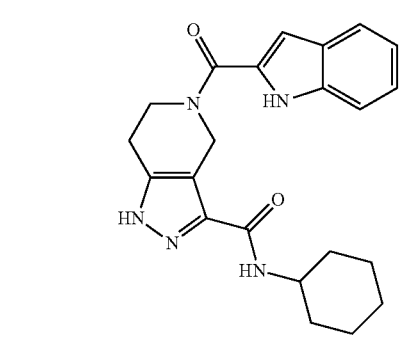 [SMILES: O=C(NC1CCCCC1)c1n[nH]c2c1CN(C(=O)c1cc3ccccc3[nH]1)CC2]

Rt (Method A) 3.28 mins, m/z 392 [M+H]+

1H NMR (400 MHz, DMSO-d6) δ 13.04 (s, 1H), 11.63 (s, 1H), 7.73 (d, J=8.3 Hz, 1H), 7.64 (d, J=7.9 Hz, 1H), 7.42 (d, J=8.2 Hz, 1H), 7.20 (t, J=7.5 Hz, 1H), 7.06 (t, J=7.4 Hz, 1H), 6.87 (s, 1H), 5.30-4.59 (m, 2H), 4.14-3.82 (m, 2H), 3.82-3.56 (m, 1H), 3.07-2.73 (m, 2H), 1.81-1.62 (m, 4H), 1.62-1.52 (m, 1H), 1.42-1.18 (m, 4H), 1.18-1.03 (m, 1H).

Example 88

Intentionally left blank

Example 89

1-[5-(1H-indole-2-carbonyl)-1H,4H,5H,6H,7H-pyrazolo[4,3-c]pyridine-3-carbonyl]azetidine-3-carboxamide

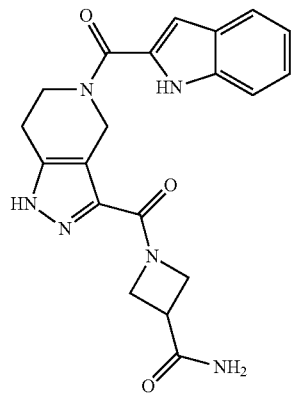 [SMILES: NC(=O)C1CN(C(=O)c2n[nH]c3c2CN(C(=O)c2cc4ccccc4[nH]2)CC3)C1]

Rt (Method A) 2.55 mins, m/z 393 [M+H]+

1H NMR (400 MHz, DMSO-d6) δ 13.13 (s, 1H), 11.63 (s, 1H), 7.64 (d, J=8.0 Hz, 1H), 7.48 (s, 1H), 7.42 (d, J=8.2 Hz, 1H), 7.23-7.16 (m, 1H), 7.11-6.99 (m, 2H), 6.87 (s, 1H), 5.20-4.64 (m, 2H), 4.64-4.48 (m, 1H), 4.48-4.37 (m, 1H), 4.18-3.78 (m, 4H), 2.99-2.76 (m, 2H). one signal (1H) coincided with water signal Example 90

Intentionally left blank

Example 91

N-benzyl-5-(1H-indole-2-carbonyl)-1H,4H,5H,6H,7H-pyrazolo[4,3-c]pyridin-3-amine

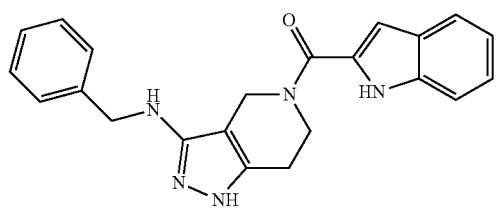 [SMILES: O=C(c1cc2ccccc2[nH]1)N1CCc2[nH]nc(NCc3ccccc3)c2C1]

Rt (Method D) 3.09 mins, m/z 372 [M+H]+

1H NMR (400 MHz, DMSO-d6) δ 11.60 (s, 1H), 11.51-9.61 (bs, 1H), 7.62 (d, J=8.0 Hz, 1H), 7.48-7.13 (m, 7H), 7.05 (t, J=7.4 Hz, 1H), 6.88 (s, 1H), 5.81-5.62 (m, 1H), 4.35-4.15 (m, 2H), 4.07-3.78 (m, 2H), 2.92-2.62 (m, 2H).

Examples 92 to 94

Intentionally left blank

Example 95

5-(1H-indole-2-carbonyl)-N-methyl-N-[(oxolan-3-yl)methyl]-1H,4H,5H,6H,7H-pyrazolo[4,3-c]pyridine-3-carboxamide

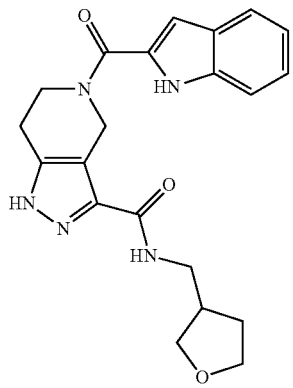 [SMILES: O=C(NCC1CCOC1)c1n[nH]c2c1CN(C(=O)c1cc3ccccc3[nH]1)CC2]

Rt (Method A) 2.77 mins, m/z 408 [M+H]+

Example 96

5-(1H-indole-2-carbonyl)-N-[(oxolan-3-yl)methyl]-1H,4H,5H,6H,7H-pyrazolo[4,3-c]pyridine-3-carboxamide Rt (Method A) 2.77 mins, m/z 394 [M+H]+

Example 97

5-(1H-indole-2-carbonyl)-N-methyl-N-[(oxolan-2-yl)methyl]-1H,4H,5H,6H,7H-pyrazolo[4,3-c]pyridine-3-carboxamide

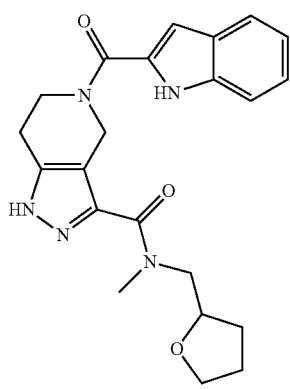 [SMILES: CN(CC1CCCO1)C(=O)c1n[nH]c2c1CN(C(=O)c1cc3ccccc3[nH]1)CC2]

Rt (Method A) 2.86 mins, m/z 408 [M+H]+

Example 98

2-[3-(4-methylpiperazine-1-carbonyl)-1H,4H,5H,6H,7H-pyrazolo[4,3-c]pyridine-5-carbonyl]-1H-indole

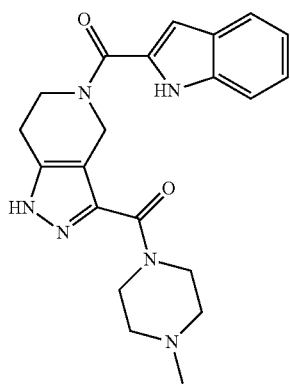 [SMILES: CN1CCN(C(=O)c2n[nH]c3c2CN(C(=O)c2cc4ccccc4[nH]2)CC3)CC1]

Rt (Method A) 2.68 mins, m/z 393 [M+H]+

1H NMR (400 MHz, DMSO-d6) δ 13.06 (s, 1H), 11.63 (s, 1H), 7.64 (d, J=8.0 Hz, 1H), 7.42 (d, J=8.2 Hz, 1H), 7.24-7.16 (m, 1H), 7.06 (dd, J=7.4 Hz, 1H), 6.87 (s, 1H), 5.18-4.50 (m, 2H), 4.23-3.82 (m, 4H), 3.78-3.45 (m, 2H), 2.97-2.80 (m, 2H), 2.37-2.24 (m, 4H), 2.17 (s, 3H).

Example 99

2-[3-(pyrrolidine-1-carbonyl)-1H,4H,5H,6H,7H-pyrazolo[4,3-c]pyridine-5-carbonyl]-1H-indole

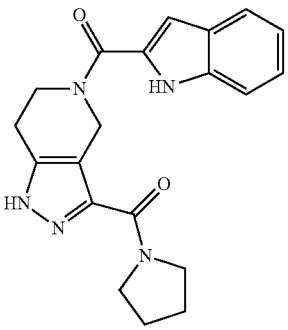 [SMILES: O=C(c1cc2ccccc2[nH]1)N1CCc2[nH]nc(C(=O)N3CCCC3)c2C1]

Rt (Method A) 2.88 mins, m/z 364 [M+H]+

Example 100

N-(2-hydroxyethyl)-5-(1H-indole-2-carbonyl)-N-methyl-1H,4H,5H,6H,7H-pyrazolo[4,3-c]pyridine-3-carboxamide

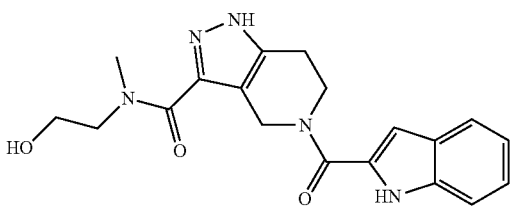

Rt (Method A) 2.59 mins, m/z 368 [M+H]+

Example 101

5-(1H-indole-2-carbonyl)-N-(2-methanesulfonyl-ethyl)-1H,4H,5H,6H7H-pyrazolo[4,3-c]pyridine-3-carboxamide

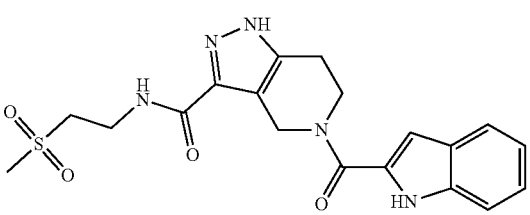 [SMILES: CS(=O)(=O)CCNC(=O)c1n[nH]c2c1CN(C(=O)c1cc3ccccc3[nH]1)CC2]

Rt (Method A) 2.69 mins, m/z 416 [M+H]+

1H NMR (400 MHz, DMSO-d6) δ 13.15 (s, 1H), 11.64 (s, 1H), 8.37-8.26 (m, 1H), 7.65 (d, J=7.9 Hz, 1H), 7.42 (d, J=8.2 Hz, 1H), 7.23-7.16 (m, 1H), 7.11-7.02 (m, 1H), 6.88 (s, 1H), 5.35-4.57 (m, 2H), 4.11-3.88 (m, 2H), 3.72-3.54 (m, 2H), 3.36-3.14 (m, 2H), 2.95-2.76 (m, 2H). one signal (2H) coincides with water signal Example 102

N-(3-hydroxypropyl)-5-(1H-indole-2-carbonyl)-N-methyl-1H,4H,5H,6H,7H-pyrazolo[4,3-c]pyridine-3-carboxamide

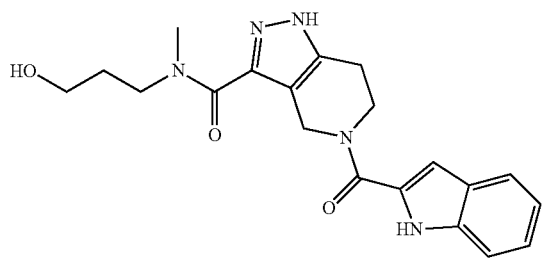 [SMILES: CN(CCCO)C(=O)c1n[nH]c2c1CN(C(=O)c1cc3ccccc3[nH]1)CC2]

Rt (Method A) 2.63 mins, m/z 382 [M+H]+

Example 103

N-ethyl-5-(1H-indole-2-carbonyl)-N-methyl-1H,4H,5H,6H,7H-pyrazolo[4,3-c]pyridine-3-carboxamide

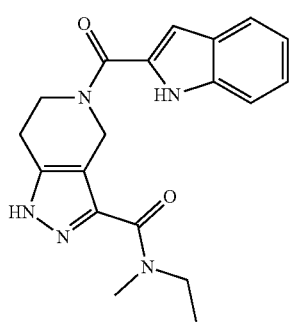 [SMILES: CCN(C)C(=O)c1n[nH]c2c1CN(C(=O)c1cc3ccccc3[nH]1)CC2]

Rt (Method A) 2.84 mins, m/z 352 [M+H]+

Example 104

5-(1H-indole-2-carbonyl)-N-(2-methoxyethyl)-1H,4H,5H,6H,7H-pyrazolo[4,3-c]pyridine-3-carboxamide

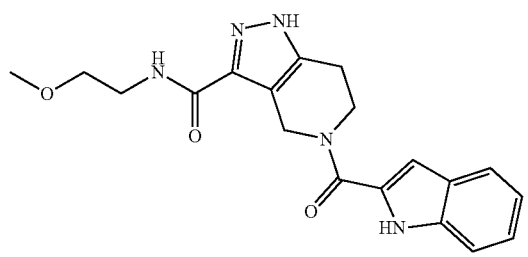 [SMILES: COCCNC(=O)c1n[nH]c2c1CN(C(=O)c1cc3ccccc3[nH]1)CC2]

Rt (Method A) 2.76 mins, m/z 368 [M+H]+

Example 105

N-(3-hydroxypropyl)-5-(1H-indole-2-carbonyl)-1H,4H,5H,6H,7H-pyrazolo[4,3-c]pyridine-3-carboxamide

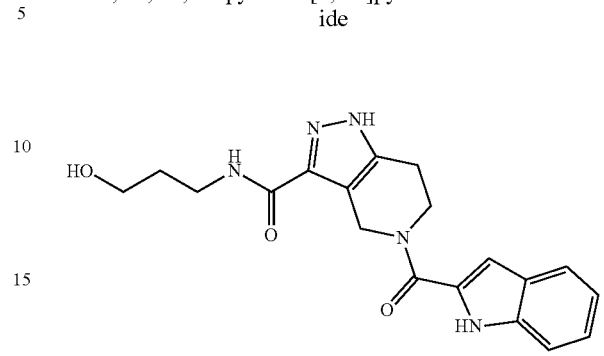

Rt (Method A) 2.61 mins, m/z 368 [M+H]+

Example 106

5-(1H-indole-2-carbonyl)-1H,4H,5H,6H,7H-pyrazolo[4,3-c]pyridine-3-carboxamide

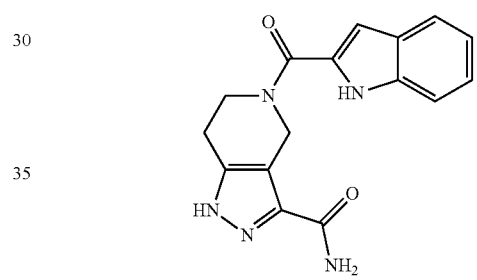

Rt (Method A) 2.59 mins, m/z 310 [M+H]+
1H NMR (400 MHz, DMSO-d6) δ 13.04 (s, 1H), 11.63 (s, 1H), 7.64 (d, J=8.0 Hz, 1H), 7.46-7.38 (m, 2H), 7.24-7.13 (m, 2H), 7.10-7.01 (m, 1H), 6.88 (s, 1H), 5.12-4.68 (m, 2H), 4.08-3.86 (m, 2H), 3.00-2.78 (m, 2H).

Example 107

N-(2-hydroxyethyl)-5-(1H-indole-2-carbonyl)-1H,4H,5H,6H,7H-pyrazolo[4,3-c]pyridine-3-carboxamide

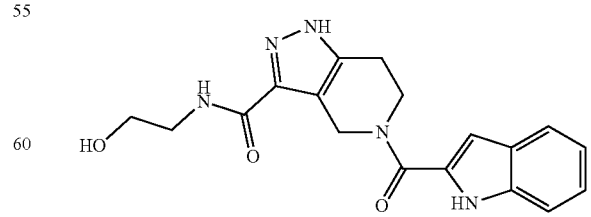

Rt (Method A) 2.58 mins, m/z 354 [M+H]+
1H NMR (400 MHz, DMSO-d6) δ 13.09 (s, 1H), 11.63 (s, 1H), 7.92 (s, 1H), 7.64 (d, J=7.9 Hz, 1H), 7.43 (d, J=8.2 Hz, 1H), 7.23-7.16 (m, 1H), 7.09-7.03 (m, 1H), 6.88 (s, 1H), 5.19-4.64 (m, 3H), 3.98 (bs, 2H), 3.51-3.42 (m, 2H), 3.30-3.24 (m, 2H), 2.89 (bs, 2H).

Example 108

2-[3-(morpholine-4-carbonyl)-1H,4H,5H,6H,7H-pyrazolo[4,3-c]pyridine-5-carbonyl]-1H-indole

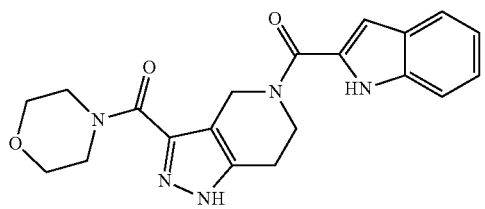 [SMILES: O=C(c1cc2ccccc2[nH]1)N1CCc2[nH]nc(C(=O)N3CCOCC3)c2C1]

Rt (Method A) 2.72 mins, m/z 380 [M+H]+

1H NMR (400 MHz, DMSO-d6) δ 13.10 (s, 1H), 11.63 (s, 1H), 7.64 (d, J=7.9 Hz, 1H), 7.42 (d, J=8.2 Hz, 1H), 7.19 (dd, J=7.5 Hz, 1H), 7.06 (dd, J=7.4 Hz, 1H), 6.88 (s, 1H), 5.27-4.50 (m, 2H), 4.28-4.05 (m, 2H), 4.05-3.87 (m, 2H), 3.76-3.48 (m, 6H), 3.02-2.75 (m, 2H).

Example 109

N-ethyl-5-(1H-indole-2-carbonyl)-1H,4H,5H,6H,7H-pyrazolo[4,3-c]pyridine-3-carboxamide

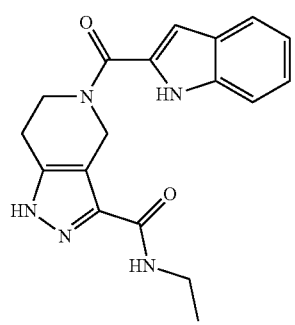 [SMILES: CCNC(=O)c1n[nH]c2c1CN(C(=O)c1cc3ccccc3[nH]1)CC2]

Rt (Method A) 2.81 mins, m/z 338 [M+H]+ 1H NMR (400 MHz, DMSO-d6) δ 13.05 (s, 1H), 11.63 (s, 1H), 8.14-8.02 (m, 1H), 7.65 (d, J=7.9 Hz, 1H), 7.42 (d, J=8.2 Hz, 1H), 7.24-7.16 (m, 1H), 7.11-7.03 (m, 1H), 6.88 (s, 1H), 5.22-4.66 (m, 2H), 4.09-3.87 (m, 2H), 3.27-3.10 (m, 2H), 3.02-2.76 (m, 2H), 1.13-0.97 (m, 3H).

Example 110

1-[5-(1H-indole-2-carbonyl)-1H,4H,5H,6H,7H-pyrazolo[4,3-c]pyridine-3-carbonyl]azetidine-3-carboxylic acid

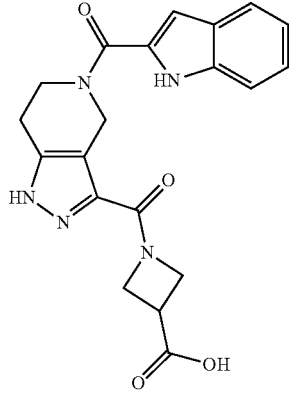 [SMILES: O=C(O)C1CN(C(=O)c2n[nH]c3c2CN(C(=O)c2cc4ccccc4[nH]2)CC3)C1]

Rt (Method A) 2.2 mins, m/z 394 [M+H]+

Example 111 methyl 1-[5-(1H-indole-2-carbonyl)-1H,4H,5H,6H,7H-pyrazolo[4,3-c]pyridine-3-carbonyl]azetidine-3-carboxylate

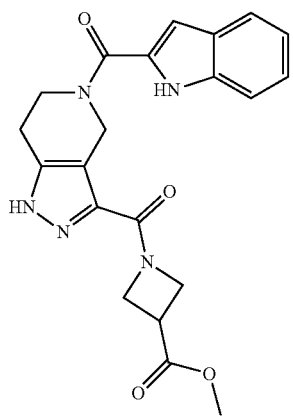 [SMILES: COC(=O)C1CN(C(=O)c2n[nH]c3c2CN(C(=O)c2cc4ccccc4[nH]2)CC3)C1]

Rt (Method A) 2.84 mins, m/z 408 [M+H]+

Example 112

2-[3-(piperidine-1-carbonyl)-1H,4H,5H,6H,7H-pyrazolo[4,3-c]pyridine-5-carbonyl]-1H-indole

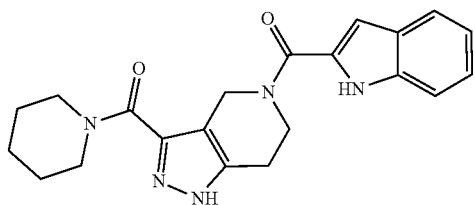 [SMILES: O=C(c1cc2ccccc2[nH]1)N1CCc2[nH]nc(C(=O)N3CCCCC3)c2C1]

Rt (Method A) 2.97 mins, m/z 378 [M+H]+

Example 113

5-(4-chloro-1H-indole-2-carbonyl)-N-methoxy-N-methyl-1H,4H,5H,6H,7H-pyrazolo[4,3-c]pyridine-3-carboxamide

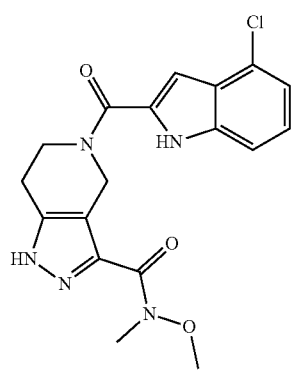 [SMILES: CON(C)C(=O)c1n[nH]c2c1CN(C(=O)c1cc3c(Cl)cccc3[nH]1)CC2]

Rt (Method A) 3 mins, m/z 388/390 [M+H]+

Example 114

4-fluoro-2-{1H,4H,5H,6H,7H-pyrazolo[4,3-c]pyridine-5-carbonyl}-1H-indole

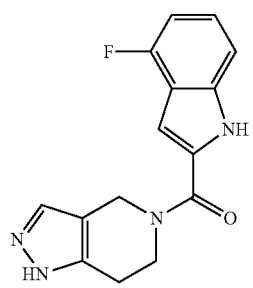 [SMILES: O=C(c1cc2c(F)cccc2[nH]1)N1CCc2[nH]ncc2C1]

Rt (Method A) 2.83 mins, m/z 285 [M+H]+

Example 115

5-(1H-indole-2-carbonyl)-1H,4H,5H,6H,7H-pyrazolo[4,3-c]pyridin-3-amine

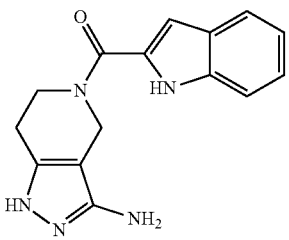 [SMILES: Nc1n[nH]c2c1CN(C(=O)c1cc3ccccc3[nH]1)CC2]

Rt (Method A) 2.55 mins, m/z 282 [M+H]+

Example 116

2-[3-(3-methyl-1,2,4-oxadiazol-5-yl)-1H,4H,5H,6H,7H-pyrazolo[4,3-c]pyridine-5-carbonyl]-1H-indole

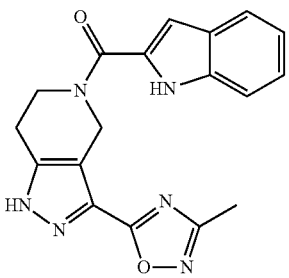 [SMILES: Cc1noc(-c2n[nH]c3c2CN(C(=O)c2cc4ccccc4[nH]2)CC3)n1]

Rt (Method A) 2.97 mins, m/z 349 [M+H]+

Example 117

11-(4,6-difluoro-1H-indole-2-carbonyl)-4,5,11-triazatricyclo[6.2.1.0$^{2,6}$]undeca-2(6),3-diene

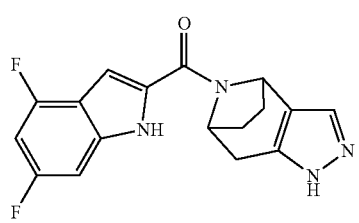 [SMILES: O=C(c1cc2c(F)cc(F)cc2[nH]1)N1C2CCC1c1cn[nH]c1C2]

Rt (Method A) 3.01 mins, m/z 329 [M+H]+

Example 118

[5-(1H-indole-2-carbonyl)-1H,4H,5H,6H,7H-pyrazolo[4,3-c]pyridin-3-yl]methanol

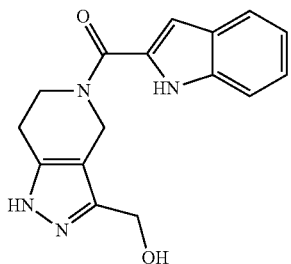 [SMILES: O=C(c1cc2ccccc2[nH]1)N1CCc2[nH]nc(CO)c2C1]

Rt (Method A) 2.58 mins, m/z 297 [M+H]+

Example 119

6-bromo-2-{1H,4H,5H,6H,7H-pyrazolo[4,3-c]pyridine-5-carbonyl}-1H-indole

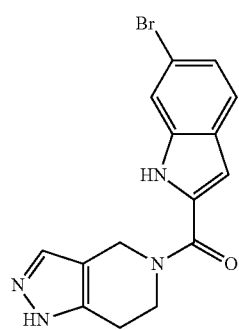 [SMILES: O=C(c1cc2ccc(Br)cc2[nH]1)N1CCc2[nH]ncc2C1]

Rt (Method A) 3.3 mins, m/z 345/347 [M+H]+

Example 120

7-chloro-2-{1H,4H,5H,6H,7H-pyrazolo[4,3-c]pyridine-5-carbonyl}-1H-indole

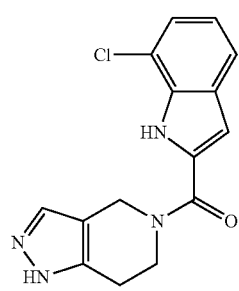 [SMILES: O=C(c1cc2cccc(Cl)c2[nH]1)N1CCc2[nH]ncc2C1]

Rt (Method A) 3.21 mins, m/z 301/303 [M+H]+

Example 121

Intentionally left blank

Example 122

5-chloro-2-{1H,4H,5H,6H,7H-pyrazolo[4,3-c]pyridine-5-carbonyl}-1H-indole

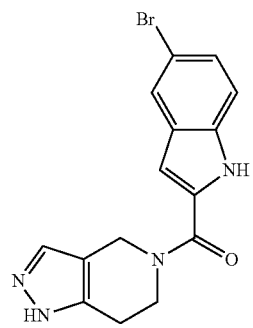 [SMILES: O=C(c1cc2cc(Br)ccc2[nH]1)N1CCc2[nH]ncc2C1]

Rt (Method A) 3.22 mins, m/z 301/303 [M+H]+

Example 123

11-(1H-indole-2-carbonyl)-4,5,11-triazatricyclo[6.2.1.0²,⁶]undeca-2(6),3-diene

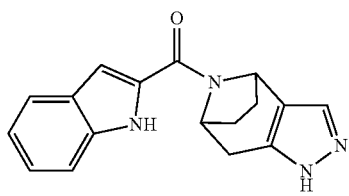 [SMILES: O=C(c1cc2ccccc2[nH]1)N1C2CCC1c1cn[nH]c1C2]

Rt (Method A) 3.34 mins, m/z 293 [M+H]+

Example 124

2-[3-(pyrazolidine-1-carbonyl)-1H,4H,5H,6H,7H-pyrazolo[4,3-c]pyridine-5-carbonyl]-1H-indole

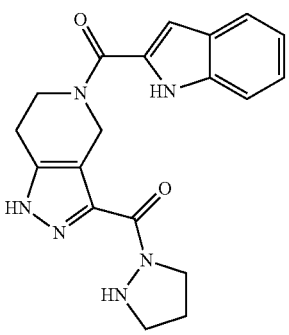 [SMILES: O=C(c1cc2ccccc2[nH]1)N1CCc2[nH]nc(C(=O)N3CCCN3)c2C1]

Rt (Method A) 2.99 mins, m/z 365 [M+H]+

Example 125

5-(4,7-difluoro-1H-indole-2-carbonyl)-N-methoxy-N-methyl-1H,4H,5H,6H,7H-pyrazolo[4,3-c]pyridine-3-carboxamide

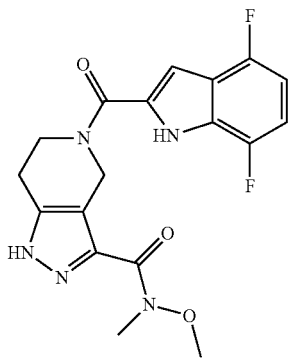 [SMILES: CON(C)C(=O)c1n[nH]c2c1CN(C(=O)c1cc3c(F)ccc(F)c3[nH]1)CC2]

Rt (Method A) 3.21 mins, m/z 390 [M+H]+

Example 126

5-(4-chloro-6-fluoro-1H-indole-2-carbonyl)-N-methoxy-N-methyl-1H,4H,5H,6H,7H-pyrazolo[4,3-c]pyridine-3-carboxamide

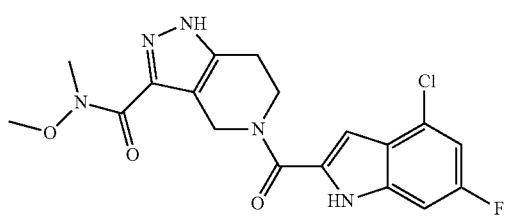 [SMILES: CON(C)C(=O)c1n[nH]c2c1CN(C(=O)c1cc3c(Cl)cc(F)cc3[nH]1)CC2]

Rt (Method A) 3.41 mins, m/z 406/408 [M+H]+

Example 127

5-(4,6-difluoro-1H-indole-2-carbonyl)-N-methoxy-N-methyl-1H4H,5H,6H,7H-pyrazolo[4,3-c]pyridine-3-carboxamide

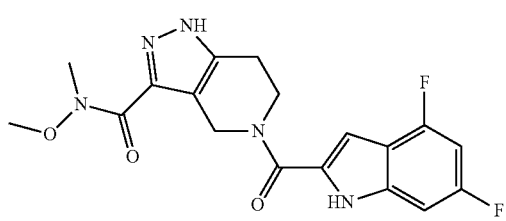 [SMILES: CON(C)C(=O)c1n[nH]c2c1CN(C(=O)c1cc3c(F)cc(F)cc3[nH]1)CC2]

Rt (Method A) 3.26 mins, m/z 390 [M+H]+

Example 128

5-(6-fluoro-4-methyl-1H-indole-2-carbonyl)-N-methoxy-N-methyl-1H,4H,5H,6H,7H-pyrazolo[4,3-c]pyridine-3-carboxamide

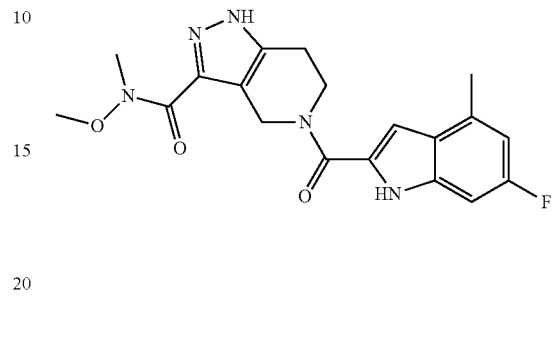

Rt (Method A) 3.3 mins, m/z 386 [M+H]+

Example 129

N-methoxy-N-methyl-5-[4-(trifluoromethyl)-1H-indole-2-carbonyl]-1H,4H,5H,6H,7H-pyrazolo[4,3-c]pyridine-3-carboxamide

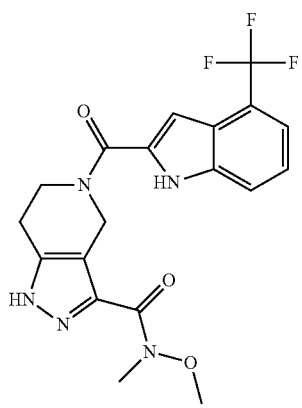 [SMILES: CON(C)C(=O)c1n[nH]c2c1CN(C(=O)c1cc3c(C(F)(F)F)cccc3[nH]1)CC2]

Rt (Method A) 3.38 mins, m/z 422 [M+H]+

Example 130

Intentionally left blank

Example 131

N-methoxy-N-methyl-5-(4-methyl-1H-indole-2-carbonyl)-1H,4H,5H,6H,7H-pyrazolo[4,3-c]pyridine-3-carboxamide

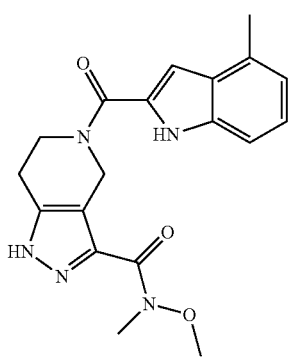 [SMILES: CON(C)C(=O)c1n[nH]c2c1CN(C(=O)c1cc3c(C)cccc3[nH]1)CC2]

Rt (Method A) 3.18 mins, m/z 368 [M+H]+

Example 132 methyl 1-[5-(1H-indole-2-carbonyl)-1H,4H,5H,6H,7H-pyrazolo[4,3-c]pyridine-3-carbonyl]piperidine-4-carboxylate

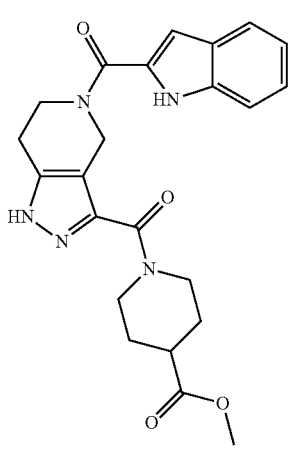 [SMILES: COC(=O)C1CCN(C(=O)c2n[nH]c3c2CN(C(=O)c2cc4ccccc4[nH]2)CC3)CC1]

Rt (Method B) 2.92 mins, m/z 436 [M+H]+

1H NMR (400 MHz, DMSO-d6) δ 13.06 (s, 1H), 11.63 (d, J=2.0 Hz, 1H), 7.64 (d, J=7.9 Hz, 1H), 7.42 (d, J=8.3 Hz, 1H), 7.19 (t, J=7.4 Hz, 1H), 7.06 (t, J=7.5 Hz, 1H), 6.87 (s, 1H), 5.30-4.53 (m, 3H), 4.52-4.15 (m, 1H), 4.10-3.84 (m, 2H), 3.61 (s, 3H), 3.30-3.13 (m, 1H), 3.06-2.75 (m, 3H), 2.72-2.61 (m, 1H), 1.98-1.78 (m, 2H), 1.61-1.41 (m, 2H).

Example 133

2-[3-(1,2-oxazolidine-2-carbonyl)-1H,4H,5H,6H,7H-pyrazolo[4,3-c]pyridine-5-carbonyl]-1H-indole

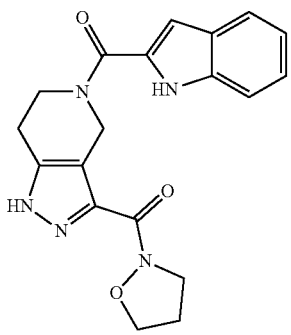 [SMILES: O=C(c1cc2ccccc2[nH]1)N1CCc2[nH]nc(C(=O)N3CCCO3)c2C1]

Rt (Method A) 3.09 mins, m/z 356 [M+H]+

Example 134

Intentionally left blank

Example 135

6-fluoro-4-methyl-2-{1H,4H,5H,6H,7H-pyrazolo[4,3-c]pyridine-5-carbonyl}-1H-indole

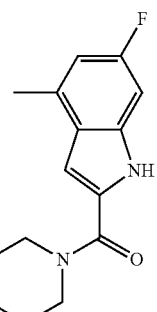

Rt (Method A) 3.07 mins, m/z 299 [M+H]+

Example 136

4-methyl-2-{1H,4H,5H,6H,7H-pyrazolo[4,3-c]pyridine-5-carbonyl}-1H-indole

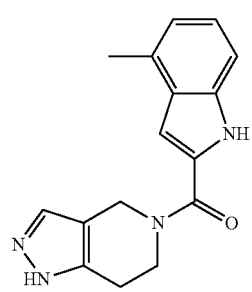

Rt (Method A) 3.02 mins, m/z 281 [M+H]+

Example 137

Intentionally left blank

Example 138

5-(1H-indole-2-carbonyl)-N-methoxy-N-methyl-1H,4H,5H,6H,7H-pyrazolo[4,3-c]pyridine-3-carboxamide

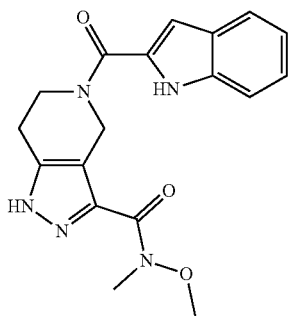 [SMILES: CON(C)C(=O)c1n[nH]c2c1CN(C(=O)c1cc3ccccc3[nH]1)CC2]

Rt (Method A) 3.07 mins, m/z 354 [M+H]+

Example 139

5-(1H-indole-2-carbonyl)-1H,4H,5H,6H,7H-pyrazolo[4,3-c]pyridine-3-carboxylic acid

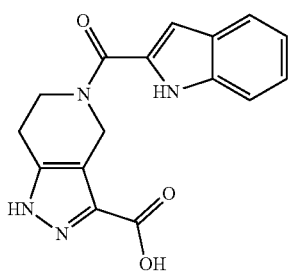 [SMILES: O=C(O)c1n[nH]c2c1CN(C(=O)c1cc3ccccc3[nH]1)CC2]

Rt (Method A) 2.2 mins, m/z 311 [M+H]+

Example 140 ethyl 5-(1H-indole-2-carbonyl)-1H,4H,5H,6H,7H-pyrazolo[4,3-c]pyridine-3-carboxylate

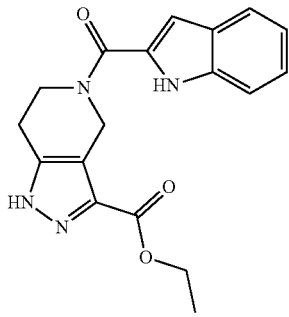 [SMILES: CCOC(=O)c1n[nH]c2c1CN(C(=O)c1cc3ccccc3[nH]1)CC2]

Rt (Method A) 3.12 mins, m/z 339 [M+H]+

Example 141

Intentionally left blank

Example 142

4-chloro-6-fluoro-2-{1H,4H,5H,6H,7H-pyrazolo[4,3-c]pyridine-5-carbonyl}-1H-indole

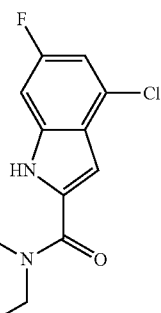
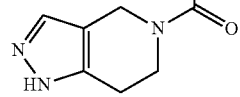

Rt (Method A) 3.17 mins, m/z 319/321 [M+H]+

Example 143

N-(1-hydroxy-2-methylpropan-2-yl)-5-(1H-indole-2-carbonyl)-N-methyl-1H,4H,5H,6H,7H-pyrazolo[4,3-c]pyridine-3-carboxamide

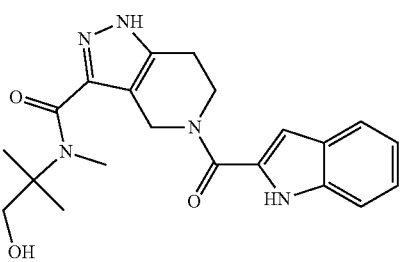 [SMILES: CN(C(=O)c1n[nH]c2c1CN(C(=O)c1cc3ccccc3[nH]1)CC2)C(C)(C)CO]

Rt (Method A) 2.76 mins, m/z 396 [M+H]+

1H NMR (400 MHz, DMSO-d6) δ 13.04 (s, 1H), 11.62 (s, 1H), 7.63 (d, J=7.8 Hz, 1H), 7.42 (d, J=8.2 Hz, 1H), 7.19 (t, J=7.1 Hz, 1H), 7.06 (t, J=7.6 Hz, 1H), 6.86 (s, 1H), 5.24-4.46 (m, 3H), 4.12-3.85 (m, 3H), 3.49-3.37 (m, 2H), 3.14-2.72 (m, 4H), 1.16-0.95 (m, 6H).

Example 144

5-[4-(1,1-difluoroethyl)-7-fluoro-1H-indole-2-carbonyl]-N-(2-hydroxyethyl)-N-methyl-1H,4H,5H,6H,7H-pyrazolo[4,3-c]pyridine-3-carboxamide

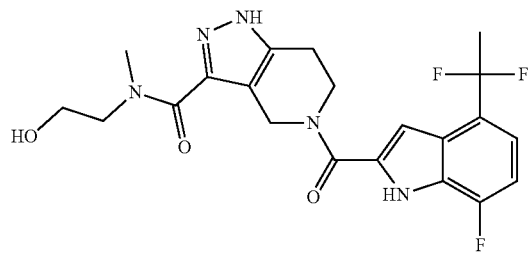 [SMILES: CN(CCO)C(=O)c1n[nH]c2c1CN(C(=O)c1cc3c(C(C)(F)F)ccc(F)c3[nH]1)CC2]

Rt (Method A) 2.91 mins, m/z 448 [M+H]+

1H NMR (400 MHz, DMSO-d6) δ 13.03 (d, J=9.1 Hz, 1H), 12.45 (s, 1H), 7.22 (dd, J=8.2, 4.3 Hz, 1H), 7.10 (dd, J=10.9, 8.1 Hz, 1H), 6.90-6.85 (m, 1H), 5.12-4.50 (m, 3H), 4.01-3.77 (m, 3H), 3.66-3.39 (m, 4H), 3.07-2.76 (m, 4H), 2.07 (t, J=18.8 Hz, 3H).

Example 145

1-{4-[5-(1H-indole-2-carbonyl)-1H,4H,5H,6H,7H-pyrazolo[4,3-c]pyridine-3-carbonyl]piperazin-1-yl}ethan-1-one

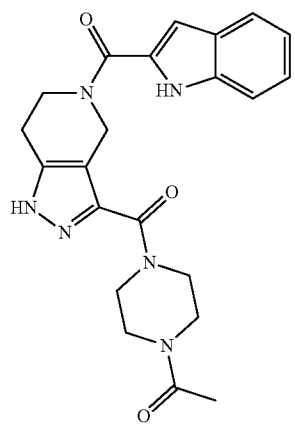 [SMILES: CC(=O)N1CCN(C(=O)c2n[nH]c3c2CN(C(=O)c2cc4ccccc4[nH]2)CC3)CC1]

Rt (Method A) 2.65 mins, m/z 421 [M+H]+

1H NMR (400 MHz, DMSO-d6) δ 13.13 (s, 1H), 11.63 (s, 1H), 7.64 (d, J=7.9 Hz, 1H), 7.42 (d, J=8.2 Hz, 1H), 7.23-7.16 (m, 1H), 7.09-7.03 (m, 1H), 6.88 (s, 1H), 5.14-4.59 (m, 2H), 4.24-3.85 (m, 4H), 3.73-3.44 (m, 6H), 3.00-2.78 (m, 2H), 2.02 (s, 3H).

Example 146

2-{3-[(2R,6R)-2,6-dimethylpiperidine-1-carbonyl]-1H,4H,5H,6H,7H-pyrazolo[4,3-c]pyridine-5-carbonyl}-1H-indole

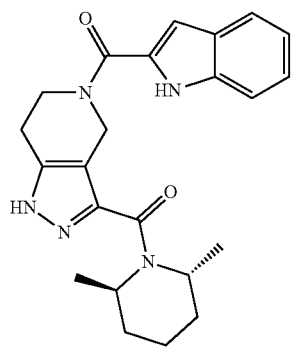 [SMILES: C[C@@H]1CCC[C@@H](C)N1C(=O)c1n[nH]c2c1CN(C(=O)c1cc3ccccc3[nH]1)CC2]

Rt (Method A) 3.27 mins, m/z 406 [M+H]+

Example 147

2-{3-[(2S)-2-methylpiperidine-1-carbonyl]-1H,4H,5H,6H,7H-pyrazolo[4,3-c]pyridine-5-carbonyl}-1H-indole

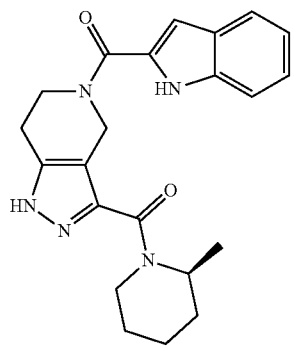 [SMILES: C[C@H]1CCCCN1C(=O)c1n[nH]c2c1CN(C(=O)c1cc3ccccc3[nH]1)CC2]

Rt (Method A) 3.12 mins, m/z 392 [M+H]+

Example 148

2-{3-[(2R)-2-methylpiperidine-1-carbonyl]-1H,4H,5H,6H,7H-pyrazolo[4,3-c]pyridine-5-carbonyl}-1H-indole

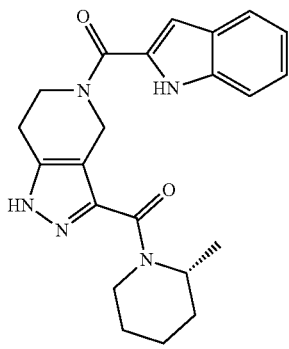 [SMILES: C[C@@H]1CCCCN1C(=O)c1n[nH]c2c1CN(C(=O)c1cc3ccccc3[nH]1)CC2]

Rt (Method A) 3.12 mins, m/z 392 [M+H]+

Example 149

N-(2-{1-[5-(1H-indole-2-carbonyl)-1H,4H,5H,6H,7H-pyrazolo[4,3-c]pyridin-3-yl]-N-methylformamido}ethyl)acetamide

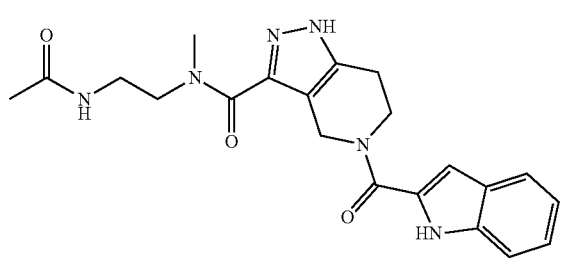 [SMILES: CC(=O)NCCN(C)C(=O)c1n[nH]c2c1CN(C(=O)c1cc3ccccc3[nH]1)CC2]

Rt (Method A) 2.58 mins, m/z 409 [M+H]+

Example 150

5-(1H-indole-2-carbonyl)-N-(2-methanesulfonylethyl)-N-methyl-1H,4H,5H,6H,7H-pyrazolo[4,3-c]pyridine-3-carboxamide

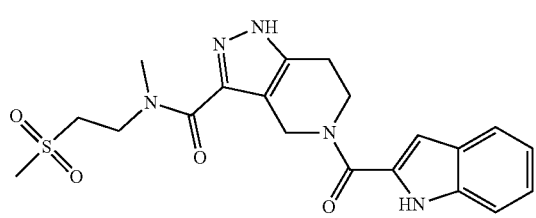 [SMILES: CN(CCS(C)(=O)=O)C(=O)c1n[nH]c2c1CN(C(=O)c1cc3ccccc3[nH]1)CC2]

Rt (Method A) 2.72 mins, m/z 430 [M+H]+

Example 151

2-(3-{5-azaspiro[3.4]octane-5-carbonyl}-1H,4H,5H,6H,7H-pyrazolo[4,3-c]pyridine-5-carbonyl)-1H-indole

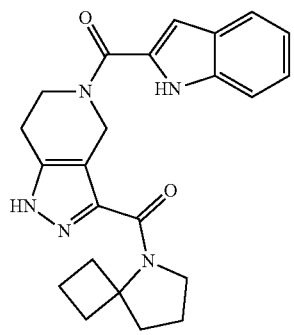 [SMILES: O=C(c1cc2ccccc2[nH]1)N1CCc2[nH]nc(C(=O)N3CCCC34CCC4)c2C1]

Rt (Method A) 3.38 mins, m/z 404 [M+H]+

Example 152

2-{3-[(3aR,6aR)-hexahydro-2H-furo[2,3-c]pyrrole-5-carbonyl]-1H,4H,5H,6H,7H-pyrazolo[4,3-c]pyridine-5-carbonyl}-1H-indole

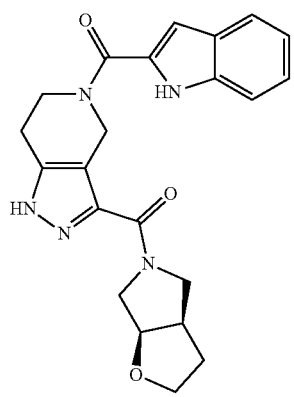 [SMILES: O=C(c1cc2ccccc2[nH]1)N1CCc2[nH]nc(C(=O)N3C[C@H]4CCO[C@H]4C3)c2C1]

Rt (Method A) 2.81 mins, m/z 406 [M+H]+

Example 153

2-(3-{hexahydro-1H-furo[3,4-c]pyrrole-5-carbonyl}-1H,4H,5H,6H,7H-pyrazolo[4,3-c]pyridine-5-carbonyl)-1H-indole

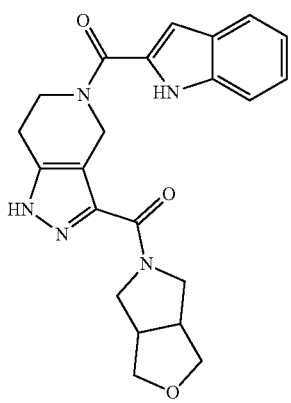 [SMILES: O=C(c1cc2ccccc2[nH]1)N1CCc2[nH]nc(C(=O)N3CC4COCC4C3)c2C1]

Rt (Method A) 2.77 mins, m/z 406 [M+H]+

Example 154

5-(1H-indole-2-carbonyl)-N-[1-(methoxymethyl)cyclobutyl]-N-methyl-1H,4H,5H,6H,7H-pyrazolo[4,3-c]pyridine-3-carboxamide

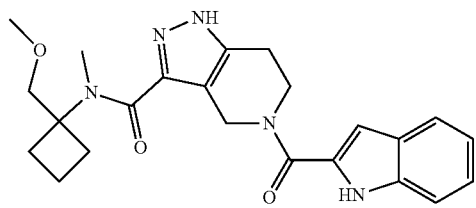 [SMILES: COCC1(N(C)C(=O)c2n[nH]c3c2CN(C(=O)c2cc4ccccc4[nH]2)CC3)CCC1]

Rt (Method A) 3.14 mins, m/z 422 [M+H]+

Example 155

5-(1H-indole-2-carbonyl)-N-[1-(methoxymethyl)cyclopropyl]-N-methyl-1H,4H,5H,6H,7H-pyrazolo[4,3-c]pyridine-3-carboxamide

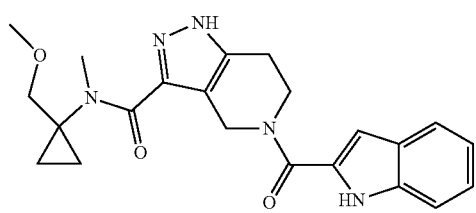 [SMILES: COCC1(N(C)C(=O)c2n[nH]c3c2CN(C(=O)c2cc4ccccc4[nH]2)CC3)CC1]

Rt (Method A) 3.00 mins, m/z 408 [M+H]+

Example 156

(3R)-1-[5-(1H-indole-2-carbonyl)-1H,4H,5H,6H,7H-pyrazolo[4,3-c]pyridine-3-carbonyl]pyrrolidin-3-ol

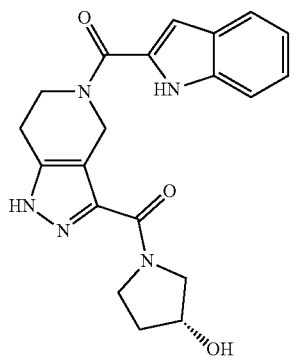 [SMILES: O=C(c1cc2ccccc2[nH]1)N1CCc2[nH]nc(C(=O)N3CC[C@@H](O)C3)c2C1]

Rt (Method A) 2.61 mins, m/z 380 [M+H]+

1H NMR (400 MHz, DMSO-d6) δ 13.07 (s, 1H), 11.62 (s, 1H), 7.64 (d, J=8.0 Hz, 1H), 7.42 (d, J=8.2 Hz, 1H), 7.22-7.16 (m, 1H), 7.06 (ddd, J=8.0, 7.0, 1.0 Hz, 1H), 6.87 (s, 1H), 5.11-4.66 (m, 3H), 4.36-4.20 (m, 1H), 4.10-3.73 (m, 4H), 3.62-3.38 (m, 2H), 3.04-2.75 (m, 2H), 1.97-1.67 (m, 2H).

Example 157

(3S)-1-[5-(1H-indole-2-carbonyl)-1H,4H,5H,6H,7H-pyrazolo[4,3-c]pyridine-3-carbonyl]pyrrolidin-3-ol

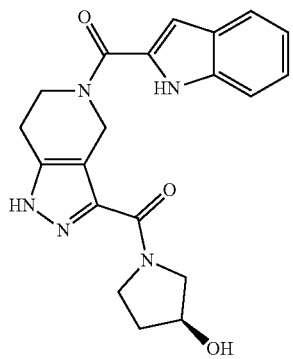 [SMILES: O=C(c1cc2ccccc2[nH]1)N1CCc2[nH]nc(C(=O)N3CC[C@H](O)C3)c2C1]

Rt (Method A) 2.61 mins, m/z 380 [M+H]+

Example 158

4-[5-(1H-indole-2-carbonyl)-1H,4H,5H,6H,7H-pyrazolo[4,3-c]pyridine-3-carbonyl]-1lambda6-thiomorpholine-1,1-dione

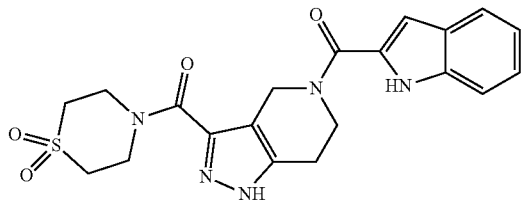 [SMILES: O=C(c1cc2ccccc2[nH]1)N1CCc2[nH]nc(C(=O)N3CCS(=O)(=O)CC3)c2C1]

Rt (Method A) 2.79 mins, m/z 428 [M+H]+

Example 159

2-[3-(thiomorpholine-4-carbonyl)-1H,4H,5H,6H,7H-pyrazolo[4,3-c]pyridine-5-carbonyl]-1H-indole

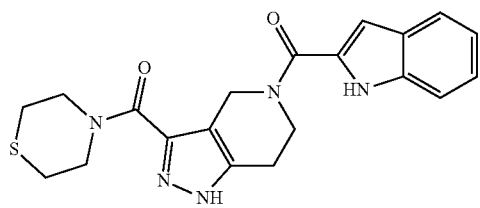 [SMILES: O=C(c1cc2ccccc2[nH]1)N1CCc2[nH]nc(C(=O)N3CCSCC3)c2C1]

Rt (Method A) 3.01 mins, m/z 396 [M+H]+
1H NMR (400 MHz, DMSO-d6) δ 13.11 (s, 1H), 11.63 (s, 1H), 7.64 (d, J=8.0 Hz, 1H), 7.42 (d, J=8.3 Hz, 1H), 7.23-7.16 (m, 1H), 7.09-7.02 (m, 1H), 6.87 (s, 1H), 5.14-4.58 (m, 2H), 4.43-4.12 (m, 2H), 4.10-3.70 (m, 4H), 3.03-2.78 (m, 2H), 2.69-2.60 (m, 4H).

Example 160

2-[3-(4-methoxypiperidine-1-carbonyl)-1H,4H,5H,6H,7H-pyrazolo[4,3-c]pyridine-5-carbonyl]-1H-indole

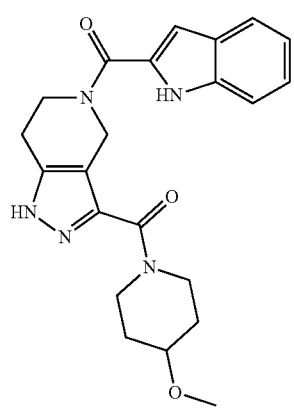 [SMILES: COC1CCN(C(=O)c2n[nH]c3c2CN(C(=O)c2cc4ccccc4[nH]2)CC3)CC1]

Rt (Method A) 2.86 mins, m/z 408 [M+H]+

Example 161

(3R)-1-[5-(1H-indole-2-carbonyl)-1H,4H,5H,6H,7H-pyrazolo[4,3-c]pyridine-3-carbonyl]piperidin-3-ol

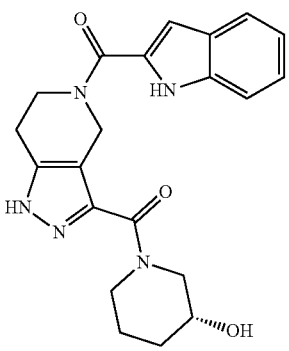 [SMILES: O=C(c1cc2ccccc2[nH]1)N1CCc2[nH]nc(C(=O)N3CCC[C@@H](O)C3)c2C1]

Rt (Method A) 2.68 mins, m/z 394 [M+H]+

Example 162

(3S)-1-[5-(1H-indole-2-carbonyl)-1H,4H,5H,6H,7H-pyrazolo[4,3-c]pyridine-3-carbonyl]piperidin-3-ol

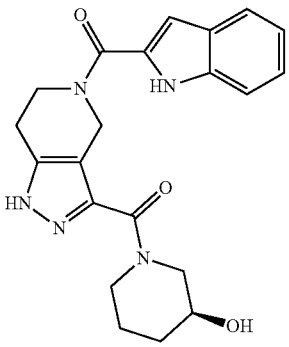 [SMILES: O=C(c1cc2ccccc2[nH]1)N1CCc2[nH]nc(C(=O)N3CCC[C@H](O)C3)c2C1]

Rt (Method A) 2.69 mins, m/z 394 [M+H]+

Example 163

1-{4-[5-(1H-indole-2-carbonyl)-1H,4H,5H,6H,7H-pyrazolo[4,3-c]pyridine-3-carbonyl]-3,3-dimethylpiperazin-1-yl}ethan-1-one

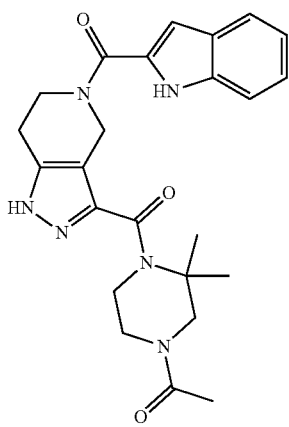 [SMILES: CC(=O)N1CCN(C(=O)c2n[nH]c3c2CN(C(=O)c2cc4ccccc4[nH]2)CC3)C(C)(C)C1]

Rt (Method A) 2.76 mins, m/z 449 [M+H]+

Example 164

1-{4-[5-(1H-indole-2-carbonyl)-1H,4H,5H,6H,7H-pyrazolo[4,3-c]pyridine-3-carbonyl]-3-methylpiperazin-1-yl}ethan-1-one

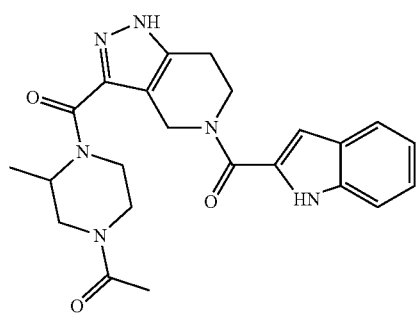 [SMILES: CC(=O)N1CCN(C(=O)c2n[nH]c3c2CN(C(=O)c2cc4ccccc4[nH]2)CC3)C(C)C1]

Rt (Method A) 2.7 mins, m/z 435 [M+H]+

Example 165

2-[3-(2,2-dimethylpiperidine-1-carbonyl)-1H,4H,5H,6H,7H-pyrazolo[4,3-c]pyridine-5-carbonyl]-1H-indole

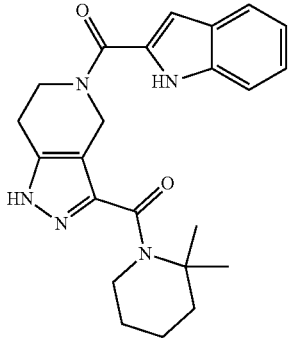 [SMILES: CC1(C)CCCCN1C(=O)c1n[nH]c2c1CN(C(=O)c1cc3ccccc3[nH]1)CC2]

Rt (Method A) 3.29 mins, m/z 406 [M+H]+

Example 166

5-(6-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

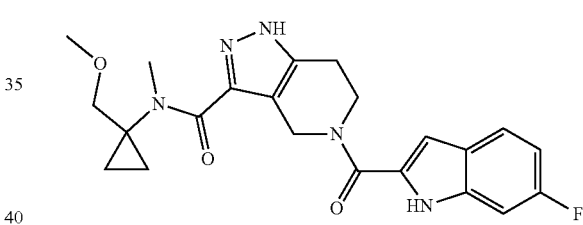

Rt (Method B) 3.01 mins, m/z 426 [M+H]+
1H NMR (400 MHz, DMSO-d6) ? 12.97 (s, 1H), 11.71 (s, 1H), 7.66 (dd, J=8.8, 5.6 Hz, 1H), 7.14 (dd, J=9.8, 2.3 Hz, 1H), 6.98-6.88 (m, 2H), 4.80 (m, 2H), 3.97 (m, 3H), 3.48 (m, 2H), 3.26 (m, 3H), 2.93 (m, 4H), 0.83 (m, 4H).

Example 167

2-{3-cyclobutyl-1H,4H,5H,6H,7H-pyrazolo[4,3-c]pyridine-5-carbonyl}-1H-indole

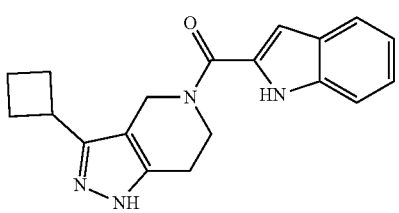 [SMILES: O=C(c1cc2ccccc2[nH]1)N1CCc2[nH]nc(C3CCC3)c2C1]

Rt (Method A) 3.16 mins, m/z 321 [M+H]+
1H NMR (400 MHz, DMSO-d6) δ 12.32 (s, 1H), 11.61 (s, 1H), 7.63 (d, J=7.9 Hz, 1H), 7.43 (d, J=8.3 Hz, 1H), 7.23-7.16 (m, 1H), 7.09-7.02 (m, 1H), 6.88 (s, 1H), 4.99-

4.45 (m, 2H), 4.04-3.88 (m, 2H), 3.57-3.40 (m, 1H), 2.84-2.74 (m, 2H), 2.27-2.12 (m, 4H), 2.03-1.90 (m, 1H), 1.88-1.71 (m, 1H).

Example 168

2-(3-{1-methyl-1H,4H,5H,6H-pyrrolo[3,4-c]pyrazole-5-carbonyl}-1H,4H,5H,6H,7H-pyrazolo[4,3-c]pyridine-5-carbonyl)-1H-indole

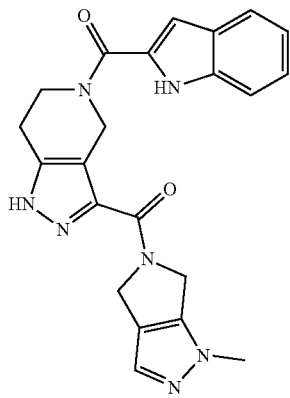 [SMILES: Cn1ncc2c1CN(C(=O)c1n[nH]c3c1CN(C(=O)c1cc4ccccc4[nH]1)CC3)C2]

Rt (Method B) 2.83 mins, m/z 416 [M+H]+

1H NMR (400 MHz, DMSO-d6) δ 13.20 (s, 1H), 11.63 (s, 1H), 7.65 (d, J=8.1 Hz, 1H), 7.53 (d, J=12.4 Hz, 1H), 7.42 (d, J=8.2 Hz, 1H), 7.19 (t, J=7.4 Hz, 1H), 7.06 (t, J=7.4 Hz, 1H), 6.89 (s, 1H), 5.20-4.66 (m, 4H), 4.63-4.43 (m, 2H), 4.11-3.92 (m, 2H), 3.83 (s, 3H), 3.05-2.69 (m, 2H).

Example 169

5-(1H-indole-2-carbonyl)-N-methyl-N-(1-methylpiperidin-4-yl)-1H,4H,5H,6H,7H-pyrazolo[4,3-c]pyridine-3-carboxamide

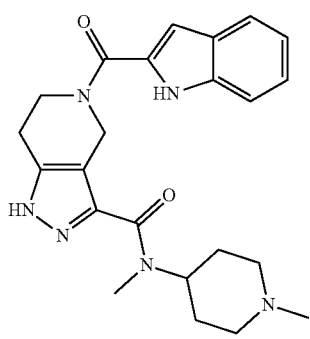 [SMILES: CN1CCC(N(C)C(=O)c2n[nH]c3c2CN(C(=O)c2cc4ccccc4[nH]2)CC3)CC1]

Rt (Method A) 2.77 mins, m/z 421 [M+H]+

1H NMR (400 MHz, DMSO-d6) δ 13.04 (s, 1H), 11.66-11.60 (m, 1H), 7.64 (d, J=7.9 Hz, 1H), 7.42 (d, J=8.0 Hz, 1H), 7.23-7.16 (m, 1H), 7.10-7.02 (m, 1H), 6.87 (s, 1H), 5.16-4.15 (m, 3H), 4.12-3.82 (m, 2H), 3.25-3.09 (m, 1H), 3.00-2.71 (m, 6H), 2.19-2.08 (m, 3H), 2.00-1.67 (m, 4H), 1.67-1.38 (m, 2H).

Example 170

N-cyclohexyl-5-(1H-indole-2-carbonyl)-N-methyl-1H,4H,5H,6H,7H-pyrazolo[4,3-c]pyridine-3-carboxamide

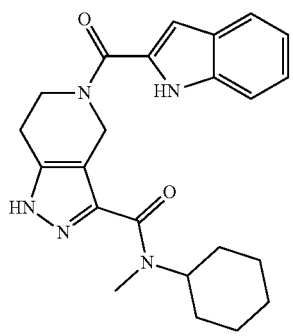 [SMILES: CN(C(=O)c1n[nH]c2c1CN(C(=O)c1cc3ccccc3[nH]1)CC2)C1CCCCC1]

Rt (Method A) 3.29 mins, m/z 406 [M+H]+

1H NMR (400 MHz, DMSO-d6) δ 13.03 (s, 1H), 11.63 (s, 1H), 7.64 (d, J=7.9 Hz, 1H), 7.42 (d, J=8.2 Hz, 1H), 7.23-7.16 (m, 1H), 7.09-7.02 (m, 1H), 6.87 (s, 1H), 5.16-4.21 (m, 3H), 4.09-3.85 (m, 2H), 3.24-3.10 (m, 1H), 2.95-2.76 (m, 3H), 1.88-0.94 (m, 11H).

Example 171 tert-butyl 2-{1-[5-(1H-indole-2-carbonyl)-1H,4H,5H,6H,7H-pyrazolo[4,3-c]pyridin-3-yl]-N-methylformamido}acetate

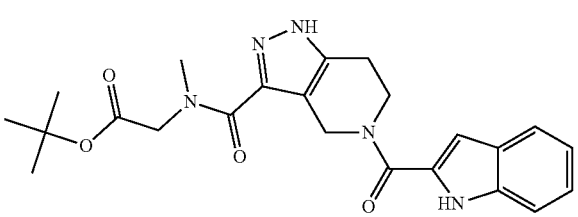 [SMILES: CN(CC(=O)OC(C)(C)C)C(=O)c1n[nH]c2c1CN(C(=O)c1cc3ccccc3[nH]1)CC2]

Rt (Method A) 3.24 mins, m/z 438 [M+H]+

1H NMR (400 MHz, DMSO-d6) δ 13.64-12.49 (m, 1H), 11.62 (s, 1H), 7.64 (t, J=7.3 Hz, 1H), 7.42 (d, J=8.2 Hz, 1H), 7.19 (t, J=7.6 Hz, 1H), 7.05 (t, J=7.6 Hz, 1H), 6.87 (s, 1H), 5.11-4.59 (m, 3H), 4.16-3.88 (m, 3H), 3.42-3.38 (m, 1H), 2.99-2.75 (m, 4H), 1.36 (s, 9H).

Example 172

5-[4-(difluoromethyl)-7-fluoro-1H-indole-2-carbonyl]-N-(2-hydroxyethyl)-N-methyl-1H,4H,5H,6H,7H-pyrazolo[4,3-c]pyridine-3-carboxamide

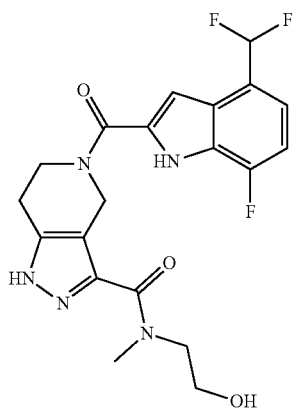 [SMILES: CN(CCO)C(=O)c1n[nH]c2c1CN(C(=O)c1cc3c(C(F)F)ccc(F)c3[nH]1)CC2]

Rt (Method A) 2.8 mins, m/z 436 [M+H]+

1H NMR (400 MHz, DMSO-d6) δ 13.04 (s, 1H), 12.51 (s, 1H), 7.47-7.06 (m, 3H), 6.97 (s, 1H), 5.01-4.53 (m, 3H), 4.08-3.71 (m, 3H), 3.71-3.38 (m, 4H), 3.15-2.75 (m, 4H).

Example 173

5-(1H-indole-2-carbonyl)-N-methyl-N-[(1r,4r)-4-hydroxycyclohexyl]-1H,4H,5H,6H,7H-pyrazolo[4,3-c]pyridine-3-carboxamide

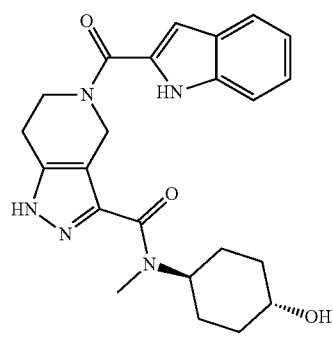 [SMILES: CN(C(=O)c1n[nH]c2c1CN(C(=O)c1cc3ccccc3[nH]1)CC2)[C@H]1CC[C@H](O)CC1]

Rt (Method A) 2.68 mins, m/z 422 [M+H]+

Example 174

5-(1H-indole-2-carbonyl)-N-methyl-N-[(1s,4s)-4-hydroxycyclohexyl]-1H,4H,5H,6H,7H-pyrazolo[4,3-c]pyridine-3-carboxamide

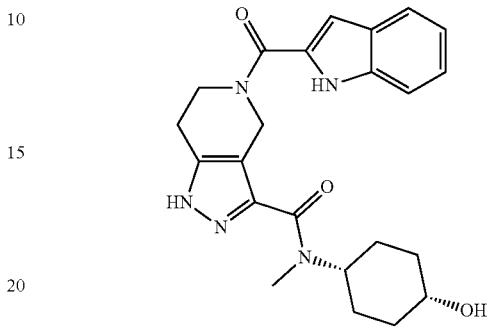

Rt (Method A) 2.69 mins, m/z 422 [M+H]+

Example 175

[(±)-3-[5-(1H-indole-2-carbonyl)-1H,4H,5H,6H,7H-pyrazolo[4,3-c]pyridine-3-carbonyl]-3-azabicyclo[3.1.0]hexan-6-yl]methanol

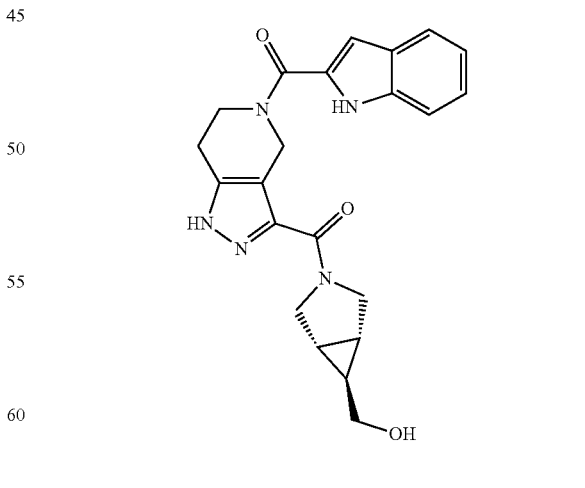

Rt (Method A) 2.67 mins, m/z 406 [M+H]+

Example 176

(±)-3-[5-(1H-indole-2-carbonyl)-1H,4H,5H,6H,7H-pyrazolo[4,3-c]pyridine-3-carbonyl]-3-azabicyclo[3.1.0]hexan-6-ol

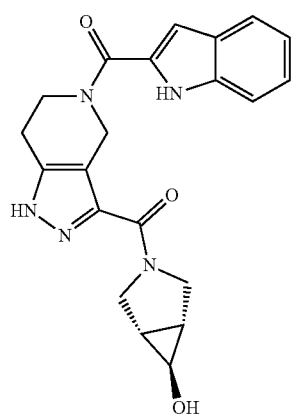 [SMILES: O=C(c1cc2ccccc2[nH]1)N1CCc2[nH]nc(C(=O)N3C[C@@H]4[C@@H](O)[C@@H]4C3)c2C1]

Rt (Method A) 2.65 mins, m/z 392 [M+H]+

1H NMR (400 MHz, DMSO-d6) δ 13.09 (s, 1H), 11.65-11.59 (m, 1H), 7.64 (d, J=8.0 Hz, 1H), 7.42 (d, J=8.3 Hz, 1H), 7.22-7.16 (m, 1H), 7.09-7.02 (m, 1H), 6.86 (s, 1H), 5.47-5.40 (m, 1H), 5.16-4.55 (m, 2H), 4.25-4.14 (m, 1H), 4.09-3.87 (m, 2H), 3.86-3.77 (m, 1H), 3.76-3.62 (m, 1H), 3.53-3.39 (m, 1H), 3.04-2.73 (m, 3H), 1.72-1.64 (m, 1H), 1.61-1.53 (m, 1H).

Example 177 ammonium 2-{1-[5-(1H-indole-2-carbonyl)-1H,4H,5H,6H,7H-pyrazolo[4,3-c]pyridin-3-yl]-N-methylformamido}ethane-1-sulfonate

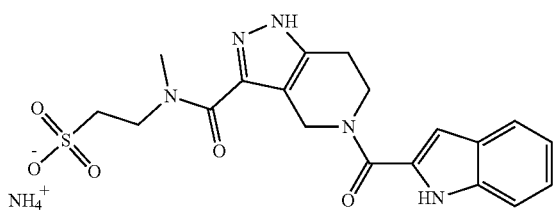

Rt (Method A) 2.27 mins, m/z 432 [M+H]+

Example 178

N-benzyl-5-(1H-indole-2-carbonyl)-N-methyl-1H4H,5H,6H,7H-pyrazolo[4,3-c]pyridine-3-carboxamide

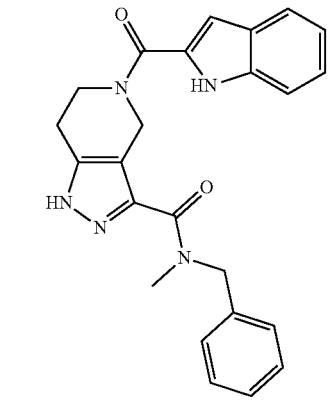 [SMILES: CN(Cc1ccccc1)C(=O)c1n[nH]c2c1CN(C(=O)c1cc3ccccc3[nH]1)CC2]

Rt (Method A) 3.26 mins, m/z 414 [M+H]+

Example 179

Intentionally left blank

Example 180

[(2S)-1-[5-(1H-indole-2-carbonyl)-1H,4H,5H,6H,7H-pyrazolo[4,3-c]pyridine-3-carbonyl]pyrrolidin-2-yl]methanol

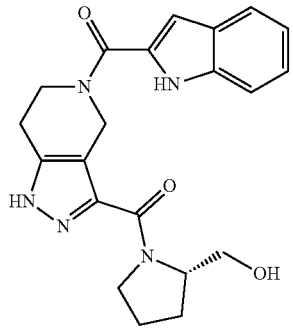 [SMILES: O=C(c1cc2ccccc2[nH]1)N1CCc2[nH]nc(C(=O)N3CCC[C@H]3CO)c2C1]

Rt (Method A) 2.76 mins, m/z 394 [M+H]+

Example 181

2-(3-{1H,4H,5H,6H-pyrrolo[3,4-c]pyrazole-5-carbonyl}-1H,4H,5H,6H,7H-pyrazolo[4,3-c]pyridine-5-carbonyl)-1H-indole

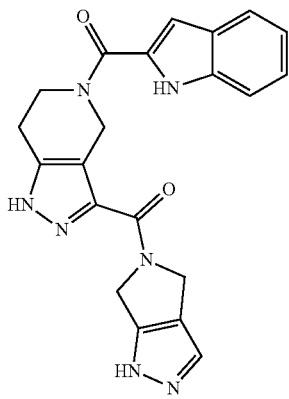 [SMILES: O=C(c1cc2ccccc2[nH]1)N1CCc2[nH]nc(C(=O)N3Cc4cn[nH]c4C3)c2C1]

Rt (Method A) 2.74 mins, m/z 402 [M+H]+

1H NMR (400 MHz, DMSO-d6) δ 13.21 (s, 1H), 12.71 (s, 1H), 11.64 (s, 1H), 7.65 (d, J=8.0 Hz, 1H), 7.55 (d, J=14.0 Hz, 1H), 7.42 (d, J=8.3 Hz, 1H), 7.23-7.16 (m, 1H), 7.09-7.03 (m, 1H), 6.89 (s, 1H), 5.24-4.71 (m, 4H), 4.66-4.48 (m, 2H), 4.13-3.88 (m, 2H), 3.06-2.79 (m, 2H).

Example 182

2-(3-{1-oxa-6-azaspiro[3.4]octane-6-carbonyl}-1H,4H,5H,6H,7H-pyrazolo[4,3-c]pyridine-5-carbonyl)-1H-indole

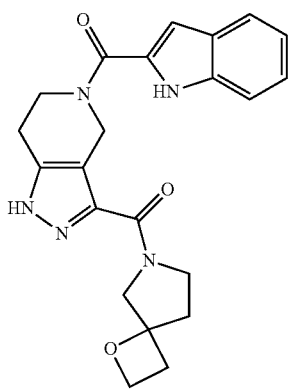 [SMILES: O=C(c1cc2ccccc2[nH]1)N1CCc2[nH]nc(C(=O)N3CCC4(CCO4)C3)c2C1]

Rt (Method A) 2.78 mins, m/z 406 [M+H]+

Example 183

2-(3-{2-oxa-6-azaspiro[3.4]octane-6-carbonyl}-1H,4H,5H,6H,7H-pyrazolo[4,3-c]pyridine-5-carbonyl)-1H-indole

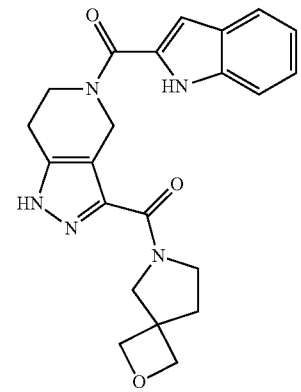 [SMILES: O=C(c1cc2ccccc2[nH]1)N1CCc2[nH]nc(C(=O)N3CCC4(COC4)C3)c2C1]

Rt (Method A) 2.75 mins, m/z 406 [M+H]+

Example 184

2-(3-{4-azaspiro[2.4]heptane-4-carbonyl}-1H,4H,5H,6H,7H-pyrazolo[4,3-c]pyridine-5-carbonyl)-1H-indole

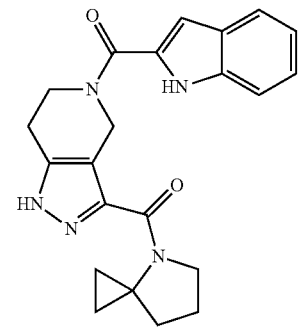 [SMILES: O=C(c1cc2ccccc2[nH]1)N1CCc2[nH]nc(C(=O)N3CCCC34CC4)c2C1]

Rt (Method A) 3.21 mins, m/z 390 [M+H]+

Example 185

N-ethyl-5-(1H-indole-2-carbonyl)-N-(oxetan-3-yl)-1H,4H,5H,6H,7H-pyrazolo[4,3-c]pyridine-3-carboxamide

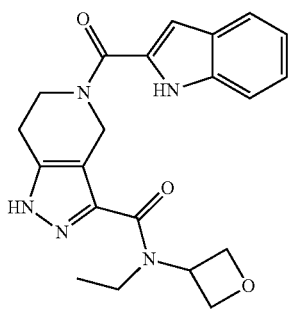 [SMILES: CCN(C(=O)c1n[nH]c2c1CN(C(=O)c1cc3ccccc3[nH]1)CC2)C1COC1]

Rt (Method A) 2.82 mins, m/z 394 [M+H]+

Example 186

2-[3-(3,3-difluoropyrrolidine-1-carbonyl)-1H,4H,5H,6H,7H-pyrazolo[4,3-c]pyridine-5-carbonyl]-1H-indole

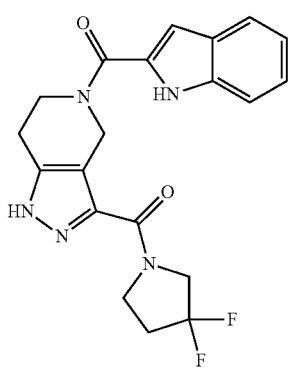 [SMILES: O=C(c1cc2ccccc2[nH]1)N1CCc2[nH]nc(C(=O)N3CCC(F)(F)C3)c2C1]

Rt (Method A) 3.11 mins, m/z 400 [M+H]+

Example 187

2-[3-(3,3-difluoropiperidine-1-carbonyl)-1H,4H,5H,6H,7H-pyrazolo[4,3-c]pyridine-5-carbonyl]-1H-indole

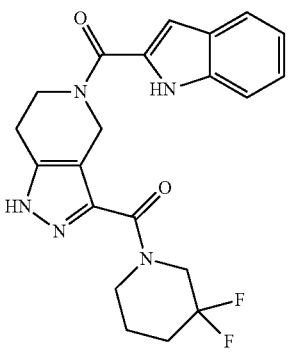 [SMILES: O=C(c1cc2ccccc2[nH]1)N1CCc2[nH]nc(C(=O)N3CCCC(F)(F)C3)c2C1]

Rt (Method A) 3.11 mins, m/z 414 [M+H]+

Example 188

5-(1H-indole-2-carbonyl)-N-methyl-N-(oxetan-3-yl)-1H,4H,5H,6H,7H-pyrazolo[4,3-c]pyridine-3-carboxamide

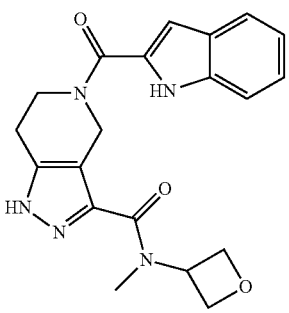 [SMILES: CN(C(=O)c1n[nH]c2c1CN(C(=O)c1cc3ccccc3[nH]1)CC2)C1COC1]

Rt (Method A) 2.7 mins, m/z 380 [M+H]+

Example 189

5-(1H-indole-2-carbonyl)-N-methyl-N-(oxolan-3-yl)-1H4H,5H,6H,7H-pyrazolo[4,3-c]pyridine-3-carboxamide

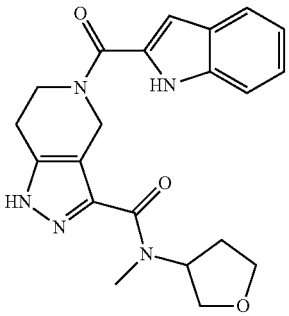 [SMILES: CN(C(=O)c1n[nH]c2c1CN(C(=O)c1cc3ccccc3[nH]1)CC2)C1CCOC1]

Rt (Method A) 2.77 mins, m/z 394 [M+H]+

Example 190

2-[3-(4,4-difluoropiperidine-1-carbonyl)-1H,4H,5H,6H,7H-pyrazolo[4,3-c]pyridine-5-carbonyl]-1H-indole

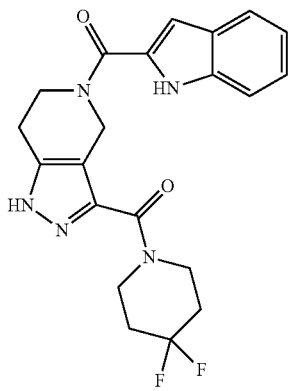 [SMILES: O=C(c1cc2ccccc2[nH]1)N1CCc2[nH]nc(C(=O)N3CCC(F)(F)CC3)c2C1]

Rt (Method A) 3.13 mins, m/z 414 [M+H]+

1H NMR (400 MHz, DMSO-d6) δ 13.15 (s, 1H), 11.63 (s, 1H), 7.64 (d, J=7.9 Hz, 1H), 7.42 (d, J=8.3 Hz, 1H), 7.23-7.16 (m, 1H), 7.09-7.02 (m, 1H), 6.88 (s, 1H), 5.18-4.57 (m, 2H), 4.40-4.10 (m, 2H), 4.08-3.87 (m, 2H), 3.87-3.57 (m, 2H), 3.04-2.73 (m, 2H), 2.10-1.91 (m, 4H).

Example 191 tert-butyl N-[(3R)-1-[5-(1H-indole-2-carbonyl)-1H,4H,5H,6H,7H-pyrazolo[4,3-c]pyridine-3-carbonyl]pyrrolidin-3-yl]carbamate

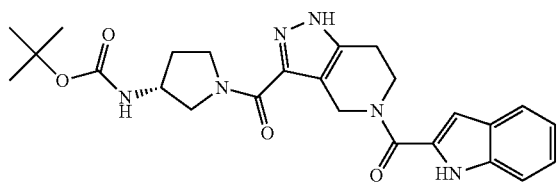 [SMILES: CC(C)(C)OC(=O)N[C@@H]1CCN(C(=O)c2n[nH]c3c2CN(C(=O)c2cc4ccccc4[nH]2)CC3)C1]

Rt (Method A) 3.14 mins, m/z 479 [M+H]+

Example 192

N-[(±)-2-hydroxycyclohexyl]-5-(1H-indole-2-carbonyl)-N-methyl-1H,4H,5H,6H,7H-pyrazolo[4,3-c]pyridine-3-carboxamide

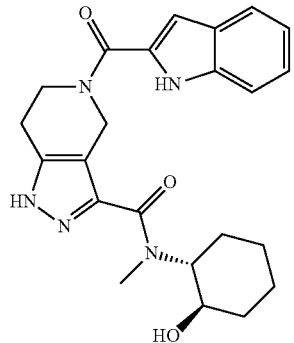 [SMILES: CN(C(=O)c1n[nH]c2c1CN(C(=O)c1cc3ccccc3[nH]1)CC2)[C@@H]1CCCC[C@H]1O]

Rt (Method A) 2.93 mins, m/z 422 [M+H]+

Example 193

5-(1H-indole-2-carbonyl)-N-methyl-N-(oxan-3-yl)-1H,4H,5H,6H,7H-pyrazolo[4,3-c]pyridine-3-carboxamide

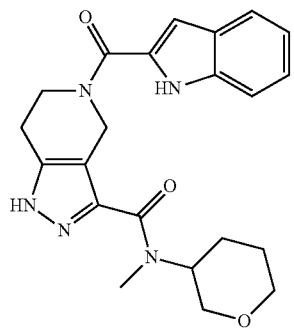 [SMILES: CN(C(=O)c1n[nH]c2c1CN(C(=O)c1cc3ccccc3[nH]1)CC2)C1CCCOC1]

Rt (Method A) 2.88 mins, m/z 408 [M+H]+

Example 194 tert-butyl N-[(3S)-1-[5-(1H-indole-2-carbonyl)-1H,4H,5H,6H,7H-pyrazolo[4,3-c]pyridine-3-carbonyl]pyrrolidin-3-yl]carbamate

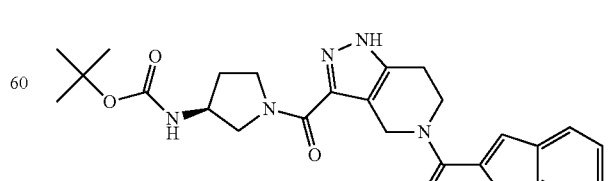

Rt (Method A) 3.14 mins, m/z 479 [M+H]+

Example 195

2-(3-{7-oxa-4-azaspiro[2.5]octane-4-carbonyl}-1H, 4H,5H,6H,7H-pyrazolo[4,3-c]pyridine-5-carbonyl)-1H-indole

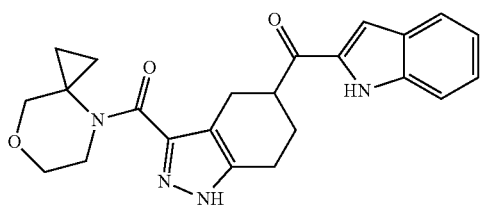 [SMILES: O=C(c1cc2ccccc2[nH]1)C1CCc2[nH]nc(C(=O)N3CCOCC34CC4)c2C1]

Rt (Method A) 2.81 mins, m/z 406 [M+H]+

Example 196

5-(4-chloro-1H-indole-2-carbonyl)-N-(2-hydroxy-ethoxy)-N-methyl-1H,4H,5H,6H,7H-pyrazolo[4,3-c]pyridine-3-carboxamide

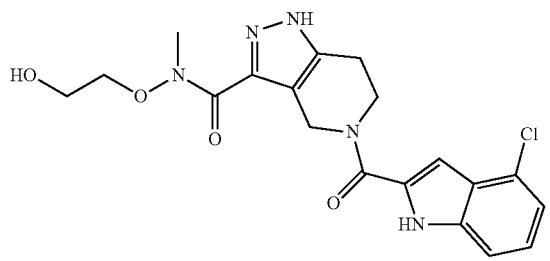 [SMILES: CN(OCCO)C(=O)c1n[nH]c2c1CN(C(=O)c1cc3c(Cl)cccc3[nH]1)CC2]

Rt (Method A) 2.99 mins, m/z 418/420 [M+H]+
1H NMR (400 MHz, DMSO-d6) δ 12.04 (s, 1H), 7.41 (d, J=8.0 Hz, 1H), 7.20 (t, J=7.8 Hz, 1H), 7.15 (d, J=7.3 Hz, 1H), 6.84 (s, 1H), 5.28-4.58 (m, 2H), 4.12-3.87 (m, 4H), 3.74-3.56 (m, 2H), 3.42-3.32 (m, 3H), 3.00-2.76 (m, 2H).

Example 197

N-(2-hydroxyethoxy)-N-methyl-5-(4-methyl-1H-indole-2-carbonyl)-1H,4H,5H,6H,7H-pyrazolo[4,3-c]pyridine-3-carboxamide

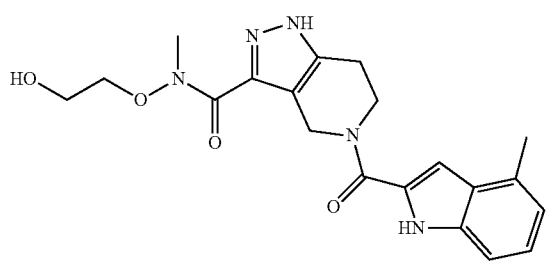 [SMILES: Cc1cccc2[nH]c(C(=O)N3CCc4[nH]nc(C(=O)N(C)OCCO)c4C3)cc12]

Rt (Method A) 2.89 mins, m/z 398 [M+H]+
1H NMR (400 MHz, DMSO-d6) δ 14.62-11.98 (m, 1H), 11.60 (s, 1H), 7.24 (d, J=8.2 Hz, 1H), 7.12-7.05 (m, 1H), 6.90-6.81 (m, 2H), 5.31-4.60 (m, 2H), 4.21-3.88 (m, 4H), 3.75-3.54 (m, 2H), 3.40-3.31 (m, 3H), 2.99-2.76 (m, 2H).

Example 198

N-(2-hydroxyethoxy)-5-(1H-indole-2-carbonyl)-N-methyl-1H,4H,5H,6H,7H-pyrazolo[4,3-c]pyridine-3-carboxamide

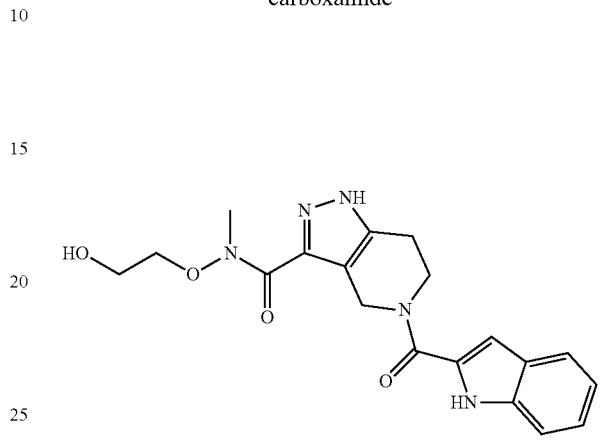

Rt (Method A) 2.77 mins, m/z 384 [M+H]+
1H NMR (400 MHz, DMSO-d6) δ 14.62-11.93 (m, 1H), 11.63 (s, 1H), 7.65 (d, J=8.0 Hz, 1H), 7.42 (d, J=8.2 Hz, 1H), 7.23-7.16 (m, 1H), 7.09-7.02 (m, 1H), 6.88 (s, 1H), 5.21-4.63 (m, 2H), 4.09-3.90 (m, 4H), 3.72-3.56 (m, 2H), 3.41-3.26 (m, 3H), 2.97-2.77 (m, 2H).

Example 199

5-(1H-indole-2-carbonyl)-N-methyl-N-(oxan-4-yl)-1H,4H,5H,6H,7H-pyrazolo[4,3-c]pyridine-3-carboxamide

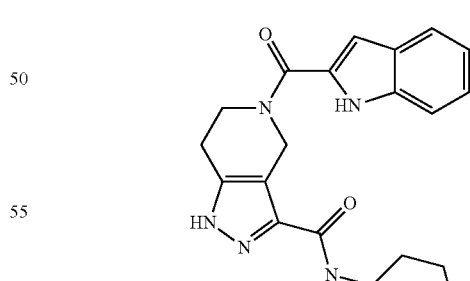

Rt (Method A) 2.79 mins, m/z 408 [M+H]+

Example 200

N-[(1R,2S)-2-hydroxycyclohexyl]-5-(1H-indole-2-carbonyl)-N-methyl-1H,4H,5H,6H,7H-pyrazolo[4,3-c]pyridine-3-carboxamide

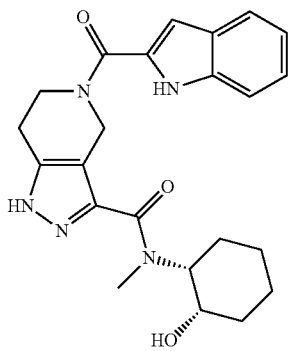 [SMILES: CN(C(=O)c1n[nH]c2c1CN(C(=O)c1cc3ccccc3[nH]1)CC2)[C@@H]1CCCC[C@@H]1O]

Rt (Method B) 2.91 mins, m/z 422 [M+H]+

1H NMR (400 MHz, DMSO-d6) δ 13.01 (s, 1H), 11.81-11.46 (m, 1H), 7.64 (d, J=8.0 Hz, 1H), 7.42 (d, J=8.3 Hz, 1H), 7.22-7.16 (m, 1H), 7.09-7.03 (m, 1H), 6.87 (s, 1H), 5.26-4.42 (m, 3H), 4.35-3.83 (m, 3H), 3.56-3.35 (m, 1H), 3.11-2.73 (m, 3H), 2.14-1.90 (m, 1H), 1.84-1.02 (m, 9H).

Example 201

5-(1H-indole-2-carbonyl)-N-[1-(methoxymethyl)cyclopropyl]-N-(2H3)methyl-1H,4H,5H,6H,7H-pyrazolo[4,3-c]pyridine-3-carboxamide

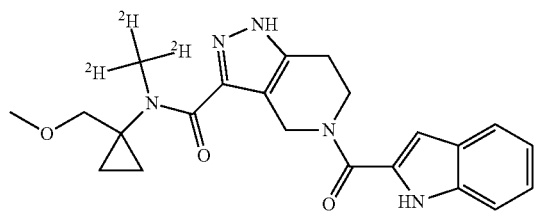 [SMILES: [2H]C([2H])([2H])N(C(=O)c1n[nH]c2c1CN(C(=O)c1cc3ccccc3[nH]1)CC2)C1(COC)CC1]

Rt (Method A) 2.92 mins, m/z 411 [M+H]+

1H NMR (400 MHz, DMSO-d6) δ 13.27-12.86 (m, 1H), 11.64 (s, 1H), 7.64 (d, J=8.0 Hz, 1H), 7.43 (d, J=8.2 Hz, 1H), 7.23-7.16 (m, 1H), 7.10-7.03 (m, 1H), 6.88 (s, 1H), 5.10-4.61 (m, 2H), 4.52-3.39 (m, 4H), 3.31-3.21 (m, 3H), 3.00-2.79 (m, 2H), 0.92-0.50 (m, 4H).

Example 202

5-(1H-indole-2-carbonyl)-N-[1-(methoxymethyl)cyclopropyl]-1H,4H,5H,6H,7H-pyrazolo[4,3-c]pyridine-3-carboxamide

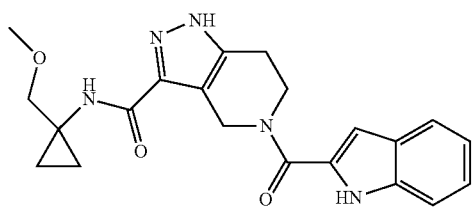 [SMILES: COCC1(NC(=O)c2n[nH]c3c2CN(C(=O)c2cc4ccccc4[nH]2)CC3)CC1]

Rt (Method A) 2.81 mins, m/z 394 [M+H]+

1H NMR (400 MHz, DMSO-d6) δ 13.21-12.92 (m, 1H), 11.64 (s, 1H), 8.17-8.04 (m, 1H), 7.65 (d, J=8.1 Hz, 1H), 7.43 (d, J=8.3 Hz, 1H), 7.23-7.16 (m, 1H), 7.10-7.03 (m, 1H), 6.89 (s, 1H), 5.19-4.64 (m, 2H), 4.10-3.85 (m, 2H), 3.44-3.39 (m, 2H), 3.24 (s, 3H), 2.99-2.75 (m, 2H), 0.80-0.66 (m, 4H).

Example 203

2-[3-(cyclopentyloxy)-1H,4H,5H,6H,7H-pyrazolo[4,3-c]pyridine-5-carbonyl]-1H-indole

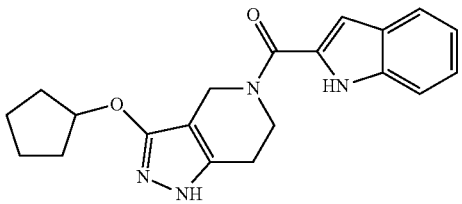 [SMILES: O=C(c1cc2ccccc2[nH]1)N1CCc2[nH]nc(OC3CCCC3)c2C1]

Rt (Method A) 3.32 mins, m/z 351 [M+H]+

1H NMR (400 MHz, DMSO-d6) δ 11.74-11.48 (m, 2H), 7.63 (d, J=8.0 Hz, 1H), 7.42 (d, J=8.2 Hz, 1H), 7.19 (t, J=7.6 Hz, 1H), 7.06 (t, J=7.5 Hz, 1H), 6.88 (s, 1H), 5.03-4.85 (m, 1H), 4.82-4.19 (m, 2H), 4.12-3.75 (m, 2H), 2.96-2.58 (m, 2H), 1.91-1.44 (m, 8H).

Example 204

5-(5-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

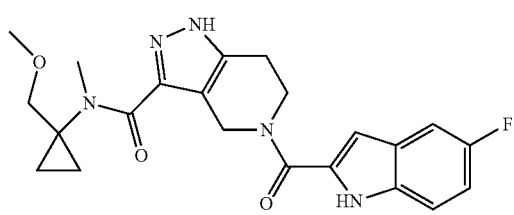 [SMILES: COCC1(N(C)C(=O)c2n[nH]c3c2CN(C(=O)c2cc4cc(F)ccc4[nH]2)CC3)CC1]

Rt (Method B) 3.00 mins, m/z 426 [M+H]+

1H NMR (400 MHz, DMSO-d6) δ 12.99 (m, 1H), 11.74 (s, 1H), 7.42 (m, 2H), 7.05 (td, J=9.2, 2.6 Hz, 1H), 6.86 (s, 1H), 4.78 (m, 2H), 3.96 (m, 3H), 3.48 (m, 1H), 3.33 (m, 1H), 3.26 (m, 3H), 2.93 (m, 4H), 0.78 (m, 4H).

Example 205

5-[4-(1,1-difluoroethyl)-6-fluoro-1H-indole-2-carbonyl]-N-[1-(methoxymethyl)cyclopropyl]-N-methyl-1H,4H,5H,6H,7H-pyrazolo[4,3-c]pyridine-3-carboxamide

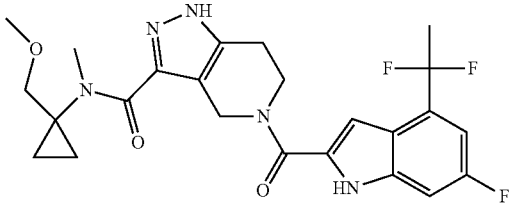 [SMILES: COCC1(N(C)C(=O)c2n[nH]c3c2CN(C(=O)c2cc4c(C(C)(F)F)cc(F)cc4[nH]2)CC3)CC1]

Rt (Method B) 3.21 mins, m/z 490 [M+H]+

1H NMR (400 MHz, DMSO-d6) δ 12.93 (s, 1H), 12.01 (s, 1H), 7.29 (dd, J=9.3, 2.2 Hz, 1H), 7.11 (dd, J=10.2, 2.2 Hz, 1H), 6.87 (s, 1H), 4.82 (m, 2H), 3.97 (m, 3H), 3.48 (m, 1H), 3.27 (m, 4H), 2.99 (m, 2H), 2.86 (m, 2H), 2.08 (t, J=18.9 Hz, 3H), 0.80 (m, 4H).

Example 206

5-(1H-indole-2-carbonyl)-N-{1-[(2H3)methoxymethyl]cyclopropyl}-N-methyl-1H,4H,5H,6H,7H-pyrazolo[4,3-c]pyridine-3-carboxamide

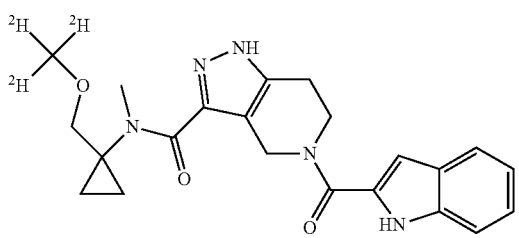 [SMILES: [2H]C([2H])([2H])OCC1(N(C)C(=O)c2n[nH]c3c2CN(C(=O)c2cc4ccccc4[nH]2)CC3)CC1]

Rt (Method A) 1.21 mins, m/z 411 [M+H]+

1H NMR (400 MHz, DMSO-d6) δ 12.99 (d, J=27.1 Hz, 1H), 11.62 (s, 1H), 7.64 (d, J=7.9 Hz, 1H), 7.42 (d, J=8.2 Hz, 1H), 7.19 (ddd, J=8.1, 6.9, 1.2 Hz, 1H), 7.06 (t, J=7.5 Hz, 1H), 6.87 (s, 1H), 4.80 (s, 2H), 3.97 (s, 2H), 3.47 (s, 2H), 2.93 (d, J=44.9 Hz, 4H), 0.78 (d, J=35.3 Hz, 4H).

Example 207

N-[1-(ethoxymethyl)cyclopropyl]-5-(1H-indole-2-carbonyl)-N-methyl-1H,4H,5H,6H,7H-pyrazolo[4,3-c]pyridine-3-carboxamide

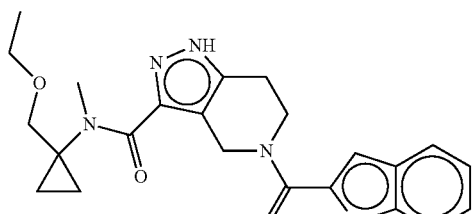

Rt (Method A) 1.30 mins, m/z 422 [M+H]+

1H NMR (400 MHz, DMSO-d6) δ 12.96 (s, 1H), 11.62 (s, 1H), 7.64 (d, J=8.0 Hz, 1H), 7.42 (d, J=8.2 Hz, 1H), 7.19 (ddd, J=8.3, 6.9, 1.1 Hz, 1H), 7.06 (ddd, J=8.1, 7.2, 1.0 Hz, 1H), 6.87 (s, 1H), 4.81 (s, 2H), 3.97 (s, 2H), 3.47 (d, J=35.9 Hz, 4H), 2.94 (d, J=49.4 Hz, 4H), 1.09 (s, 3H), 0.77 (d, J=33.7 Hz, 4H).

Example 208

5-(1H-indole-2-carbonyl)-N-methyl-N-{1-[(propan-2-yloxy)methyl]cyclopropyl}-1H,4H,5H,6H,7H-pyrazolo[4,3-c]pyridine-3-carboxamide

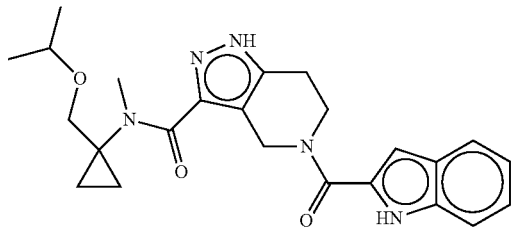

Rt (Method A) 1.38 mins, m/z 436 [M+H]+ 1H NMR (400 MHz, Methanol-d4) δ 7.63 (d, J=8.1 Hz, 1H), 7.43 (d, J=8.3 Hz, 1H), 7.22 (ddd, J=8.3, 7.0, 1.2 Hz, 1H), 7.10-7.03 (m, 1H), 6.92 (s, 1H), 4.99 (s, 2H), 4.28 (s, 1H), 4.08 (s, 1H), 3.90 (d, J=56.7 Hz, 1H), 3.58 (s, 1H), 3.09 (s, 2H), 2.94 (s, 2H), 1.27 (s, 3H), 0.95 (dd, J=88.7, 44.5 Hz, 8H).

Example 209

2-{3-[(3,3-difluoroazetidin-1-yl)sulfonyl]-1H,4H,5H,6H,7H-pyrazolo[4,3-c]pyridine-5-carbonyl}-1H-indole

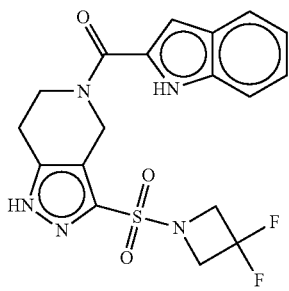

Rt (Method A) 3.18 mins, m/z 422 [M+H]+
1H NMR (400 MHz, DMSO-d6) δ 14.36-13.13 (m, 1H), 11.66 (s, 1H), 7.64 (d, J=8.1 Hz, 1H), 7.43 (d, J=8.2 Hz, 1H), 7.23-7.17 (m, 1H), 7.09-7.03 (m, 1H), 6.90 (s, 1H), 5.14-4.57 (m, 2H), 4.35 (t, J=12.5 Hz, 4H), 4.14-3.94 (m, 2H), 3.10-2.91 (m, 2H).

Example 210

2-[3-(pyrrolidine-1-sulfonyl)-1H,4H,5H,6H,7H-pyrazolo[4,3-c]pyridine-5-carbonyl]-1H-indole

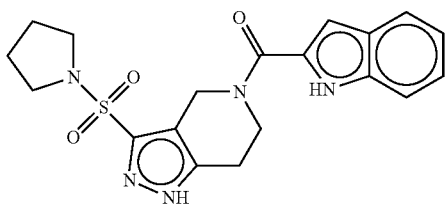

Rt (Method A) 3.1 mins, m/z 400 [M+H]+
1H NMR (400 MHz, DMSO-d6) δ 13.98-13.21 (m, 1H), 11.64 (s, 1H), 7.64 (d, J=8.2 Hz, 1H), 7.43 (d, J=8.3 Hz, 1H), 7.23-7.17 (m, 1H), 7.09-7.03 (m, 1H), 6.89 (s, 1H), 5.02-4.62 (m, 2H), 4.10-3.92 (m, 2H), 3.28-3.11 (m, 4H), 3.04-2.84 (m, 2H), 1.77-1.58 (m, 4H).

Example 211

2-{3-methanesulfonyl-1H,4H,5H,6H,7H-pyrazolo[4,3-c]pyridine-5-carbonyl}-1H-indole

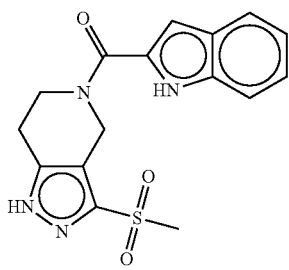

Rt (Method A) 2.79 mins, m/z 345 [M+H]+
1H NMR (400 MHz, DMSO-d6) δ 13.93-13.52 (m, 1H), 11.65 (s, 1H), 7.64 (d, J=8.0 Hz, 1H), 7.43 (d, J=8.1 Hz, 1H), 7.25-7.15 (m, 1H), 7.10-7.03 (m, 1H), 6.90 (s, 1H), 5.08-4.66 (m, 2H), 4.12-3.91 (m, 2H), 3.21 (s, 3H), 3.06-2.90 (m, 2H).

Example 212

5-(1H-indole-2-carbonyl)-N-(2-methoxyethyl)-N-methyl-1H,4H,5H,6H,7H-pyrazolo[4,3-c]pyridine-3-sulfonamide

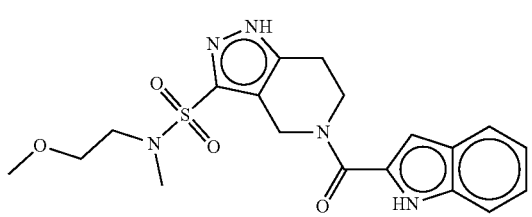

Rt (Method A) 3.01 mins, m/z 418 [M+H]+
1H NMR (400 MHz, DMSO-d6) δ 13.83-13.23 (m, 1H), 11.65 (s, 1H), 7.64 (d, J=8.1 Hz, 1H), 7.43 (d, J=8.2 Hz, 1H), 7.20 (t, J=7.7 Hz, 1H), 7.06 (t, J=7.5 Hz, 1H), 6.89 (s, 1H), 5.03-4.65 (m, 2H), 4.07-3.92 (m, 2H), 3.50-3.38 (m, 2H), 3.25-3.13 (m, 5H), 3.01-2.86 (m, 2H), 2.80-2.72 (m, 3H).

Example 213

Intentionally left blank

Example 214

2-(3-{4-azaspiro[2.4]heptane-4-carbonyl}-1H,4H,5H,6H,7H-pyrazolo[4,3-c]pyridine-5-carbonyl)-4-ethyl-6-fluoro-1H-indole

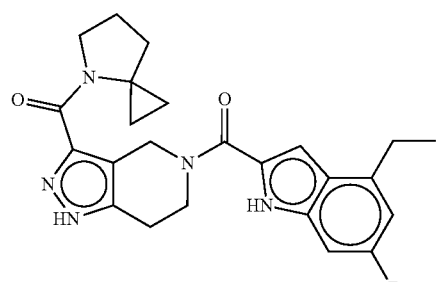

Rt (Method A) 3.46 mins, m/z 436 [M+H]+
1H NMR (400 MHz, DMSO-d6) δ 13.00 (s, 1H), 11.67 (s, 1H), 7.01-6.89 (m, 2H), 6.77 (d, J=10.7 Hz, 1H), 5.15-4.55 (m, 2H), 4.13-3.86 (m, 4H), 3.00-2.78 (m, 4H), 1.98-1.74 (m, 6H), 1.28 (t, J=7.6 Hz, 3H), 0.54-0.39 (m, 2H).

Example 215

2-(3-{4-azaspiro[2.4]heptane-4-carbonyl}-1H,4H,5H,6H,7H-pyrazolo[4,3-c]pyridine-5-carbonyl)-4-chloro-6-fluoro-1H-indole

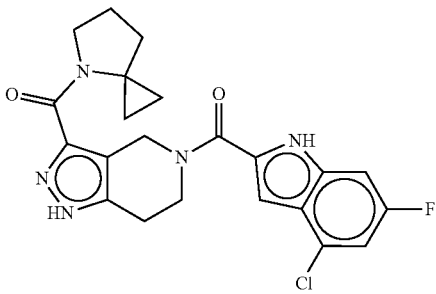

Rt (Method A) 3.53 mins, m/z 442/444 [M+H]+

1H NMR (400 MHz, DMSO-d6) δ 13.01 (s, 1H), 12.12 (s, 1H), 7.20-7.13 (m, 2H), 6.85 (s, 1H), 5.07-4.57 (m, 2H), 4.09-3.85 (m, 4H), 3.00-2.74 (m, 2H), 1.98-1.77 (m, 6H), 0.55-0.43 (m, 2H).

Example 216

2-(3-{4-azaspiro[2.4]heptane-4-carbonyl}-1H,4H,5H,6H,7H-pyrazolo[4,3-c]pyridine-5-carbonyl)-4-chloro-1H-indole

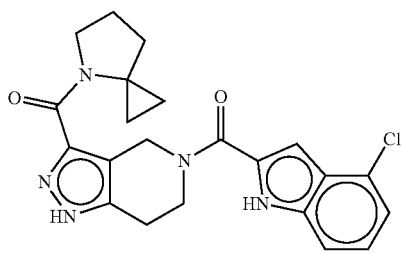

Rt (Method A) 3.48 mins, m/z 424/426 [M+H]+

1H NMR (400 MHz, DMSO-d6) δ 13.01 (s, 1H), 12.02 (s, 1H), 7.40 (d, J=7.9 Hz, 1H), 7.20 (t, J=7.8 Hz, 1H), 7.14 (d, J=7.3 Hz, 1H), 6.83 (s, 1H), 5.07-4.57 (m, 2H), 4.09-3.86 (m, 4H), 2.99-2.78 (m, 2H), 1.98-1.76 (m, 6H), 0.57-0.41 (m, 2H).

Example 217

4-chloro-2-[3-(3,3-difluoropyrrolidine-1-carbonyl)-1H,4H,5H,6H,7H-pyrazolo[4,3-c]pyridine-5-carbonyl]-5-fluoro-1H-indole

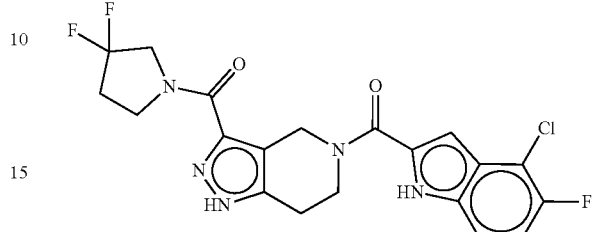

Rt (Method A) 3.34 mins, m/z 452/454 [M+H]+

1H NMR (400 MHz, DMSO-d6) δ 13.22 (s, 1H), 12.13 (s, 1H), 7.41 (dd, J=9.0, 3.9 Hz, 1H), 7.25 (t, J=9.4 Hz, 1H), 6.88 (s, 1H), 5.16-4.65 (m, 2H), 4.38-4.26 (m, 1H), 4.23-4.09 (m, 1H), 4.08-3.75 (m, 3H), 3.75-3.61 (m, 1H), 3.02-2.77 (m, 2H), 2.46-2.31 (m, 2H).

Example 218

5-(1H-indole-2-carbonyl)-2H,4H,5H,6H7H-pyrazolo[4,3-c]pyridin-3-ol

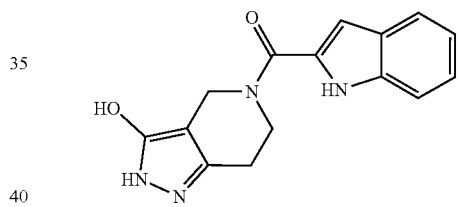

Rt (Method B) 2.45 mins, m/z 283 [M+H]+

1H NMR (400 MHz, DMSO-d6) δ 11.81-10.84 (m, 2H), 10.34-9.02 (m, 1H), 7.63 (d, J=7.8 Hz, 1H), 7.42 (d, J=8.3 Hz, 1H), 7.19 (t, J=7.7 Hz, 1H), 7.06 (t, J=7.6 Hz, 1H), 6.87 (s, 1H), 4.93-4.26 (m, 2H), 4.10-3.74 (m, 2H), 2.91-2.62 (m, 2H).

Example 219

{1-[N-methyl 5-(1H-indole-2-carbonyl)-1H,4H,5H,6H,7H-pyrazolo[4,3-c]pyridine-3-amido]cyclopropyl}methyl benzoate

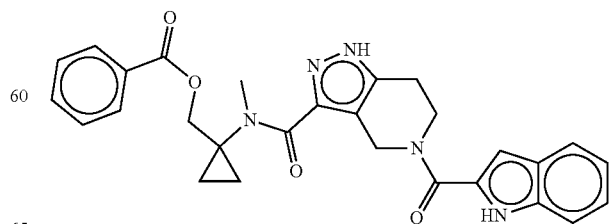

Rt (Method A) 3.46 mins, m/z 498 [M+H]+

1H NMR (400 MHz, DMSO-d6) δ 13.07 (s, 1H), 11.63 (s, 1H), 8.08-7.92 (m, 2H), 7.77-7.47 (m, 4H), 7.42 (d, J=8.0 Hz, 1H), 7.19 (t, J=7.6 Hz, 1H), 7.05 (t, J=7.4 Hz, 1H), 6.86 (s, 1H), 5.47-3.78 (m, 5H), 3.52-3.34 (m, 2H), 3.16-2.99 (m, 2H), 2.98-2.78 (m, 2H), 1.10-0.68 (m, 4H).

Example 220

N-cyclopropyl-5-(1H-indole-2-carbonyl)-1H,4H,5H,6H,7H-pyrazolo[4,3-c]pyridine-3-carboxamide

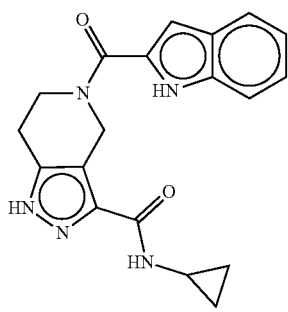

Rt (Method A) 2.9 mins, m/z 350 [M+H]+

1H NMR (400 MHz, DMSO-d6) δ 13.01 (s, 1H), 11.62 (s, 1H), 8.09 (d, J=4.4 Hz, 1H), 7.65 (d, J=7.9 Hz, 1H), 7.43 (d, J=8.2 Hz, 1H), 7.20 (t, J=7.5 Hz, 1H), 7.06 (t, J=7.5 Hz, 1H), 6.88 (s, 1H), 4.92 (m, 2H), 3.98 (m, 2H), 2.82 (m, 3H), 0.67-0.52 (m, 4H).

Example 221

5-(1H-indole-2-carbonyl)-N-methyl-N-(1-phenylcyclopropyl)-1H,4H,5H,6H,7H-pyrazolo[4,3-c]pyridine-3-carboxamide

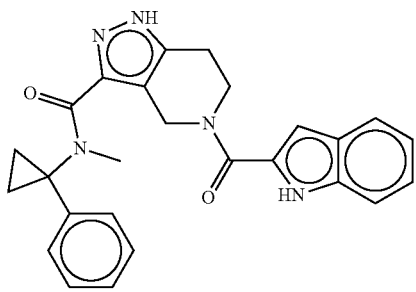

Rt (Method A) 2.02 mins, m/z 440 [M+H]+

1H NMR (400 MHz, DMSO-d6) δ 13.31-12.71 (m, 1H), 11.63 (s, 1H), 7.63 (d, J=8.0 Hz, 1H), 7.42 (d, J=8.3 Hz, 1H), 7.33-6.94 (m, 7H), 6.87 (s, 1H), 5.25-4.48 (m, 2H), 4.21-3.68 (m, 2H), 3.45-3.24 (m, 2H), 3.13-2.70 (m, 3H), 1.46-1.07 (m, 4H).

Example 222

2-[3-(3,3-difluoroazetidine-1-carbonyl)-1H,4H,5H,6H,7H-pyrazolo[4,3-c]pyridine-5-carbonyl]-1H-indole

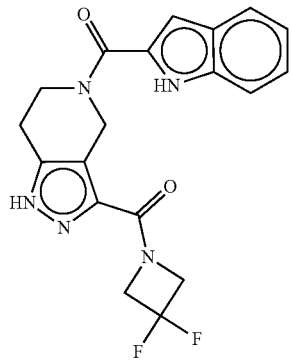

Rt (Method A) 3.12 mins, m/z 386 [M+H]+

1H NMR (400 MHz, DMSO-d6) δ 13.25 (s, 1H), 11.62 (s, 1H), 7.64 (d, J=7.9 Hz, 1H), 7.42 (d, J=8.1 Hz, 1H), 7.19 (ddd, J=8.2, 7.0, 1.1 Hz, 1H), 7.06 (t, J=7.6 Hz, 1H), 6.87 (s, 1H), 4.84 (m, 4H), 4.41 (s, 2H), 3.98 (s, 2H), 2.89 (s, 2H).

Example 223

2-[3-(3,3,4,4-tetrafluoropyrrolidine-1-carbonyl)-1H,4H,5H,6H,7H-pyrazolo[4,3-c]pyridine-5-carbonyl]-1H-indole

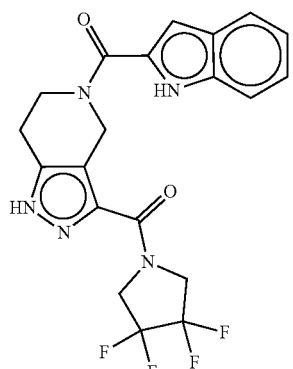

Rt (Method A) 3.42 mins, m/z 436 [M+H]+

1H NMR (400 MHz, DMSO-d6) δ 13.34 (s, 1H), 11.62 (s, 1H), 7.64 (d, J=7.9 Hz, 1H), 7.42 (d, J=8.1 Hz, 1H), 7.19 (ddd, J=8.2, 6.9, 1.1 Hz, 1H), 7.06 (t, J=7.5 Hz, 1H), 6.88 (s, 1H), 5.34-4.49 (m, 4H), 4.08 (d, J=78.4 Hz, 4H), 2.91 (s, 2H).

Example 224

2-{3-[(3S)-3-fluoropyrrolidine-1-carbonyl]-1H,4H,5H,6H,7H-pyrazolo[4,3-c]pyridine-5-carbonyl}-1H-indole

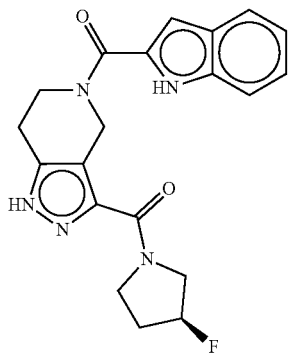

Rt (Method A) 2.95 mins, m/z 382 [M+H]+

1H NMR (400 MHz, DMSO-d6) δ 13.12 (s, 1H), 11.62 (s, 1H), 7.64 (d, J=8.0 Hz, 1H), 7.42 (d, J=8.2 Hz, 1H), 7.23-7.16 (m, 1H), 7.06 (t, J=7.5 Hz, 1H), 6.87 (s, 1H), 5.35 (dd, J=53.0, 21.1 Hz, 1H), 4.94 (m, 2H), 4.49-4.19 (m, 1H), 4.17-3.44 (m, 5H), 2.89 (s, 2H), 2.12 (d, J=34.1 Hz, 2H).

Example 225

2-{3-[(3R)-3-fluoropyrrolidine-1-carbonyl]-1H,4H,5H,6H,7H-pyrazolo[4,3-c]pyridine-5-carbonyl}-1H-indole

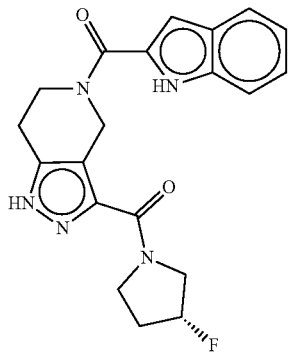

Rt (Method A) 2.94 mins, m/z 382 [M+H]+

1H NMR (400 MHz, DMSO-d6) δ 13.10 (s, 1H), 11.62 (s, 1H), 7.64 (d, J=7.9 Hz, 1H), 7.42 (d, J=8.2 Hz, 1H), 7.19 (ddd, J=8.0, 6.9, 1.1 Hz, 1H), 7.06 (t, J=7.4 Hz, 1H), 6.87 (s, 1H), 5.35 (dd, J=53.1, 21.0 Hz, 1H), 4.92 (m, 2H), 4.42-4.13 (m, 1H), 4.05-3.46 (m, 5H), 2.89 (s, 2H), 2.31-1.80 (m, 2H).

Example 226 methyl 2-{1-[N-methyl 5-(1H-indole-2-carbonyl)-1H,4H,5H,6H,7H-pyrazolo[4,3-c]pyridine-3-amido]cyclopropyl}acetate

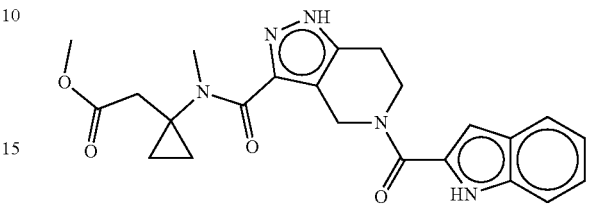

Rt (Method A) 2.98 mins, m/z 436 [M+H]+

1H NMR (400 MHz, DMSO-d6) δ 13.04 (s, 1H), 11.63 (s, 1H), 7.64 (d, J=8.0 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.21-4.38 (m, 2H), 4.16-3.84 (m, 2H), 3.70-3.38 (m, 3H), 3.29-3.22 (m, 2H), 3.07-2.70 (m, 3H), 2.64-2.51 (m, 2H), 0.99-0.66 (m, 4H).

Example 227

2-[3-(3,3-difluoropyrrolidine-1-carbonyl)-1H,4H,5H,6H,7H-pyrazolo[4,3-c]pyridine-5-carbonyl]-4-ethyl-6-fluoro-1H-indole

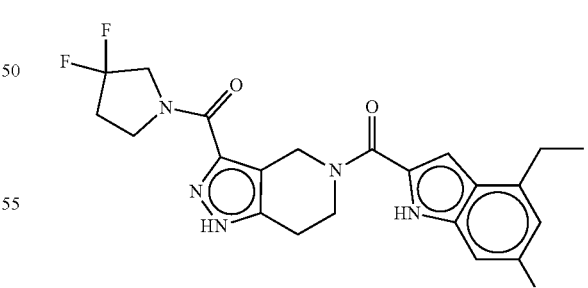

Rt (Method A) 3.44 mins, m/z 446 [M+H]+ 1H NMR (400 MHz, DMSO-d6) δ 13.47-12.98 (m, 1H), 11.81-11.60 (m, 1H), 7.00-6.91 (m, 2H), 6.77 (dd, 1H), 5.17-4.63 (m, 2H), 4.33 (t, J=13.1 Hz, 1H), 4.23-4.09 (m, 1H), 4.08-3.92 (m, 2H), 3.92-3.80 (m, 1H), 3.73-3.63 (m, 1H), 2.94-2.84 (m, 4H), 2.47-2.30 (m, 2H), 1.28 (t, J=7.6 Hz, 3H).

Example 228

2-[3-(3,3-difluoropyrrolidine-1-carbonyl)-1H,4H,5H,6H,7H-pyrazolo[4,3-c]pyridine-5-carbonyl]-4-ethyl-1H-indole

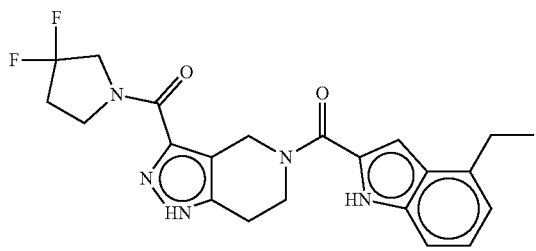

Rt (Method A) 3.38 mins, m/z 428 [M+H]+

1H NMR (400 MHz, DMSO-d6) δ 13.21 (s, 1H), 11.59 (s, 1H), 7.25 (d, J=8.2 Hz, 1H), 7.11 (t, J=7.6 Hz, 1H), 6.92-6.85 (m, 2H), 5.16-4.63 (m, 2H), 4.33 (t, J=13.1 Hz, 1H), 4.24-4.07 (m, 1H), 4.06-3.92 (m, 2H), 3.92-3.78 (m, 1H), 3.76-3.59 (m, 1H), 2.95-2.83 (m, 4H), 2.47-2.29 (m, 2H), 1.29 (t, J=7.6 Hz, 3H).

Example 230

4-chloro-2-[3-(3,3-difluoropyrrolidine-1-carbonyl)-1H,4H,5H,6H,7H-pyrazolo[4,3-c]pyridine-5-carbonyl]-1H-indole

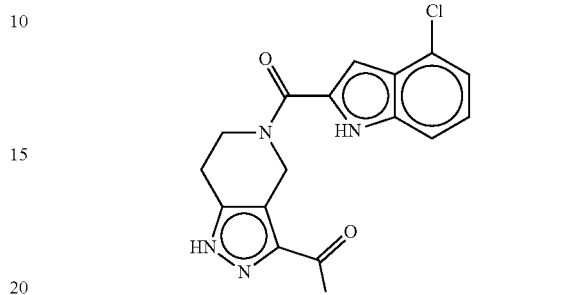

Rt (Method A) 3.33 mins, m/z 434/436 [M+H]+

1H NMR (400 MHz, DMSO-d6) δ 13.22 (s, 1H), 12.04 (s, 1H), 7.41 (d, J=7.9 Hz, 1H), 7.20 (t, J=7.8 Hz, 1H), 7.15 (d, J=7.4 Hz, 1H), 6.85 (s, 1H), 5.19-4.55 (m, 2H), 4.41-4.23 (m, 1H), 4.23-4.07 (m, 1H), 4.07-3.76 (m, 3H), 3.75-3.60 (m, 1H), 3.00-2.76 (m, 2H), 2.45-2.30 (m, 2H).

Example 229

4-chloro-2-[3-(3,3-difluoropyrrolidine-1-carbonyl)-1H,4H,5H,6H,7H-pyrazolo[4,3-c]pyridine-5-carbonyl]-6-fluoro-1H-indole

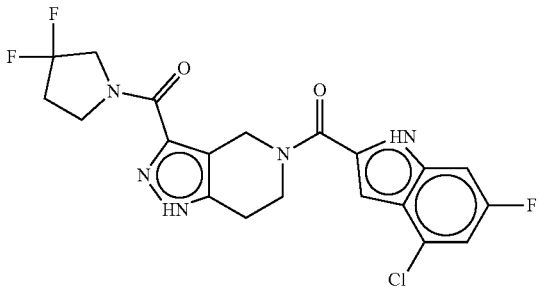

Rt (Method A) 3.41 mins, m/z 452/454 [M+H]+

1H NMR (400 MHz, DMSO-d6) δ 13.64-12.72 (m, 1H), 12.72-11.87 (m, 1H), 7.21-7.14 (m, 2H), 6.86 (s, 1H), 5.20-4.60 (m, 2H), 4.33 (t, J=13.3 Hz, 1H), 4.22-4.11 (m, 1H), 4.06-3.79 (m, 3H), 3.75-3.63 (m, 1H), 3.05-2.79 (m, 2H), 2.47-2.31 (m, 2H).

Example 231

2-[3-(3,3-difluoropyrrolidine-1-carbonyl)-1H,4H,5H,6H,7H-pyrazolo[4,3-c]pyridine-5-carbonyl]-4,5-difluoro-1H-indole

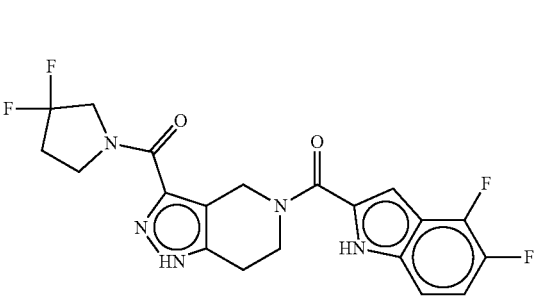

Rt (Method A) 3.27 mins, m/z 436 [M+H]+

1H NMR (400 MHz, DMSO-d6) δ 13.59-12.66 (m, 1H), 12.66-11.81 (m, 1H), 7.27-7.20 (m, 2H), 6.98 (s, 1H), 5.21-4.58 (m, 2H), 4.47-4.24 (m, 1H), 4.23-4.09 (m, 1H), 4.08-3.79 (m, 3H), 3.79-3.57 (m, 1H), 3.10-2.75 (m, 2H), 2.48-2.30 (m, 2H).

Example 232

N-cyclopropyl-5-(1H-indole-2-carbonyl)-N-methyl-1H,4H,5H,6H,7H-pyrazolo[4,3-c]pyridine-3-carboxamide

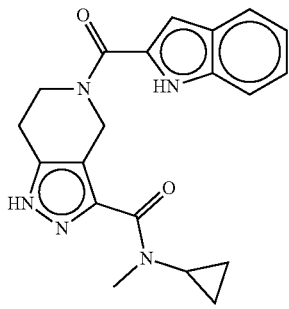

Rt (Method A) 2.93 mins, m/z 364 [M+H]+

1H NMR (400 MHz, DMSO-d6) δ 13.00 (s, 1H), 11.63 (s, 1H), 7.64 (d, J=8.0 Hz, 1H), 7.42 (d, J=8.3 Hz, 1H), 7.19 (t, J=7.5 Hz, 1H), 7.06 (t, J=7.5 Hz, 1H), 6.87 (s, 1H), 5.25-4.52 (m, 2H), 4.08-3.88 (m, 2H), 3.24-2.69 (m, 6H), 0.70-0.45 (m, 4H).

Examples 233 to 235

Intentionally left blank

Example 236

1-{4-[5-(1H-indole-2-carbonyl)-2H,4H,5H,6H,7H-pyrazolo[4,3-c]pyridine-3-carbonyl]-4,7-diazaspiro[2.5]octan-7-yl}ethan-1-one

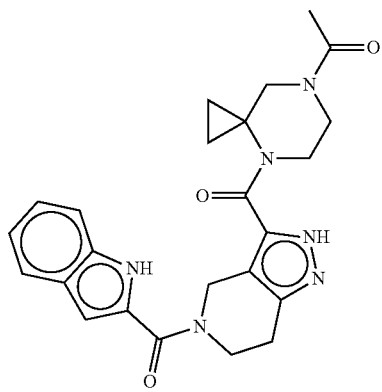

Rt (Method A) 2.79 mins, m/z 447 [M+H]+

1H NMR (400 MHz, DMSO-d6) δ 13.09 (s, 1H), 11.63 (s, 1H), 7.64 (d, J=7.9 Hz, 1H), 7.42 (d, J=8.1 Hz, 1H), 7.20 (t, J=7.5 Hz, 1H), 7.06 (t, J=7.5 Hz, 1H), 6.88 (s, 1H), 5.24-4.45 (m, 2H), 4.33-3.72 (m, 4H), 3.62-3.40 (m, 4H), 3.10-2.70 (m, 2H), 2.06-1.91 (m, 3H), 1.02-0.61 (m, 4H).

Example 237

N-[1-(2-carbamoylethyl)cyclopropyl]-5-(1H-indole-2-carbonyl)-N-methyl-1H,4H,5H,6H,7H-pyrazolo[4,3-c]pyridine-3-carboxamide

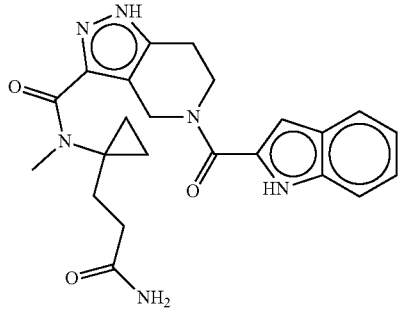

Rt (Method A) 2.76 mins, m/z 435 [M+H]+

1H NMR (400 MHz, DMSO-d6) δ 13.00 (s, 1H), 11.63 (s, 1H), 7.65 (d, J=8.2 Hz, 1H), 7.43 (d, J=8.2 Hz, 1H), 7.28 (s, 1H), 7.20 (t, J=7.4 Hz, 1H), 7.06 (t, J=7.5 Hz, 1H), 6.89 (s, 1H), 6.69 (s, 1H), 5.25-4.50 (m, 2H), 4.16-3.82 (m, 2H), 3.31-3.18 (m, 2H), 3.06-2.61 (m, 4H), 2.28-2.06 (m, 2H), 1.93-1.65 (m, 1H), 0.97-0.43 (m, 4H).

Example 238

5-(4,6-difluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

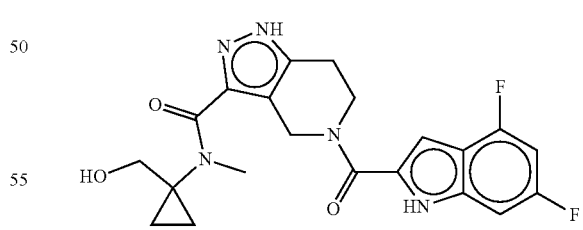

Rt (Method A) 2.92 mins, m/z 430 [M+H]+ 1H NMR (400 MHz, DMSO-d6) δ 13.05 (s, 1H), 12.08 (s, 1H), 7.08-6.99 (m, 1H), 6.99-6.86 (m, 2H), 5.51-4.51 (m, 3H), 4.17-3.47 (m, 4H), 3.11-2.75 (m, 4H), 0.97-0.37 (m, 4H). one signal (1H) coincides with water signal.

Example 239

5-(4-chloro-5-fluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

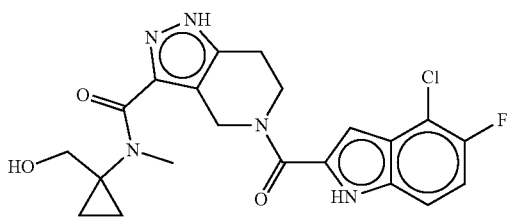

Rt (Method A) 2.99 mins, m/z 446/448 [M+H]+ 1H NMR (400 MHz, DMSO-d6) δ 13.06 (s, 1H), 12.13 (s, 1H), 7.41 (dd, J=8.9, 3.9 Hz, 1H), 7.24 (t, J=9.4 Hz, 1H), 6.87 (s, 1H), 5.58-4.50 (m, 3H), 4.09-3.47 (m, 4H), 3.14-2.74 (m, 4H), 0.94-0.44 (m, 4H). one signal (1H) coincides with water signal.

Example 240

5-(4,5-difluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

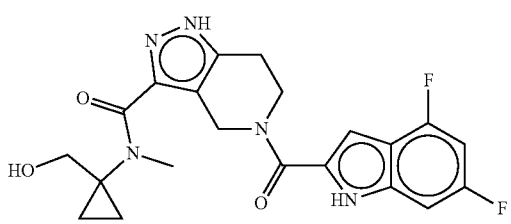

Rt (Method A) 2.9 mins, m/z 430 [M+H]+ 1H NMR (400 MHz, DMSO-d6) δ 13.05 (s, 1H), 12.07 (s, 1H), 7.37-7.08 (m, 2H), 6.97 (s, 1H), 5.49-4.39 (m, 3H), 4.38-3.44 (m, 4H), 3.09-2.73 (m, 4H), 0.96-0.42 (m, 4H). One signal coincides with water signal.

Example 241

5-(4-chloro-6-fluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

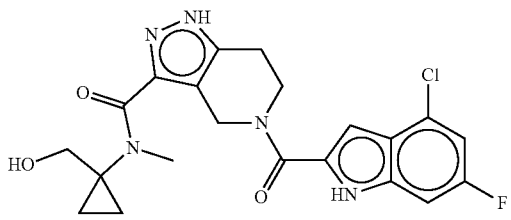

Rt (Method A) 3.03 mins, m/z 446/448 [M+H]+ 1H NMR (400 MHz, DMSO-d6) δ 13.49-12.59 (m, 1H), 12.54-11.82 (m, 1H), 7.21-7.14 (m, 2H), 6.85 (s, 1H), 5.37-4.49 (m, 3H), 4.28-3.46 (m, 4H), 3.08-2.76 (m, 4H), 0.76 (d, J=42.1 Hz, 4H). One signal coincides with water signal.

Example 242

5-(6-chloro-5-fluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

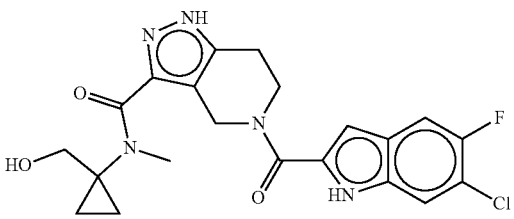

Rt (Method A) 2.99 mins, m/z 446/448 [M+H]+ 1H NMR (400 MHz, DMSO-d6) δ 13.35-12.78 (m, 1H), 11.89 (s, 1H), 7.80-7.59 (m, 1H), 7.54 (d, J=6.5 Hz, 1H), 6.91 (s, 1H), 5.69-4.49 (m, 3H), 4.13-3.46 (m, 4H), 3.10-2.71 (m, 4H), 0.94-0.39 (m, 4H). One signal (1H) coincides with water signal.

Example 243

5-(6-fluoro-4-methyl-1H-indole-2-carbonyl)-N-[1-(hydroxymethyl)cyclopropyl]-N-methyl-1H,4H,5H,6H,7H-pyrazolo[4,3-c]pyridine-3-carboxamide

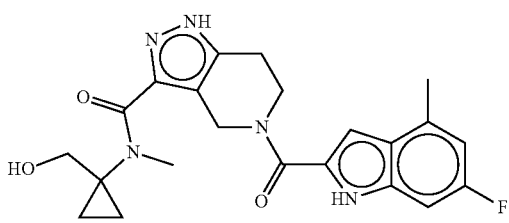

Rt (Method A) 3.04 mins, m/z 426 [M+H]+ 1H NMR (400 MHz, DMSO-d6) δ 13.04 (s, 1H), 11.68 (d, J=2.2 Hz, 1H), 7.00-6.87 (m, 2H), 6.80-6.70 (m, 1H), 5.61-4.54 (m, 3H), 4.13-3.48 (m, 4H), 3.39-3.34 (m, 1H), 3.09-2.77 (m, 4H), 0.95-0.47 (m, 4H). One signal (3H) coincides with DMSO signal

Example 244

3-{1-[5-(1H-indole-2-carbonyl)-2H,4H,5H,6H,7H-pyrazolo[4,3-c]pyridin-3-yl]-N-methylformamido}-N-methanesulfonylpropanamide

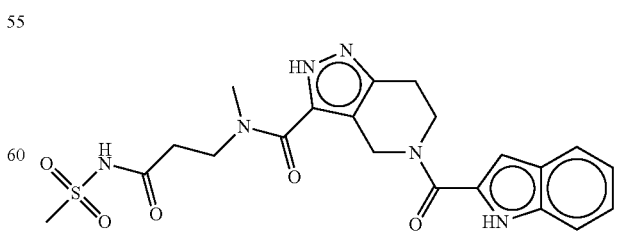

Rt (Method A) 2.34 mins, m/z 471 [M+H]+
1H NMR (400 MHz, DMSO-d6) δ 13.58-12.78 (m, 1H), 12.51-11.45 (m, 2H), 7.65 (d, J=8.0 Hz, 1H), 7.42 (d, J=8.1

Hz, 1H), 7.19 (t, J=7.5 Hz, 1H), 7.06 (t, J=7.5 Hz, 1H), 6.87 (s, 1H), 5.24-4.58 (m, 2H), 4.20-3.82 (m, 3H), 3.70-3.50 (m, 1H), 3.39-3.36 (m, 1H), 3.28-2.73 (m, 7H), 2.60-2.54 (m, 1H).

Example 245

3-{1-[N-methyl 5-(1H-indole-2-carbonyl)-1H,4H,5H,6H,7H-pyrazolo[4,3-c]pyridine-3-amido]cyclopropyl}propanoic acid

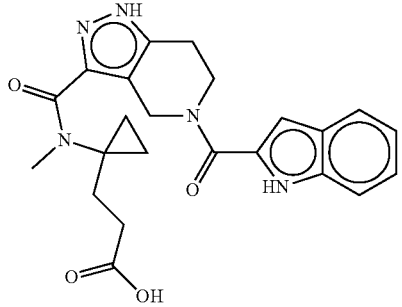

Rt (Method B) 2.82 mins, m/z 436 [M+H]+

1H NMR (400 MHz, DMSO-d6) δ 13.01 (s, 1H), 12.08 (s, 1H), 11.63 (s, 1H), 7.64 (d, J=8.1 Hz, 1H), 7.42 (d, J=8.1 Hz, 1H), 7.19 (t, J=7.4 Hz, 1H), 7.06 (t, J=7.5 Hz, 1H), 6.88 (s, 1H), 5.26-4.39 (m, 2H), 4.19-3.75 (m, 2H), 3.30-3.15 (m, 2H), 3.09-2.73 (m, 3H), 2.40-2.23 (m, 2H), 1.97-1.55 (m, 2H), 0.92-0.48 (m, 4H).

Example 246 ethyl 3-{1-[N-methyl 5-(1H-indole-2-carbonyl)-1H,4H,5H,6H,7H-pyrazolo[4,3-c]pyridine-3-amido]cyclopropyl}propanoate

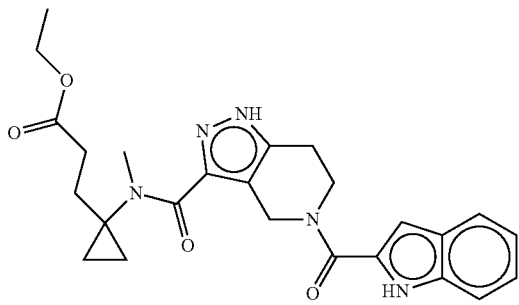

Rt (Method A) 3.23 mins, m/z 464 [M+H]+

1H NMR (400 MHz, DMSO-d6) δ 12.99 (s, 1H), 11.63 (s, 1H), 7.64 (d, J=7.9 Hz, 1H), 7.42 (d, J=8.2 Hz, 1H), 7.19 (t, J=7.5 Hz, 1H), 7.06 (t, J=7.4 Hz, 1H), 6.88 (s, 1H), 5.29-4.41 (m, 2H), 4.16-3.80 (m, 4H), 3.29-3.18 (m, 2H), 3.08-2.74 (m, 3H), 2.47-2.34 (m, 2H), 2.01-1.50 (m, 2H), 1.30-0.98 (m, 3H), 0.92-0.46 (m, 4H).

Example 247

N-(cyclopropanesulfonyl)-3-{1-[5-(1H-indole-2-carbonyl)-2H,4H,5H,6H,7H-pyrazolo[4,3-c]pyridin-3-yl]-N-methylformamido}propanamide

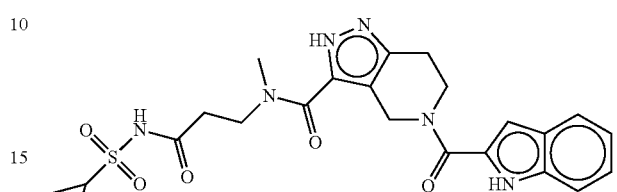

Rt (Method B) 2.82 mins, m/z 499 [M+H]+

1H NMR (400 MHz, DMSO-d6) δ 13.73-12.49 (m, 1H), 11.74-11.57 (m, 1H), 7.65 (d, J=8.1 Hz, 1H), 7.42 (d, J=8.1 Hz, 1H), 7.23-7.16 (m, 1H), 7.06 (t, J=7.5 Hz, 1H), 6.88 (s, 1H), 5.35-4.47 (m, 2H), 3.98 (s, 3H), 3.68-3.51 (m, 1H), 3.50-3.35 (m, 1H), 3.08-2.75 (m, 5H), 2.66-2.55 (m, 1H), 1.96-1.43 (m, 1H), 1.05-0.82 (m, 4H).

Example 248

5-(1H-indole-2-carbonyl)-N-[1-(2-methoxyethyl)cyclopropyl]-N-methyl-2H,4H,5H,6H,7H-pyrazolo[4,3-c]pyridine-3-carboxamide

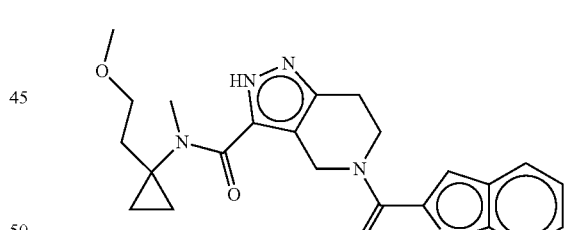

Rt (Method A) 3.04 mins, m/z 422 [M+H]+

1H NMR (400 MHz, DMSO-d6) δ 12.97 (s, 1H), 11.63 (s, 1H), 7.64 (d, J=8.1 Hz, 1H), 7.42 (d, J=8.3 Hz, 1H), 7.23-7.16 (m, 1H), 7.09-7.02 (m, 1H), 6.87 (s, 1H), 5.19-4.51 (m, 2H), 4.21-3.78 (m, 2H), 3.39 (s, 2H), 3.29-3.07 (m, 5H), 2.98-2.76 (m, 3H), 2.02-1.41 (m, 2H), 0.89-0.49 (m, 4H).

Example 249

N-[3-(hydroxymethyl)oxetan-3-yl]-5-(1H-indole-2-carbonyl)-N-methyl-2H,4H,5H,6H,7H-pyrazolo[4,3-c]pyridine-3-carboxamide

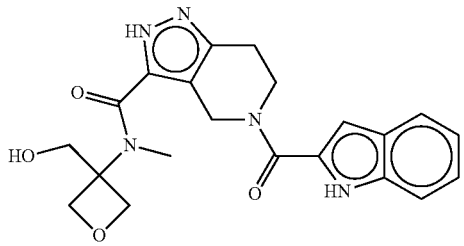

Rt (Method A) 2.64 mins, m/z 410 [M+H]+

1H NMR (400 MHz, DMSO-d6) δ 13.12 (s, 1H), 11.71-11.52 (m, 1H), 7.64 (d, J=8.0 Hz, 1H), 7.42 (d, J=8.2 Hz, 1H), 7.23-7.15 (m, 1H), 7.06 (t, J=7.5 Hz, 1H), 6.99-6.83 (m, 1H), 5.53-3.33 (m, 12H), 3.28-3.19 (m, 2H), 3.06-2.75 (m, 2H).

Example 250

1-[N-methyl 5-(1H-indole-2-carbonyl)-2H,4H,5H,6H,7H-pyrazolo[4,3-c]pyridine-3-amido]cyclopropane-1-carboxylic acid

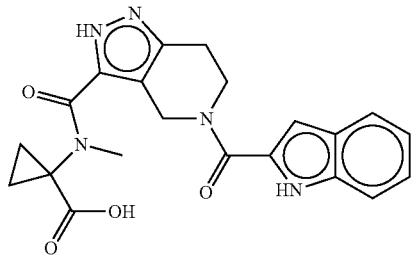

Rt (Method A) 2.77 mins, m/z 408 [M+H]+

1H NMR (400 MHz, DMSO-d6) δ 13.26-12.79 (m, 1H), 12.42 (s, 1H), 11.71-11.53 (m, 1H), 7.64 (d, J=7.7 Hz, 1H), 7.42 (d, J=8.3 Hz, 1H), 7.19 (t, J=7.6 Hz, 1H), 7.06 (t, J=7.5 Hz, 1H), 6.87 (d, J=8.4 Hz, 1H), 5.18-4.47 (m, 2H), 4.32-3.62 (m, 2H), 3.38 (s, 1H), 2.94 (d, J=39.5 Hz, 4H), 1.58-0.78 (m, 5H).

Example 251

5-(1H-indole-2-carbonyl)-N-methyl-N-(3-methyl-oxetan-3-yl)-2H,4H,5H,6H,7H-pyrazolo[4,3-c]pyridine-3-carboxamide

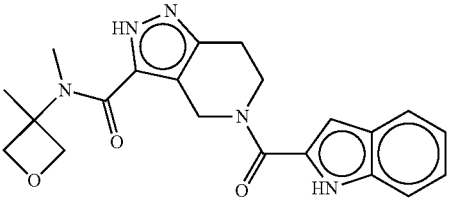

Rt (Method A) 2.83 mins, m/z 394 [M+H]+

1H NMR (400 MHz, DMSO-d6) δ 13.13 (s, 1H), 11.63 (s, 1H), 7.64 (d, J=8.0 Hz, 1H), 7.42 (d, J=8.2 Hz, 1H), 7.27-7.16 (m, 1H), 7.06 (t, J=7.4 Hz, 1H), 6.88 (s, 1H), 5.21-4.48 (m, 4H), 4.44-3.80 (m, 4H), 3.23-2.75 (m, 5H), 2.02-1.39 (m, 3H).

Example 252

N-[(1S,2S)-2-hydroxycyclopentyl]-5-(1H-indole-2-carbonyl)-N-methyl-2H,4H,5H,6H,7H-pyrazolo[4,3-c]pyridine-3-carboxamide

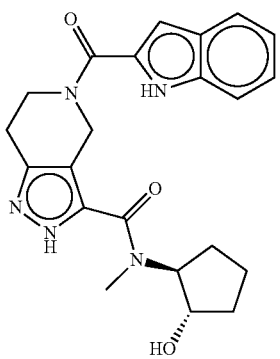

Rt (Method A) 2.85 mins, m/z 408 [M+H]+

1H NMR (400 MHz, DMSO-d6) δ 13.01 (s, 1H), 11.63 (s, 1H), 7.64 (d, J=7.9 Hz, 1H), 7.42 (d, J=8.2 Hz, 1H), 7.23-7.15 (m, 1H), 7.06 (t, J=7.5 Hz, 1H), 6.87 (s, 1H), 5.48-4.32 (m, 4H), 4.18-3.55 (m, 3H), 3.28-2.75 (m, 5H), 2.01-1.27 (m, 6H).

Example 253

N-(2,3-dihydroxypropyl)-5-(1H-indole-2-carbonyl)-N-methyl-2H,4H,5H,6H,7H-pyrazolo[4,3-c]pyridine-3-carboxamide

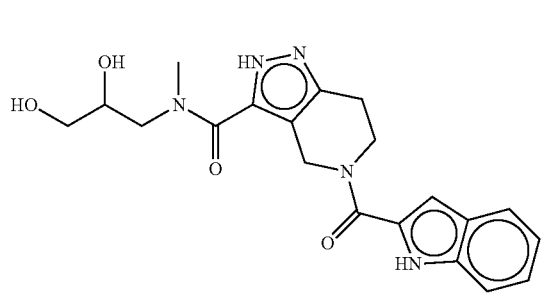

Rt (Method A) 2.58 mins, m/z 396 [M+H]+

1H NMR (400 MHz, DMSO-d6) δ 13.05 (s, 1H), 11.79-11.54 (m, 1H), 7.65 (d, J=8.0 Hz, 1H), 7.42 (d, J=8.2 Hz, 1H), 7.23-7.15 (m, 1H), 7.06 (t, J=7.4 Hz, 1H), 6.87 (s, 1H), 5.31-4.27 (m, 4H), 4.10-3.38 (m, 6H), 3.30 (s, 2H), 3.10-2.78 (m, 4H).

Example 254

N-[(1-hydroxycyclobutyl)methyl]-5-(1H-indole-2-carbonyl)-N-methyl-1H,4H,5H,6H,7H-pyrazolo[4,3-c]pyridine-3-carboxamide

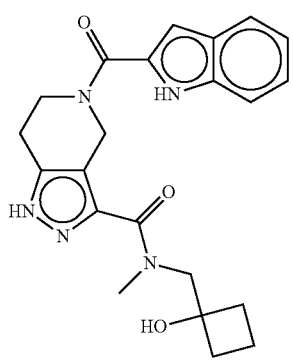

Rt (Method A) 2.88 mins, m/z 408 [M+H]+

1H NMR (400 MHz, DMSO-d6) δ 13.04 (s, 1H), 11.63 (s, 1H), 7.64 (d, J=7.9 Hz, 1H), 7.42 (d, J=8.1 Hz, 1H), 7.23-7.15 (m, 1H), 7.06 (t, J=7.5 Hz, 1H), 6.87 (s, 1H), 5.57-4.50 (m, 3H), 4.31-3.75 (m, 3H), 3.73-3.51 (m, 1H), 3.50-3.36 (m, 1.5H), 3.10-2.79 (m, 3.5H), 2.05-1.74 (m, 4H), 1.68-1.22 (m, 2H).

Example 255

N-(2-ethoxyethyl)-5-(1H-indole-2-carbonyl)-N-methyl-1H,4H,5H,6H,7H-pyrazolo[4,3-c]pyridine-3-carboxamide

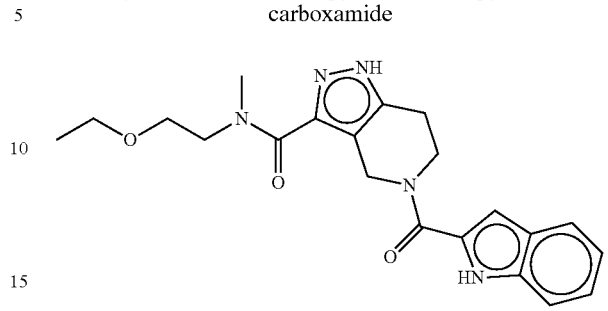

Rt (Method A) 2.95 mins, m/z 396 [M+H]+

1H NMR (400 MHz, DMSO-d6) δ 13.04 (s, 1H), 11.63 (s, 1H), 7.64 (d, J=7.9 Hz, 1H), 7.42 (d, J=8.2 Hz, 1H), 7.23-7.15 (m, 1H), 7.06 (t, J=7.4 Hz, 1H), 6.87 (s, 1H), 5.28-4.43 (m, 2H), 4.23-3.79 (m, 3H), 3.63-3.36 (m, 5H), 3.06-2.79 (m, 4H), 1.19-0.88 (m, 3H).

Example 256

N-(2-cyclopropyl-2-hydroxyethyl)-5-(1H-indole-2-carbonyl)-N-methyl-1H,4H,5H,6H,7H-pyrazolo[4,3-c]pyridine-3-carboxamide

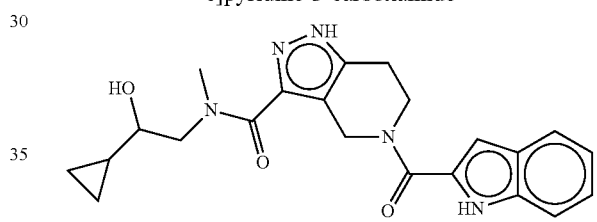

Rt (Method A) 2.86 mins, m/z 408 [M+H]+ 1H NMR (400 MHz, DMSO-d6) δ 13.03 (s, 1H), 11.80-11.44 (m, 1H), 7.64 (d, J=7.9 Hz, 1H), 7.42 (d, J=8.2 Hz, 1H), 7.23-7.15 (m, 1H), 7.06 (t, J=7.4 Hz, 1H), 6.96-6.75 (m, 1H), 5.27-4.43 (m, 3H), 4.25-3.80 (m, 3H), 3.77-3.51 (m, 1H), 3.46-3.37 (m, 1H), 3.23-3.09 (m, 1H), 3.08-2.76 (m, 4H), 0.90-0.59 (m, 1H), 0.48-0.09 (m, 4H).

Example 257

2-(3-{4-benzyl-4,7-diazaspiro[2.5]octane-7-carbonyl}-2H,4H,5H,6H,7H-pyrazolo[4,3-c]pyridine-5-carbonyl)-1H-indole

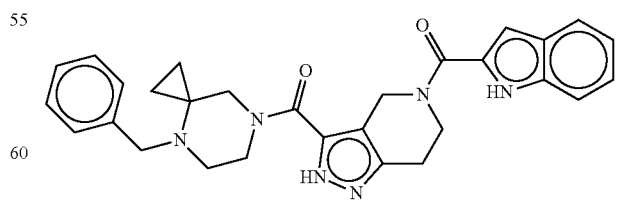

Rt (Method A) 3.52 mins, m/z 495 [M+H]+

1H NMR (400 MHz, DMSO-d6) δ 13.04 (s, 1H), 11.63 (s, 1H), 7.64 (d, J=8.0 Hz, 1H), 7.42 (d, J=8.1 Hz, 1H), 7.34-7.16 (m, 6H), 7.06 (t, J=7.5 Hz, 1H), 6.87 (s, 1H), 5.14-4.58 (m, 2H), 4.26-3.80 (m, 6H), 3.77-3.45 (m, 2H), 3.03-2.77 (m, 2H), 2.75-2.63 (m, 2H), 0.72-0.46 (m, 4H).

Example 258 tert-butyl 1-[N-methyl 5-(1H-indole-2-carbonyl)-2H,4H,5H,6H,7H-pyrazolo[4,3-c]pyridine-3-amido]cyclopropane-1-carboxylate

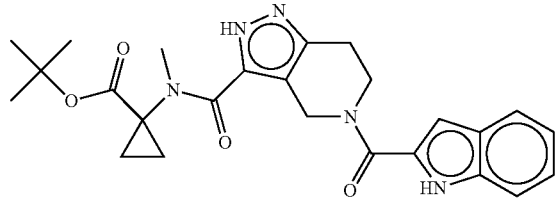

Rt (Method A) 3.39 mins, m/z 464 [M+H]+

1H NMR (400 MHz, DMSO-d6) δ 13.20-12.91 (m, 1H), 11.72-11.54 (m, 1H), 7.63 (t, J=7.3 Hz, 1H), 7.42 (d, J=8.4 Hz, 1H), 7.19 (t, J=7.5 Hz, 1H), 7.05 (t, J=7.5 Hz, 1H), 6.86 (s, 1H), 5.21-4.55 (m, 2H), 4.24-3.70 (m, 2H), 3.07-2.74 (m, 4H), 1.51-0.91 (m, 14H).

Example 260

N-[1-(methoxymethyl)cyclopropyl]-N-methyl-5-(4-methyl-1H-indole-2-carbonyl)-1H,4H,5H,6H,7H-pyrazolo[4,3-c]pyridine-3-carboxamide

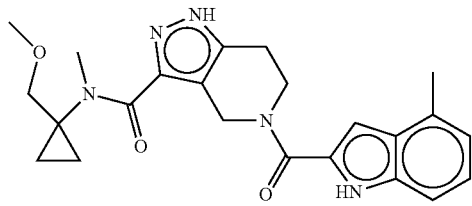

Prepared as described for AIC224714 starting from 4-methyl-1H-indole-2-carboxylic acid.

Rt (Method A) 3.13 mins, m/z 420 [M+H]+

1H NMR (400 MHz, DMSO-d6) δ 13.23-12.73 (m, 1H), 11.68-11.48 (m, 1H), 7.24 (d, J=8.3 Hz, 1H), 7.13-7.04 (m, 1H), 6.90-6.82 (m, 2H), 5.11-3.79 (m, 4H), 3.63-3.40 (m, 1H), 3.28-3.17 (m, 3H), 3.09-2.77 (m, 4H), 0.93-0.60 (m, 4H). one signal (3H) coincides with DMSO signal, one signal (2H) coincides with water signal Example 259

(3R)-1-[5-(1H-indole-2-carbonyl)-2H,4H,5H,6H,7H-pyrazolo[4,3-c]pyridine-3-carbonyl]pyrrolidin-3-amine

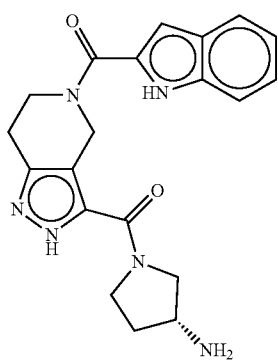

Rt (Method A) 2.63 mins, m/z 379 [M+H]+

1H NMR (400 MHz, Methanol-d4) δ 7.62 (d, J=8.0 Hz, 1H), 7.43 (d, J=8.2 Hz, 1H), 7.26-7.17 (m, 1H), 7.07 (t, J=7.5 Hz, 1H), 6.93 (s, 1H), 5.25-5.03 (m, 2H), 4.21-3.35 (m, 7H), 3.07-2.79 (m, 2H), 2.22-2.04 (m, 1H), 1.88-1.67 (m, 1H).

Example 261

(3S)-1-[5-(1H-indole-2-carbonyl)-2H,4H,5H,6H,7H-pyrazolo[4,3-c]pyridine-3-carbonyl]pyrrolidin-3-amine

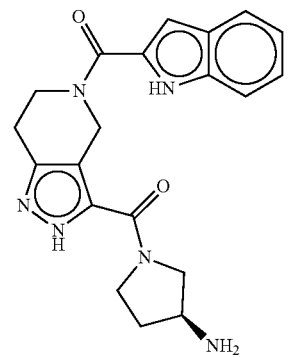

Rt (Method A) 2.63 mins, m/z 379 [M+H]+

1H NMR (400 MHz, Methanol-d4) δ 7.62 (d, J=7.9 Hz, 1H), 7.43 (d, J=8.3 Hz, 1H), 7.21 (t, J=7.7 Hz, 1H), 7.07 (t, J=7.5 Hz, 1H), 6.93 (s, 1H), 5.51-4.99 (m, 2H), 4.21-3.36 (m, 7H), 2.93 (m, 2H), 2.29-2.02 (m, 1H), 1.89-1.68 (m, 1H).

Example 262

5-(4-chloro-1H-indole-2-carbonyl)-N-[1-(methoxymethyl)cyclopropyl]-N-methyl-1H,4H,5H,6H,7H-pyrazolo[4,3-c]pyridine-3-carboxamide

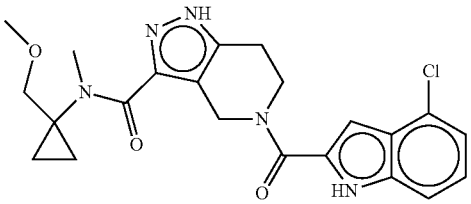

To a solution of 4-chloro-1H-indole-2-carboxylic acid (0.029 g, 0.148 mmol) and HATU (0.062 g, 0.163 mmol) in dry DMF (1 ml) was added triethylamine (0.103 ml, 0.741 mmol) and N-(1(methoxymethyl)cyclopropyl)-N-methyl-4,5,6,7-tetrahydro-1H-pyrazolo[4,3-c]pyridine-3-carboxamide dihydrochloride (0.05 g, 0.148 mmol). The mixture was stirred for 3.5 h, a few drops of water were added and filtered. The filtrate was purified directly by reverse phase HPLC to give the desired product (0.042 g, 64% yield).

(Rt (Method A) 3.22 mins, m/z 442/444 [M+H]+

1H NMR (400 MHz, DMSO-d6) δ 12.99 (s, 1H), 12.04 (s, 1H), 7.41 (d, J=8.0 Hz, 1H), 7.31-7.03 (m, 2H), 6.83 (s, 1H), 5.38-4.54 (m, 2H), 4.48-3.69 (m, 2H), 3.66-3.14 (m, 6H), 3.14-2.76 (m, 4H), 1.03-0.38 (m, 4H).

Example 263

5-(6-chloro-1H-indole-2-carbonyl)-N-[1-(methoxymethyl)cyclopropyl]-N-methyl-1H,4H,5H,6H,7H-pyrazolo[4,3-c]pyridine-3-carboxamide

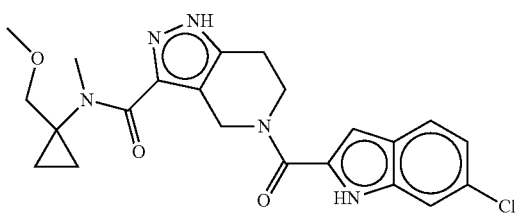

Prepared as described for Example 262 starting from 6-chloro-1H-indole-2-carboxylic acid.

Rt (Method A) 3.23 mins, m/z 442/444 [M+H]+

1H NMR (400 MHz, DMSO-d6) δ 13.72-11.20 (m, 2H), 7.67 (d, J=8.5 Hz, 1H), 7.43 (d, J=1.8 Hz, 1H), 7.08 (dd, J=8.4, 1.9 Hz, 1H), 7.01-6.81 (m, 1H), 5.33-4.49 (m, 2H), 4.48-3.68 (m, 2H), 3.75-3.13 (m, 6H), 3.10-2.61 (m, 4H), 1.02-0.30 (m, 4H)

Example 264

5-(4-chloro-6-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

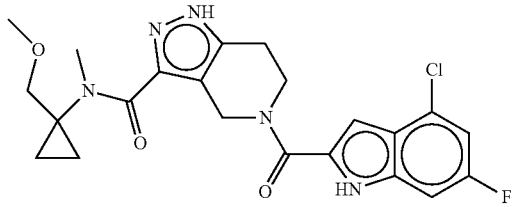

Prepared as described for Example 262, starting from 4-chloro-6-fluoro-1H-indole-2-carboxylic acid.

Rt (Method A) 3.31 mins, m/z 460/462 [M+H]+

1H NMR (400 MHz, DMSO-d6) δ 13.54-11.48 (m, 2H), 7.18 (s, 1H), 7.16 (s, 1H), 6.85 (s, 1H), 5.29-4.52 (m, 2H), 4.50-3.71 (m, 2H), 3.70-3.12 (m, 6H), 3.11-2.60 (m, 4H), 1.09-0.36 (m, 4H).

Example 265

5-(6-chloro-5-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

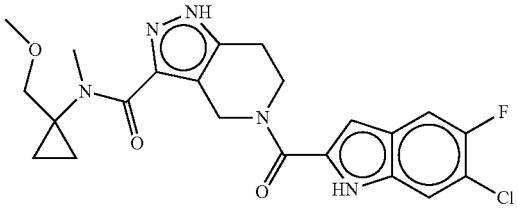

Prepared as described for Example 262 starting from 6-chloro-5-fluoro-1H-indole-2-carboxylic acid.

Rt (Method A) 3.27 mins, m/z 460/462 [M+H]+

1H NMR (400 MHz, DMSO-d6) δ 13.37-11.49 (m, 2H), 7.76-7.59 (m, 1H), 7.54 (d, J=6.4 Hz, 1H), 6.91 (s, 1H), 5.27-4.55 (m, 2H), 4.53-3.70 (m, 2H), 3.69-3.14 (m, 6H), 3.11-2.62 (m, 4H), 1.14-0.30 (m, 4H).

Example 266

5-(4,6-difluoro-1H-indole-2-carbonyl)-N-[1-(methoxymethyl)cyclopropyl]-N-methyl-1H,4H,5H,6H,7H-pyrazolo[4,3-c]pyridine-3-carboxamide

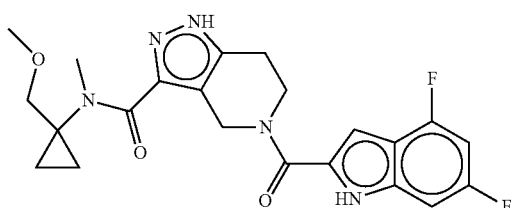

Prepared as described for Example 262 starting from 4,6-difluoro-1H-indole-2-carboxylic acid.

Rt (Method A) 3.18 mins, m/z 444 [M+H]+

1H NMR (400 MHz, DMSO-d6) δ 13.54-11.39 (m, 2H), 7.04 (dd, J=9.4, 2.1 Hz, 1H), 6.99-6.86 (m, 2H), 5.36-4.52 (m, 2H), 4.52-3.72 (m, 2H), 3.70-3.14 (m, 6H), 3.14-2.62 (m, 4H), 1.07-0.44 (m, 4H).

Example 267

5-(4,5-difluoro-1H-indole-2-carbonyl)-N-[1-(methoxymethyl)cyclopropyl]-N-methyl-1H,4H,5H,6H,7H-pyrazolo[4,3-c]pyridine-3-carboxamide

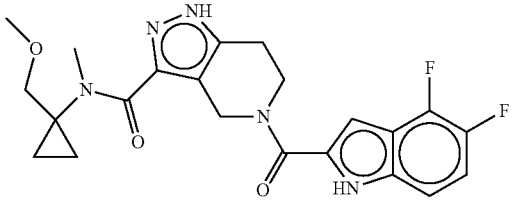

Prepared as described for Example 262 starting from 4,5-difluoro-1H-indole-2-carboxylic acid.

Rt (Method A) 3.15 mins, m/z 444 [M+H]+

1H NMR (400 MHz, DMSO-d6) δ 13.53-11.66 (m, 2H), 7.30-7.16 (m, 2H), 6.97 (s, 1H), 5.36 –4.53 (m, 2H), 4.52-3.78 (m, 2H), 3.68-3.16 (m, 6H), 3.16-2.76 (m, 4H), 1.12-0.43 (m, 4H).

Example 268

5-(4-chloro-5-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

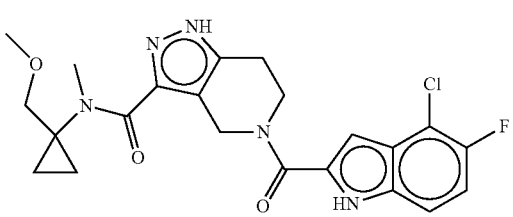

Prepared as described for Example 262 starting from 4-chloro-5-fluoro-1H-indole-2-carboxylic acid.

Rt (Method A) 3.26 mins, m/z 360/362 [M+H]+

1H NMR (400 MHz, DMSO-d6) δ 12.97 (s, 1H), 12.13 (s, 1H), 7.41 (dd, J=8.8, 3.9 Hz, 1H), 7.23 (t, 1H), 6.87 (s, 1H), 5.40-4.52 (m, 2H), 4.45-3.76 (m, 2H), 3.76-3.11 (m, 6H), 3.11-2.60 (m, 4H), 1.16-0.35 (m, 4H).

Example 269

5-(6-fluoro-4-methyl-1H-indole-2-carbonyl)-N-[1-(methoxymethyl)cyclopropyl]-N-methyl-1H,4H,5H,6H,7H-pyrazolo[4,3-c]pyridine-3-carboxamide

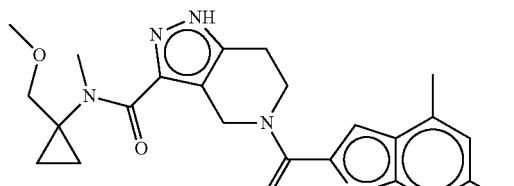

Prepared as described for Example 262 starting from 6-fluoro-4-methyl-1H-indole-2-carboxylic acid.

Rt (Method A) 3.2 mins, m/z 440 [M+H]+

1H NMR (400 MHz, DMSO-d6) δ 14.02-10.95 (m, 2H), 7.06-6.85 (m, 2H), 6.76 (dd, J=10.5, 2.1 Hz, 1H), 5.50-4.54 (m, 2H), 4.54-3.77 (m, 2H), 3.77-3.11 (m, 8H), 3.11-2.59 (m, 4H), 2.56-2.44 (m, 1H), 1.02-0.35 (m, 4H).

Example 270

5-(4-ethyl-1H-indole-2-carbonyl)-N-[1-(methoxymethyl)cyclopropyl]-N-methyl-1H,4H,5H,6H,7H-pyrazolo[4,3-c]pyridine-3-carboxamide

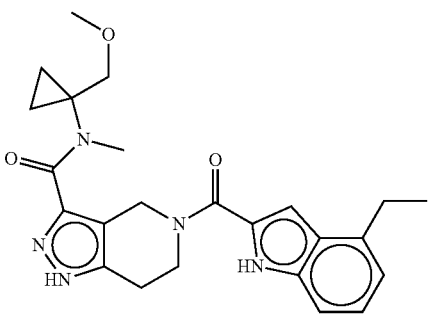

Prepared as described for Example 262 starting from 4-ethyl-H-indole-2-carboxylic acid.

Rt (Method A) 3.28 mins, m/z 436 [M+H]+

1H NMR (400 MHz, DMSO-d6) δ 12.97 (s, 1H), 11.59 (s, 1H), 7.25 (d, J=8.1 Hz, 1H), 7.11 (dd, J=8.2, 7.1 Hz, 1H), 7.02-6.74 (m, 2H), 5.46-4.49 (m, 2H), 4.47-3.75 (m, 2H), 3.75-3.13 (m, 6H), 3.10-2.60 (m, 5H), 1.28 (t, J=7.6 Hz, 3H), 1.02-0.32 (m, 4H).

Example 271

5-(4-ethyl-6-fluoro-1H-indole-2-carbonyl)-N-[1-(hydroxymethyl)cyclopropyl]-N-methyl-1H,4H,5H,6H,7H-pyrazolo[4,3-c]pyridine-3-carboxamide

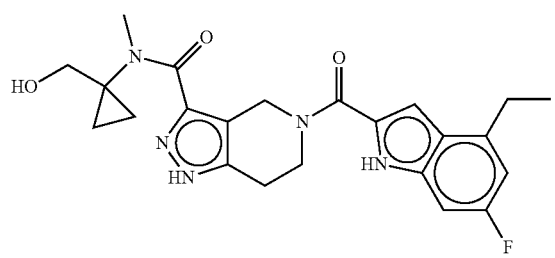

Rt (Method A) 3.15 mins, m/z 440 [M+H]+

1H NMR (400 MHz, DMSO-d6) δ 13.04 (bs, 1H), 11.68 (s, 1H), 6.96 (dd, J=9.7, 2.4 Hz, 1H), 6.93 (s, 1H), 6.77 (dd, J=10.8, 2.3 Hz, 1H), 5.63-5.29 (m, 1H), 5.23-4.49 (m, 2H), 4.15-3.85 (m, 2H), 3.82-3.39 (m, 3H), 3.11-2.95 (m, 2H), 2.95-2.74 (m, 4H), 1.28 (t, J=7.6 Hz, 3H), 0.93-0.35 (m, 4H)—mixture of conformers, OH not fully visible.

Example 272

5-(4-ethyl-6-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

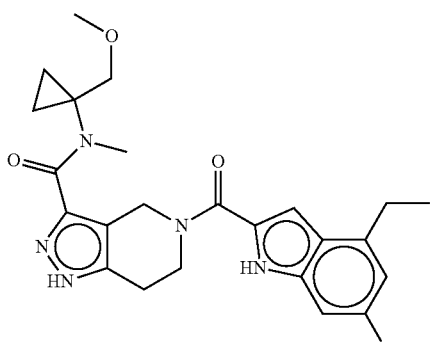

Prepared as described for Example 262 starting from 4-ethyl-6-fluoro-1H-indole-2-carboxylic acid.

Rt (Method A) 3.34 mins, m/z 454 [M+H]+

1H NMR (400 MHz, DMSO-d6) δ 13.68-10.84 (m, 2H), 7.04-6.84 (m, 2H), 6.77 (dd, J=10.8, 2.3 Hz, 1H), 5.47-4.44 (m, 2H), 4.43-3.75 (m, 2H), 3.75-3.12 (m, 8H), 3.12-2.71 (m, 6H), 1.28 (t, J=7.5 Hz, 3H), 0.96-0.52 (m, 4H).

Example 273 ethoxy({1-[5-(1H-indole-2-carbonyl)-1H,4H,5H,6H,7H-pyrazolo[4,3-c]pyridin-3-yl]ethylidene})amine

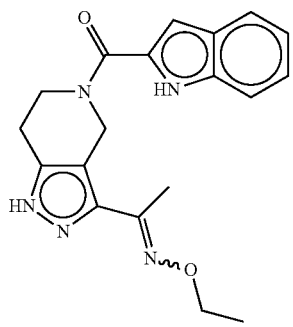

Rt (Method A) 3.38 mins, m/z 352 [M+H]+

1H NMR (400 MHz, DMSO-d6) δ 12.83 (s, 1H), 11.61 (s, 1H), 7.60 (d, J=8.0 Hz, 1H), 7.43 (d, J=8.2 Hz, 1H), 7.26-7.14 (m, 1H), 7.10-6.98 (m, 1H), 6.87 (s, 1H), 5.32-4.46 (m, 2H), 4.13 (q, J=6.9 Hz, 2H), 4.06-3.85 (m, 2H), 3.00-2.69 (m, 2H), 2.14 (s, 3H), 1.25 (t, J=7.0 Hz, 3H).

Example 274

{1-[5-(1H-indole-2-carbonyl)-1H,4H,5H,6H,7H-pyrazolo[4,3-c]pyridin-3-yl]ethylidene}(methoxy)amine

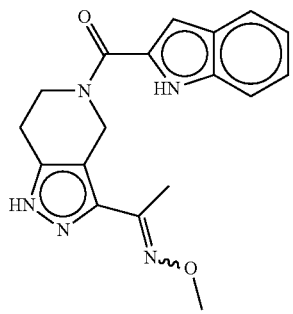

Rt (Method A) 3.25 mins, m/z 338 [M+H]+

1H NMR (400 MHz, DMSO-d6) δ 12.87 (s, 1H), 11.60 (s, 1H), 7.62 (d, J=8.0 Hz, 1H), 7.43 (d, J=8.1 Hz, 1H), 7.26-7.14 (m, 1H), 7.11-7.00 (m, 1H), 6.89 (s, 1H), 5.38-4.24 (m, 2H), 4.12-3.94 (m, 2H), 3.89 (s, 3H), 3.06-2.71 (m, 2H), 2.15 (s, 3H).

Example 275

3-(3-{1-[5-(1H-indole-2-carbonyl)-2H,4H,5H,6H,7H-pyrazolo[4,3-c]pyridin-3-yl]-N-methylformamido}-N-methylpropanamido)propanoic acid

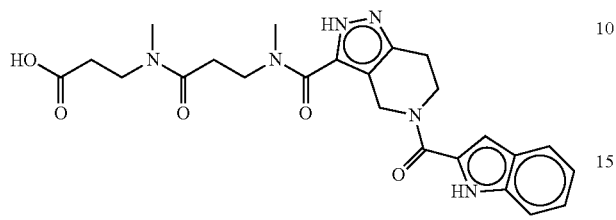

Rt (Method B) 2.62 mins, m/z 481 [M+H]+

1H NMR (400 MHz, DMSO-d6) δ 13.61-11.94 (m, 2H), 11.68-11.58 (m, 1H), 7.64 (d, J=8.1 Hz, 1H), 7.42 (d, J=8.2 Hz, 1H), 7.19 (t, J=7.7 Hz, 1H), 7.06 (t, J=7.5 Hz, 1H), 6.87 (s, 1H), 5.23-4.50 (m, 2H), 4.10-3.83 (m, 3H), 3.65-3.41 (m, 3H), 3.05-2.60 (m, 9H), 2.43-2.32 (m, 1H).

Example 276

3-{1-[5-(1H-indole-2-carbonyl)-2H,4H,5H,6H,7H-pyrazolo[4,3-c]pyridin-3-yl]-N-methylformamido}propanoic acid

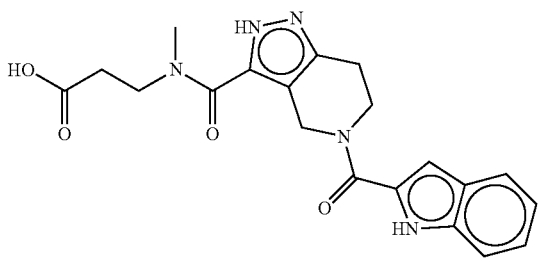

Rt (Method B) 2.65 mins, m/z 791 [M+H]+

1H NMR (400 MHz, DMSO-d6) δ 13.47-11.76 (m, 2H), 11.66-11.59 (m, 1H), 7.64 (d, J=8.1 Hz, 1H), 7.42 (d, J=8.2 Hz, 1H), 7.23-7.16 (m, 1H), 7.10-7.02 (m, 1H), 6.87 (s, 1H), 5.26-4.46 (m, 2H), 4.21-3.81 (m, 3H), 3.70-3.51 (m, 1H), 3.40-3.36 (m, 1H), 3.10-2.72 (m, 4H), 2.66-2.57 (m, 1H).

Example 277

5-(1H-indole-2-carbonyl)-N-methyl-N-[(1H-1,2,3,4-tetrazol-5-yl)methyl]-2H,4H,5H,6H,7H-pyrazolo[4,3-c]pyridine-3-carboxamide

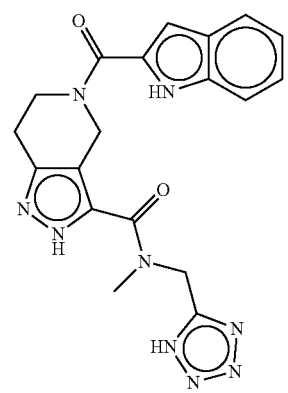

Rt (Method B) 2.68 mins, m/z 404 [M+H]+

1H NMR (400 MHz, DMSO-d6) δ 13.16 (s, 0.5H), 11.63 (s, 1H), 7.68-7.61 (m, 1H), 7.42 (d, J=8.1 Hz, 1H), 7.30-6.84 (m, 3.5H), 5.37 (s, 1H), 5.20-4.57 (m, 3H), 4.19-3.85 (m, 2H), 3.57-3.44 (m, 2H), 3.04-2.74 (m, 4H).

Example 278

5-(1H-indole-2-carbonyl)-N-methyl-N-[2-(1H-1,2,3,4-tetrazol-5-yl)ethyl]-2H,4H,5H,6H,7H-pyrazolo[4,3-c]pyridine-3-carboxamide

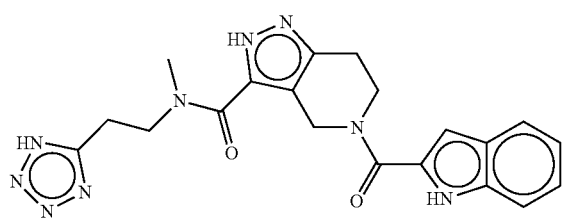

Rt (Method B) 2.62 mins, m/z 418 [M+H]+

1H NMR (400 MHz, DMSO-d6) δ 13.07 (s, 0.5H), 11.62 (s, 1H), 7.65 (d, J=8.0 Hz, 1H), 7.42 (d, J=8.1 Hz, 1H), 7.23-7.15 (m, 1H), 7.06 (t, J=7.4 Hz, 1H), 6.87 (s, 1H), 5.34-4.46 (m, 2H), 4.30-4.10 (m, 1H), 4.07-3.89 (m, 2H), 3.79-3.70 (m, 1H), 3.23-3.09 (m, 3H), 3.00-2.75 (m, 4H).

Example 279

2-(3-{4-azaspiro[2.5]octane-4-carbonyl}-2H,4H,5H,6H,7H-pyrazolo[4,3-c]pyridine-5-carbonyl)-1H-indole

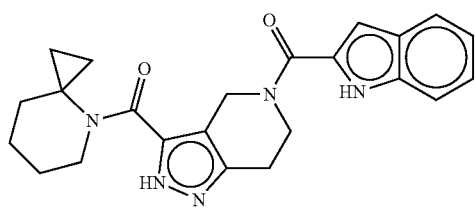

Rt (Method A) 3.14 mins, m/z 404 [M+H]+

1H NMR (400 MHz, DMSO-d6) δ 12.98 (s, 1H), 11.63 (s, 1H), 7.64 (d, J=7.9 Hz, 1H), 7.42 (d, J=8.1 Hz, 1H), 7.23-7.16 (m, 1H), 7.06 (t, J=7.4 Hz, 1H), 6.87 (s, 1H), 5.11-4.49 (m, 2H), 4.29-3.46 (m, 4H), 3.04-2.75 (m, 2H), 1.82-1.31 (m, 6H), 0.90-0.40 (m, 4H).

Example 280

N-(2-aminoethyl)-5-(1H-indole-2-carbonyl)-N-methyl-2H,4H,5H,6H,7H-pyrazolo[4,3-c]pyridine-3-carboxamide

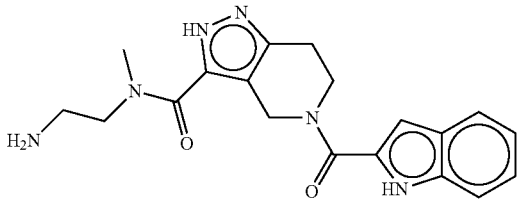

Rt (Method A) 2.68 mins, m/z 367 [M+H]+

1H NMR (400 MHz, DMSO-d6) δ 13.00 (s, 0.3H), 11.63 (s, 1H), 7.64 (d, J=8.0 Hz, 1H), 7.42 (d, J=8.3 Hz, 1H), 7.23-7.16 (m, 1H), 7.06 (t, J=7.5 Hz, 1H), 6.87 (s, 1H), 5.24-4.54 (m, 2H), 4.10-3.88 (m, 2H), 3.86-3.64 (m, 1.3H), 3.17-2.67 (m, 6.3H).

Example 281 tert-butyl N-(2-{1-[5-(1H-indole-2-carbonyl)-2H,4H,5H,6H,7H-pyrazolo[4,3-c]pyridin-3-yl]-N-methylformamido}ethyl)carbamate

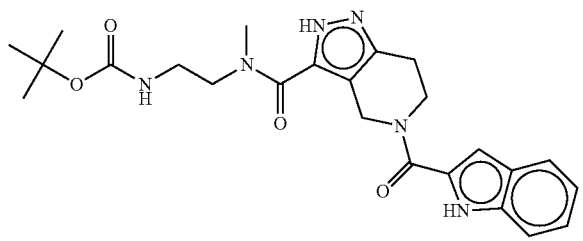

Rt (Method A) 3.1 mins, m/z 465 [M+H]+

1H NMR (400 MHz, DMSO-d6) δ 13.02 (s, 1H), 11.62 (s, 1H), 7.64 (d, J=7.9 Hz, 1H), 7.42 (d, J=8.2 Hz, 1H), 7.24-7.16 (m, 1H), 7.12-7.02 (m, 1H), 6.98-6.76 (m, 2H), 5.33-4.42 (m, 2H), 4.13-3.84 (m, 3H), 3.18-3.05 (m, 2H), 3.03-2.76 (m, 4H), 1.45-1.13 (m, 9H).

Example 282

2-{1-[5-(1H-indole-2-carbonyl)-1H,4H,5H,6H,7H-pyrazolo[4,3-c]pyridin-3-yl]-N-methylformamido}acetic acid

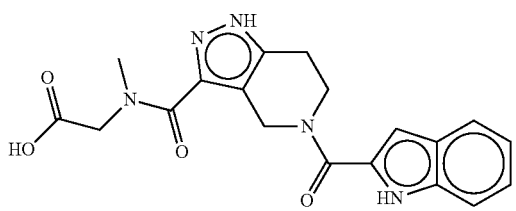

Rt (Method B) 2.67 mins, m/z 380 [M+H]+

1H NMR (400 MHz, DMSO-d6) δ 13.24-13.03 (m, 1H), 12.60 (s, 1H), 11.62 (s, 1H), 7.65 (d, J=8.0 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.26-4.57 (m, 3H), 4.23-3.86 (m, 3H), 3.47-3.37 (m, 1H), 3.09-2.75 (m, 4H).

Example 283

1-[5-(1H-indole-2-carbonyl)-1H,4H,5H,6H,7H-pyrazolo[4,3-c]pyridine-3-carbonyl]piperidine-4-carboxylic acid

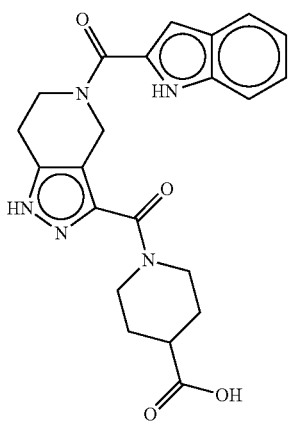

Rt (Method B) 2.7 mins, m/z 422 [M+H]+

1H NMR (400 MHz, DMSO-d6) δ 13.04 (s, 1H), 11.74-11.50 (m, 1H), 7.64 (d, J=7.9 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.21-4.52 (m, 3H), 4.44-4.16 (m, 1H), 4.05-3.85 (m, 2H), 3.07-2.76 (m, 3H), 2.59-2.51 (m, 1H), 1.94-1.79 (m, 2H), 1.49 (s, 2H).

Example 284

(2S)-1-[5-(1H-indole-2-carbonyl)-1H,4H,5H,6H,7H-pyrazolo[4,3-c]pyridine-3-carbonyl]pyrrolidine-2-carboxylic acid

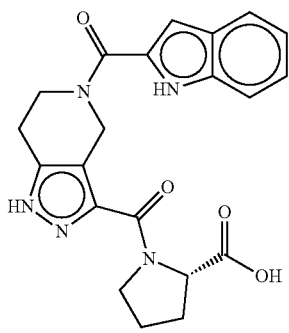

Rt (Method A) 2.76 mins, m/z 406 [M+H]+

1H NMR (400 MHz, DMSO-d6) δ 13.25-12.23 (m, 1H), 11.63 (s, 1H), 7.65 (d, J=8.1 Hz, 1H), 7.42 (d, J=8.2 Hz, 1H), 7.19 (t, J=7.5 Hz, 1H), 7.06 (t, J=7.5 Hz, 1H), 6.87 (s, 1H), 5.37-4.33 (m, 3H), 4.08-3.83 (m, 3H), 3.64-3.49 (m, 1H), 3.08-2.74 (m, 2H), 2.29-1.68 (m, 4H).

Example 285

5-(1H-indole-2-carbonyl)-N-methyl-1H,4H,5H,6H,7H-pyrazolo[4,3-c]pyridine-3-carboxamide

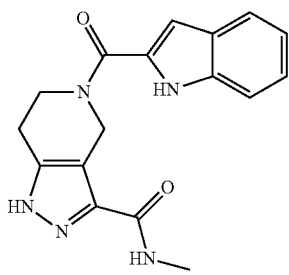 [SMILES: CNC(=O)c1n[nH]c2c1CN(C(=O)c1cc3ccccc3[nH]1)CC2]

Rt (Method A) 2.71 mins, m/z 324 [M+H]+

1H NMR (400 MHz, DMSO-d6) δ 13.05 (s, 1H), 11.63 (s, 1H), 8.04 (q, J=4.8 Hz, 1H), 7.65 (d, J=8.0 Hz, 1H), 7.43 (d, J=8.1 Hz, 1H), 7.20 (t, J=7.6 Hz, 1H), 7.06 (t, J=7.5 Hz, 1H), 6.88 (s, 1H), 5.38-4.52 (m, 2H), 4.17-3.81 (m, 2H), 2.99-2.80 (m, 2H), 2.78-2.64 (m, 3H).

Example 286 ethyl 3-(3-{1-[5-(1H-indole-2-carbonyl)-1H,4H,5H,6H,7H-pyrazolo[4,3-c]pyridin-3-yl]-N-methylformamido}-N-methylpropanamido)propanoate Rt (Method A) 2.92 mins, m/z 509 [M+H]+

1H NMR (400 MHz, DMSO-d6) δ 13.05 (s, 1H), 11.62 (s, 1H), 7.64 (d, J=8.0 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.37-4.48 (m, 2H), 4.22-3.38 (m, 9H), 3.08-2.54 (m, 10H), 2.47-2.41 (m, 1H), 1.21-1.09 (m, 3H).

Example 287 ethyl 3-{1-[5-(1H-indole-2-carbonyl)-1H,4H,5H,6H,7H-pyrazolo[4,3-c]pyridin-3-yl]-N-methylformamido}propanoate Rt (Method A) 3.01 mins, m/z 424 [M+H]+

1H NMR (400 MHz, DMSO-d6) δ 13.07 (s, 1H), 11.62 (s, 1H), 7.64 (d, J=8.1 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.31-4.40 (m, 2H), 4.12-3.35 (m, 7H), 3.08-2.54 (m, 6H), 1.26-1.00 (m, 3H).

Example 288

(E)-{cyclopropyl[5-(1H-indole-2-carbonyl)-1H,4H,5H,6H,7H-pyrazolo[4,3-c]pyridin-3-yl]methylidene}(methoxy)amine

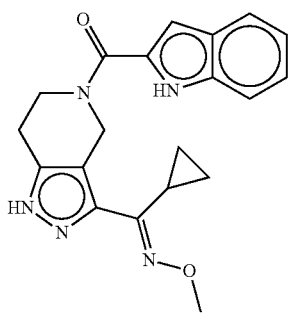

Rt (Method A) 3.26 mins, m/z 364 [M+H]+

1H NMR (400 MHz, DMSO-d6) δ 12.96 (s, 1H), 11.60 (s, 1H), 7.63 (d, J=7.9 Hz, 1H), 7.42 (d, J=8.1 Hz, 1H), 7.26-7.13 (m, 1H), 7.13-6.98 (m, 1H), 6.96-6.75 (m, 1H), 5.31-4.33 (m, 2H), 4.22-3.88 (m, 2H), 3.86-3.41 (m, 3H), 3.11-2.71 (m, 2H), 2.03-1.70 (m, 1H), 0.86-0.61 (m, 4H).

Example 289

(Z)-{cyclopropyl[5-(1H-indole-2-carbonyl)-1H,4H,5H,6H,7H-pyrazolo[4,3-c]pyridin-3-yl]methylidene}(methoxy)amine

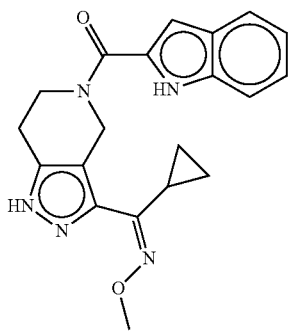

Rt (Method A) 3.44 mins, m/z 364 [M+H]+

1H NMR (400 MHz, DMSO-d6) δ 12.75 (s, 1H), 11.59 (s, 1H), 7.66-7.58 (m, 1H), 7.48-7.40 (m, 1H), 7.24-7.14 (m, 1H), 7.10-7.01 (m, 1H), 6.92-6.81 (m, 1H), 5.21-4.34 (m, 2H), 4.13-3.91 (m, 2H), 3.87 (s, 3H), 3.01-2.68 (m, 2H), 2.44-2.28 (m, 1H), 1.51-1.35 (m, 2H), 0.94-0.69 (m, 2H).

Example 290

5-(4-chloro-1H-indole-2-carbonyl)-N-[1-(hydroxymethyl)cyclopropyl]-N-methyl-1H,4H,5H,6H,7H-pyrazolo[4,3-c]pyridine-3-carboxamide

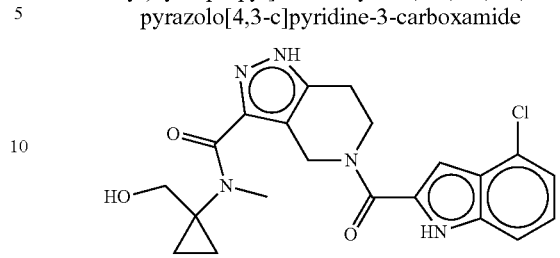

Rt (Method A) 3.02 mins, m/z 428/430 [M+H]+

1H NMR (400 MHz, DMSO-d6) δ 13.04 (bs, 1H), 12.03 (s, 1H), 7.41 (d, J=8.1 Hz, 1H), 7.20 (dd, J=7.8 Hz, 1H), 7.15 (d, J=7.4 Hz, 1H), 6.83 (s, 1H), 5.19-4.47 (m, 2H), 4.20-3.85 (m, 2H), 3.83-3.39 (m, 4H), 3.11-2.71 (m, 4H), 1.01-0.36 (m, 4H)—one signal (1H) coincides with H2O signal.

Example 291

5-(4-ethyl-1H-indole-2-carbonyl)-N-[1-(hydroxymethyl)cyclopropyl]-N-methyl-1H,4H,5H,6H,7H-pyrazolo[4,3-c]pyridine-3-carboxamide

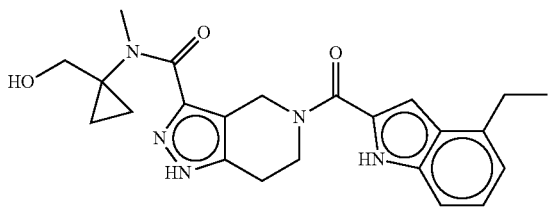

Rt (Method A) 3.07 mins, m/z 422 [M+H]+

1H NMR (400 MHz, DMSO-d6) δ 13.03 (bs, 1H), 11.59 (s, 1H), 7.25 (d, J=8.2 Hz, 1H), 7.11 (t, J=7.6 Hz, 1H), 6.98-6.74 (m, 2H), 5.12-4.57 (m, 2H), 4.23-3.84 (m, 2H), 3.83-3.37 (m, 4H), 3.11-2.94 (m, 2H), 2.94-2.77 (m, 4H), 1.28 (t, J=7.5 Hz, 3H), 0.97-0.28 (m, 4H)—one signal (1H) coincides with H2O signal.

Example 292

N-(2-cyanoethyl)-5-(1H-indole-2-carbonyl)-N-methyl-1H,4H,5H,6H,7H-pyrazolo[4,3-c]pyridine-3-carboxamide

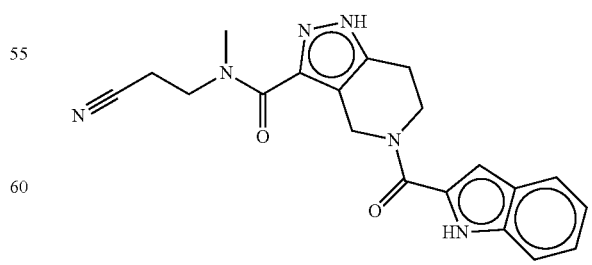

Rt (Method A) 2.82 mins, m/z 377 [M+H]+

1H NMR (400 MHz, DMSO-d6) δ 13.16 (s, 1H), 11.63 (s, 1H), 7.64 (d, J=8.1 Hz, 1H), 7.42 (d, J=8.3 Hz, 1H), 7.23-7.16 (m, 1H), 7.06 (t, J=7.5 Hz, 1H), 6.87 (s, 1H), 5.26-4.54 (m, 2H), 4.23-3.42 (m, 5H), 3.08-2.76 (m, 6H).

Example 293

N-cyclopropyl-5-(1H-indole-2-carbonyl)-N-(oxan-4-yl)-1H,4H,5H,6H,7H-pyrazolo[4,3-c]pyridine-3-carboxamide

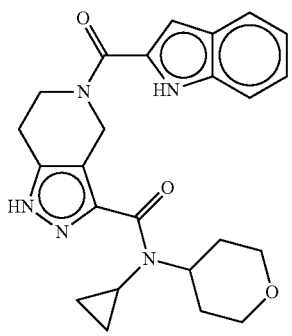

Rt (Method A) 2.9 mins, m/z 434 [M+H]+

1H NMR (400 MHz, DMSO-d6) δ 12.96 (s, 1H), 11.63 (s, 1H), 7.64 (d, J=8.0 Hz, 1H), 7.42 (d, J=8.3 Hz, 1H), 7.24-7.15 (m, 1H), 7.06 (t, J=7.4 Hz, 1H), 6.88 (s, 1H), 5.23-4.45 (m, 2H), 4.31-4.10 (m, 1H), 4.09-3.84 (m, 4H), 3.09-2.69 (m, 3H), 2.15-1.93 (m, 2H), 1.83-1.63 (m, 2H), 0.77-0.59 (m, 2H), 0.56-0.39 (m, 2H).

Example 294

N-ethyl-5-(1H-indole-2-carbonyl)-N-(2-methoxyethyl)-1H,4H,5H,6H,7H-pyrazolo[4,3-c]pyridine-3-carboxamide

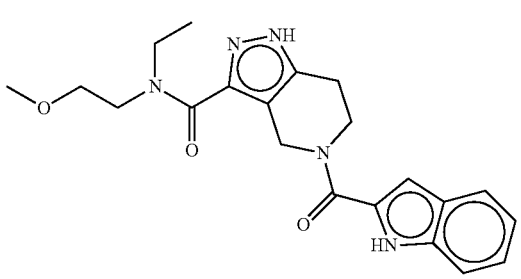

Rt (Method A) 2.96 mins, m/z 369 [M+H]+

1H NMR (400 MHz, DMSO-d6) δ 13.06 (s, 1H), 11.63 (s, 1H), 7.64 (d, J=7.9 Hz, 1H), 7.42 (d, J=8.1 Hz, 1H), 7.27-7.16 (m, 1H), 7.06 (t, J=7.5 Hz, 1H), 6.87 (s, 1H), 5.21-4.51 (m, 2H), 4.09-3.80 (m, 4H), 3.61-3.39 (m, 4H), 3.28-3.11 (m, 3H), 3.06-2.72 (m, 2H), 1.21-1.01 (m, 3H).

Example 295 tert-butyl (2S)-1-[5-(1H-indole-2-carbonyl)-1H,4H,5H,6H,7H-pyrazolo[4,3-c]pyridine-3-carbonyl]pyrrolidine-2-carboxylate

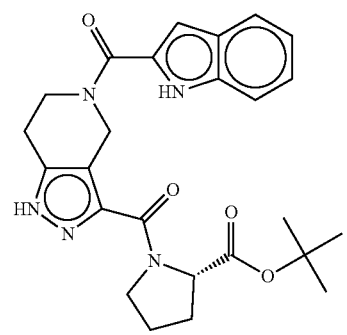

Rt (Method A) 3.34 mins, m/z 462 [M+H]+

1H NMR (400 MHz, DMSO-d6) δ 13.23-13.00 (m, 1H), 11.63 (s, 1H), 7.63 (t, J=8.1 Hz, 1H), 7.42 (d, J=8.1 Hz, 1H), 7.19 (t, J=7.7 Hz, 1H), 7.09-7.02 (m, 1H), 6.90-6.83 (m, 1H), 5.30-4.52 (m, 2.5H), 4.40-4.26 (m, 0.5H), 14.14-3.81 (m, 3H), 3.63-3.47 (m, 1H), 3.06-2.71 (m, 2H), 2.31-2.08 (m, 1H), 2.07-1.62 (m, 3H), 1.39-1.23 (m, 9H).

Example 296

N-ethyl-5-(1H-indole-2-carbonyl)-N-[1-(methoxymethyl)cyclopropyl]-1H,4H,5H,6H,7H-pyrazolo[4,3-c]pyridine-3-carboxamide

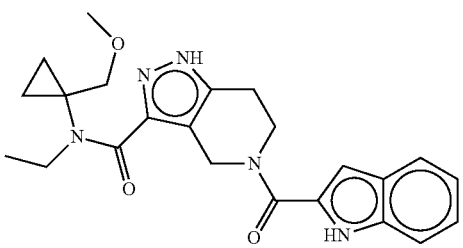

Rt (Method A) 3.07 mins, m/z 422.1 [M+H]+

1H NMR (400 MHz, DMSO-d6) δ 13.18-12.77 (m, 1H), 11.63 (s, 1H), 7.64 (d, J=8.0 Hz, 1H), 7.42 (d, J=8.3 Hz, 1H), 7.23-7.16 (m, 1H), 7.09-7.02 (m, 1H), 6.87 (s, 1H), 5.07-4.60 (m, 2H), 4.36-3.80 (m, 4H), 3.75-3.42 (m, 2H), 3.25 (s, 3H), 3.02-2.77 (m, 2H), 1.18-1.06 (m, 3H), 0.94-0.69 (m, 4H).

Example 297

5-(4,7-difluoro-1H-indole-2-carbonyl)-N-[1-(methoxymethyl)cyclopropyl]-N-methyl-1H,4H,5H,6H,7H-pyrazolo[4,3-c]pyridine-3-carboxamide

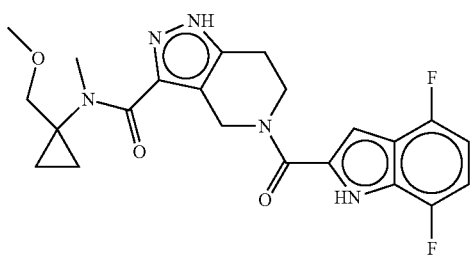

Rt (Method B) 3.04 mins, m/z 444.2 [M+H]+

1H NMR (400 MHz, DMSO-d6) δ 12.98 (s, 1H), 12.46 (s, 1H), 7.05-6.88 (m, 2H), 6.80 (d, J=9.6 Hz, 1H), 4.73 (m, 2H), 3.93 (m, 3H), 3.48 (m, 1H), 3.27 (m, 4H), 2.92 (m, 4H), 0.78 (m, 4H).

Example 298

5-[4-(difluoromethyl)-6-fluoro-1H-indole-2-carbonyl]-N-[1-(methoxymethyl)cyclopropyl]-N-methyl-1H,4H,5H,6H,7H-pyrazolo[4,3-c]pyridine-3-carboxamide

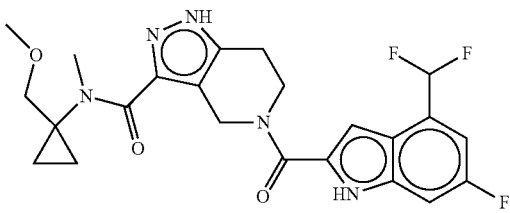

Rt (Method B) 3.11 mins, m/z 476.2 [M+H]+

1H NMR (400 MHz, DMSO-d6) δ 12.99 (m, 1H), 12.09 (s, 1H), 7.52-7.16 (m, 3H), 6.99 (s, 1H), 4.80 (m, 2H), 3.97 (m, 3H), 3.48 (m, 1H), 3.26 (m, 4H), 2.93 (m, 4H), 0.78 (m, 4H).

Example 299

5-[4-(difluoromethyl)-1H-indole-2-carbonyl]-N-[1-(methoxymethyl)cyclopropyl]-N-methyl-1H,4H,5H,6H,7H-pyrazolo[4,3-c]pyridine-3-carboxamide

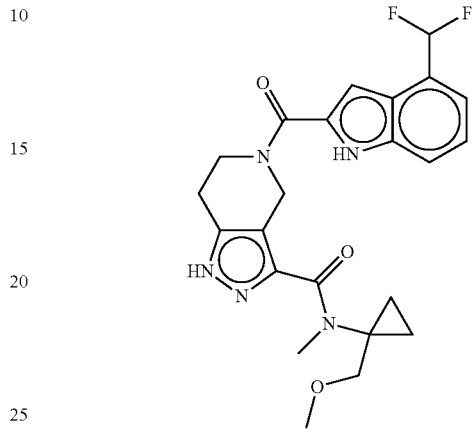

Rt (Method B) 3.03 mins, m/z 458.2 [M+H]+

1H NMR (400 MHz, DMSO-d6) δ 12.97 (s, 1H), 12.01 (s, 1H), 7.63-7.56 (m, 1H), 7.48-7.13 (m, 3H), 6.96 (s, 1H), 4.81 (m, 2H), 3.98 (m, 3H), 3.48 (m, 1H), 3.26 (m, 4H), 2.93 (m, 4H), 0.81 (m, 4H).

Example 300

5-(5,6-difluoro-1H-indole-2-carbonyl)-N-[1-(methoxymethyl)cyclopropyl]-N-methyl-1H,4H,5H,6H,7H-pyrazolo[4,3-c]pyridine-3-carboxamide

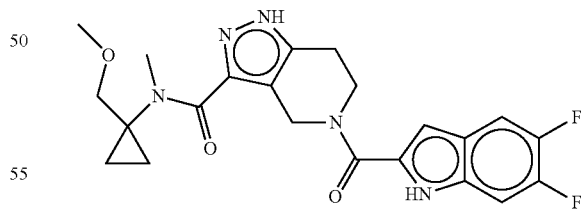

Rt (Method B) 3.06 mins, m/z 444.2 [M+H]+

1H NMR (400 MHz, DMSO-d6) δ 11.91 (m, 2H), 7.65 (s, 1H), 7.34 (dd, J=11.0, 7.0 Hz, 1H), 6.89 (s, 1H), 4.79 (m, 2H), 3.96 (m, 3H), 3.48 (m, 1H), 3.26 (m, 4H), 2.93 (m, 4H), 0.81 (m, 4H).

Example 301

5-[4-(1,1-difluoroethyl)-1H-indole-2-carbonyl]-N-[1-(methoxymethyl)cyclopropyl]-N-methyl-1H,4H,5H,6H,7H-pyrazolo[4,3-c]pyridine-3-carboxamide

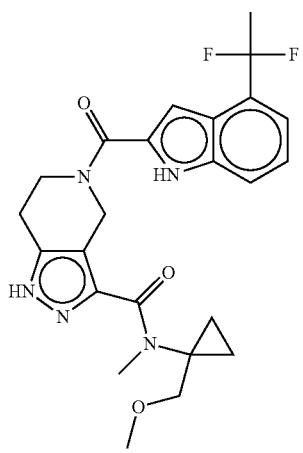

Rt (Method B) 3.13 mins, m/z 372.1 [M+H]+

1H NMR (400 MHz, DMSO-d6) δ 12.97 (s, 1H), 11.95 (s, 1H), 7.55 (d, J=7.9 Hz, 1H), 7.25 (m, 2H), 6.86 (s, 1H), 4.84 (m, 2H), 3.97 (m, 3H), 3.47 (m, 1H), 3.26 (m, 4H), 2.92 (m, 4H), 2.07 (t, J=18.8 Hz, 3H), 0.78 (m, 4H).

Example 302

N-[1-(methoxymethyl)cyclopropyl]-N-methyl-5-[4-(trifluoromethyl)-1H-indole-2-carbonyl]-1H,4H,5H,6H,7H-pyrazolo[4,3-c]pyridine-3-carboxamide

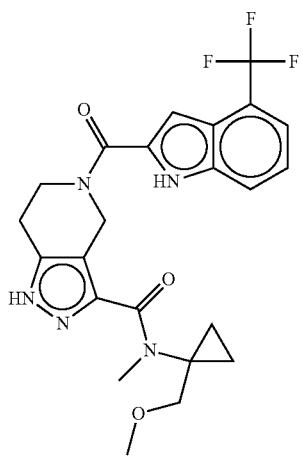

Rt (Method B) 3.21 mins, m/z 476.2 [M+H]+

1H NMR (400 MHz, DMSO-d6) δ 12.99 (m, 1H), 12.22 (s, 1H), 7.73 (d, J=8.2 Hz, 1H), 7.52-7.28 (m, 2H), 6.95-6.73 (m, 1H), 4.82 (m, 2H), 3.96 (m, 3H), 3.47 (m, 1H), 3.26 (m, 4H), 2.92 (m, 4H), 0.78 (m, 4H).

Example 303

N-(2,2-difluoroethyl)-5-(1H-indole-2-carbonyl)-N-[1-(methoxymethyl)cyclopropyl]-1H,4H,5H,6H,7H-pyrazolo[4,3-c]pyridine-3-carboxamide

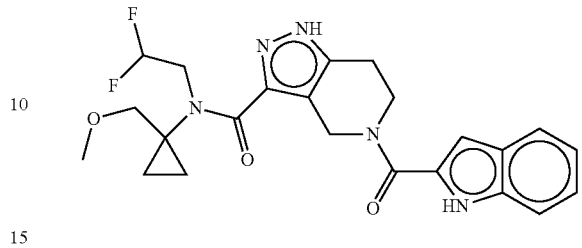

Rt (Method A) 3.28 mins, m/z 458.1 [M+H]+

1H NMR (400 MHz, DMSO-d6) δ 13.15 (s, 1H), 11.63 (s, 1H), 7.64 (d, J=8.0 Hz, 1H), 7.42 (d, J=8.3 Hz, 1H), 7.19 (t, J=7.5 Hz, 1H), 7.06 (t, J=7.5 Hz, 1H), 6.88 (s, 1H), 6.24 (t, J=57.0 Hz, 1H), 5.26-4.57 (m, 2H), 4.57-3.36 (m, 6H), 3.25 (s, 3H), 3.02-2.74 (m, 2H), 1.03-0.61 (m, 4H).

Example 304

5-(1H-indole-2-carbonyl)-N-[1-(methoxymethyl)cyclopropyl]-N-(propan-2-yl)-1H,4H,5H,6H,7H-pyrazolo[4,3-c]pyridine-3-carboxamide

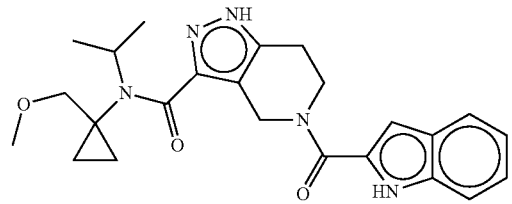

Rt (Method A) 3.25 mins, m/z 436.2 [M+H]+

1H NMR (400 MHz, DMSO-d6) δ 12.89 (s, 1H), 11.63 (s, 1H), 7.63 (d, J=8.0 Hz, 1H), 7.42 (d, J=8.3 Hz, 1H), 7.19 (t, J=7.6 Hz, 1H), 7.06 (t, J=7.5 Hz, 1H), 6.87 (s, 1H), 5.04-4.45 (m, 2H), 4.45-3.41 (m, 5H), 3.29-3.13 (m, 3H), 3.06-2.72 (m, 2H), 1.54-1.26 (m, 6H), 1.03-0.43 (m, 4H).

Example 305

5-(6-chloro-4-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

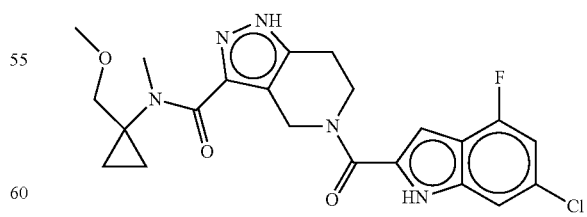

Rt (Method B) 3.24 mins, m/z 460/462 [M+H]+

1H NMR (400 MHz, DMSO-d6) δ 12.97 (s, 1H), 12.13 (s, 1H), 7.30 (d, J=1.6 Hz, 1H), 7.08-6.85 (m, 2H), 4.73 (m, 2H), 3.96 (m, 3H), 3.48 (m, 1H), 3.29 (m, 4H), 2.94 (m, 4H), 0.79 (m, 4H).

Example 306

5-(4-chloro-7-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

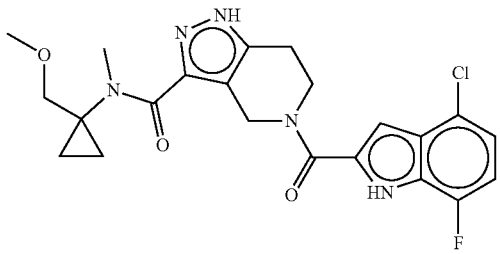

Rt (Method B) 3.17 mins, m/z 460/462 [M+H]+
1H NMR (400 MHz, DMSO-d6) δ 12.97 (s, 1H), 12.53 (s, 1H), 7.23-6.96 (m, 2H), 6.84 (d, J=2.9 Hz, 1H), 4.77 (m, 2H), 3.92 (m, 3H), 3.48 (m, 1H), 3.27 (m, 4H), 2.92 (m, 4H), 0.78 (m, 4H).

Example 307

N-[1-(methoxymethyl)cyclopropyl]-N-methyl-5-(4,5,7-trifluoro-1H-indole-2-carbonyl)-1H,4H,5H,6H,7H-pyrazolo[4,3-c]pyridine-3-carboxamide

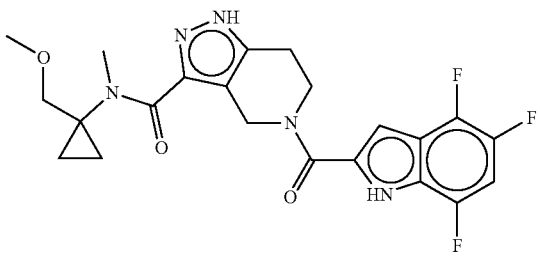

Rt (Method B) 3.14 mins, m/z 462 [M+H]+
1H NMR (400 MHz, DMSO-d6) δ 12.98 (s, 1H), 12.68 (s, 1H), 7.14 (td, J=10.6, 5.0 Hz, 1H), 6.96 (s, 1H), 4.73 (m, 2H), 3.91 (m, 3H), 3.48 (m, 1H), 3.26 (m, 4H), 2.93 (m, 4H), 0.78 (m, 4H).

Example 308

5-(7-fluoro-1H-indole-2-carbonyl)-N-[1-(methoxymethyl)cyclopropyl]-N-methyl-1H,4H,5H,6H,7H-pyrazolo[4,3-c]pyridine-3-carboxamide

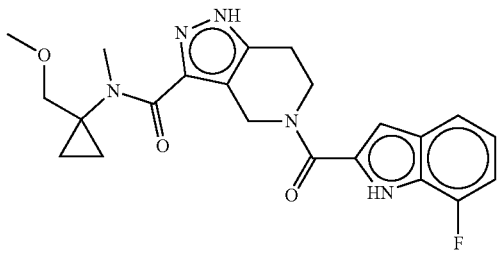

Rt (Method B) 2.97 mins, m/z 426 [M+H]+
1H NMR (400 MHz, DMSO-d6) δ 12.91 (s, 1H), 12.09 (s, 1H), 7.54-7.36 (m, 1H), 7.02 (m, 2H), 6.90 (s, 1H), 4.76 (m, 2H), 3.93 (m, 3H), 3.46 (m, 1H), 3.27 (m, 4H), 2.92 (m, 4H), 1.02-0.43 (m, 4H).

Example 309

5-(5,7-difluoro-1H-indole-2-carbonyl)-N-[1-(methoxymethyl)cyclopropyl]-N-methyl-1H,4H,5H,6H,7H-pyrazolo[4,3-c]pyridine-3-carboxamide

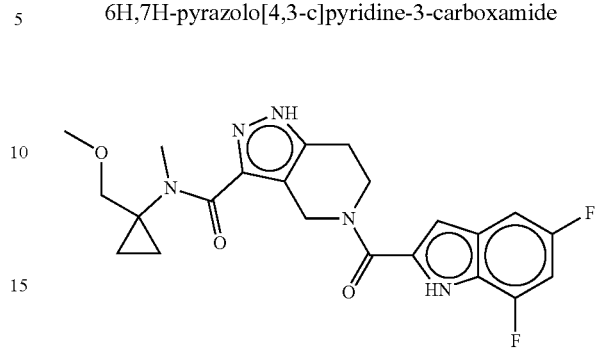

Rt (Method B) 3.04 mins, m/z 444 [M+H]+
1H NMR (400 MHz, DMSO-d6) δ 12.98 (s, 1H), 12.24 (s, 1H), 7.28 (s, 1H), 7.06 (s, 1H), 6.89 (s, 1H), 4.74 (m, 2H), 3.92 (m, 3H), 3.46 (m, 1H), 3.27 (m, 4H), 2.92 (m, 4H), 0.77 (m, 4H).

Example 310

5-(1H-indole-2-carbonyl)-N-methyl-N-[1-(trifluoromethyl)cyclopropyl]-1H,4H,5H,6H,7H-pyrazolo[4,3-c]pyridine-3-carboxamide

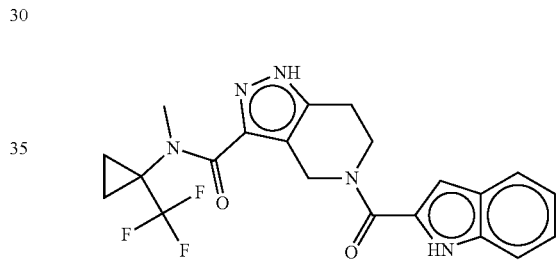

Rt (Method B) 3.19 mins, m/z 432 [M+H]+
1H NMR (400 MHz, DMSO-d6) δ 13.16 (s, 1H), 11.65-11.59 (m, 1H), 7.64 (d, J=8.0 Hz, 1H), 7.42 (d, J=8.3 Hz, 1H), 7.23-7.16 (m, 1H), 7.06 (t, J=7.4 Hz, 1H), 6.88 (s, 1H), 5.08-4.63 (m, 2H), 4.12-3.85 (m, 2H), 3.50-2.77 (m, 5H), 1.58-1.13 (m, 4H).

Example 311

5-(1H-indole-2-carbonyl)-N-methyl-N-[1-(pyridin-2-yl)cyclopropyl]-1H,4H,5H,6H,7H-pyrazolo[4,3-c]pyridine-3-carboxamide

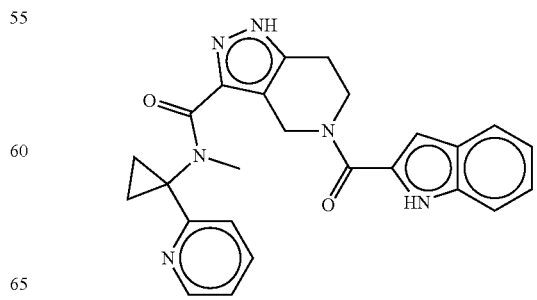

Rt (Method B) 2.63 mins, m/z 441 [M+H]+ 1H NMR (400 MHz, DMSO-d6) δ 13.32-12.71 (m, 1H), 11.61 (s, 1H), 8.49-8.39 (m, 1H), 7.73-7.57 (m, 2H), 7.42 (d, J=8.2 Hz, 1H), 7.34-7.10 (m, 3H), 7.09-7.01 (m, 1H), 6.87 (s, 1H), 5.13-4.63 (m, 2H), 4.11-3.78 (m, 2H), 3.50-3.01 (m, 3H), 2.98-2.70 (m, 2H), 1.63-1.41 (m, 2H), 1.38-1.10 (m, 2H).

Example 312

5-(1H-indole-2-carbonyl)-N-methyl-N-(prop-2-yn-1-yl)-1H,4H,5H,6H,7H-pyrazolo[4,3-c]pyridine-3-carboxamide

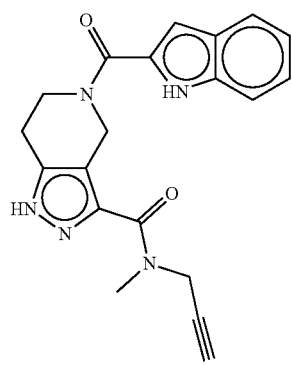

Rt (Method A) 2.92 mins, m/z 362 [M+H]+

1H NMR (400 MHz, DMSO-d6) δ 13.18 (d, J=9.6 Hz, 1H), 11.65 (s, 1H), 7.65 (d, J=8.0 Hz, 1H), 7.42 (d, J=8.2 Hz, 1H), 7.19 (t, J=7.6 Hz, 1H), 7.06 (t, J=7.5 Hz, 1H), 6.88 (s, 1H), 5.24-4.50 (m, 3H), 4.26 (s, 1H), 3.98 (m, 2H), 3.41 (s, 1H), 3.22 (s, 1H), 2.93 (m, 4H).

Example 313

5-(1H-indole-2-carbonyl)-N-[1-(methoxymethyl)cyclopropyl]-N-(2,2,2-trifluoroethyl)-1H,4H,5H,6H,7H-pyrazolo[4,3-c]pyridine-3-carboxamide

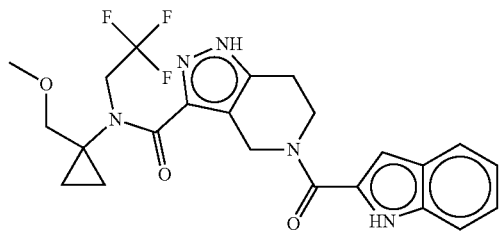

Rt (Method A) 3.33 mins, m/z 476 [M+H]+

1H NMR (400 MHz, DMSO-d6) δ 13.20 (s, 1H), 11.64 (s, 1H), 7.64 (d, J=7.9 Hz, 1H), 7.42 (d, J=8.1 Hz, 1H), 7.23-7.16 (m, 1H), 7.09-7.02 (m, 1H), 6.88 (s, 1H), 5.18-3.47 (m, 8H), 3.28-3.16 (m, 3H), 3.00-2.78 (m, 2H), 1.05-0.69 (m, 4H).

Example 314

Intentionally left blank

Example 315

5-(1H-indole-2-carbonyl)-N-methyl-N-{1-[(prop-2-yn-1-yloxy)methyl]cyclopropyl}-1H,4H,5H,6H,7H-pyrazolo[4,3-c]pyridine-3-carboxamide

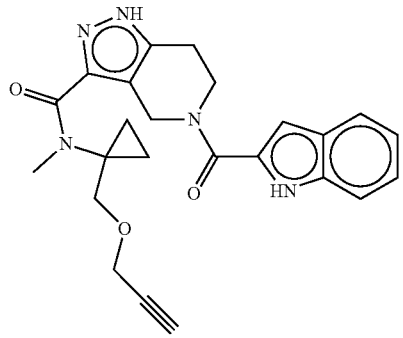

Rt (Method A) 3.06 mins, m/z 432 [M+H]+

1H NMR (400 MHz, DMSO-d6) δ 13.33-12.75 (m, 1H), 11.62 (s, 1H), 7.64 (d, J=7.9 Hz, 1H), 7.42 (d, J=8.2 Hz, 1H), 7.19 (t, J=7.6 Hz, 1H), 7.06 (t, J=7.5 Hz, 1H), 6.95-6.80 (m, 1H), 5.27-4.60 (m, 2H), 4.60-4.31 (m, 1H), 4.23-4.09 (m, 2H), 4.09-3.81 (m, 2H), 3.71-3.53 (m, 1H), 3.48-3.37 (m, 1H), 2.99 (s, 2H), 2.88 (s, 2H), 1.06-0.39 (m, 4H)—one signal (1H) coincides with DMSO signal.

Example 316

5-(1H-indole-2-carbonyl)-N-methyl-N-[(1-methyl-1H-1,2,3-triazol-4-yl)methyl]-1H,4H,5H,6H,7H-pyrazolo[4,3-c]pyridine-3-carboxamide

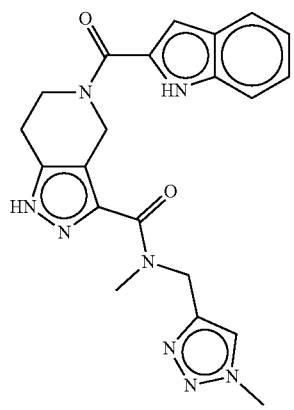

Rt (Method J) 1.02 mins, m/z 419 [M+H]+

1H NMR (400 MHz, DMSO-d6) δ 13.10 (s, 1H), 11.63 (s, 1H), 7.90 (m, 1H), 7.65 (d, J=8.0 Hz, 1H), 7.43 (d, J=8.2 Hz, 1H), 7.20 (t, J=7.6 Hz, 1H), 7.06 (t, J=7.5 Hz, 1H), 6.88 (s, 1H), 5.21 (s, 1H), 4.91 (m, 2H), 4.64 (s, 1H), 3.99 (m, 5H), 3.38 (m, 2H), 2.90 (m, 3H).

Example 317

2-[3-(5-ethenyl-1,3-thiazol-4-yl)-1H,4H,5H,6H,7H-pyrazolo[4,3-c]pyridine-5-carbonyl]-1H-indole

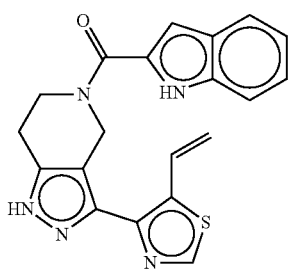

Rt (Method A) 3.24 mins, m/z 376 [M+H]+

1H NMR (400 MHz, DMSO-d6) δ 12.95 (s, 1H), 11.62 (s, 1H), 9.06 (s, 1H), 7.97-7.74 (m, 1H), 7.63 (d, J=8.0 Hz, 1H), 7.43 (d, J=8.2 Hz, 1H), 7.24-7.15 (m, 1H), 7.09-7.01 (m, 1H), 6.89 (s, 1H), 5.60 (d, J=17.5 Hz, 1H), 5.35 (d, J=11.0 Hz, 1H), 5.10-4.77 (m, 2H), 4.12-3.94 (m, 2H), 3.06-2.87 (m, 2H).

Example 318

N-{1-[(difluoromethoxy)methyl]cyclopropyl}-5-(1H-indole-2-carbonyl)-N-methyl-1H,4H,5H,6H,7H-pyrazolo[4,3-c]pyridine-3-carboxamide

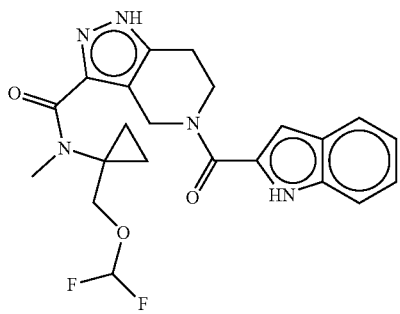

Rt (Method B) 3.11 mins, m/z 444 [M+H]+

1H NMR (400 MHz, DMSO-d6) δ 13.02 (s, 1H), 11.62 (s, 1H), 7.64 (d, J=7.8 Hz, 1H), 7.42 (d, J=8.2 Hz, 1H), 7.23-7.16 (m, 1H), 7.06 (t, J=7.5 Hz, 1H), 6.92-6.44 (m, 2H), 5.23-4.55 (m, 2H), 4.14-3.83 (m, 3H), 3.64-3.50 (m, 1H), 3.07-2.78 (m, 4H), 0.98-0.61 (m, 4H).

Example 319

N-cyclopropyl-5-(7-fluoro-1H-indole-2-carbonyl)-N-methyl-2H,4H,5H,6H,7H-pyrazolo[4,3-c]pyridine-3-carboxamide

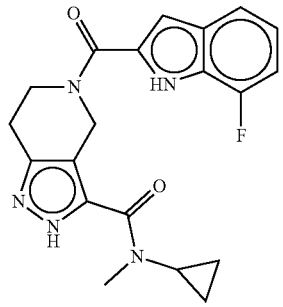

Rt (Method J) 1.15 mins, m/z 382 [M+H]+
No NMR available

Example 320

N-cyclopropyl-5-(6-fluoro-1H-indole-2-carbonyl)-N-methyl-2H,4H,5H,6H,7H-pyrazolo[4,3-c]pyridine-3-carboxamide

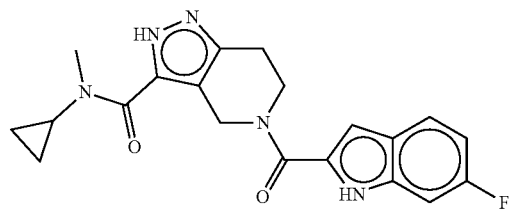

Rt (Method J) 1.17 mins, m/z 382 [M+H]+

1H NMR (400 MHz, DMSO-d6) δ 12.98 (s, 1H), 11.71 (s, 1H), 7.65 (ddd, J=13.7, 8.8, 5.5 Hz, 1H), 7.14 (dd, J=9.9, 2.4 Hz, 1H), 7.01-6.84 (m, 2H), 5.15-4.47 (m, 2H), 3.95 (d, J=21.0 Hz, 2H), 3.22-2.74 (m, 6H), 0.59 (d, J=53.1 Hz, 4H).

Example 321

N-cyclopropyl-5-(5-fluoro-1H-indole-2-carbonyl)-N-methyl-2H,4H,5H,6H,7H-pyrazolo[4,3-c]pyridine-3-carboxamide

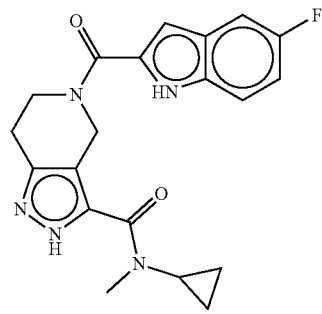

Rt (Method J) 1.16 mins, m/z 382 [M+H]+
No NMR available

Example 322

N-cyclopropyl-5-(4-fluoro-1H-indole-2-carbonyl)-N-methyl-2H,4H,5H,6H,7H-pyrazolo[4,3-c]pyridine-3-carboxamide

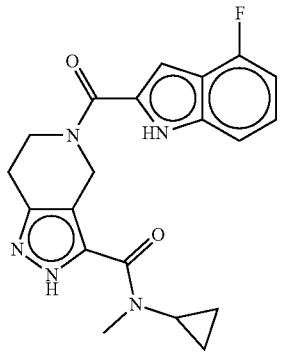

Rt (Method J) 1.18 mins, m/z 382 [M+H]+
No NMR available

Example 323

N-cyclopropyl-5-(4,6-difluoro-1H-indole-2-carbonyl)-N-methyl-2H,4H,5H,6H,7H-pyrazolo[4,3-c]pyridine-3-carboxamide

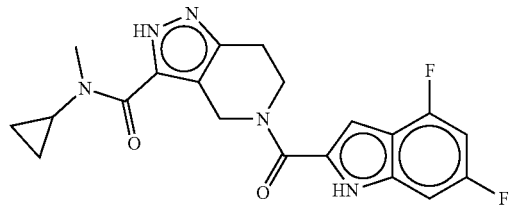

Rt (Method J) 1.23 mins, m/z 400 [M+H]+
No NMR available

Example 324

5-(4-chloro-5-fluoro-1H-indole-2-carbonyl)-N-cyclopropyl-N-methyl-2H,4H,5H,6H,7H-pyrazolo[4,3-c]pyridine-3-carboxamide

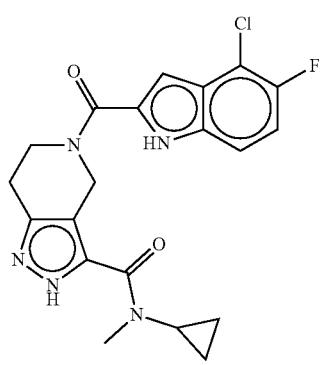

Rt (Method J) 1.28 mins, m/z 416/418 [M+H]+
No NMR available

Example 325

5-(6-chloro-1H-indole-2-carbonyl)-N-cyclopropyl-N-methyl-2H,4H,5H,6H,7H-pyrazolo[4,3-c]pyridine-3-carboxamide

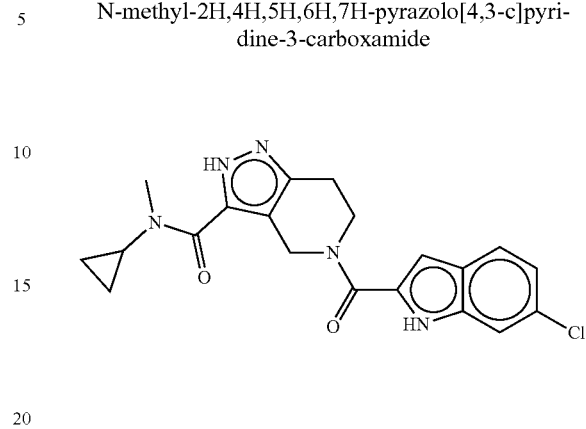

Rt (Method J) 1.27 mins, m/z 398/400 [M+H]+

1H NMR (400 MHz, DMSO-d6) δ 12.98 (s, 1H), 11.79 (s, 1H), 7.67 (d, J=8.5 Hz, 1H), 7.43 (d, J=1.9 Hz, 1H), 7.08 (dd, J=8.5, 2.0 Hz, 1H), 6.92 (s, 1H), 5.12-4.50 (m, 2H), 3.98 (s, 2H), 2.94 (d, J=51.1 Hz, 6H), 0.79-0.59 (m, 2H), 0.52 (s, 2H).

Example 326

5-(4-chloro-1H-indole-2-carbonyl)-N-cyclopropyl-N-methyl-2H,4H,5H,6H,7H-pyrazolo[4,3-c]pyridine-3-carboxamide

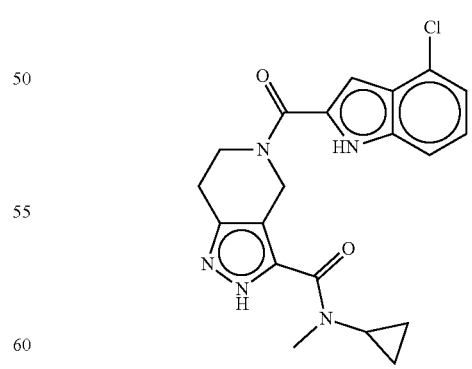

Rt (Method J) 1.25 mins, m/z 398/400 [M+H]+
No NMR available

Example 327

N-cyclopropyl-5-(6-fluoro-4-methyl-1H-indole-2-carbonyl)-N-methyl-2H,4H,5H,6H,7H-pyrazolo[4,3-c]pyridine-3-carboxamide

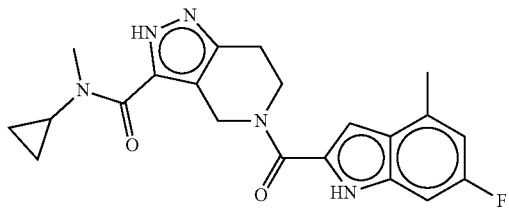

Rt (Method J) 1.24 mins, m/z 396 [M+H]+
No NMR available

Example 328

N-cyclopropyl-5-(4-ethyl-1H-indole-2-carbonyl)-N-methyl-2H,4H,5H,6H,7H-pyrazolo[4,3-c]pyridine-3-carboxamide

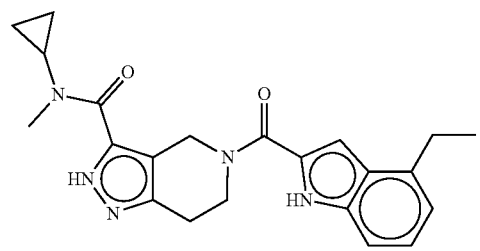

Rt (Method J) 1.29 mins, m/z 392 [M+H]+
No NMR available

Example 329

5-(6-chloro-5-fluoro-1H-indole-2-carbonyl)-N-cyclopropyl-N-methyl-2H,4H,5H,6H,7H-pyrazolo[4,3-c]pyridine-3-carboxamide

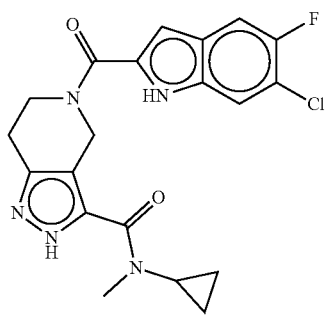

Rt (Method J) 1.29 mins, m/z 416/418 [M+H]+
No NMR available

Example 330

N-cyclopropyl-5-(4-ethyl-6-fluoro-1H-indole-2-carbonyl)-N-methyl-2H,4H,5H,6H,7H-pyrazolo[4,3-c]pyridine-3-carboxamide

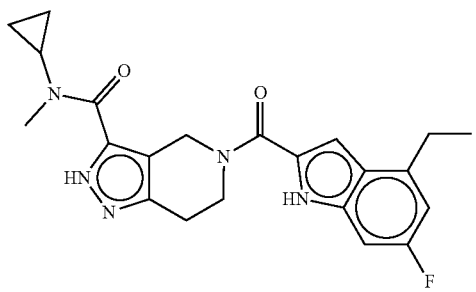

Rt (Method J) 1.33 mins, m/z 410 [M+H]+

1H NMR (400 MHz, DMSO-d6) δ 12.97 (s, 1H), 11.68 (s, 1H), 7.03-6.83 (m, 2H), 6.77 (dd, J=10.8, 2.3 Hz, 1H), 5.16-4.58 (m, 2H), 3.99 (s, 2H), 3.00 (s, 3H), 2.89 (q, J=7.5 Hz, 4H), 1.28 (t, J=7.5 Hz, 3H), 0.66 (d, J=7.1 Hz, 2H), 0.52 (s, 2H).

Example 331

2-(3-{bicyclo[1.1.1]pentan-1-yl}-1H,4H,5H,6H,7H-pyrazolo[4,3-c]pyridine-5-carbonyl)-4-ethyl-1H-indole

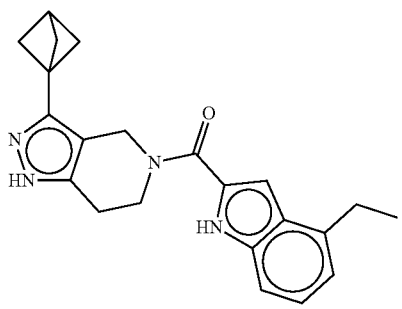

Rt (Method A) 3.38 mins, m/z 361 [M+H]+

1H NMR (400 MHz, DMSO-d6) δ 12.61-12.18 (m, 1H), 11.57 (s, 1H), 7.26 (d, J=8.2 Hz, 1H), 7.15-7.08 (m, 1H), 6.93-6.89 (m, 1H), 6.87 (d, J=7.1 Hz, 1H), 5.20-4.48 (m, 2H), 4.01-3.89 (m, 2H), 2.89 (q, J=7.6 Hz, 2H), 2.83-2.71 (m, 2H), 2.54-2.51 (m, 1H), 2.16-1.99 (m, 6H), 1.29 (t, J=7.5 Hz, 3H).

Example 332

2-(3-{bicyclo[1.1.1]pentan-1-yl}-1H,4H,5H,6H,7H-pyrazolo[4,3-c]pyridine-5-carbonyl)-4,5-difluoro-1H-indole

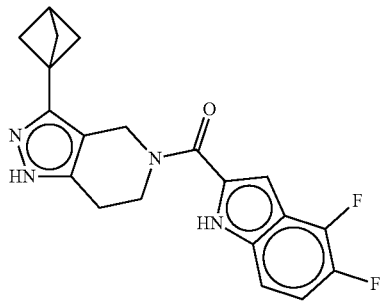

Rt (Method A) 3.26 mins, m/z 369 [M+H]+

1H NMR (400 MHz, DMSO-d6) δ 12.63-12.17 (m, 1H), 12.03 (s, 1H), 7.29-7.19 (m, 2H), 6.96 (s, 1H), 5.08-4.39 (m, 2H), 3.97-3.90 (m, 2H), 2.90-2.70 (m, 2H), 2.55-2.52 (m, 1H), 2.09 (s, 6H).

Example 333

2-(3-{bicyclo[1.1.1]pentan-1-yl}-1H,4H,5H,6H,7H-pyrazolo[4,3-c]pyridine-5-carbonyl)-4,6-difluoro-1H-indole

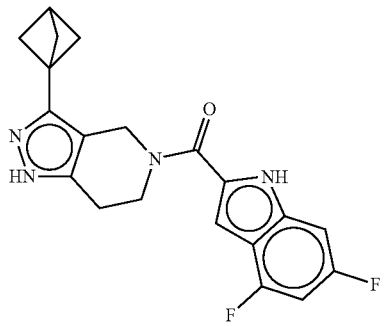

Rt (Method A) 3.29 mins, m/z 369 [M+H]+

1H NMR (400 MHz, DMSO-d6) δ 12.70-12.18 (m, 1H), 12.02 (s, 1H), 7.05 (dd, J=9.6, 2.1 Hz, 1H), 6.96-6.86 (m, 2H), 5.06-4.46 (m, 2H), 4.02-3.87 (m, 2H), 2.88-2.69 (m, 2H), 2.54-2.52 (m, 1H), 2.15-2.01 (m, 6H).

Example 334

2-(3-{bicyclo[1.1.1]pentan-1-yl}-1H,4H,5H,6H,7H-pyrazolo[4,3-c]pyridine-5-carbonyl)-4-ethyl-6-fluoro-1H-indole

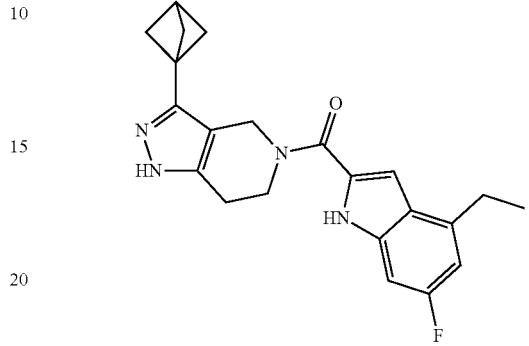

Rt (Method A) 3.43 mins, m/z 379 [M+H]+

1H NMR (400 MHz, DMSO-d6) δ 12.50-12.20 (m, 1H), 11.65 (s, 1H), 6.97 (dd, J=9.8, 2.3 Hz, 1H), 6.95-6.91 (m, 1H), 6.77 (dd, J=10.7, 2.2 Hz, 1H), 5.06-4.49 (m, 2H), 3.99-3.90 (m, 2H), 2.89 (q, J=7.6 Hz, 2H), 2.83-2.70 (m, 2H), 2.53-2.52 (m, 1H), 2.17-2.00 (m, 6H), 1.28 (t, J=7.5 Hz, 3H).

Example 335

2-(3-{bicyclo[1.1.1]pentan-1-yl}-1H,4H,5H,6H,7H-pyrazolo[4,3-c]pyridine-5-carbonyl)-4-chloro-6-fluoro-1H-indole

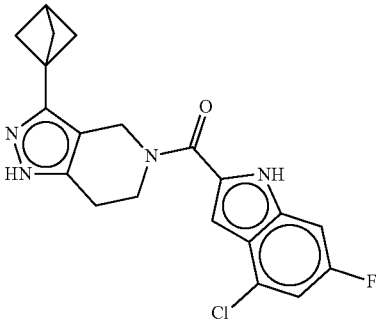

Rt (Method A) 3.43 mins, m/z 385/387 [M+H]+

1H NMR (400 MHz, DMSO-d6) δ 12.56-12.23 (m, 1H), 12.09 (s, 1H), 7.21-7.13 (m, 2H), 6.83 (s, 1H), 5.09-4.41 (m, 2H), 4.00-3.91 (m, 2H), 2.85-2.73 (m, 2H), 2.55-2.52 (m, 1H), 2.17-2.01 (m, 6H).

Example 336

2-(3-{bicyclo[1.1.1]pentan-1-yl}-1H,4H,5H,6H,7H-pyrazolo[4,3-c]pyridine-5-carbonyl)-6-fluoro-4-methyl-1H-indole

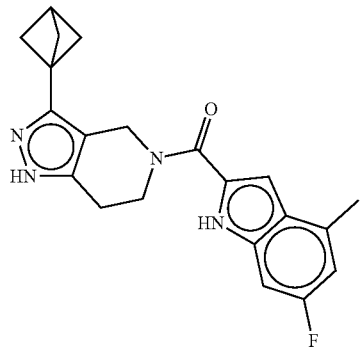

Rt (Method A) 3.31 mins, m/z 365 [M+H]+

1H NMR (400 MHz, DMSO-d6) δ 12.61-12.17 (m, 1H), 11.65 (s, 1H), 7.00-6.93 (m, 1H), 6.90 (s, 1H), 6.79-6.72 (m, 1H), 4.93-4.55 (m, 2H), 4.00-3.92 (m, 2H), 2.82-2.74 (m, 2H), 2.54-2.52 (m, 1H), 2.15-2.04 (m, 6H), one signal (3H) coincides with DMSO signal.

Example 337

4-ethyl-2-[3-(oxolan-2-yl)-1H,4H,5H,6H,7H-pyrazolo[4,3-c]pyridine-5-carbonyl]-1H-indole

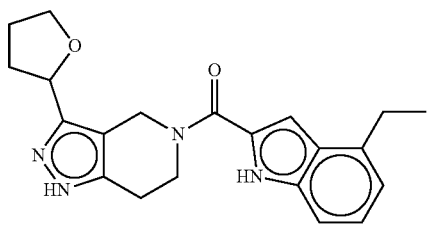

Rt (Method A) 3.1 mins, m/z 365 [M+H]+

1H NMR (400 MHz, DMSO-d6) δ 12.70-12.22 (m, 1H), 11.57 (s, 1H), 7.25 (d, J=8.3 Hz, 1H), 7.15-7.07 (m, 1H), 6.92-6.89 (m, 1H), 6.87 (d, J=7.0 Hz, 1H), 5.12-4.52 (m, 3H), 4.09-3.65 (m, 4H), 2.88 (q, J=7.5 Hz, 2H), 2.84-2.74 (m, 2H), 2.25-2.05 (m, 1H), 2.02-1.77 (m, 3H), 1.28 (t, J=7.5 Hz, 3H).

Example 338

4,5-difluoro-2-[3-(oxolan-2-yl)-1H,4H,5H,6H,7H-pyrazolo[4,3-c]pyridine-5-carbonyl]-1H-indole

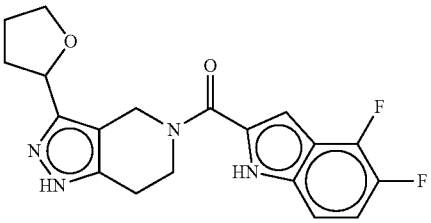

Rt (Method A) 2.99 mins, m/z 373 [M+H]+

1H NMR (400 MHz, DMSO-d6) δ 12.63-12.33 (m, 1H), 12.04 (s, 1H), 7.29-7.18 (m, 2H), 6.97 (s, 1H), 5.12-4.45 (m, 3H), 4.10-3.57 (m, 4H), 2.97-2.70 (m, 2H), 2.26-2.05 (m, 1H), 2.05-1.81 (m, 3H).

Example 339

4,6-difluoro-2-[3-(oxolan-2-yl)-1H,4H,5H,6H,7H-pyrazolo[4,3-c]pyridine-5-carbonyl]-1H-indole

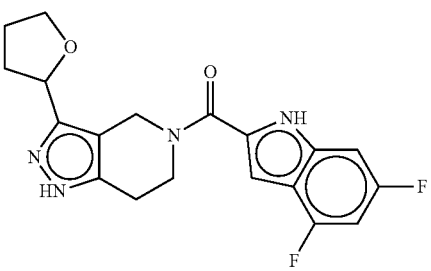

Rt (Method A) 3.01 mins, m/z 373 [M+H]+

1H NMR (400 MHz, DMSO-d6) δ 12.61-12.29 (m, 1H), 12.04 (s, 1H), 7.04 (dd, J=9.4, 2.1 Hz, 1H), 6.95-6.87 (m, 2H), 5.06-4.37 (m, 3H), 4.09-3.63 (m, 4H), 2.98-2.74 (m, 2H), 2.27-2.05 (m, 1H), 2.05-1.81 (m, 3H).

Example 340

4-ethyl-6-fluoro-2-[3-(oxolan-2-yl)-1H,4H,5H,6H,7H-pyrazolo[4,3-c]pyridine-5-carbonyl]-1H-indole

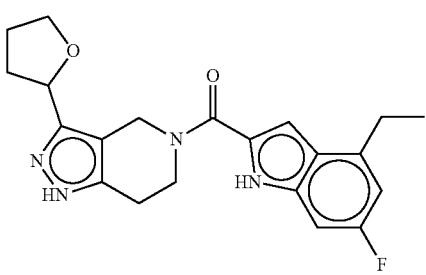

Rt (Method A) 3.16 mins, m/z 383 [M+H]+

1H NMR (400 MHz, DMSO-d6) δ 12.73-12.22 (m, 1H), 11.65 (s, 1H), 6.97 (dd, J=9.6, 2.3 Hz, 1H), 6.94 (d, J=2.2 Hz, 1H), 6.77 (dd, J=10.6, 2.3 Hz, 1H), 5.06-4.55 (m, 3H), 4.08-3.67 (m, 4H), 2.98-2.71 (m, 4H), 2.27-2.03 (m, 1H), 1.99-1.81 (m, 3H), 1.28 (t, J=7.5 Hz, 3H).

Example 341

4-chloro-6-fluoro-2-[3-(oxolan-2-yl)-1H,4H,5H,6H,7H-pyrazolo[4,3-c]pyridine-5-carbonyl]-1H-indole

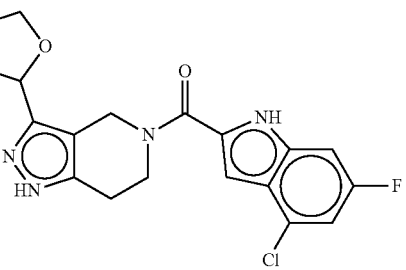

Rt (Method A) 3.13 mins, m/z 389/391 [M+H]+

1H NMR (400 MHz, DMSO-d6) δ 12.64-12.30 (m, 1H), 12.08 (s, 1H), 7.21-7.14 (m, 2H), 6.86 (s, 1H), 5.05-4.50 (m, 3H), 4.08-3.67 (m, 4H), 2.93-2.72 (m, 2H), 2.29-2.05 (m, 1H), 2.03-1.77 (m, 3H).

Example 342

6-fluoro-4-methyl-2-[3-(oxolan-2-yl)-1H,4H,5H,6H,7H-pyrazolo[4,3-c]pyridine-5-carbonyl]-1H-indole

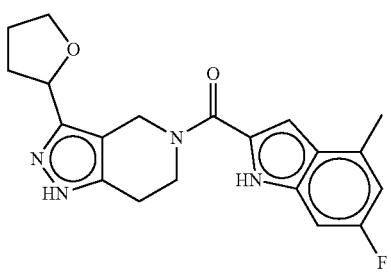

Rt (Method A) 3.03 mins, m/z 369 [M+H]+

1H NMR (400 MHz, DMSO-d6) δ 12.70-12.27 (m, 1H), 11.65 (s, 1H), 6.96 (dd, J=10.0, 2.3 Hz, 1H), 6.91 (d, J=2.3 Hz, 1H), 6.75 (dd, J=10.5, 2.3 Hz, 1H), 5.00-4.46 (m, 3H), 4.12-3.62 (m, 4H), 2.85-2.77 (m, 2H), 2.25-2.06 (m, 1H), 2.02-1.84 (m, 3H), one signal (3H) coincides with DMSO signal.

Example 343

2-(3-{bicyclo[1.1.1]pentan-1-yl}-1H,4H,5H,6H,7H-pyrazolo[4,3-c]pyridine-5-carbonyl)-1H-indole

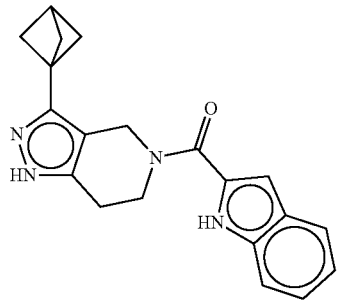

Rt (Method A) 3.13 mins, m/z 333 [M+H]+

1H NMR (400 MHz, DMSO-d6) δ 12.61-12.20 (m, 1H), 11.59 (s, 1H), 7.64 (d, J=8.1 Hz, 1H), 7.43 (d, J=8.3 Hz, 1H), 7.23-7.16 (m, 1H), 7.09-7.02 (m, 1H), 6.90-6.85 (m, 1H), 5.13-4.29 (m, 2H), 3.99-3.91 (m, 2H), 2.87-2.69 (m, 2H), 2.55-2.51 (m, 1H), 2.20-1.97 (m, 6H).

Example 344

2-[3-(oxolan-2-yl)-1H,4H,5H,6H,7H-pyrazolo[4,3-c]pyridine-5-carbonyl]-1H-indole

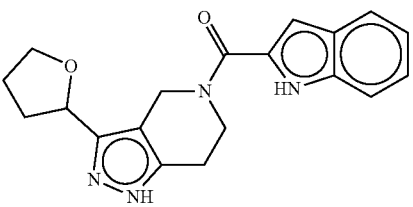

Rt (Method A) 2.83 mins, m/z 337 [M+H]+

1H NMR (400 MHz, DMSO-d6) δ 12.68-12.22 (m, 1H), 11.60 (s, 1H), 7.63 (d, J=7.9 Hz, 1H), 7.43 (d, J=8.2 Hz, 1H), 7.23-7.16 (m, 1H), 7.10-7.02 (m, 1H), 6.90-6.85 (m, 1H), 5.01-4.51 (m, 3H), 4.10-3.66 (m, 4H), 2.91-2.73 (m, 2H), 2.23-2.05 (m, 1H), 2.04-1.80 (m, 3H).

Example 345

5-(1H-indole-2-carbonyl)-N-[1-(methanesulfonylmethyl)cyclopropyl]-N-methyl-1H,4H,5H,6H,7H-pyrazolo[4,3-c]pyridine-3-carboxamide

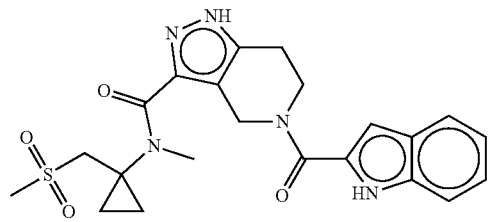

Rt (Method A) 1.08 mins, m/z 456 [M+H]+

1H NMR (400 MHz, DMSO-d6) δ 13.05 (s, 1H), 11.61 (s, 1H), 7.64 (d, J=7.9 Hz, 1H), 7.43 (d, J=8.2 Hz, 1H), 7.19 (ddd, J=8.1, 6.8, 1.2 Hz, 1H), 7.06 (t, J=7.5 Hz, 1H), 6.88 (s, 1H), 5.20-4.66 (m, 2H), 4.14-3.84 (m, 2H), 3.51 (s, 1H), 3.17 (s, 1H), 3.01 (s, 4H), 2.88 (s, 2H), 1.04 (d, J=24.1 Hz, 3H), 0.75 (d, J=37.5 Hz, 1H).

Example 346

5-(1H-indole-2-carbonyl)-N-methyl-N-{1-[(methylsulfanyl)methyl]cyclopropyl}-1H,4H,5H,6H,7H-pyrazolo[4,3-c]pyridine-3-carboxamide

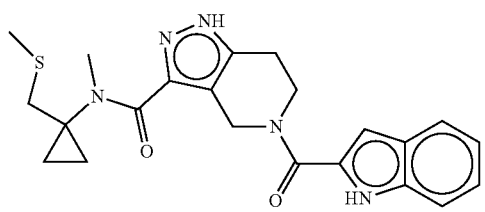

Rt (Method A) 1.33 mins, m/z 424 [M+H]+

1H NMR (400 MHz, DMSO-d6) δ 13.01 (s, 1H), 11.62 (s, 1H), 7.64 (d, J=8.0 Hz, 1H), 7.42 (d, J=8.3 Hz, 1H), 7.19 (dd, J=8.3, 6.7 Hz, 1H), 7.06 (t, J=7.4 Hz, 1H), 6.87 (s, 1H), 5.25-4.52 (m, 2H), 3.97 (s, 2H), 3.63 (s, 1H), 3.03 (s, 2H), 2.88 (s, 3H), 2.09 (d, J=9.7 Hz, 3H), 0.82 (d, J=33.5 Hz, 4H).

Example 347

2-(3-{7,7-difluoro-4-azaspiro[2.5]octane-4-carbonyl}-1H,4H,5H,6H,7H-pyrazolo[4,3-c]pyridine-5-carbonyl)-1H-indole

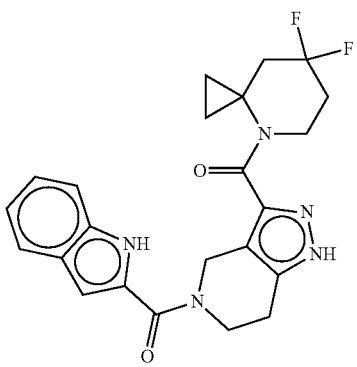

Rt (Method B) 3.14 mins, m/z 440 [M+H]+

1H NMR (400 MHz, DMSO-d6) δ 11.61 (s, 1H), 7.65-7.59 (m, 2H), 7.42 (d, J=8.3 Hz, 1H), 7.19 (t, J=7.6 Hz, 1H), 7.05 (t, J=7.4 Hz, 1H), 6.91-6.86 (m, 1H), 5.09-4.30 (m, 2H), 4.12-3.93 (m, 2H), 3.60 (s, 2H), 3.27 (s, 3H), 2.70-2.61 (m, 2H), 2.22-2.11 (m, 2H), 2.11-1.98 (m, 2H), 1.92-1.65 (m, 2H).

Example 348

5-(1H-indole-2-carbonyl)-N-methyl-N-[1-(5-methyl-1,3,4-oxadiazol-2-yl)cyclopropyl]-1H,4H,5H,6H,7H-pyrazolo[4,3-c]pyridine-3-carboxamide

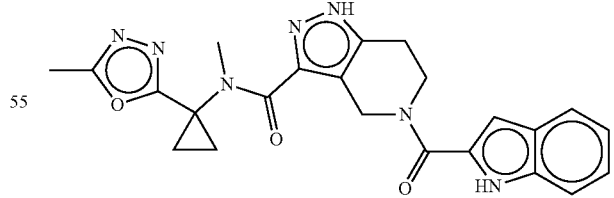

Rt (Method B) 2.76 mins, m/z 446 [M+H]+

1H NMR (400 MHz, DMSO-d6) δ 13.08 (d, J=81.8 Hz, 1H), 11.62 (s, 1H), 7.64 (d, J=7.9 Hz, 1H), 7.42 (d, J=8.2 Hz, 1H), 7.19 (m, J=8.2, 6.9 Hz, 1H), 7.06 (t, J=7.5 Hz, 1H), 6.87 (s, 1H), 4.88 (m, 2H), 3.99 (s, 2H), 3.51 (s, 1.5H), 3.11 (s, 1.5H), 2.86 (s, 2H), 2.43 (s, 3H), 1.83-1.17 (m, 4H).

Example 349

N-(cyclopropylmethyl)-5-(1H-indole-2-carbonyl)-N-methyl-1H,4H,5H,6H,7H-pyrazolo[4,3-c]pyridine-3-carboxamide

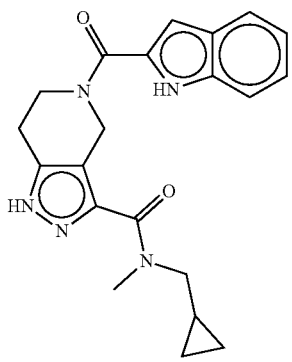

Rt (Method B) 2.966 mins, m/z 378 [M+H]+
No NMR available

Example 350

5-(1H-indole-2-carbonyl)-N-methyl-N-(2-phenylethyl)-1H,4H,5H,6H,7H-pyrazolo[4,3-c]pyridine-3-carboxamide

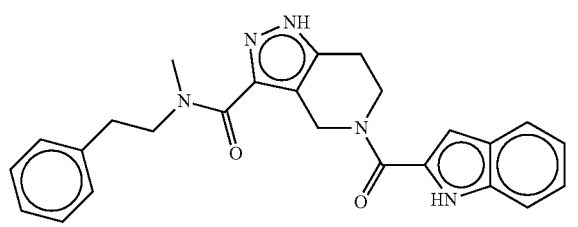

Rt (Method B) 3.128 mins, m/z 428 [M+H]+
1H NMR (400 MHz, DMSO-d6) δ 13.04 (s, 1H), 11.63 (s, 1H), 7.65 (d, J=8.0 Hz, 1H), 7.43 (d, J=8.3 Hz, 1H), 7.32-6.99 (m, 7H), 6.87 (s, 1H), 5.05-4.55 (m, 2H), 4.13-3.88 (m, 3H), 3.67-3.56 (m, 1H), 3.31-3.25 (m, 2H), 3.01-2.78 (m, 5H).

Example 351

5-(1H-indole-2-carbonyl)-N-methyl-N-[(5-methyl-furan-2-yl)methyl]-1H,4H,5H,6H,7H-pyrazolo[4,3-c]pyridine-3-carboxamide

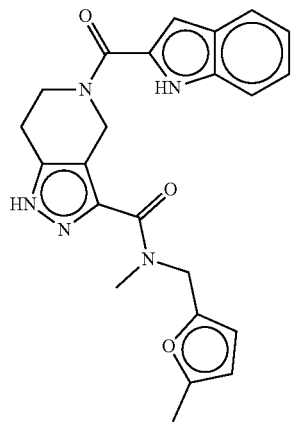

Rt (Method B) 3.121 mins, m/z 418 [M+H]+
No NMR available

Example 352

5-(1H-indole-2-carbonyl)-N-methyl-N-[(1-methyl-1H-pyrazol-5-yl)methyl]-1H,4H,5H,6H,7H-pyrazolo[4,3-c]pyridine-3-carboxamide

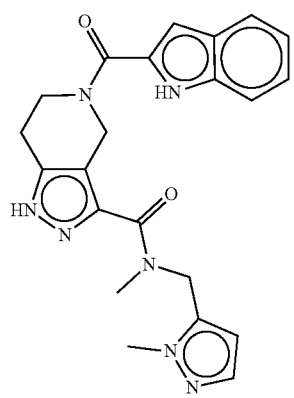

Rt (Method B) 2.744 mins, m/z 418 [M+H]+
No NMR available

Example 353

5-(1H-indole-2-carbonyl)-N-methyl-N-[(pyrazin-2-yl)methyl]-1H,4H,5H,6H,7H-pyrazolo[4,3-c]pyridine-3-carboxamide

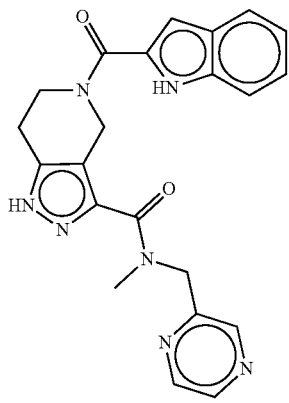

Rt (Method B) 2.692 mins, m/z 416 [M+H]+
No NMR available

Example 354

5-(1H-indole-2-carbonyl)-N-methyl-N-[(pyridin-4-yl)methyl]-1H,4H,5H,6H,7H-pyrazolo[4,3-c]pyridine-3-carboxamide

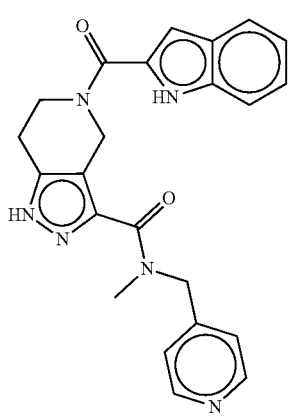

Rt (Method B) 2.228 mins, m/z 415 [M+H]+
1H NMR (400 MHz, DMSO-d6) δ 13.10 (s, 1H), 11.63 (s, 1H), 8.49 (d, J=4.6 Hz, 2H), 7.64 (d, J=7.4 Hz, 1H), 7.43 (d, J=8.3 Hz, 1H), 7.28-7.16 (m, 3H), 7.06 (t, J=7.4 Hz, 1H), 6.89 (s, 1H), 5.23 (s, 1H), 5.15-4.74 (m, 2H), 4.68 (s, 1H), 4.04-3.92 (m, 2H), 3.42-3.34 (m, 2H), 2.89 (s, 3H).

Example 355

5-(1H-indole-2-carbonyl)-N-methyl-N-[(pyridin-3-yl)methyl]-1H,4H,5H,6H,7H-pyrazolo[4,3-c]pyridine-3-carboxamide

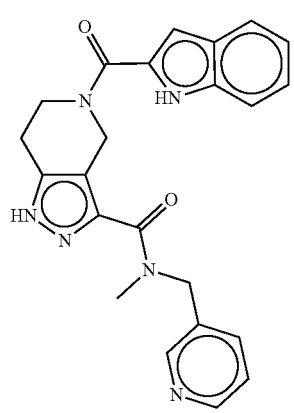

Rt (Method B) 2.294 mins, m/z 415 [M+H]+
No NMR available

Example 356

5-(1H-indole-2-carbonyl)-N-methyl-N-[(pyridin-2-yl)methyl]-1H,4H,5H,6H,7H-pyrazolo[4,3-c]pyridine-3-carboxamide

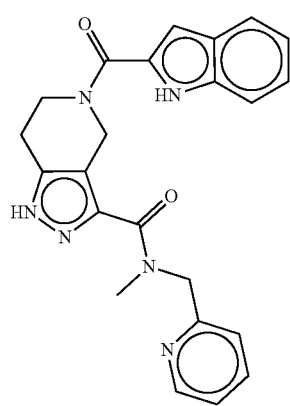

Rt (Method B) 2.47 mins, m/z 415 [M+H]+
No NMR available

Example 357 ammonium 3-[5-(1H-indole-2-carbonyl)-1H,4H,5H,6H,7H-pyrazolo[4,3-c]pyridin-3-yl]bicyclo[1.1.1]pentane-1-carboxylate

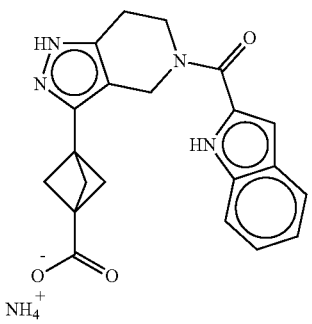

Rt (Method A) 2.28 mins, m/z 377 [M+H]+

1H NMR (400 MHz, DMSO-d6) δ 11.60 (s, 1H), 7.65 (d, J=7.9 Hz, 1H), 7.43 (d, J=8.3 Hz, 1H), 7.23-7.15 (m, 1H), 7.09-7.01 (m, 1H), 6.89 (s, 1H), 4.98-4.57 (m, 2H), 4.01-3.90 (m, 2H), 2.85-2.72 (m, 2H), 2.16 (s, 6H) (two signals (5H) coincides with water signal).

Example 358 methyl 3-[5-(1H-indole-2-carbonyl)-1H,4H,5H,6H,7H-pyrazolo[4,3-c]pyridin-3-yl]bicyclo[1.1.1]pentane-1-carboxylate

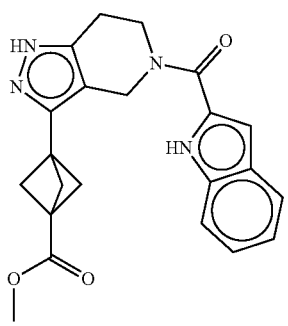

Rt (Method A) 2.99 mins, m/z 391 [M+H]+

1H NMR (400 MHz, DMSO-d6) δ 12.81-12.27 (m, 1H), 11.60 (s, 1H), 7.65 (d, J=8.0 Hz, 1H), 7.43 (d, J=8.2 Hz, 1H), 7.24-7.16 (m, 1H), 7.10-7.02 (m, 1H), 6.90 (s, 1H), 5.06-4.48 (m, 2H), 4.10-3.86 (m, 2H), 3.63 (s, 3H), 2.94-2.71 (m, 2H), 2.30 (s, 6H).

Example 359

5-(1H-indole-2-carbonyl)-N-methyl-N-{1-[(2,2,2-trifluoroethoxy)methyl]cyclopropyl}-1H,4H,5H,6H,7H-pyrazolo[4,3-c]pyridine-3-carboxamide

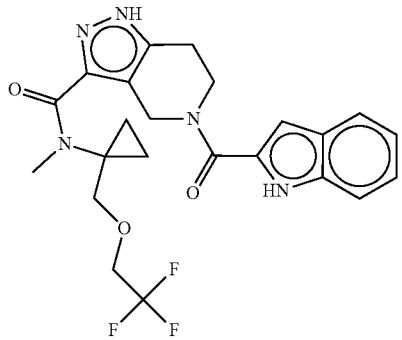

Rt (Method A) 1.4 mins, m/z 476 [M+H]+

1H NMR (400 MHz, DMSO-d6) δ 13.00 (s, 1H), 11.62 (s, 1H), 7.64 (d, J=8.0 Hz, 1H), 7.42 (d, J=8.3 Hz, 1H), 7.19 (t, J=7.6 Hz, 1H), 7.06 (t, J=7.4 Hz, 1H), 6.87 (s, 1H), 5.09-4.55 (m, 2H), 4.10 (t, J=9.4 Hz, 2H), 4.06-3.88 (m, 2H), 3.74 (s, 1H), 2.94 (d, J=48.7 Hz, 3H), 1.07-0.36 (m, 4H) (N-methyl peak not observed).

Example 360

N-{1-[(2,2-difluoroethoxy)methyl]cyclopropyl}-5-(1H-indole-2-carbonyl)-N-methyl-1H,4H,5H,6H,7H-pyrazolo[4,3-c]pyridine-3-carboxamide

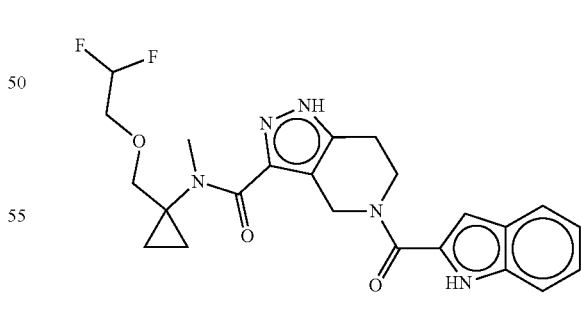

Rt (Method A) 1.31 mins, m/z 458 [M+H]+

1H NMR (400 MHz, DMSO-d6) δ 12.97 (s, 1H), 11.62 (s, 1H), 7.64 (d, J=7.9 Hz, 1H), 7.42 (d, J=8.1 Hz, 1H), 7.19 (t, J=7.6 Hz, 1H), 7.06 (t, J=7.5 Hz, 1H), 6.87 (s, 1H), 6.12 (t, J=53.8 Hz, 1H), 5.04-4.60 (m, 2H), 4.10-3.87 (m, 2H), 3.71 (t, J=15.5 Hz, 3H), 2.94 (d, J=49.8 Hz, 3H), 1.01-0.46 (m, 4H) (N-methyl peak not observed).

Example 361

N-[1-(cyanomethyl)cyclopropyl]-5-(1H-indole-2-carbonyl)-N-methyl-1H,4H,5H,6H,7H-pyrazolo[4,3-c]pyridine-3-carboxamide

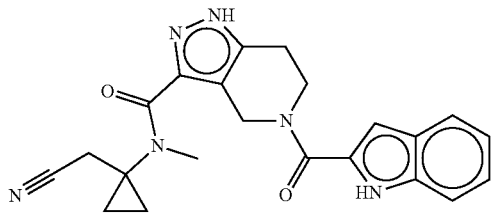

Rt (Method A) 1.2 mins, m/z 403 [M+H]+

1H NMR (400 MHz, DMSO-d6) δ 13.08 (s, 1H), 11.62 (s, 1H), 7.64 (d, J=7.9 Hz, 1H), 7.42 (d, J=8.1 Hz, 1H), 7.19 (ddd, J=8.1, 6.9, 1.2 Hz, 1H), 7.06 (t, J=7.5 Hz, 1H), 6.87 (s, 1H), 4.82 (s, 2H), 4.24-3.57 (m, 3H), 3.19-2.74 (m, 6H), 1.10-0.59 (m, 4H).

Example 362

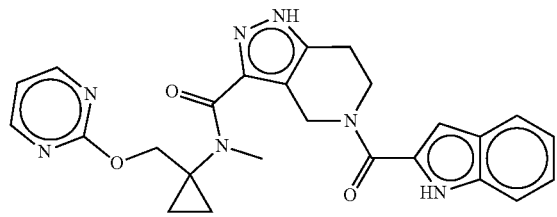

Rt (Method B) 2.88 mins, m/z 472 [M+H]+

1H NMR (400 MHz, DMSO-d6) δ 13.00 (s, 1H), 11.62 (s, 1H), 8.57 (m, 2H), 7.64 (d, J=7.9 Hz, 1H), 7.42 (d, J=8.3 Hz, 1H), 7.19 (t, J=7.6 Hz, 1H), 7.07 (m, 2H), 6.87 (s, 1H), 5.49-4.66 (m, 4H), 3.97 (m, 3H), 3.05 (m, 2H), 2.88 (m, 2H), 0.85 (m, 4H).

Example 363

5-(4,6-difluoro-1H-indole-2-carbonyl)-N-[1-(ethoxymethyl)cyclopropyl]-N-methyl-2H,4H,5H,6H,7H-pyrazolo[4,3-c]pyridine-3-carboxamide

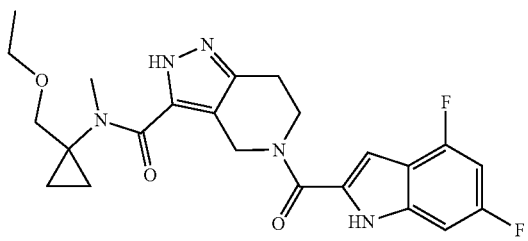 [SMILES: CCOCC1(N(C)C(=O)c2[nH]nc3c2CN(C(=O)c2cc4c(F)cc(F)cc4[nH]2)CC3)CC1]

Rt (Method A) 3.28 mins, m/z 458 [M+H]+

1H NMR (400 MHz, DMSO-d6) δ 12.93 (s, 1H), 12.09 (s, 1H), 7.04 (m, 1H), 6.90 (m, 2H), 4.76 (m, 2H), 3.97 (m, 2H), 3.45 (m, 3H), 2.94 (m, 4H), 1.10 (m, 3H), 0.81 (m, 4H).

Example 364

5-(4-chloro-5-fluoro-1H-indole-2-carbonyl)-N-[1-(ethoxymethyl)cyclopropyl]-N-methyl-2H,4H,5H,6H,7H-pyrazolo[4,3-c]pyridine-3-carboxamide

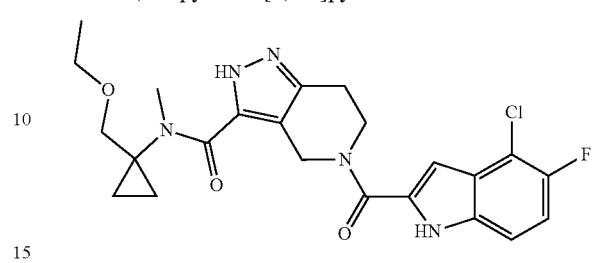

Rt (Method A) 3.35 mins, m/z 474/476 [M+H]+

1H NMR (400 MHz, DMSO-d6) δ 12.96 (s, 1H), 12.12 (s, 1H), 7.41 (m, 1H), 7.28-7.15 (m, 1H), 6.86 (s, 1H), 4.77 m, 2H), 3.97 (m, 2H), 3.45 (m, 3H), 2.93 (m, 4H), 1.10 (m, 3H), 0.78 (m, 4H).

Example 365

5-(4-chloro-6-fluoro-1H-indole-2-carbonyl)-N-[1-(ethoxymethyl)cyclopropyl]-N-methyl-2H,4H,5H,6H,7H-pyrazolo[4,3-c]pyridine-3-carboxamide

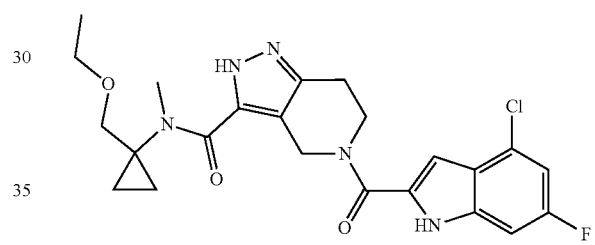

Rt (Method A) 3.4 mins, m/z 474/476 [M+H]+

1H NMR (400 MHz, DMSO-d6) δ 12.94 (s, 1H), 12.14 (s, 1H), 7.16 (m, 2H), 6.84 (s, 1H), 4.80 (m, 2H), 3.97 (m, 2H), 3.45 (m, 5H), 2.94 (m, 4H), 1.10 (m, 3H), 0.79 (m, 4H).

Example 366

N-[1-(ethoxymethyl)cyclopropyl]-5-(6-fluoro-4-methyl-1H-indole-2-carbonyl)-N-methyl-2H,4H,5H,6H,7H-pyrazolo[4,3-c]pyridine-3-carboxamide

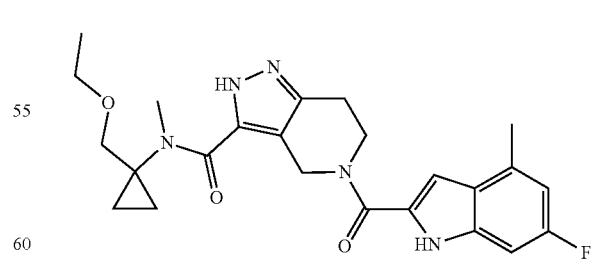

Rt (Method A) 3.29 mins, m/z 454 [M+H]+

1H NMR (400 MHz, DMSO-d6) δ 12.83 (s, 1H), 11.69 (s, 1H), 6.96 (m, 1H), 6.90 (s, 1H), 6.74 (m, 1H), 4.80 (m, 2H), 3.98 (m, 2H), 3.49 (m, 5H), 2.94 (m, 4H), 1.10 (m, 3H), 0.81 (m, 4H).

Example 367

N-[1-(ethoxymethyl)cyclopropyl]-5-(7-fluoro-1H-indole-2-carbonyl)-N-methyl-2H,4H,5H,6H,7H-pyrazolo[4,3-c]pyridine-3-carboxamide

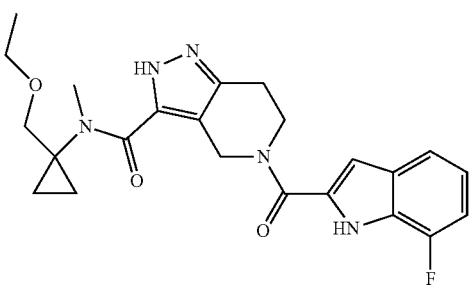 [SMILES: CCOCC1(N(C)C(=O)c2[nH]nc3c2CN(C(=O)c2cc4cccc(F)c4[nH]2)CC3)CC1]

Rt (Method A) 3.18 mins, m/z 440 [M+H]+ 1H NMR (400 MHz, DMSO-d6) δ 12.97 (s, 1H), 12.06 (s, 1H), 7.44 (m, 1H), 7.00 (m, 2H), 6.90 (m, 1H), 4.73 (m, 2H), 3.93 (m, 2H), 3.45 (m, 3H), 2.99 (m, 2H), 2.86 (m, 2H), 1.10 (m, 3H), 0.79 (m, 4H).

Example 368

5-(1H-indole-2-carbonyl)-N-methyl-N-[1-(1,3-oxazol-4-yl)cyclopropyl]-2H,4H,5H,6H,7H-pyrazolo[4,3-c]pyridine-3-carboxamide

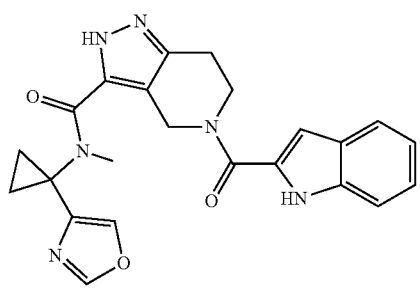 [SMILES: CN(C(=O)c1[nH]nc2c1CN(C(=O)c1cc3ccccc3[nH]1)CC2)C1(c2cocn2)CC1]

Rt (Method B) 2.88 mins, m/z 431 [M+H]+
1H NMR (400 MHz, DMSO-d6) δ 12.99 (s, 1H), 11.62 (s, 1H), 8.23 (s, 1H), 7.89 (s, 1H), 7.64 (d, J=7.9 Hz, 1H), 7.42 (d, J=8.3 Hz, 1H), 7.19 (t, J=7.6 Hz, 1H), 7.06 (t, J=7.5 Hz, 1H), 6.87 (s, 1H), 5.26-4.58 (m, 2H), 4.18-3.80 (m, 2H), 3.48-3.38 (m, 2H), 3.15-2.73 (m, 3H), 1.39-1.01 (m, 4H).

Example 369

N-[1-(ethoxymethyl)cyclopropyl]-5-(4-fluoro-1H-indole-2-carbonyl)-N-methyl-2H,4H,5H,6H,7H-pyrazolo[4,3-c]pyridine-3-carboxamide

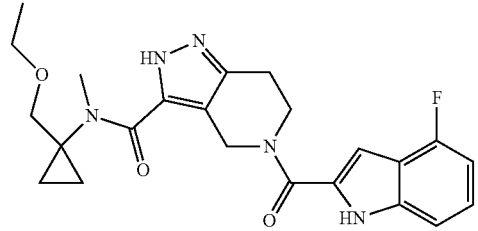 [SMILES: CCOCC1(N(C)C(=O)c2[nH]nc3c2CN(C(=O)c2cc4c(F)cccc4[nH]2)CC3)CC1]

Rt (Method A) 3.2 mins, m/z 440 [M+H]+

1H NMR (400 MHz, DMSO-d6) δ 12.86 (s, 1H), 12.16 (s, 1H), 7.27 (d, J=8.2 Hz, 1H), 7.17 (m, 1H), 6.96-6.79 (m, 2H), 4.94 (m, 2H), 3.97 (m, 2H), 3.39 (m, 5H), 2.94 (m, 4H), 1.11 (m, 3H), 0.95-0.42 (m, 4H).

Example 370

5-(6-chloro-1H-indole-2-carbonyl)-N-[1-(ethoxymethyl)cyclopropyl]-N-methyl-2H,4H,5H,6H,7H-pyrazolo[4,3-c]pyridine-3-carboxamide

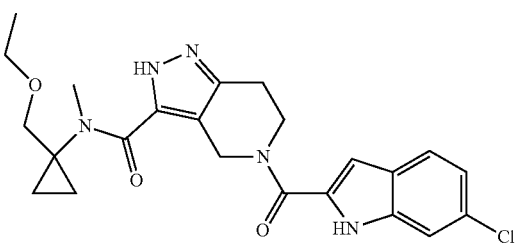 [SMILES: CCOCC1(N(C)C(=O)c2[nH]nc3c2CN(C(=O)c2cc4ccc(Cl)cc4[nH]2)CC3)CC1]

Rt (Method A) 3.33 mins, m/z 456/458 [M+H]+

1H NMR (400 MHz, DMSO-d6) δ 12.41 (m, 2H), 7.67 (d, J=8.5 Hz, 1H), 7.44 (s, 1H), 7.08 (dd, J=8.4, 1.9 Hz, 1H), 6.92 (s, 1H), 4.87 (m, 2H), 3.97 (m, 2H), 3.48 (m, 5H), 2.94 (m, 4H), 1.10 (m, 3H), 0.93-0.47 (m, 4H).

Example 371

5-(4-chloro-1H-indole-2-carbonyl)-N-[1-(ethoxymethyl)cyclopropyl]-N-methyl-2H,4H,5H,6H,7H-pyrazolo[4,3-c]pyridine-3-carboxamide

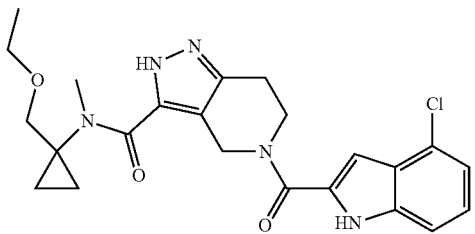 [SMILES: CCOCC1(N(C)C(=O)c2[nH]nc3c2CN(C(=O)c2cc4c(Cl)cccc4[nH]2)CC3)CC1]

Rt (Method A) 3.32 mins, m/z 456/458 [M+H]+

1H NMR (400 MHz, DMSO-d6) δ 12.90 (s, 1H), 12.14 (s, 1H), 7.41 (d, J=7.9 Hz, 1H), 7.24-7.10 (m, 2H), 6.83 (s, 1H), 4.84 (m, 2H), 3.98 (m, 2H), 3.44 (m, 5H), 2.94 (m, 4H), 1.11 (m, 3H), 0.81 (m, 4H).

Example 373

5-(6-chloro-5-fluoro-1H-indole-2-carbonyl)-N-[1-(ethoxymethyl)cyclopropyl]-N-methyl-2H,4H,5H,6H,7H-pyrazolo[4,3-c]pyridine-3-carboxamide

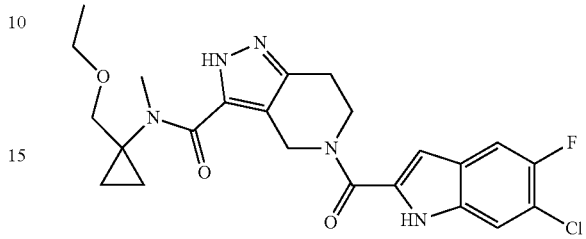

Rt (Method A) 3.17 mins, m/z 474/476 [M+H]+

1H NMR (400 MHz, DMSO-d6) δ 12.86 (s, 1H), 12.03 (s, 1H), 7.65 (d, J=10.0 Hz, 1H), 7.54 (d, J=6.4 Hz, 1H), 6.90 (s, 1H), 4.84 (m, 2H), 3.96 (m, 2H), 3.74-3.37 (m, 5H), 2.94 (m, 4H), 1.11 (m, 3H), 0.93-0.39 (m, 4H).

Example 372

N-[1-(ethoxymethyl)cyclopropyl]-5-(4-ethyl-1H-indole-2-carbonyl)-N-methyl-2H,4H,5H,6H,7H-pyrazolo[4,3-c]pyridine-3-carboxamide

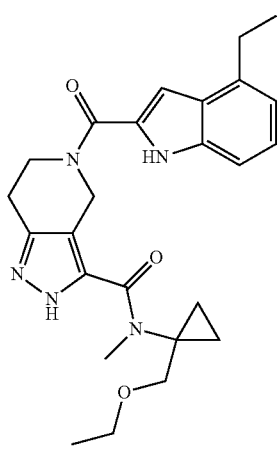 [SMILES: CCOCC1(N(C)C(=O)c2[nH]nc3c2CN(C(=O)c2cc4c(CC)cccc4[nH]2)CC3)CC1]

Rt (Method A) 3.36 mins, m/z 450 [M+H]+

1H NMR (400 MHz, DMSO-d6) δ 12.95 (s, 1H), 11.59 (s, 1H), 7.25 (d, J=8.2 Hz, 1H), 7.11 (t, J=7.6 Hz, 1H), 6.95-6.83 (m, 2H), 4.83 (m, 2H), 3.98 (m, 2H), 3.44 (m, 5H), 3.13-2.71 (m, 6H), 1.28 (t, J=7.5 Hz, 3H), 1.19-0.97 (m, 3H), 0.79 (m, 4H).

Example 374

N-[1-(ethoxymethyl)cyclopropyl]-5-(4-ethyl-6-fluoro-1H-indole-2-carbonyl)-N-methyl-2H,4H,5H,6H,7H-pyrazolo[4,3-c]pyridine-3-carboxamide

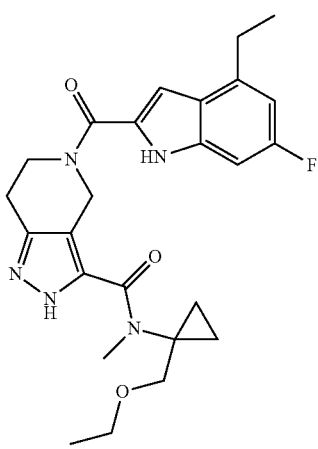 [SMILES: CCOCC1(N(C)C(=O)c2[nH]nc3c2CN(C(=O)c2cc4c(CC)cc(F)cc4[nH]2)CC3)CC1]

Rt (Method A) 3.42 mins, m/z 468 [M+H]+

1H NMR (400 MHz, DMSO-d6) δ 12.80 (s, 1H), 11.75 (s, 1H), 7.02-6.85 (m, 2H), 6.77 (m, 1H), 4.81 (m, 2H), 3.98 (m, 2H), 3.48 (m, 5H), 3.10-2.71 (m, 6H), 1.28 (t, J=7.5 Hz, 3H), 1.08 (m, 3H), 0.79 (m, 4H).

Example 375

N-[1-(ethoxymethyl)cyclopropyl]-5-(5-fluoro-1H-indole-2-carbonyl)-N-methyl-2H,4H,5H,6H,7H-pyrazolo[4,3-c]pyridine-3-carboxamide

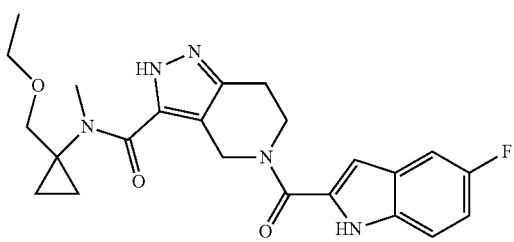 [SMILES: CCOCC1(N(C)C(=O)c2[nH]nc3c2CN(C(=O)c2cc4cc(F)ccc4[nH]2)CC3)CC1]

Rt (Method A) 3.17 mins, m/z 440 [M+H]+
1H NMR (400 MHz, DMSO-d6) δ 12.90 (s, 1H), 11.80 (s, 1H), 7.41 (m, 2H), 7.06 (m, 1H), 6.86 (s, 1H), 4.76 (m, 2H), 3.96 (m, 2H), 3.48 (m, 5H), 3.11-2.64 (m, 4H), 1.10 (m, 3H), 0.78 (m, 4H).

Example 376

5-(4-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

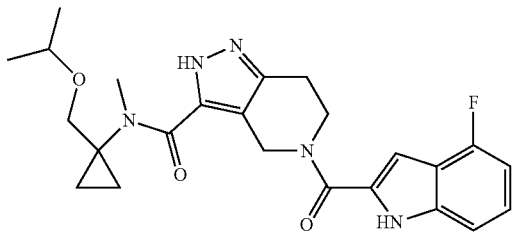 [SMILES: CC(C)OCC1(N(C)C(=O)c2[nH]nc3c2CN(C(=O)c2cc4c(F)cccc4[nH]2)CC3)CC1]

Rt (Method A) 3.31 mins, m/z 454 [M+H]+
1H NMR (400 MHz, DMSO-d6) δ 12.10 (s, 1H), 7.27 (d, J=8.3 Hz, 1H), 7.18 (m, 1H), 6.94-6.76 (m, 2H), 4.76 (m, 2H), 3.97 (m, 2H), 3.63 (m, 4H), 2.94 (m, 4H), 1.05 (m, 6H), 0.78 (m, 4H).

Example 377

2-{3-cyclobutyl-2H,4H,5H,6H,7H-pyrazolo[4,3-c]pyridine-5-carbonyl}-4-(difluoromethyl)-1H-indole

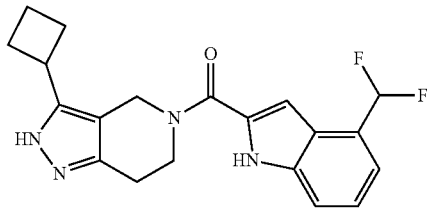 [SMILES: O=C(c1cc2c(C(F)F)cccc2[nH]1)N1CCc2n[nH]c(C3CCC3)c2C1]

Rt (Method A) 3.17 mins, m/z 371 [M+H]+ No NMR available

Example 378

2-{3-cyclobutyl-2H,4H,5H,6H,7H-pyrazolo[4,3-c]pyridine-5-carbonyl}-4-ethyl-6-fluoro-1H-indole

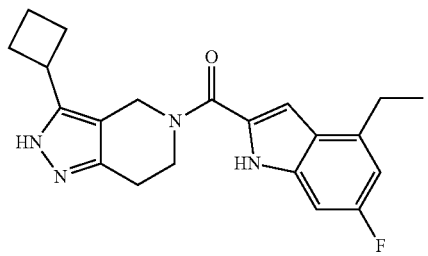 [SMILES: CCc1cc(F)cc2[nH]c(C(=O)N3CCc4n[nH]c(C5CCC5)c4C3)cc12]

Rt (Method A) 3.4 mins, m/z 367 [M+H]+
No NMR available

Example 379

(2-{3-cyclobutyl-2H,4H,5H,6H,7H-pyrazolo[4,3-c]pyridine-5-carbonyl}-1H-indol-4-yl)methanol

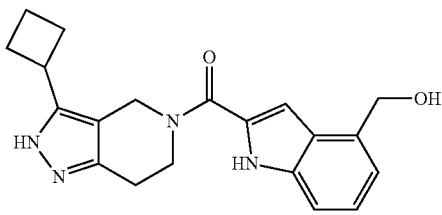 [SMILES: O=C(c1cc2c(CO)cccc2[nH]1)N1CCc2n[nH]c(C3CCC3)c2C1]

Rt (Method A) 2.67 mins, m/z 351 [M+H]+
No NMR available

Example 380

2-{3-cyclobutyl-2H,4H,5H,6H,7H-pyrazolo[4,3-c]pyridine-5-carbonyl}-4-(propan-2-yl)-1H-indole

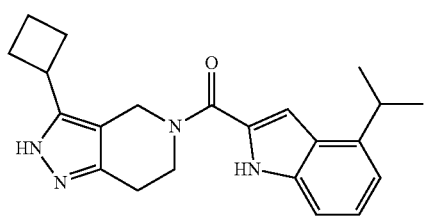 [SMILES: CC(C)c1cccc2[nH]c(C(=O)N3CCc4n[nH]c(C5CCC5)c4C3)cc12]

Rt (Method A) 3.45 mins, m/z 363 [M+H]+
1H NMR (400 MHz, DMSO-d6) δ 12.46-12.09 (m, 1H), 11.57 (s, 1H), 7.25 (d, J=8.2 Hz, 1H), 7.13 (t, J=7.7 Hz, 1H), 6.96-6.89 (m, 2H), 5.09-4.47 (m, 2H), 4.06-3.87 (m, 2H), 3.56-3.42 (m, 1H), 3.41-3.33 (m, 1H), 2.89-2.70 (m, 2H), 2.27-2.13 (m, 4H), 2.00-1.89 (m, 1H), 1.88-1.73 (m, 1H), 1.32 (d, J=6.9 Hz, 6H).

Example 381

2-{3-cyclobutyl-2H,4H,5H,6H,7H-pyrazolo[4,3-c]pyridine-5-carbonyl}-4-ethyl-1H-indole

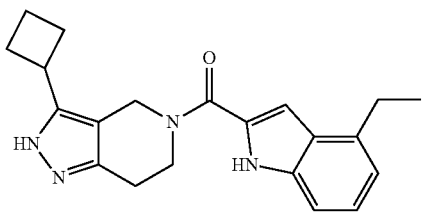 [SMILES: CCc1cccc2[nH]c(C(=O)N3CCc4n[nH]c(C5CCC5)c4C3)cc12]

Rt (Method A) 3.35 mins, m/z 349 [M+H]+
No NMR available

Example 382

2-{3-cyclobutyl-2H,4H,5H,6H,7H-pyrazolo[4,3-c]pyridine-5-carbonyl}-4-methyl-1H-indole

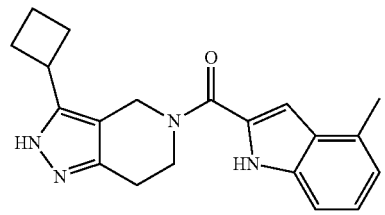 [SMILES: Cc1cccc2[nH]c(C(=O)N3CCc4n[nH]c(C5CCC5)c4C3)cc12]

Rt (Method A) 3.22 mins, m/z 335 [M+H]+
No NMR available

Example 383

4-chloro-2-{3-cyclobutyl-2H,4H,5H,6H,7H-pyrazolo[4,3-c]pyridine-5-carbonyl}-6-fluoro-1H-indole

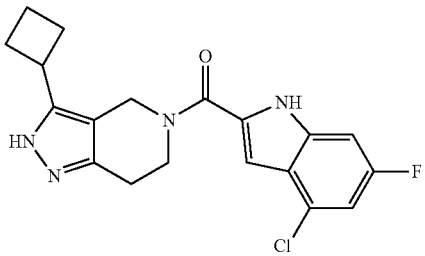 [SMILES: O=C(c1cc2c(Cl)cc(F)cc2[nH]1)N1CCc2n[nH]c(C3CCC3)c2C1]

Rt (Method A) 3.39 mins, m/z 373/375 [M+H]+
No NMR available

Example 384

6-chloro-2-{3-cyclobutyl-2H,4H,5H,6H,7H-pyrazolo[4,3-c]pyridine-5-carbonyl}-7-fluoro-1H-indole

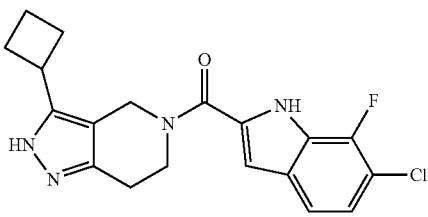 [SMILES: O=C(c1cc2ccc(Cl)c(F)c2[nH]1)N1CCc2n[nH]c(C3CCC3)c2C1]

Rt (Method A) 3.35 mins, m/z 373/375 [M+H]+
No NMR available

Example 385

6-chloro-2-{3-cyclobutyl-2H,4H,5H,6H,7H-pyrazolo[4,3-c]pyridine-5-carbonyl}-5-fluoro-1H-indole

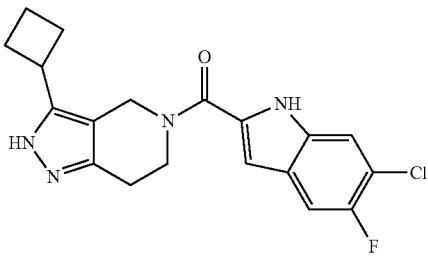 [SMILES: O=C(c1cc2cc(F)c(Cl)cc2[nH]1)N1CCc2n[nH]c(C3CCC3)c2C1]

Rt (Method A) 3.33 mins, m/z 373/375 [M+H]+
No NMR available

Example 386

6-chloro-2-{3-cyclobutyl-2H,4H,5H,6H,7H-pyrazolo[4,3-c]pyridine-5-carbonyl}-1H-indole

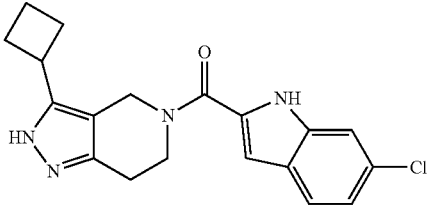 [SMILES: O=C(c1cc2ccc(Cl)cc2[nH]1)N1CCc2n[nH]c(C3CCC3)c2C1]

Rt (Method A) 3.31 mins, m/z 355/357 [M+H]+
No NMR available

Example 387

4-chloro-2-{3-cyclobutyl-2H,4H,5H,6H,7H-pyrazolo[4,3-c]pyridine-5-carbonyl}-1H-indole

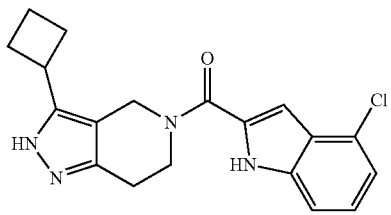 [SMILES: O=C(c1cc2c(Cl)cccc2[nH]1)N1CCc2n[nH]c(C3CCC3)c2C1]

Rt (Method A) 3.29 mins, m/z 355/357 [M+H]+

1H NMR (400 MHz, DMSO-d6) δ 12.50-12.17 (m, 1H), 12.01 (s, 1H), 7.41 (d, J=8.0 Hz, 1H), 7.20 (t, J=7.8 Hz, 1H), 7.14 (d, J=7.4 Hz, 1H), 6.82 (s, 1H), 5.06-4.47 (m, 2H), 4.04-3.86 (m, 2H), 3.59-3.39 (m, 1H), 2.88-2.71 (m, 2H), 2.29-2.10 (m, 4H), 2.01-1.90 (m, 1H), 1.87-1.73 (m, 1H).

Example 388

2-{3-cyclobutyl-2H,4H,5H,6H,7H-pyrazolo[4,3-c]pyridine-5-carbonyl}-4,6-difluoro-1H-indole

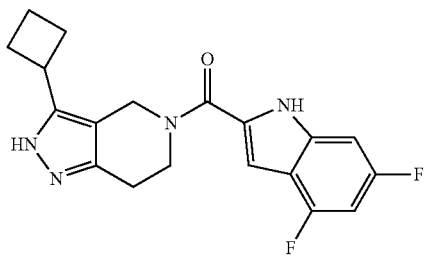 [SMILES: O=C(c1cc2c(F)cc(F)cc2[nH]1)N1CCc2n[nH]c(C3CCC3)c2C1]

Rt (Method A) 3.26 mins, m/z 357 [M+H]+
No NMR available

Example 389

2-{3-cyclobutyl-2H,4H,5H,6H,7H-pyrazolo[4,3-c]pyridine-5-carbonyl}-6,7-difluoro-1H-indole

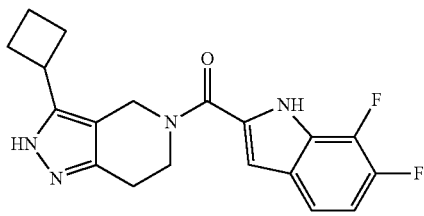 [SMILES: O=C(c1cc2ccc(F)c(F)c2[nH]1)N1CCc2n[nH]c(C3CCC3)c2C1]

Rt (Method A) 3.21 mins, m/z 357 [M+H]+
No NMR available

Example 390

2-{3-cyclobutyl-2H,4H,5H,6H,7H-pyrazolo[4,3-c]pyridine-5-carbonyl}-5,6-difluoro-1H-indole

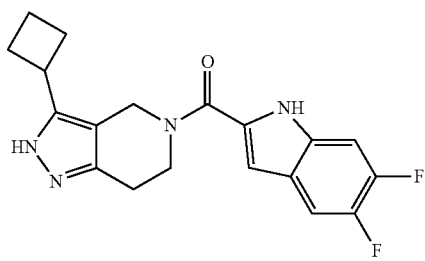 [SMILES: O=C(c1cc2cc(F)c(F)cc2[nH]1)N1CCc2n[nH]c(C3CCC3)c2C1]

Rt (Method A) 3.21 mins, m/z 357 [M+H]+
No NMR available

Example 391

2-{3-cyclobutyl-2H,4H,5H,6H,7H-pyrazolo[4,3-c]pyridine-5-carbonyl}-4,5-difluoro-1H-indole

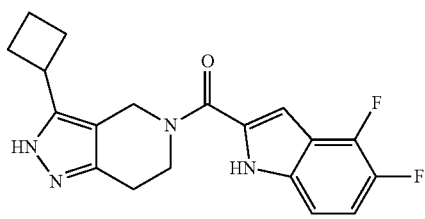

Rt (Method A) 3.23 mins, m/z 357 [M+H]+
No NMR available

Example 392

2-{3-cyclobutyl-2H,4H,5H,6H,7H-pyrazolo[4,3-c]pyridine-5-carbonyl}-7-fluoro-1H-indole

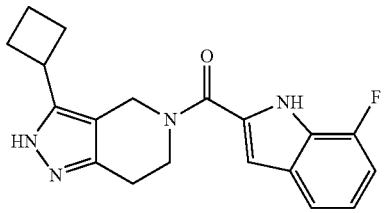 [SMILES: O=C(c1cc2cccc(F)c2[nH]1)N1CCc2n[nH]c(C3CCC3)c2C1]

Rt (Method A) 3.15 mins, m/z 339 [M+H]+
No NMR available

Example 393

2-{3-cyclobutyl-2H,4H,5H,6H,7H-pyrazolo[4,3-c]pyridine-5-carbonyl}-6-fluoro-1H-indole

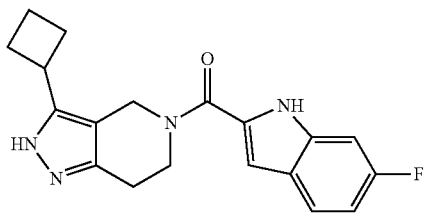 [SMILES: O=C(c1cc2ccc(F)cc2[nH]1)N1CCc2n[nH]c(C3CCC3)c2C1]

Rt (Method A) 3.16 mins, m/z 339 [M+H]+
No NMR available

Example 394

2-{3-cyclobutyl-2H,4H,5H,6H,7H-pyrazolo[4,3-c]pyridine-5-carbonyl}-5-fluoro-1H-indole

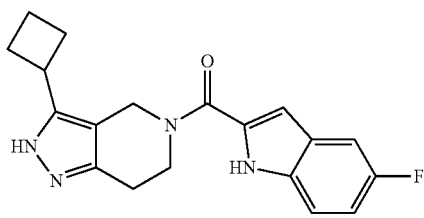 [SMILES: O=C(c1cc2cc(F)ccc2[nH]1)N1CCc2n[nH]c(C3CCC3)c2C1]

Rt (Method A) 3.14 mins, m/z 339 [M+H]+
No NMR available

Example 395

N-[1-(ethoxymethyl)cyclopropyl]-5-(6-fluoro-1H-indole-2-carbonyl)-N-methyl-2H,4H,5H,6H,7H-pyrazolo[4,3-c]pyridine-3-carboxamide

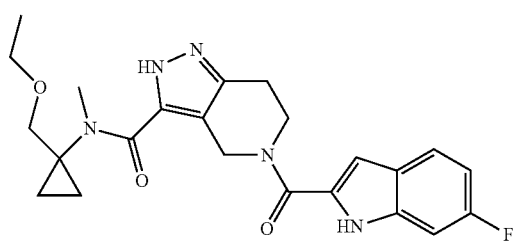 [SMILES: CCOCC1(N(C)C(=O)c2[nH]nc3c2CN(C(=O)c2cc4ccc(F)cc4[nH]2)CC3)CC1]

Rt (Method A) 3.2 mins, m/z 440 [M+H]+
1H NMR (400 MHz, DMSO-d6) δ 12.96 (s, 1H), 11.72 (s, 1H), 7.66 (dd, J=8.8, 5.5 Hz, 1H), 7.14 (dd, J=10.0, 2.4 Hz, 1H), 6.98-6.85 (m, 2H), 4.88 (m, 2H), 3.97 (m, 2H), 3.51 (m, 5H), 2.94 (m, 4H), 1.10 (m, 3H), 0.78 (m, 4H).

Example 396

2-{3-cyclobutyl-1H,4H,5H,6H,7H-pyrazolo[4,3-c]pyridine-5-carbonyl}-4,7-difluoro-1H-indole

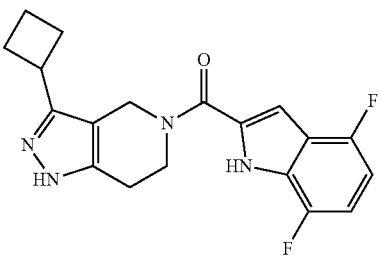 [SMILES: O=C(c1cc2c(F)ccc(F)c2[nH]1)N1CCc2[nH]nc(C3CCC3)c2C1]

Rt (Method A) 3.2 mins, m/z 357 [M+H]+
1H NMR (400 MHz, DMSO-d6) δ 13.66-11.12 (m, 2H), 7.06-6.96 (m, 1H), 6.92 (s, 1H), 6.86-6.77 (m, 1H), 4.97-4.49 (m, 2H), 3.96-3.82 (m, 2H), 2.88-2.70 (m, 2H), 2.31-2.05 (m, 4H), 2.05-1.69 (m, 2H). One signal (1H) coincides with water signal.

Example 397

2-{3-cyclobutyl-2H,4H,5H,6H,7H-pyrazolo[4,3-c]pyridine-5-carbonyl}-4-fluoro-1H-indole

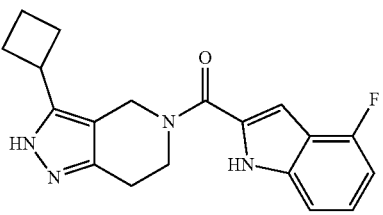 [SMILES: O=C(c1cc2c(F)cccc2[nH]1)N1CCc2n[nH]c(C3CCC3)c2C1]

Rt (Method A) 3.17 mins, m/z 339 [M+H]+
1H NMR (400 MHz, DMSO-d6) δ 12.35 (s, 1H), 11.95 (s, 1H), 7.27 (d, J=8.2 Hz, 1H), 7.17 (td, J=8.0, 5.2 Hz, 1H), 6.91 (s, 1H), 6.84 (dd, J=10.7, 7.6 Hz, 1H), 5.08-4.43 (m, 2H), 4.06-3.82 (m, 2H), 3.59-3.41 (m, 1H), 2.92-2.69 (m, 2H), 2.30-2.07 (m, 4H), 2.03-1.89 (m, 1H), 1.88-1.72 (m, 1H).

Example 398

5-(1H-indole-2-carbonyl)-N-methyl-N-[1-(3-methyl-1,2,4-oxadiazol-5-yl)cyclopropyl]-2H,4H,5H,6H,7H-pyrazolo[4,3-c]pyridine-3-carboxamide

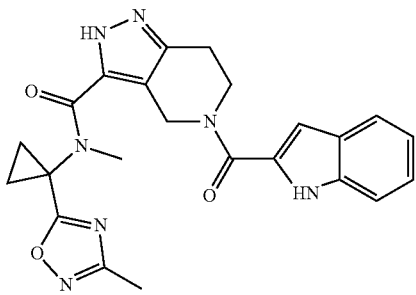 [SMILES: Cc1noc(C2(N(C)C(=O)c3[nH]nc4c3CN(C(=O)c3cc5ccccc5[nH]3)CC4)CC2)n1]

Rt (Method A) 3.03 mins, m/z 446 [M+H]+
1H NMR (400 MHz, DMSO-d6) δ 13.06 (s, 1H), 11.62 (s, 1H), 7.64 (d, J=8.0 Hz, 1H), 7.42 (d, J=8.2 Hz, 1H), 7.19 (t, J=7.6 Hz, 1H), 7.06 (t, J=7.5 Hz, 1H), 6.87 (s, 1H), 5.24-4.52 (m, 2H), 4.22-3.67 (m, 2H), 3.61-3.45 (m, 1H), 3.20-3.04 (m, 2H), 2.99-2.71 (m, 2H), 2.27 (s, 3H), 1.88-1.30 (m, 4H).

Example 399

2-{3-cyclobutyl-2H,4H,5H,6H,7H-pyrazolo[4,3-c]pyridine-5-carbonyl}-4-(1,1-difluoroethyl)-6-fluoro-1H-indole

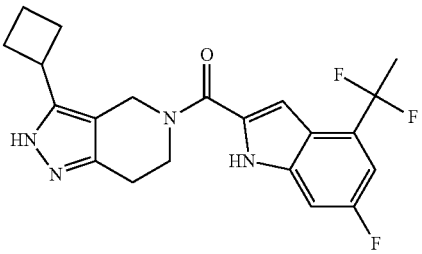 [SMILES: CC(F)(F)c1cc(F)cc2[nH]c(C(=O)N3CCc4n[nH]c(C5CCC5)c4C3)cc12]

Rt (Method A) 3.35 mins, m/z 403 [M+H]+
No NMR available

Example 400

2-{3-cyclobutyl-2H,4H,5H,6H,7H-pyrazolo[4,3-c]pyridine-5-carbonyl}-4-(difluoromethyl)-6-fluoro-1H-indole

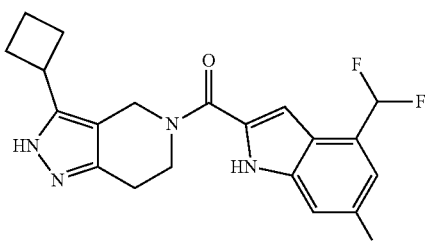

Rt (Method A) 3.25 mins, m/z 389 [M+H]+
No NMR available

Example 401

2-(3-{6,6-difluoro-4-azaspiro[2.4]heptane-4-carbonyl}-2H,4H,5H,6H,7H-pyrazolo[4,3-c]pyridine-5-carbonyl)-1H-indole

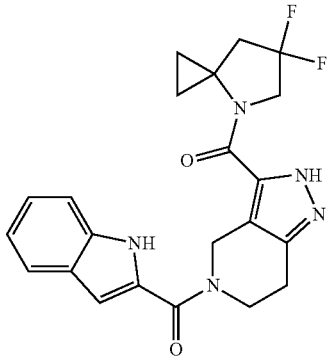 [SMILES: O=C(c1cc2ccccc2[nH]1)N1CCc2n[nH]c(C(=O)N3CC(F)(F)CC34CC4)c2C1]

Rt (Method A) 3.35 mins, m/z 426 [M+H]+
1H NMR (400 MHz, DMSO-d6) δ 13.19 (s, 1H), 11.62 (s, 1H), 7.64 (d, J=8.0 Hz, 1H), 7.42 (d, J=8.1 Hz, 1H), 7.19 (t, J=7.6 Hz, 1H), 7.06 (t, J=7.5 Hz, 1H), 6.87 (s, 1H), 4.83 (m, 2H), 4.47 (t, J=13.3 Hz, 2H), 3.96 (m, 2H), 2.89 (m, 2H), 2.46 m, 2H), 1.93 (m, 2H), 0.64 (m, 2H).

Example 402

5-(1H-indole-2-carbonyl)-N-methyl-N-[1-(1,2-oxazol-5-yl)cyclopropyl]-2H,4H,5H,6H,7H-pyrazolo[4,3-c]pyridine-3-carboxamide

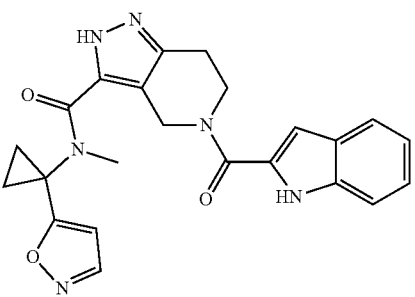 [SMILES: CN(C(=O)c1[nH]nc2c1CN(C(=O)c1cc3ccccc3[nH]1)CC2)C1(c2ccno2)CC1]

Rt (Method A) 3.03 mins, m/z 431 [M+H]+
1H NMR (400 MHz, DMSO-d6) δ 13.30-12.77 (m, 1H), 11.62 (s, 1H), 8.40 (s, 1H), 7.64 (d, J=7.9 Hz, 1H), 7.42 (d, J=8.1 Hz, 1H), 7.25-7.14 (m, 1H), 7.06 (t, J=7.5 Hz, 1H), 6.87 (s, 1H), 6.21 (s, 1H), 5.17-4.56 (m, 2H), 4.16-3.76 (m, 2H), 3.58-3.38 (m, 2H), 3.20-3.00 (m, 1H), 3.00-2.71 (m, 2H), 1.69-1.19 (m, 4H).

Example 403

5-(4,6-difluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

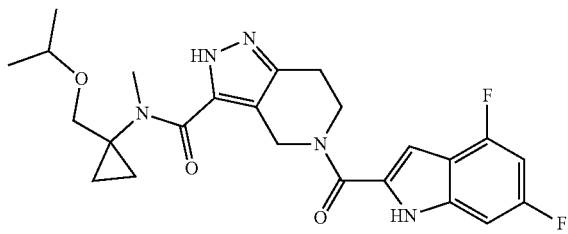 [SMILES: CC(C)OCC1(N(C)C(=O)c2[nH]nc3c2CN(C(=O)c2cc4c(F)cc(F)cc4[nH]2)CC3)CC1]

Rt (Method J) 1.48 mins, m/z 472 [M+H]+
No NMR available

Example 404

5-(4-chloro-5-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

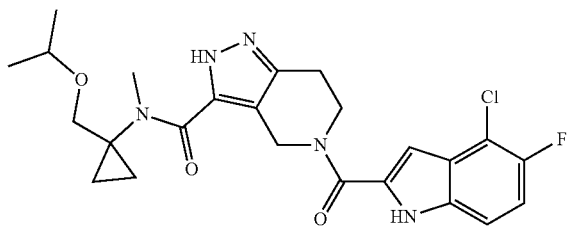 [SMILES: CC(C)OCC1(N(C)C(=O)c2[nH]nc3c2CN(C(=O)c2cc4c(Cl)c(F)ccc4[nH]2)CC3)CC1]

Rt (Method J) 1.52 mins, m/z 488/490 [M+H]+
No NMR available

Example 405

5-(6-chloro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

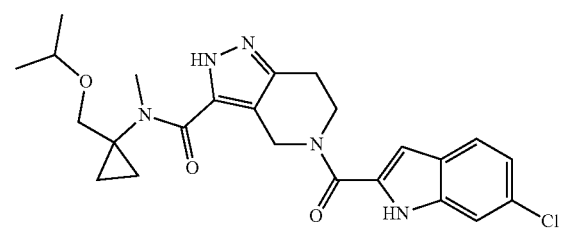 [SMILES: CC(C)OCC1(N(C)C(=O)c2[nH]nc3c2CN(C(=O)c2cc4ccc(Cl)cc4[nH]2)CC3)CC1]

Rt (Method J) 1.51 mins, m/z 470/472 [M+H]+
No NMR available

Example 406

5-(4-chloro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

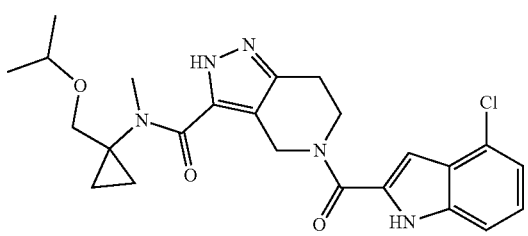 [SMILES: CC(C)OCC1(N(C)C(=O)c2[nH]nc3c2CN(C(=O)c2cc4c(Cl)cccc4[nH]2)CC3)CC1]

Rt (Method J) 1.51 mins, m/z 470/472 [M+H]+
No NMR available

Example 407

5-(6-fluoro-4-methyl-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

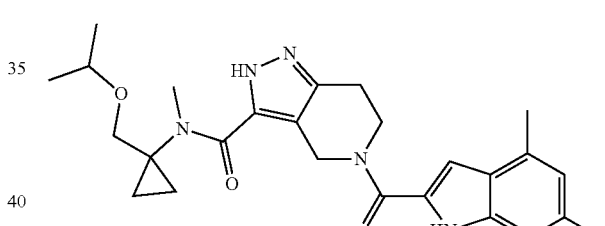

Rt (Method J) 1.48 mins, m/z 468 [M+H]+
No NMR available

Example 408

5-(4-ethyl-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

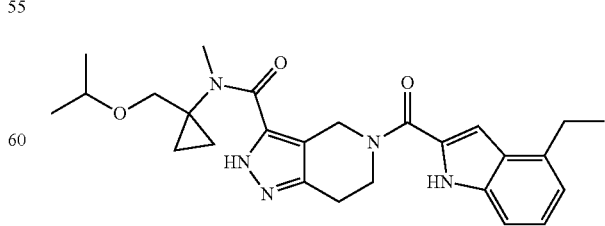

Rt (Method J) 1.54 mins, m/z 464 [M+H]+
No NMR available

Example 409

5-(6-chloro-5-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

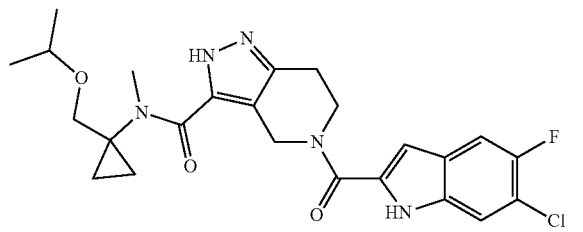 [SMILES: CC(C)OCC1(N(C)C(=O)c2[nH]nc3c2CN(C(=O)c2cc4cc(F)c(Cl)cc4[nH]2)CC3)CC1]

Rt (Method J) 1.52 mins, m/z 488/490 [M+H]+
No NMR available

Example 410

5-(4-chloro-6-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

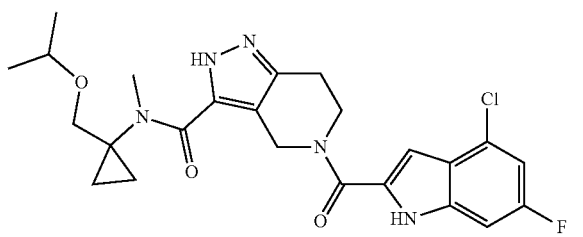 [SMILES: CC(C)OCC1(N(C)C(=O)c2[nH]nc3c2CN(C(=O)c2cc4c(Cl)cc(F)cc4[nH]2)CC3)CC1]

Rt (Method J) 1.56 mins, m/z 488/490 [M+H]+
1H NMR (400 MHz, DMSO-d6) δ 12.98 (s, 1H), 12.11 (s, 1H), 7.22-7.11 (m, 2H), 6.85 (s, 1H), 5.28-4.52 (m, 2H), 3.97 (m, 2H), 3.75-3.33 (m, 4H), 3.15-2.72 (m, 4H), 1.31-0.90 (m, 6H), 0.88-0.47 (m, 4H).

Example 411

5-(4-ethyl-6-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

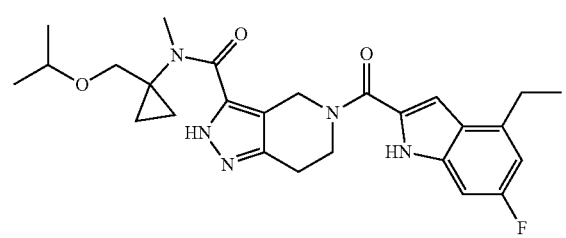 [SMILES: CCc1cc(F)cc2[nH]c(C(=O)N3CCc4n[nH]c(C(=O)N(C)C5(COC(C)C)CC5)c4C3)cc12]

Rt (Method J) 1.57 mins, m/z 482 [M+H]+
No NMR available

Example 412

5-(7-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboxamide

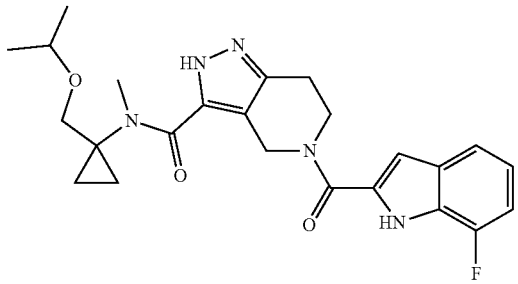 [SMILES: CC(C)OCC1(N(C)C(=O)c2[nH]nc3c2CN(C(=O)c2cc4cccc(F)c4[nH]2)CC3)CC1]

Rt (Method J) 1.4 mins, m/z 454 [M+H]+
No NMR available

Example 413

5-(6-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboximide

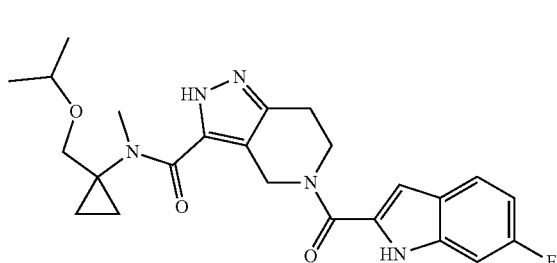 [SMILES: CC(C)OCC1(N(C)C(=O)c2[nH]nc3c2CN(C(=O)c2cc4cc(F)ccc4[nH]2)CC3)CC1]

Rt (Method J) 1.41 mins, m/z 454 [M+H]+
1H NMR (400 MHz, DMSO-d6) δ 12.96 (s, 1H), 11.76 (s, 1H), 7.72-7.61 (m, 1H), 7.18-7.10 (m, 1H), 6.99-6.82 (m, 2H), 5.33-4.49 (m, 2H), 3.97 (m, 2H), 3.77-3.35 (m, 4H), 3.11-2.70 (m, 4H), 1.41-0.40 (m, 10H).

Example 414

5-(5-fluoro-1H-indole-2-carbonyl)-N-methyl-N-{1-[(propan-2-yloxy)methyl]cyclopropyl}-2H,4H,5H,6H,7H-pyrazolo[4,3-c]pyridine-3-carboximide

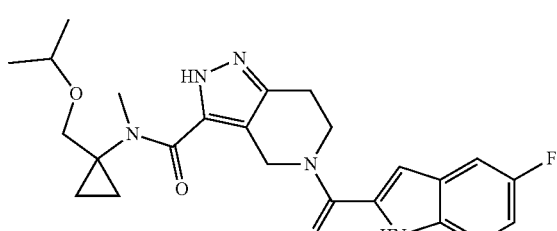

Rt (Method J) 1.4 mins, m/z 454 [M+H]+
No NMR available

Example 415

5-(6-chloro-7-fluoro-1H-indole-2-carbonyl)-N-[1-(methoxymethyl)cyclopropyl]-N-methyl-2H,4H,5H,6H,7H-pyrazolo[4,3-c]pyridine-3-carboxamide

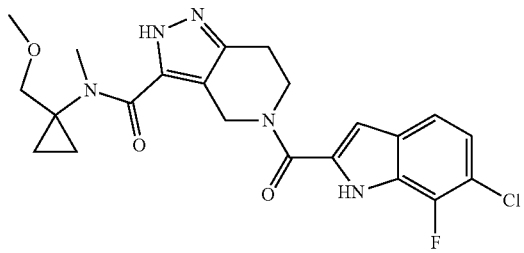 [SMILES: COCC1(N(C)C(=O)c2[nH]nc3c2CN(C(=O)c2cc4ccc(Cl)c(F)c4[nH]2)CC3)CC1]

Rt (Method A) 3.22 mins, m/z 460/462 [M+H]+

1H NMR (400 MHz, DMSO-d6) δ 12.97 (s, 1H), 12.35 (s, 1H), 7.48 (d, J=8.6 Hz, 1H), 7.18-7.10 (m, 1H), 6.94 (s, 1H), 5.14-4.52 (m, 2H), 3.93 (m, 2H), 3.60-3.41 (m, 1H), 3.30-3.11 (m, 4H), 3.11-2.68 (m, 4H), 1.02-0.45 (m, 4H).

Example 417

N-{1-[(difluoromethoxy)methyl]cyclopropyl}-N-methyl-5-(4-methyl-1H-indole-2-carbonyl)-2H,4H,5H,6H,7H-pyrazolo[4,3-c]pyridine-3-carboxamide

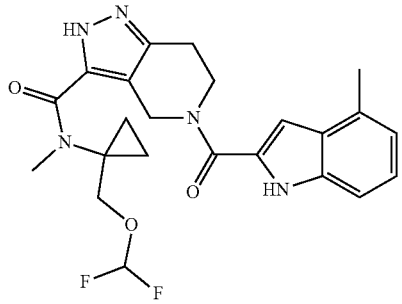

Rt (Method H) 1.54 mins, m/z 458 [M+H]+

1H NMR (400 MHz, DMSO-d6) δ 13.05 (s, 1H), 11.60 (d, J=2.2 Hz, 1H), 7.24 (d, J=8.2 Hz, 1H), 7.17-7.03 (m, 1H), 6.98-6.39 (m, 3H), 4.91 (m, 3H), 4.00 (m, 3H), 3.56 (m, 1H), 2.94 (m, 4H), 0.88 (m, 4H).

Example 416

5-(1H-indole-2-carbonyl)-N-methyl-N-[1-(1,2-oxazol-3-yl)cyclopropyl]-2H,4H,5H,6H,7H-pyrazolo[4,3-c]pyridine-3-carboxamide

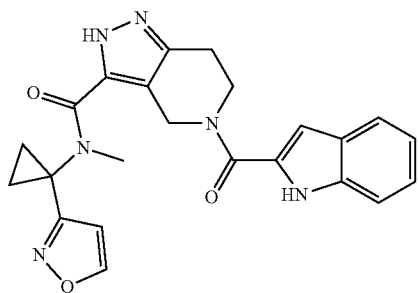 [SMILES: CN(C(=O)c1[nH]nc2c1CN(C(=O)c1cc3ccccc3[nH]1)CC2)C1(c2ccon2)CC1]

Rt (Method A) 2.97 mins, m/z 421 [M+H]+

1H NMR (400 MHz, DMSO-d6) δ 13.03 (m, 1H), 11.62 (s, 1H), 8.74 (s, 1H), 7.64 (d, J=8.0 Hz, 1H), 7.42 (d, J=8.2 Hz, 1H), 7.19 (t, J=7.6 Hz, 1H), 7.06 (t, J=7.4 Hz, 1H), 6.87 (s, 1H), 6.38 (d, J=12.8 Hz, 1H), 4.85 (m, 2H), 3.98 (m, 2H), 3.44 (m, 1.6H), 3.06 (m, 1.4H), 2.89 (m, 2H), 1.31 (m, 4H).

Example 418

5-(4-chloro-1H-indole-2-carbonyl)-N-{1-[(difluoromethoxy)methyl]cyclopropyl}-N-methyl-2H,4H,5H,6H,7H-pyrazolo[4,3-c]pyridine-3-carboxamide

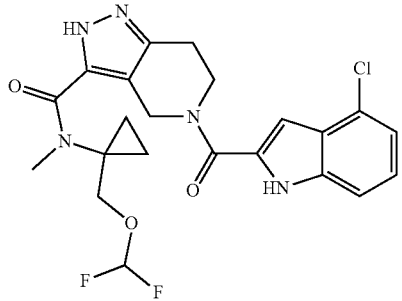 [SMILES: CN(C(=O)c1[nH]nc2c1CN(C(=O)c1cc3c(Cl)cccc3[nH]1)CC2)C1(COC(F)F)CC1]

Rt (Method H) 1.59 mins, m/z 478/480 [M+H]+

1H NMR (400 MHz, DMSO-d6) δ 13.05 (s, 1H), 12.04 (s, 1H), 7.41 (d, J=8.0 Hz, 1H), 7.23-7.12 (m, 2H), 6.83 (m, 2H), 4.98 (m, 3H), 3.99 (m, 3.2H), 3.55 (m, 0.8H), 2.93 (m, 4H), 0.89 (m, 4H).

Example 419

5-(5,6-difluoro-1H-indole-2-carbonyl)-N-{1-[(difluoromethoxy)methyl]cyclopropyl}-N-methyl-2H,4H,5H,6H,7H-pyrazolo[4,3-c]pyridine-3-carboxamide

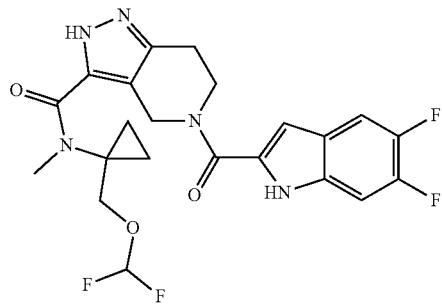 [SMILES: CN(C(=O)c1[nH]nc2c1CN(C(=O)c1cc3cc(F)c(F)cc3[nH]1)CC2)C1(COC(F)F)CC1]

Rt (Method H) 1.53 mins, m/z 480 [M+H]+

1H NMR (400 MHz, DMSO-d6) δ 13.03 (s, 1H), 11.84 (s, 1H), 7.65 (s, 1H), 7.35 (m, 1H), 6.80 (m, 2H), 4.87 (m, 3H), 3.97 (m, 3H), 3.55 (m, 1H), 2.93 (m, 4H), 0.89 (m, 4H).

Example 420

5-(4,6-difluoro-1H-indole-2-carbonyl)-N-{1-[(difluoromethoxy)methyl]cyclopropyl}-N-methyl-2H,4H,5H,6H,7H-pyrazolo[4,3-c]pyridine-3-carboxamide

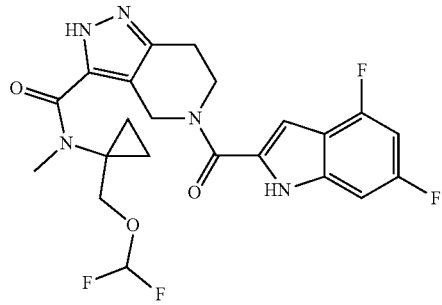 [SMILES: CN(C(=O)c1[nH]nc2c1CN(C(=O)c1cc3c(F)cc(F)cc3[nH]1)CC2)C1(COC(F)F)CC1]

Rt (Method H) 1.55 mins, m/z 480 [M+H]+

1H NMR (400 MHz, DMSO-d6) δ 13.04 (s, 1H), 12.08 (s, 1H), 7.04 (m, J=9.3, 2.1 Hz, 1H), 6.99-6.34 (m, 3H), 4.87 (m, 3H), 3.97 (m, 3.3H), 3.56 (m, 0.7H), 2.94 (m, 4H), 0.89 (m, 4H).

Example 421

N-{1-[(difluoromethoxy)methyl]cyclopropyl}-5-(4-fluoro-1H-indole-2-carbonyl)-N-methyl-2H,4H,5H,6H,7H-pyrazolo[4,3-c]pyridine-3-carboxamide

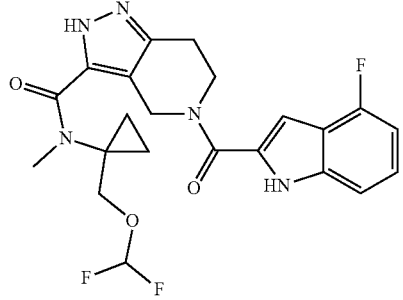 [SMILES: CN(C(=O)c1[nH]nc2c1CN(C(=O)c1cc3c(F)cccc3[nH]1)CC2)C1(COC(F)F)CC1]

Rt (Method H) 1.5 mins, m/z 462 [M+H]+

1H NMR (400 MHz, DMSO-d6) δ 13.05 (s, 1H), 11.99 (s, 1H), 7.27 (d, J=8.2 Hz, 1H), 7.18 (m, J=8.0, 5.2 Hz, 1H), 6.99-6.36 (m, 3H), 4.87 (m, 3H), 3.98 (m, 3.3H), 3.55 (m, 0.7H), 2.94 (m, 4H), 0.89 (m, 4H).

Example 422

N-{1-[(difluoromethoxy)methyl]cyclopropyl}-5-(5-fluoro-1H-indole-2-carbonyl)-N-methyl-2H,4H,5H,6H,7H-pyrazolo[4,3-c]pyridine-3-carboxamide

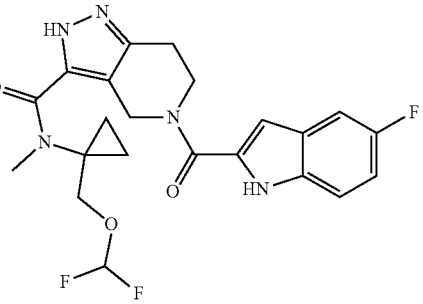

Rt (Method H) 1.49 mins, m/z 462 [M+H]+

1H NMR (400 MHz, DMSO-d6) δ 13.05 (s, 1H), 11.75 (s, 1H), 7.41 (m, 2H), 7.06 (m, 1H), 6.79 (m, 2H), 4.87 (m, 3H), 3.98 (m, 3.3H), 3.56 (m, 0.7H), 2.93 (m, 4H), 0.89 (m, 4H).

Example 423

N-{1-[(difluoromethoxy)methyl]cyclopropyl}-5-(6-fluoro-1H-indole-2-carbonyl)-N-methyl-2H,4H,5H,6H,7H-pyrazolo[4,3-c]pyridine-3-carboxamide

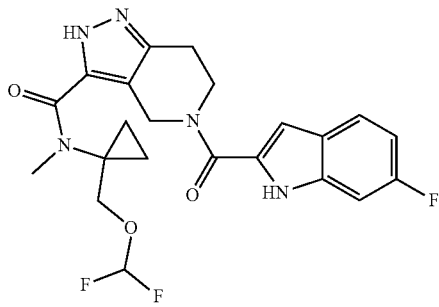 [SMILES: CN(C(=O)c1[nH]nc2c1CN(C(=O)c1cc3ccc(F)cc3[nH]1)CC2)C1(COC(F)F)CC1]

Rt (Method H) 1.5 mins, m/z 462 [M+H]+

1H NMR (400 MHz, DMSO-d6) δ 13.03 (s, 1H), 11.71 (s, 1H), 7.66 (dd, J=8.7, 5.5 Hz, 1H), 7.14 (dd, J=9.9, 2.4 Hz, 1H), 7.00-6.38 (m, 3H), 4.89 (m, 2.6H), 3.98 (m, 3H), 3.56 (m, 0.6H), 3.36 (m, 0.8H) 3.16-2.69 (m, 4H), 0.88 (m, 4H).

Example 424

N-{1-[(difluoromethoxy)methyl]cyclopropyl}-5-(7-fluoro-1H-indole-2-carbonyl)-N-methyl-2H,4H,5H,6H,7H-pyrazolo[4,3-c]pyridine-3-carboxamide

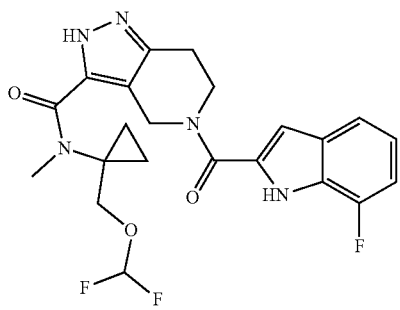 [SMILES: CN(C(=O)c1[nH]nc2c1CN(C(=O)c1cc3cccc(F)c3[nH]1)CC2)C1(COC(F)F)CC1]

Rt (Method H) 1.48 mins, m/z 462 [M+H]+

1H NMR (400 MHz, DMSO-d6) δ 13.04 (s, 1H), 12.09 (s, 1H), 7.58-7.34 (m, 1H), 7.10-6.96 (m, 2H), 6.80 (m, 2H), 4.86 (m, 2.6H), 3.93 (m, 3.1H), 3.55 (m, 1H), 2.93 (m, 4H), 0.88 (m, 4H).

Example 425

5-(6-chloro-5-fluoro-1H-indole-2-carbonyl)-N-{1-[(difluoromethoxy)methyl]cyclopropyl}-N-methyl-2H,4H,5H,6H,7H-pyrazolo[4,3-c]pyridine-3-carboxamide

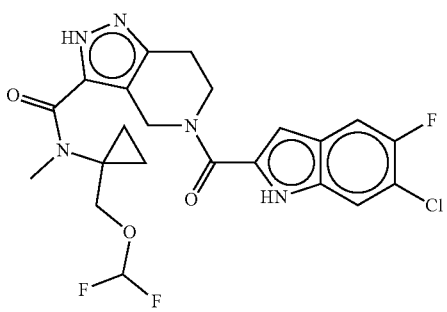

Rt (Method B) 3.33 mins, m/z 496/498 [M+H]+

1H NMR (400 MHz, DMSO-d6) δ 13.03 (s, 1H), 11.89 (s, 1H), 7.65 (d, J=9.9 Hz, 1H), 7.54 (d, J=6.5 Hz, 1H), 6.80 (m, 2H), 4.86 (m, 2.5H), 3.97 (m, 3H), 3.55 (m, 0.5H), 2.93 (m, 4H), 0.89 (m, 4H).

Example 426

5-(4,5-difluoro-1H-indole-2-carbonyl)-N-{1-[(difluoromethoxy)methyl]cyclopropyl}-N-methyl-2H,4H,5H,6H,7H-pyrazolo[4,3-c]pyridine-3-carboxamide

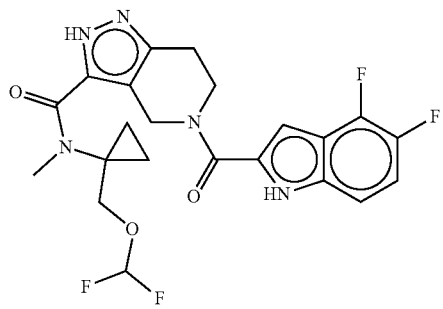

Rt (Method B) 3.24 mins, m/z 480 [M+H]+

1H NMR (400 MHz, DMSO-d6) δ 13.05 (s, 1H), 12.08 (s, 1H), 7.24 (m, 2H), 6.84 (m, 2H), 4.86 (m, 2.6H), 3.97 (m, 3H), 3.56 (m, 0.6H), 2.97 (m, 4H), 0.89 (m, 4H).

Example 427

2-(3-{7-fluoro-4-azaspiro[2.5]octane-4-carbonyl}-2H,4H,5H,6H,7H-pyrazolo[4,3-c]pyridine-5-carbonyl)-1H-indole

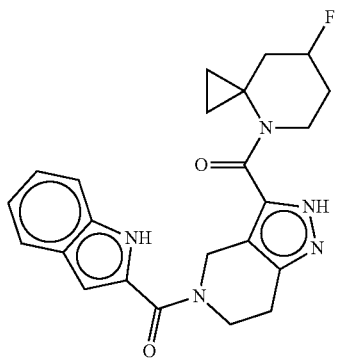

Rt (Method J) 1.25 mins, m/z 422 [M+H]+

1H NMR (400 MHz, DMSO-d6) δ 12.99 (s, 1H), 11.63 (s, 1H), 7.64 (d, J=8.0 Hz, 1H), 7.43 (d, J=8.3 Hz, 1H), 7.20 (t, J=7.6 Hz, 1H), 7.06 (t, J=7.4 Hz, 1H), 6.88 (s, 1H), 5.02-4.60 (m, 3H), 4.52-4.09 (m, 1H), 4.06-3.91 (m, 2H), 3.88-3.57 (m, 1H), 2.96-2.72 (m, 2H), 2.01-1.50 (m, 3H), 1.66-1.43 (m, 1H), 1.21-0.40 (m, 4H).

Example 428

5-(1H-indole-2-carbonyl)-N-methyl-N-[1-(oxolan-2-yl)cyclopropyl]-2H,4H,5H,6H,7H-pyrazolo[4,3-c]pyridine-3-carboxamide

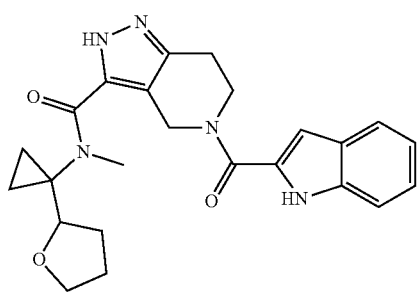 [SMILES: CN(C(=O)c1[nH]nc2c1CN(C(=O)c1cc3ccccc3[nH]1)CC2)C1(C2CCCO2)CC1]

Rt (Method B) 3.01 mins, m/z 434 [M+H]+

1H NMR (400 MHz, DMSO-d6) δ 13.02 (m, 1H), 11.63 (s, 1H), 7.64 (d, J=8.0 Hz, 1H), 7.42 (d, J=8.3 Hz, 1H), 7.19 (m, 1H), 7.06 (t, J=7.5 Hz, 1H), 6.87 (s, 1H), 5.24-4.48 (m, 2H), 4.20-3.47 (m, 5H), 2.93 (m, 3H), 2.15-1.48 (m, 4H), 1.09-0.47 (m, 4H).

Example 429

2-({1-[5-(1H-indole-2-carbonyl)-2H,4H,5H,6H,7H-pyrazolo[4,3-c]pyridin-3-yl]-N-methylformamido}methyl)benzoic acid

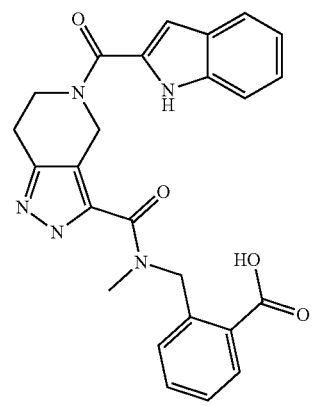

Rt (Method B) 3.01 mins, m/z 458 [M+H]+

1H NMR (400 MHz, DMSO-d6) δ 13.06 (m, 2H), 11.64 (s, 1H), 7.89 (d, J=7.4 Hz, 1H), 7.63 (d, J=8.9 Hz, 1H), 7.31 (m, 5H), 7.07 (m, 1H), 6.89 (s, 1H), 5.50 (m, 1H), 5.00 (m, 3H), 4.01 (m, 3H), 3.39 (m, 1H), 2.92 (m, 4H).

Example 430 methyl 2-({1-[5-(1H-indole-2-carbonyl)-2H,4H,5H,6H,7H-pyrazolo[4,3-c]pyridin-3-yl]-N-methylformamido}methyl)benzoate

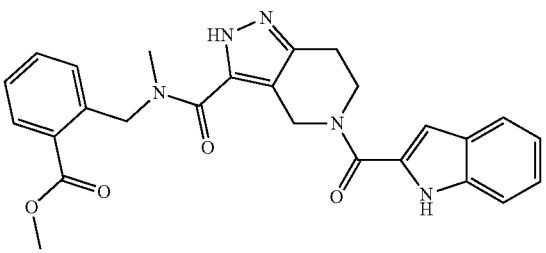 [SMILES: COC(=O)c1ccccc1CN(C)C(=O)c1[nH]nc2c1CN(C(=O)c1cc3ccccc3[nH]1)CC2]

Rt (Method A) 3.13 mins, m/z 472 [M+H]+

1H NMR (400 MHz, DMSO-d6) δ 13.07 (m, 1H), 11.64 (s, 1H), 7.89 (m, 1H), 7.73-7.30 (m, 4H), 7.20 (m, 2H), 7.06 (m, 1H), 6.89 (s, 1H), 5.48 (m, 1H), 4.96 (m, 3H), 3.97 (m, 2H), 3.82 (m, 3H), 3.36 (m, 1H), 2.91 (m, 4H).

Example 431

2-[4-methyl-3-(oxolan-2-yl)-2H,4H,5H,6H,7H-pyrazolo[4,3-c]pyridine-5-carbonyl]-1H-indole

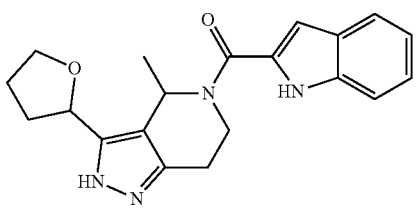 [SMILES: CC1c2c(n[nH]c2C2CCCO2)CCN1C(=O)c1cc2ccccc2[nH]1]

Rt (Method A) 2.9 mins, m/z 351 [M+H]+

1H NMR (400 MHz, DMSO-d6) δ 12.64-12.24 (m, 1H), 11.61 (s, 1H), 7.63 (d, J=7.9 Hz, 1H), 7.41 (d, J=8.2 Hz, 1H), 7.22-7.15 (m, 1H), 7.09-7.00 (m, 1H), 6.90-6.80 (m, 1H), 5.72-5.44 (m, 1H), 5.00-4.79 (m, 1H), 4.65-4.41 (m, 1H), 4.03-3.40 (m, 3H), 3.08-2.64 (m, 2H), 2.38-1.70 (m, 4H), 1.70-1.33 (m, 3H).

Example 432

2-[6-methyl-3-(oxolan-2-yl)-2H,4H,5H,6H,7H-pyrazolo[4,3-c]pyridine-5-carbonyl]-1H-indole

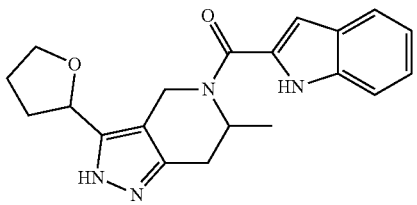 [SMILES: CC1Cc2n[nH]c(C3CCCO3)c2CN1C(=O)c1cc2ccccc2[nH]1]

Rt (Method A) 2.87 mins, m/z 351 [M+H]+

1H NMR (400 MHz, DMSO-d6) δ 12.71-12.19 (m, 1H), 11.58 (s, 1H), 7.63 (d, J=7.9 Hz, 1H), 7.42 (d, J=8.2 Hz, 1H), 7.19 (t, J=7.5 Hz, 1H), 7.05 (t, J=7.3 Hz, 1H), 6.84 (s, 1H), 5.23-5.05 (m, 2H), 5.03-4.70 (m, 1H), 4.70-4.00 (m, 1H), 4.00-3.60 (m, 2H), 3.12-2.90 (m, 1H), 2.63-2.55 (m, 1H), 2.26-2.06 (m, 1H), 2.06-1.77 (m, 3H), 1.19 (t, J=6.4 Hz, 3H).

Example 433

2-{3-cyclobutyl-4-methyl-2H,4H,5H,6H,7H-pyrazolo[4,3-c]pyridine-5-carbonyl}-1H-indole

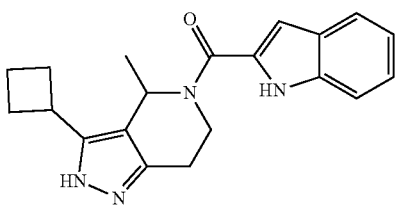 [SMILES: CC1c2c(n[nH]c2C2CCC2)CCN1C(=O)c1cc2ccccc2[nH]1]

Rt (Method A) 3.13 mins, m/z 335 [M+H]+

1H NMR (400 MHz, DMSO-d6) δ 12.73-12.02 (m, 1H), 11.61 (s, 1H), 7.63 (d, J=8.0 Hz, 1H), 7.41 (d, J=8.2 Hz, 1H), 7.19 (t, J=7.5 Hz, 1H), 7.05 (t, J=7.5 Hz, 1H), 6.85 (s, 1H), 5.54-5.33 (m, 1H), 4.66-4.40 (m, 1H), 3.64-3.41 (m, 2H), 3.04-2.63 (m, 2H), 2.38-1.69 (m, 6H), 1.68-1.26 (m, 3H).

Example 434

2-{3-cyclobutyl-6-methyl-2H,4H,5H,6H,7H-pyrazolo[4,3-c]pyridine-5-carbonyl}-1H-indole

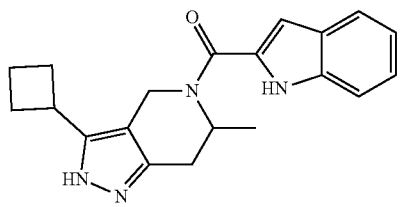 [SMILES: CC1Cc2n[nH]c(C3CCC3)c2CN1C(=O)c1cc2ccccc2[nH]1]

Rt (Method A) 3.11 mins, m/z 335 [M+H]+

1H NMR (400 MHz, DMSO-d6) δ 12.52-12.08 (m, 1H), 11.59 (s, 1H), 7.63 (d, J=7.9 Hz, 1H), 7.42 (d, J=8.2 Hz, 1H), 7.22-7.15 (m, 1H), 7.09-7.02 (m, 1H), 6.86 (s, 1H), 5.29-4.92 (m, 2H), 4.60-3.81 (m, 1H), 3.61-3.42 (m, 1H), 3.10-2.86 (m, 1H), 2.63-2.53 (m, 1H), 2.29-2.14 (m, 4H), 2.01-1.91 (m, 1H), 1.88-1.72 (m, 1H), 1.18 (d, J=6.8 Hz, 3H).

Example 435

5-(5-fluoro-4-methyl-1H-indole-2-carbonyl)-N-[1-(methoxymethyl)cyclopropyl]-N-methyl-2H,4H,5H,6H,7H-pyrazolo[4,3-c]pyridine-3-carboxamide

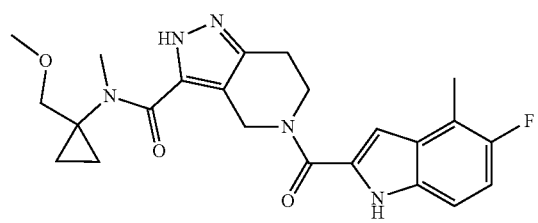 [SMILES: COCC1(N(C)C(=O)c2[nH]nc3c2CN(C(=O)c2cc4c(C)c(F)ccc4[nH]2)CC3)CC1]

Rt (Method H) 1.35 mins, m/z 440 [M+H]+

1H NMR (400 MHz, DMSO-d6) δ 13.00 (s, 1H), 11.70 (s, 1H), 7.27-7.19 (m, 1H), 7.05-6.97 (m, 1H), 6.92 (s, 1H), 5.11-4.44 (m, 2H), 4.12-3.79 (m, 2H), 3.61-3.34 (m, 3H), 3.27-3.13 (m, 4H), 3.12-2.77 (m, 4H), 2.41 (s, 3H), 0.94-0.46 (m, 4H).

Example 436

2-{3-cyclobutyl-2H,4H,5H,6H,7H-pyrazolo[4,3-c]pyridine-5-carbonyl}-4-(1,1-difluoroethyl)-1H-indole

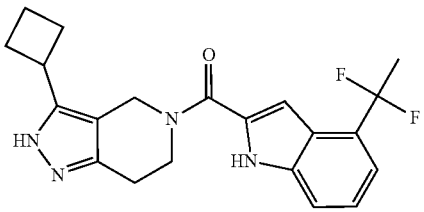 [SMILES: CC(F)(F)c1cccc2[nH]c(C(=O)N3CCc4n[nH]c(C5CCC5)c4C3)cc12]

Rt (Method A) 3.2 mins, m/z 385 [M+H]+

1H NMR (400 MHz, DMSO-d6) δ 12.51-12.14 (m, 1H), 11.96 (s, 1H), 7.55 (d, J=7.9 Hz, 1H), 7.30-7.19 (m, 2H), 6.87 (s, 1H), 5.17-4.39 (m, 2H), 4.04-3.89 (m, 2H), 3.59-3.38 (m, 1H), 2.87-2.70 (m, 2H), 2.31-2.00 (m, 7H), 2.00-1.88 (m, 1H), 1.88-1.72 (m, 1H).

Selected compounds of the invention were assayed in capsid assembly and HBV replication assays, as described below and a representative group of these active compounds is shown in Table 1.

Biochemical Capsid Assembly Assay

The screening for assembly effector activity was done based on a fluorescence quenching assay published by Zlotnick et al. (2007). The C-terminal truncated core protein containing 149 amino acids of the N-terminal assembly domain fused to a unique cysteine residue at position 150 and was expressed in E. coli using the pET expression system (Merck Chemicals, Darmstadt). Purification of core dimer protein was performed using a sequence of size exclusion chromatography steps. In brief, the cell pellet from 1 L BL21 (DE3) Rosetta2 culture expressing the coding sequence of core protein cloned NdeI/XhoI into expression plasmid pET21b was treated for 1 h on ice with a native lysis buffer (Qproteome Bacterial Protein Prep Kit; Qiagen, Hilden). After a centrifugation step the supernatant was precipitated during 2 h stirring on ice with 0.23 g/ml of solid ammonium sulfate. Following further centrifugation the resulting pellet was resolved in buffer A (100 mM Tris, pH 7.5; 100 mM NaCl; 2 mM DTT) and was subsequently loaded onto a buffer A equilibrated CaptoCore 700 column (GE HealthCare, Frankfurt). The column flow through containing the assembled HBV capsid was dialyzed against buffer N (50 mM NaHCO$_3$ pH 9.6; 5 mM DTT) before urea was added to a final concentration of 3M to dissociate the capsid into core dimers for 1.5 h on ice. The protein solution was then loaded onto a 1 L Sephacryl S300 column. After elution with buffer N core dimer containing fractions were identified by SDS-PAGE and subsequently pooled and dialyzed against 50 mM HEPES pH 7.5; mM DTT. To improve the assembly capacity of the purified core dimers a second round of assembly and disassembly starting with the addition of 5 M NaCl and including the size exclusion chromatography steps described above was performed. From the last chromatography step core dimer containing fractions were pooled and stored in aliquots at concentrations between 1.5 to 2.0 mg/ml at −80° C.

Immediately before labelling the core protein was reduced by adding freshly prepared DTT in a final concentration of 20 mM. After 40 min incubation on ice storage buffer and DTT was removed using a Sephadex G-25 column (GE HealthCare, Frankfurt) and 50 mM HEPES, pH 7.5. For labelling 1.6 mg/ml core protein was incubated at 4° C. and darkness overnight with BODIPY-FL maleimide (Invitrogen, Karlsruhe) in a final concentration of 1 mM. After labelling the free dye was removed by an additional desalting step using a Sephadex G-25 column. Labelled core dimers were stored in aliquots at 4° C. In the dimeric state the fluorescence signal of the labelled core protein is high and is quenched during the assembly of the core dimers to high molecular capsid structures. The screening assay was performed in black 384 well microtiter plates in a total assay volume of 10 µl using 50 mM HEPES pH 7.5 and 1.0 to 2.0 µM labelled core protein. Each screening compound was added in 8 different concentrations using a 0.5 log-unit serial dilution starting at a final concentration of 100 µM, 31.6 µM or 10 µM, In any case the DMSO concentration over the entire microtiter plate was 0.5%. The assembly reaction was started by the injection of NaCl to a final concentration of 300 µM which induces the assembly process to approximately 25% of the maximal quenched signal. 6 min after starting the reaction the fluorescence signal was measured using a Clariostar plate reader (BMG Labtech, Ortenberg) with an excitation of 477 nm and an emission of 525 nm. As 100% and 0% assembly control HEPES buffer containing 2.5 M and 0 M NaCl was used. Experiments were performed thrice in triplicates. EC$_{50}$ values were calculated by non-linear regression analysis using the Graph Pad Prism 6 software (GraphPad Software, La Jolla, USA).

Determination of HBV DNA from the Supernatants of HepAD38 Cells

The anti-HBV activity was analysed in the stable transfected cell line HepAD38, which has been described to secrete high levels of HBV virion particles (Ladner et al., 1997). In brief, HepAD38 cells were cultured at 37° C. at 5% CO$_2$ and 95% humidity in 200 µl maintenance medium, which was Dulbecco's modified Eagle's medium/Nutrient Mixture F-12 (Gibco, Karlsruhe), 10% fetal bovine serum (PAN Biotech Aidenbach) supplemented with 50 µg/ml penicillin/streptomycin (Gibco, Karlsruhe), 2 mM L-glutamine (PAN Biotech, Aidenbach), 400 µg/ml G418 (AppliChem, Darmstadt) and 0.3 µg/ml tetracycline. Cells were subcultured once a week in a 1:5 ratio, but were usually not passaged more than ten times. For the assay 60,000 cells were seeded in maintenance medium without any tetracycline into each well of a 96-well plate and treated with serial half-log dilutions of test compound. To minimize edge effects the outer 36 wells of the plate were not used but were filled with assay medium. On each assay plate six wells for the virus control (untreated HepAD38 cells) and six wells for the cell control (HepAD38 cells treated with 0.3 µg/ml tetracycline) were allocated, respectively. In addition, one plate set with reference inhibitors like BAY 41-4109, entecavir, and lamivudine instead of screening compounds were prepared in each experiment. In general, experiments were performed thrice in triplicates. At day 6 HBV DNA from 100 µl filtrated cell culture supernatant (AcroPrep Advance 96 Filter Plate, 0.45 µM Supor membran, PALL GmbH, Dreieich) was automatically purified on the MagNa Pure LC instrument using the MagNA Pure 96 DNA and Viral NA Small Volume Kit (Roche Diagnostics, Mannheim) according to the instructions of the manufacturer. EC50 values were calculated from relative copy numbers of HBV DNA In brief, 5 µl of the 100 µl eluate containing HBV DNA were subjected to PCR LC480 Probes Master Kit (Roche) together with 1 µM antisense primer tgcagaggtgaagcgaagtgcaca, 0.5 µM sense primer gacgtcctttgtttacgtcccgtc, 0.3 µM hybprobes acggggcgcacctctctttacgcgg-FL and LC640-ctccccgtctgtgccttctcatctgc-PH (TIBMoBiol, Berlin) to a final volume of 12.5 µl. The PCR was performed on the Light Cycler 480 real time system (Roche Diagnostics, Mannheim) using the following protocol: Pre-incubation for 1 min at 95° C., amplification: 40 cycles×(10 sec at 95° C., 50 sec at 60° C., 1 sec at 70° C.), cooling for 10 sec at 40° C. Viral load was quantitated against known standards using HBV plasmid DNA of pCH-9/3091 (Nassal et al., 1990, Cell 63: 1357-1363) and the LightCycler 480 SW 1.5 software (Roche Diagnostics, Mannheim) and $EC_{50}$ values were calculated using non-linear regression with GraphPad Prism 6 (GraphPad Software Inc., La Jolla, USA).

Cell Viability Assay

Using the AlamarBlue viability assay cytotoxicity was evaluated in HepAD38 cells in the presence of 0.3 µg/ml tetracycline, which blocks the expression of the HBV genome. Assay condition and plate layout were in analogy to the anti-HBV assay, however other controls were used. On each assay plate six wells containing untreated HepAD38 cells were used as the 100% viability control, and six wells filled with assay medium only were used as 0% viability control. In addition, a geometric concentration series of cycloheximide starting at 60 µM final assay concentration was used as positive control in each experiment. After six days incubation period Alamar Blue Presto cell viability reagent (ThermoFisher, Dreieich) was added in 1/11 dilution to each well of the assay plate. After an incubation for 30 to 45 min at 37° C. the fluorescence signal, which is proportional to the number of living cells, was read using a Tecan Spectrafluor Plus plate reader with an excitation filter 550 nm and emission filter 595 nm, respectively. Data were normalized into percentages of the untreated control (100% viability) and assay medium (0% viability) before CC50 values were calculated using non-linear regression and the GraphPad Prism 6.0 (GraphPad Software, La Jolla, USA). Mean $EC_{50}$ and $CC_{50}$ values were used to calculate the selectivity index ($SI=CC_{50}/EC_{50}$) for each test compound.

In Vivo Efficacy Models

HBV research and preclinical testing of antiviral agents are limited by the narrow species- and tissue-tropism of the virus, the paucity of infection models available and the restrictions imposed by the use of chimpanzees, the only animals fully susceptible to HBV infection. Alternative animal models are based on the use of HBV-related hepadnaviruses and various antiviral compounds have been tested in woodchuck hepatitis virus (WHV) infected woodchucks or in duck hepatitis B virus (DHBV) infected ducks or in woolly monkey HBV (WM-HBV) infected tupaia (overview in Dandri et al., 2017, Best Pract Res Clin Gastroenterol 31, 273-279). However, the use of surrogate viruses has several limitations. For example is the sequence homology between the most distantly related DHBV and HBV is only about 40% and that is why core protein assembly modifiers of the HAP family appeared inactive on DHBV and WHV but efficiently suppressed HBV (Campagna et al., 2013, J. Virol. 87, 6931-6942). Mice are not HBV permissive but major efforts have focused on the development of mouse models of HBV replication and infection, such as the generation of mice transgenic for the human HBV (HBV tg mice), the hydrodynamic injection (HDI) of HBV genomes in mice or the generation of mice having humanized livers and/or humanized immune systems and the intravenous injection of viral vectors based on adenoviruses containing HBV genomes (Ad-HBV) or the adenoassociated virus (AAV-HBV) into immune competent mice (overview in Dandri et al., 2017, Best Pract Res Clin Gastroenterol 31, 273-279). Using mice transgenic for the full HBV genome the ability of murine hepatocytes to produce infectious HBV virions could be demonstrated (Guidotti et al., 1995, J. Virol., 69: 6158-6169). Since transgenic mice are immunological tolerant to viral proteins and no liver injury was observed in HBV-producing mice, these studies demonstrated that HBV itself is not cytopathic. HBV transgenic mice have been employed to test the efficacy of several anti-HBV agents like the polymerase inhibitors and core protein assembly modifiers (Weber et al., 2002, Antiviral Research 54 69-78; Julander et al., 2003, Antivir. Res., 59: 155-161), thus proving that HBV transgenic mice are well suitable for many type of preclinical antiviral testing in vivo.

As described in Paulsen et al., 2015, PLOSone, 10: e0144383 HBV-transgenic mice (Tg [HBV1.3 fsX-3'5']) carrying a frameshift mutation (GC) at position 2916/2917 could be used to demonstrate antiviral activity of core protein assembly modifiers in vivo. In brief, The HBV-transgenic mice were checked for HBV-specific DNA in the serum by qPCR prior to the experiments (see section "Determination of HBV DNA from the supernatants of HepAD38 cells"). Each treatment group consisted of five male and five female animals approximately 10 weeks age with a titer of above $3\times10^6$ virions per ml serum. Compounds were formulated as a suspension in a suitable vehicle such as 2% DMSO/98% tylose (0.5% Methylcellulose/99.5% PBS) or 50% PEG400 and administered per os to the animals one to three times/day for a 10 day period. The vehicle served as negative control, whereas 1 µg/kg entecavir in a suitable vehicle was the positive control. Blood was obtained by retro bulbar blood sampling using an Isoflurane Vaporizer. For collection of terminal heart puncture six hours after the last treatment blood or organs, mice were anaesthetized with isoflurane and subsequently sacrificed by $CO_2$ exposure. Retro bulbar (100-150 µl) and heart puncture (400-500 µl) blood samples were collected into a Microvette 300 LH or Microvette 500 LH, respectively, followed by separation of plasma via centrifugation (10 min, 2000 g, 4° C.). Liver tissue was taken and snap frozen in liquid N2. All samples were stored at −80° C. until further use. Viral DNA was extracted from 50 µl plasma or 25 mg liver tissue and eluted in 50 µl AE buffer (plasma) using the DNeasy 96 Blood & Tissue Kit (Qiagen, Hilden) or 320 µl AE buffer (liver tissue) using the DNeasy Tissue Kit (Qiagen, Hilden) according to the manufacturer's instructions. Eluted viral DNA was subjected to qPCR using the LightCycler 480 Probes Master PCR kit (Roche, Mannheim) according to the manufacturer's instructions to determine the HBV copy number. HBV specific primers used included the forward primer 5'-CTG TAC CAA ACC TTC GGA CGG-3', the reverse primer 5'-AGG AGA AAC GGG CTG AGG C-3' and the FAM labelled probe FAM-CCA TCA TCC TGG GCT TTC GGA AAA TT-BBQ. One PCR reaction sample with a total volume of 20 µl contained 5 µl DNA eluate and 15 µl master mix (comprising 0.3 µM of the forward primer, 0.3 µM of the reverse primer, 0.15 µM of the FAM labelled probe). qPCR was carried out on the Roche LightCycler1480 using the following protocol: Pre-incubation for 1 min at 95° C., amplification: (10 sec at 95° C., 50 sec at 60° C., 1 sec at 70° C.)×45 cycles, cooling for 10 sec at 40° C. Standard curves were generated as described above. All samples were tested in duplicate. The detection limit of the assay is ~50 HBV DNA copies (using standards ranging from 250-2.5×107 copy numbers). Results are expressed as HBV DNA copies/10 µl plasma or HBV DNA copies/100 ng total liver DNA (normalized to negative control).

It has been shown in multiple studies that not only transgenic mice are a suitable model to proof the antiviral activity of new chemical entities in vivo the use of hydrodynamic injection of HBV genomes in mice as well as the use of immune deficient human liver chimeric mice infected with HBV positive patient serum have also frequently used to profile drugs targeting HBV (Li et al., 2016, Hepat. Mon. 16: e34420; Qiu et al., 2016, J. Med. Chem. 59: 7651-7666; Lutgehetmann et al., 2011, Gastroenterology, 140: 2074-2083). In addition chronic HBV infection has also been successfully established in immunecompetent mice by inoculating low doses of adenovirus-(Huang et al., 2012, Gastroenterology 142: 1447-1450) or adeno-associated virus (AAV) vectors containing the HBV genome (Dion et al., 2013, J Virol. 87: 5554-5563). This models could also be used to demonstrate the in vivo antiviral activity of novel anti-HBV agents.

TABLE 1

Biochemical and antiviral activities

| Example | $CC_{50}$ (µM) | Cell Activity | Assembly Activity |
|---|---|---|---|
| Example 1 | | Example not included | |
| Example 2 | | Example not included | |
| Example 3 | >10 | +++ | A |
| Example 4 | >10 | +++ | A |
| Example 5 | >32 | + | A |
| Example 6 | >10 | +++ | A |
| Example 7 | >10 | +++ | A |
| Example 8 | >10 | +++ | A |
| Example 9 | >10 | +++ | A |
| Example 10 | >10 | +++ | A |
| Example 11 | >10 | +++ | NT |
| Example 12 | >10 | +++ | A |
| Example 13 | >10 | +++ | NT |
| Example 14 | >10 | +++ | NT |
| Example 15 | >10 | +++ | B |
| Example 16 | >10 | +++ | A |
| Example 17 | >10 | +++ | A |
| Example 18 | 7.3 | +++ | A |
| Example 19 | >10 | +++ | A |
| Example 20 | >10 | +++ | A |
| Example 21 | >10 | +++ | C |
| Example 22 | >10 | +++ | A |
| Example 23 | >10 | +++ | A |
| Example 24 | | Example not included | |
| Example 25 | >10 | ++ | NT |
| Example 26 | >10 | +++ | A |
| Example 27 | >10 | +++ | A |
| Example 28 | >10 | +++ | A |
| Example 29 | >10 | +++ | A |
| Example 30 | >10 | +++ | A |
| Example 31 | >100 | ++ | B |
| Example 32 | >100 | +++ | A |
| Example 33 | >10 | +++ | A |
| Example 34 | >15 | +++ | C |
| Example 35 | >32 | +++ | NT |
| Example 36 | 88.0 | +++ | B |
| Example 37 | >32 | +++ | B |
| Example 38 | 100.0 | +++ | A |
| Example 39 | >32 | ++ | C |
| Example 40 | >100 | ++ | A |
| Example 41 | >100 | +++ | A |
| Example 42 | >100 | ++ | B |
| Example 43 | >32 | +++ | B |
| Example 44 | >100 | ++ | C |
| Example 45 | >100 | ++ | C |
| Example 46 | >100 | +++ | A |
| Example 47 | >100 | +++ | A |
| Example 48 | >32 | +++ | A |
| Example 49 | >100 | + | C |
| Example 50 | >32 | + | C |
| Example 51 | >100 | +++ | A |
| Example 52 | >100 | +++ | A |
| Example 53 | >100 | +++ | A |
| Example 54 | >100 | +++ | A |
| Example 55 | >32 | +++ | A |
| Example 56 | >32 | +++ | A |
| Example 57 | >100 | +++ | A |
| Example 58 | >100 | +++ | A |
| Example 59 | >32 | +++ | A |
| Example 60 | >32 | +++ | A |
| Example 61 | >100 | +++ | A |
| Example 62 | >100 | +++ | A |
| Example 63 | >100 | +++ | A |
| Example 64 | >32 | +++ | A |
| Example 65 | | Example not included | |
| Example 66 | >32 | +++ | A |
| Example 67 | >32 | +++ | A |
| Example 68 | NT | NT | NT |
| Example 69 | NT | NT | NT |
| Example 70 | >32 | ++ | A |
| Example 71 | >32 | ++ | B |
| Example 72 | | Example not included | |
| Example 73 | | Example not included | |
| Example 74 | >100 | ++ | C |
| Example 75 | >100 | +++ | B |
| Example 76 | | Example not included | |
| Example 77 | | Example not included | |
| Example 78 | | Example not included | |
| Example 79 | >100 | ++ | B |
| Example 80 | >100 | ++ | C |
| Example 81 | >100 | ++ | C |
| Example 82 | >100 | + | C |
| Example 83 | NT | NT | NT |
| Example 84 | NT | NT | NT |
| Example 85 | >100 | ++ | C |
| Example 86 | | Example not included | |
| Example 87 | >100 | ++ | NT |
| Example 88 | | Example not included | |
| Example 89 | NT | NT | NT |
| Example 90 | | Example not included | |
| Example 91 | >100 | ++ | B |
| Example 92 | | Example not included | |
| Example 93 | | Example not included | |
| Example 94 | | Example not included | |
| Example 95 | >100 | ++ | C |
| Example 96 | >100 | ++ | C |
| Example 97 | >100 | +++ | B |
| Example 98 | >32 | ++ | C |
| Example 99 | >100 | ++ | B |
| Example 100 | >100 | +++ | A |
| Example 101 | >100 | + | C |
| Example 102 | >100 | +++ | A |
| Example 103 | >100 | +++ | A |
| Example 104 | >100 | ++ | C |
| Example 105 | >100 | ++ | C |
| Example 106 | >100 | + | C |
| Example 107 | >100 | ++ | C |
| Example 108 | >100 | ++ | C |
| Example 109 | >100 | ++ | B |
| Example 110 | NT | NT | NT |
| Example 111 | NT | NT | NT |
| Example 112 | >32 | +++ | A |
| Example 113 | >100 | +++ | A |
| Example 114 | >100 | +++ | A |
| Example 115 | >100 | ++ | B |
| Example 116 | >100 | + | B |
| Example 117 | >100 | + | C |
| Example 118 | >100 | ++ | B |
| Example 119 | >100 | +++ | A |
| Example 120 | >100 | +++ | B |
| Example 121 | | Example not included | |
| Example 122 | >100 | ++ | C |
| Example 123 | NT | NT | NT |
| Example 124 | >32 | +++ | A |
| Example 125 | >100 | +++ | A |
| Example 126 | >32 | +++ | A |
| Example 127 | >100 | +++ | A |
| Example 128 | 98.0 | +++ | A |
| Example 129 | >32 | +++ | A |

TABLE 1-continued

Biochemical and antiviral activities

| Example | CC$_{50}$ (μM) | Cell Activity | Assembly Activity |
|---|---|---|---|
| Example 130 | | Example not included | |
| Example 131 | >100 | +++ | A |
| Example 132 | >10 | NT | A |
| Example 133 | >100 | + | A |
| Example 134 | | Example not included | |
| Example 135 | >100 | +++ | A |
| Example 136 | >100 | +++ | A |
| Example 137 | | Example not included | |
| Example 138 | >100 | +++ | A |
| Example 139 | NT | NT | NT |
| Example 140 | >100 | + | A |
| Example 141 | | Example not included | |
| Example 142 | >100 | +++ | A |
| Example 143 | NT | ++ | B |
| Example 144 | NT | NT | NT |
| Example 145 | NT | NT | NT |
| Example 146 | >10 | ++ | NT |
| Example 147 | >10 | +++ | B |
| Example 148 | >10 | ++ | B |
| Example 149 | >10 | ++ | C |
| Example 150 | >10 | ++ | C |
| Example 151 | >10 | ++ | NT |
| Example 152 | >10 | ++ | C |
| Example 153 | >10 | ++ | C |
| Example 154 | >10 | +++ | B |
| Example 155 | >10 | +++ | A |
| Example 156 | >10 | ++ | C |
| Example 157 | >10 | ++ | C |
| Example 158 | >10 | ++ | C |
| Example 159 | >10 | +++ | A |
| Example 160 | >10 | +++ | C |
| Example 161 | >10 | +++ | B |
| Example 162 | >10 | ++ | C |
| Example 163 | >10 | ++ | C |
| Example 164 | NT | NT | NT |
| Example 165 | >10 | +++ | B |
| Example 166 | >10 | +++ | A |
| Example 167 | >10 | +++ | A |
| Example 168 | >10 | ++ | NT |
| Example 169 | NT | NT | NT |
| Example 170 | >10 | ++ | B |
| Example 171 | >10 | ++ | C |
| Example 172 | >10 | ++ | A |
| Example 173 | >10 | ++ | C |
| Example 174 | >10 | ++ | C |
| Example 175 | >10 | ++ | B |
| Example 176 | >10 | ++ | B |
| Example 177 | NT | NT | NT |
| Example 178 | >10 | +++ | A |
| Example 179 | | Example not included | |
| Example 180 | >10 | ++ | C |
| Example 181 | >10 | ++ | B |
| Example 182 | >10 | ++ | NT |
| Example 183 | >10 | ++ | NT |
| Example 184 | >10 | +++ | A |
| Example 185 | >10 | +++ | B |
| Example 186 | >10 | +++ | NT |
| Example 187 | >10 | +++ | NT |
| Example 188 | >10 | +++ | B |
| Example 189 | >10 | ++ | C |
| Example 190 | >10 | +++ | A |
| Example 191 | >10 | ++ | A |
| Example 192 | >10 | +++ | B |
| Example 193 | >10 | ++ | C |
| Example 194 | >10 | ++ | C |
| Example 195 | >10 | +++ | B |
| Example 196 | >10 | +++ | A |
| Example 197 | >10 | +++ | A |
| Example 198 | >10 | +++ | A |
| Example 199 | >10 | ++ | C |
| Example 200 | >10 | ++ | NT |
| Example 201 | >10 | +++ | A |
| Example 202 | >10 | +++ | A |
| Example 203 | >10 | +++ | B |
| Example 204 | >10 | +++ | A |
| Example 205 | >10 | +++ | A |
| Example 206 | >10 | +++ | A |
| Example 207 | >10 | +++ | A |
| Example 208 | >10 | +++ | A |
| Example 209 | >10 | +++ | NT |
| Example 210 | >10 | +++ | NT |
| Example 211 | >10 | +++ | A |
| Example 212 | >10 | ++ | NT |
| Example 213 | | Example not included | |
| Example 214 | >10 | +++ | NT |
| Example 215 | >10 | +++ | NT |
| Example 216 | >10 | +++ | NT |
| Example 217 | >10 | +++ | NT |
| Example 218 | NT | NT | NT |
| Example 219 | >10 | +++ | NT |
| Example 220 | >10 | ++ | NT |
| Example 221 | >10 | +++ | NT |
| Example 222 | >10 | +++ | NT |
| Example 223 | >10 | ++ | NT |
| Example 224 | >10 | +++ | NT |
| Example 225 | >10 | +++ | NT |
| Example 226 | >10 | ++ | NT |
| Example 227 | >10 | +++ | NT |
| Example 228 | >10 | +++ | NT |
| Example 229 | >10 | +++ | NT |
| Example 230 | >10 | +++ | NT |
| Example 231 | >10 | +++ | NT |
| Example 232 | >10 | +++ | A |
| Example 233 | | Example not included | |
| Example 234 | | Example not included | |
| Example 235 | | Example not included | |
| Example 236 | >10 | ++ | NT |
| Example 237 | >10 | + | NT |
| Example 238 | >10 | +++ | NT |
| Example 239 | >10 | +++ | NT |
| Example 240 | >10 | +++ | NT |
| Example 241 | >10 | +++ | NT |
| Example 242 | >10 | +++ | NT |
| Example 243 | >10 | +++ | NT |
| Example 244 | >10 | + | NT |
| Example 245 | >10 | + | B |
| Example 246 | >10 | + | C |
| Example 247 | >10 | + | C |
| Example 248 | >10 | +++ | A |
| Example 249 | >10 | +++ | A |
| Example 250 | NT | NT | NT |
| Example 251 | >10 | +++ | A |
| Example 252 | >10 | +++ | A |
| Example 253 | >10 | ++ | B |
| Example 254 | >10 | +++ | A |
| Example 255 | >10 | +++ | A |
| Example 256 | >10 | +++ | A |
| Example 257 | >10 | ++ | NT |
| Example 258 | >10 | ++ | NT |
| Example 259 | >10 | ++ | NT |
| Example 260 | >10 | +++ | A |
| Example 261 | NT | NT | NT |
| Example 262 | >10 | +++ | A |
| Example 263 | >10 | +++ | A |
| Example 264 | >10 | +++ | A |
| Example 265 | >10 | +++ | A |
| Example 266 | >10 | +++ | A |
| Example 267 | >10 | +++ | A |
| Example 268 | >10 | +++ | A |
| Example 269 | >10 | +++ | A |
| Example 270 | >10 | +++ | A |
| Example 271 | >10 | +++ | A |
| Example 272 | >10 | +++ | A |
| Example 273 | >10 | ++ | C |
| Example 274 | >10 | ++ | C |
| Example 275 | >10 | ++ | NT |
| Example 276 | NT | NT | NT |
| Example 277 | NT | NT | NT |
| Example 278 | NT | NT | NT |
| Example 279 | >10 | +++ | A |
| Example 280 | >10 | +++ | C |
| Example 281 | >10 | ++ | C |

TABLE 1-continued

Biochemical and antiviral activities

| Example | CC$_{50}$ (μM) | Cell Activity | Assembly Activity |
|---|---|---|---|
| Example 282 | NT | NT | NT |
| Example 283 | NT | NT | NT |
| Example 284 | NT | NT | NT |
| Example 285 | >10 | ++ | C |
| Example 286 | NT | NT | NT |
| Example 287 | NT | NT | NT |
| Example 288 | >10 | ++ | NT |
| Example 289 | >10 | ++ | NT |
| Example 290 | >10 | +++ | A |
| Example 291 | >10 | +++ | A |
| Example 292 | >10 | ++ | A |
| Example 293 | >10 | + | NT |
| Example 294 | >10 | +++ | B |
| Example 295 | NT | NT | NT |
| Example 296 | >10 | +++ | A |
| Example 297 | >10 | +++ | A |
| Example 298 | >10 | +++ | A |
| Example 299 | >10 | +++ | A |
| Example 300 | >10 | +++ | A |
| Example 301 | >10 | +++ | A |
| Example 302 | >10 | +++ | A |
| Example 303 | >10 | +++ | A |
| Example 304 | >10 | +++ | A |
| Example 305 | >10 | +++ | A |
| Example 306 | >10 | +++ | A |
| Example 307 | >10 | +++ | A |
| Example 308 | >10 | +++ | A |
| Example 309 | >10 | +++ | A |
| Example 310 | >10 | ++ | C |
| Example 311 | >10 | +++ | A |
| Example 312 | >10 | +++ | A |
| Example 313 | >10 | +++ | A |
| Example 314 | Example not included | | |
| Example 315 | >10 | +++ | A |
| Example 316 | >10 | ++ | A |
| Example 317 | >10 | +++ | A |
| Example 318 | >10 | +++ | A |
| Example 319 | >10 | +++ | NT |
| Example 320 | >10 | +++ | NT |
| Example 321 | >10 | +++ | NT |
| Example 322 | >10 | +++ | A |
| Example 323 | >10 | +++ | A |
| Example 324 | >10 | +++ | A |
| Example 325 | >10 | +++ | A |
| Example 326 | >10 | +++ | A |
| Example 327 | >10 | +++ | A |
| Example 328 | >10 | +++ | A |
| Example 329 | >10 | +++ | A |
| Example 330 | >10 | +++ | A |
| Example 331 | >10 | +++ | A |
| Example 332 | >10 | +++ | A |
| Example 333 | >10 | +++ | A |
| Example 334 | >10 | +++ | A |
| Example 335 | >10 | +++ | NT |
| Example 336 | >10 | +++ | A |
| Example 337 | >10 | +++ | A |
| Example 338 | >10 | +++ | A |
| Example 339 | >10 | +++ | A |
| Example 340 | >10 | +++ | A |
| Example 341 | >10 | +++ | A |
| Example 342 | >10 | +++ | A |
| Example 343 | >10 | +++ | A |
| Example 344 | >10 | +++ | A |
| Example 345 | NT | NT | NT |
| Example 346 | NT | NT | NT |
| Example 347 | NT | NT | NT |
| Example 348 | NT | NT | NT |
| Example 349 | NT | NT | NT |
| Example 350 | NT | NT | NT |
| Example 351 | NT | NT | NT |
| Example 352 | NT | NT | NT |
| Example 353 | NT | NT | NT |
| Example 354 | NT | NT | NT |
| Example 355 | NT | NT | NT |
| Example 356 | NT | NT | NT |
| Example 357 | NT | NT | NT |
| Example 358 | NT | NT | NT |
| Example 359 | >10 | +++ | A |
| Example 360 | >10 | +++ | A |
| Example 361 | >10 | ++ | A |
| Example 362 | >10 | +++ | NT |
| Example 363 | >10 | +++ | A |
| Example 364 | >10 | +++ | A |
| Example 365 | >10 | +++ | A |
| Example 366 | >10 | +++ | A |
| Example 367 | >10 | +++ | A |
| Example 368 | >10 | +++ | A |
| Example 369 | NT | NT | NT |
| Example 370 | NT | NT | NT |
| Example 371 | NT | NT | NT |
| Example 372 | NT | NT | NT |
| Example 373 | NT | NT | NT |
| Example 374 | NT | NT | NT |
| Example 375 | NT | NT | NT |
| Example 376 | NT | NT | NT |
| Example 377 | NT | NT | NT |
| Example 378 | NT | NT | NT |
| Example 379 | NT | NT | NT |
| Example 380 | NT | NT | NT |
| Example 381 | NT | NT | NT |
| Example 382 | NT | NT | NT |
| Example 383 | NT | NT | NT |
| Example 384 | NT | NT | NT |
| Example 385 | NT | NT | NT |
| Example 386 | NT | NT | NT |
| Example 387 | >10 | +++ | NT |
| Example 388 | >10 | +++ | NT |
| Example 389 | >10 | +++ | NT |
| Example 390 | >10 | +++ | NT |
| Example 391 | >10 | +++ | NT |
| Example 392 | >10 | +++ | NT |
| Example 393 | >10 | +++ | NT |
| Example 394 | >10 | +++ | NT |
| Example 395 | >10 | +++ | NT |
| Example 396 | >10 | +++ | NT |
| Example 397 | >10 | +++ | NT |
| Example 398 | >10 | +++ | NT |
| Example 399 | >10 | +++ | NT |
| Example 400 | >10 | +++ | NT |
| Example 401 | >10 | +++ | NT |
| Example 402 | >10 | +++ | NT |
| Example 403 | NT | NT | NT |
| Example 404 | NT | NT | NT |
| Example 405 | NT | NT | NT |
| Example 406 | NT | NT | NT |
| Example 407 | NT | NT | NT |
| Example 408 | NT | NT | NT |
| Example 409 | NT | NT | NT |
| Example 410 | NT | NT | NT |
| Example 411 | NT | NT | NT |
| Example 412 | NT | NT | NT |
| Example 413 | NT | NT | NT |
| Example 414 | NT | NT | NT |
| Example 415 | NT | NT | NT |
| Example 416 | NT | NT | NT |
| Example 417 | NT | NT | NT |
| Example 418 | NT | NT | NT |
| Example 419 | NT | NT | NT |
| Example 420 | NT | NT | NT |
| Example 421 | NT | NT | NT |
| Example 422 | NT | NT | NT |
| Example 423 | NT | NT | NT |
| Example 424 | NT | NT | NT |
| Example 425 | NT | NT | NT |
| Example 426 | NT | NT | NT |
| Example 427 | NT | NT | NT |
| Example 428 | NT | NT | NT |

TABLE 1-continued

Biochemical and antiviral activities

| Example | CC$_{50}$ (μM) | Cell Activity | Assembly Activity |
|---|---|---|---|
| Example 429 | NT | NT | NT |
| Example 430 | NT | NT | NT |
| Example 431 | NT | NT | NT |
| Example 432 | NT | NT | NT |
| Example 433 | NT | NT | NT |
| Example 434 | NT | NT | NT |
| Example 435 | NT | NT | NT |
| Example 436 | NT | NT | NT |

In Table 1, "+++" represents an EC$_{50}$ < 1 μM; "++" represents 1 μM < EC$_{50}$ < 25 μM; "+" represents EC$_{50}$ < 100 μM (Cell activity assay), NT = inactive/no data
In Table 1, "A" represents an IC$_{50}$ < 5 μM; "B" represents 5 μM < IC$_{50}$ < 10 μM; "C" represents IC$_{50}$ < 100 μM (Assembly assay activity), NT = inactive/no data

The invention claimed is:

1. Compound of Formula Ia

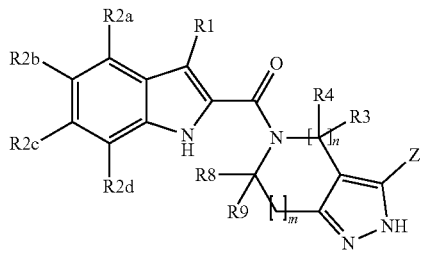

in which

Z is H, D, C(=O)N(R5)(R6), C(=O)N(R5)O(R6), C(=O)N(R5)N(R6)(R7), N(R5)(R6), N(R5)SO$_2$(R6), C(=O)O(R5), CH$_2$—N(R5)(R6), C(R5)=NO(R6), O—R5, SO2N(R5)(R6), SO$_2$—R5, alkyl, cycloalkyl, heterocycloalkyl, heteroaryl, or heteroaryl substituted with C2-C6 alkenyl, wherein cycloalkyl is optionally substituted with carboxy, carboxyl ester, halo, C1-C6 alkyl, C1-C6-haloalkyl or NH$_2$ R1 is H, D, F, Cl, Br or NH$_2$ R2a, R2b, R2c and R2d are for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C=C, C≡C, C≡N, C(CH$_3$)$_2$OH, Si(CH$_3$)$_3$, SMe, OH, with the proviso that when Z is H, R2b is not F and R2c is not Cl or CH$_3$ R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring R5, R6 and R7 are independently selected from the group comprising H, D, C1-C6-alkyl, C3-C6-cycloalkyl, C1-C4-carboxyalkyl, C1-C4-acylsulfonamido-alkyl, C1-C4-carboxamidoalkyl, C4-C7-heterocycloalkyl, C2-C6-aminoalkyl, C2-C6-hydroxyalkyl, and C2-C6-alkynyl, optionally substituted with 1, 2, or 3 groups each independently selected from OH, halo, C≡N, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C4-carboxamidoalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO$_2$-C1-C6-alkyl, or C≡N R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1 or 2 m is 0 or 1 or a pharmaceutically acceptable salt thereof or a solvate or a hydrate of a compound of Formula Ia or the pharmaceutically acceptable salt thereof or a prodrug of a compound of Formula Ia or a pharmaceutically acceptable salt or a solvate or a hydrate thereof.

2. A compound of Formula Ia according to claim 1 that is a compound of Formula II

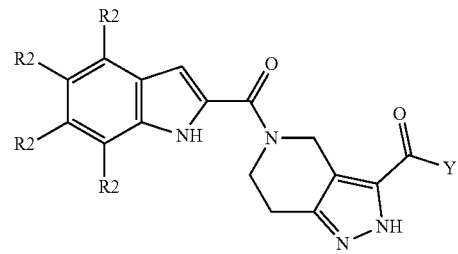

in which

Y is N(R5)(R6), N(R5)O(R6), or N(R5)N(R6)(R7)

R2 is for each position independently selected from the group comprising H, CF$_2$H, CF$_3$, CF$_2$CH$_3$, F, Cl, Br, CH$_3$, Et, and i-Pr R5, R6, and R7 are independently selected from the group comprising H, D, C1-C6-alkyl, C3-C6-cycloalkyl, C1-C4-carboxyalkyl, C4-C7-heterocycloalkyl, C1-C4-carboxamidoalkyl, C1-C4-acylsulfonamido-alkyl, C2-C6-aminoalkyl, and C2-C6-hydroxyalkyl, optionally substituted with 1, 2, or 3 groups each independently selected from OH, halo, amino, acyl, SO$_2$Me, SO$_3$H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl, C1-C6-hydroxyalkyl, and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO$_2$-C1-C6-alkyl, or C≡N R5 and R6 are optionally connected to form a C4-C7-heterocyclic ring containing 1 or 2 nitrogen, sulfur or oxygen atoms, or hetero-spirocyclic system consisting of 2 or 3 C3-C7 rings and containing 1 or 2 nitrogen, sulfur or oxygen atoms, optionally substituted with 1, 2, or 3 groups each independently selected from OH, halo, amino, acyl, SO₂Me, SO₃H, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy or a pharmaceutically acceptable salt thereof or a solvate or a hydrate of a compound of Formula II or the pharmaceutically acceptable salt thereof or a prodrug of a compound of Formula II or a pharmaceutically acceptable salt or a solvate or a hydrate thereof.

3. A compound of Formula Ia according to claim 1 that is a compound of Formula III

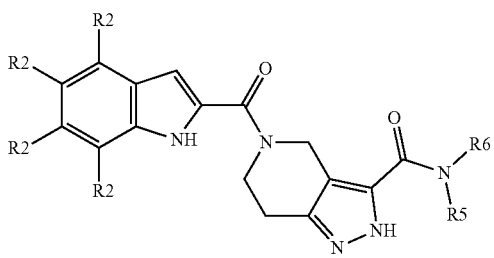

III in which

R2 is for each position independently selected from the group comprising H, CH₂F, CF₂H, CF₃, C(F)CH₃, CF₂CH₃, F, Cl, Br, CH₃, Et R5 is selected from the group comprising C1-C6-alkyl, C3-C6-cycloalkyl, C4-C7-heterocycloalkyl, C2-C6-aminoalkyl, C2-C6-hydroxyalkyl, C1-C4-carboxamidoalkyl, C1-C4-carboxyalkyl, and C1-C4-acylsulfonamido-alkyl, optionally substituted with 1, 2, or 3 groups each independently selected from OH, halo, amino, acyl, SO₂Me, SO₃H, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-alkyl-O-C1-C6-alkyl and C1-C6 alkenyloxy, wherein C1-C6-alkyl, C6-aryl and heteroaryl are optionally substituted with acyloxy, carboxy, carboxyl ester, C6-aryl, C2-C6-alkynyloxy, C1-C6-alkyl, C1-C6-haloalkyl, S-C1-C6-alkyl, SO₂-C1-C6-alkyl, or C≡N R6 is selected from the group comprising methyl and ethyl or a pharmaceutically acceptable salt thereof or a solvate or a hydrate of a compound of Formula III or the pharmaceutically acceptable salt thereof or a prodrug of a compound of Formula III or a pharmaceutically acceptable salt or a solvate or a hydrate thereof.

4. A compound of Formula Ia according to claim 1 that is a compound of Formula VI

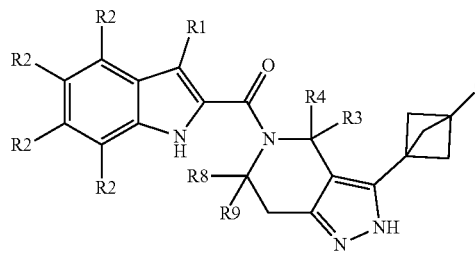

VI in which,

Q is H, carboxy, carboxyl ester, halo, C1-C6 alkyl, C1-C6-haloalkyl or NH₂

R1 is H, D, F, Cl, Br or NH₂

R2 is for each position independently selected from the group comprising H, CF₂H, CF₃, CF₂CH₃, F, Cl, Br, CH₃, Et, and i-Pr R3, R4, R8 and R9 are for each position independently selected from the group comprising H, methyl and ethyl R3 and R4 are optionally connected to form a C3-C5-cycloalkyl ring R3 and R8 are optionally connected to form a bridged heterobicyclic ring or a pharmaceutically acceptable salt thereof or a solvate or a hydrate of a compound of Formula VI or the pharmaceutically acceptable salt thereof or a prodrug of a compound of Formula VI or a pharmaceutically acceptable salt or a solvate or a hydrate thereof.

5. A compound according to claim 1 or a pharmaceutically acceptable salt thereof or a solvate or a hydrate of said compound or the pharmaceutically acceptable salt thereof or a prodrug of said compound or a pharmaceutically acceptable salt or a solvate or a hydrate thereof for use in the treatment of an HBV infection in subject.

6. A pharmaceutical composition comprising a compound according to claim 1 or a pharmaceutically acceptable salt thereof or a solvate or a hydrate of said compound or the pharmaceutically acceptable salt thereof or a prodrug of said compound or a pharmaceutically acceptable salt or a solvate or a hydrate thereof, together with a pharmaceutically acceptable carrier.

7. A method of treating an HBV infection in an individual in need thereof, comprising administering to the individual a therapeutically effective amount of a compound according to claim 1 or a pharmaceutically acceptable salt thereof or a solvate or a hydrate of said compound or the pharmaceutically acceptable salt thereof or a prodrug of said compound or a pharmaceutically acceptable salt or a solvate or a hydrate thereof.

8. Method for the preparation of a compound of Formula Ia according to claim 1 by reacting a compound of Formula IV

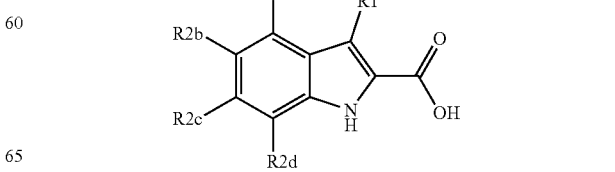

IV in which R1, R2a, R2b, R2c and R2d are as defined in claim 1, with a compound of Formula V
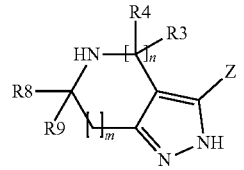
in which n, m, Z, R3, R4, R8 and R9 are as defined in claim 1.
* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Hepatitis B virus

<400> SEQUENCE: 1
ctgtaccaaa ccttcggacg g                                21

<210> SEQ ID NO 2
<211> LENGTH: 18
<212> TYPE: DNA
<213> ORGANISM: Hepatitis B virus

<400> SEQUENCE: 2
aggagaaacg ggctgagg                                    18

<210> SEQ ID NO 3
<211> LENGTH: 26
<212> TYPE: DNA
<213> ORGANISM: Hepatitis B virus

<400> SEQUENCE: 3
ccatcatcct gggctttcgg aaaatt                           26

<210> SEQ ID NO 4
<211> LENGTH: 24
<212> TYPE: DNA
<213> ORGANISM: Hepatitis B virus

<400> SEQUENCE: 4
tgcagaggtg aagcgaagtg caca                             24

<210> SEQ ID NO 5
<211> LENGTH: 24
<212> TYPE: DNA
<213> ORGANISM: Hepatitis B virus

<400> SEQUENCE: 5
gacgtccttt gtttacgtcc cgtc                             24

<210> SEQ ID NO 6
<211> LENGTH: 25
<212> TYPE: DNA
<213> ORGANISM: Hepatitis B virus

<400> SEQUENCE: 6
acggggcgca cctctcttta cgcgg                            25

<210> SEQ ID NO 7

```
<211> LENGTH: 26
<212> TYPE: DNA
<213> ORGANISM: Hepatitis B virus

<400> SEQUENCE: 7
ctccccgtct gtgccttctc atctgc                                          26
```